(12) United States Patent
Gillespie et al.

(10) Patent No.: US 8,404,859 B2
(45) Date of Patent: Mar. 26, 2013

(54) THIAZOLE AND THIOPHENE COMPOUNDS

(75) Inventors: Paul Gillespie, Westfield, NJ (US); Christophe Michoud, New York, NY (US); Kenneth Carey Rupert, Bedminster, NJ (US); Kshitij Chhabilbhai Thakkar, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/399,106

(22) Filed: Feb. 17, 2012

(65) Prior Publication Data

US 2012/0238569 A1 Sep. 20, 2012

Related U.S. Application Data

(60) Provisional application No. 61/453,208, filed on Mar. 16, 2011.

(51) Int. Cl.
*A61K 31/426* (2006.01)
*A61K 31/381* (2006.01)
*C07D 417/12* (2006.01)
*C07D 277/46* (2006.01)
*C07D 333/38* (2006.01)

(52) U.S. Cl. ..... 548/188; 548/198; 548/181; 548/304.7; 548/467; 548/361.1; 549/72; 544/310; 544/405; 514/371; 514/444; 514/471

(58) Field of Classification Search .................. 548/188, 548/198; 549/72
See application file for complete search history.

(56) References Cited

U.S. PATENT DOCUMENTS

2005/0203135 A1 9/2005 Burdick et al.
2009/0258069 A1 10/2009 Burnier et al.

FOREIGN PATENT DOCUMENTS

WO 00/21920 4/2000
WO 02/02539 1/2002
WO 2005/084695 9/2005

OTHER PUBLICATIONS

Barnes et al., European Respiratory Journal (2005), 25(6), pp. 1084-1106.*
(International Search Report PCT/EP2012/054418 Mar. 14, 2012).

* cited by examiner

*Primary Examiner* — Laura L. Stockton
(74) *Attorney, Agent, or Firm* — George W. Johnston; Dennis P. Tramaloni

(57) ABSTRACT

Provided herein are compounds of the formula (I):

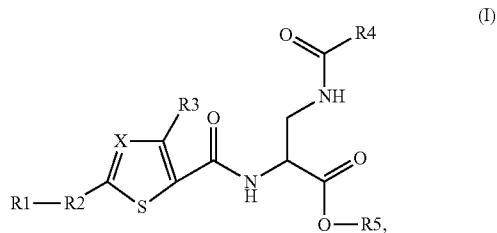

as well as pharmaceutically acceptable salts thereof, wherein the substituents are as those disclosed in the specification. These compounds, and the pharmaceutical compositions containing them, are useful for the treatment of inflammatory diseases and disorders such as, for example, asthma and COPD.

24 Claims, No Drawings

THIAZOLE AND THIOPHENE COMPOUNDS

PRIORITY TO RELATED APPLICATION(S)

This application claims the benefit of U.S. Provisional Application No. 61/453,208, filed Mar. 16, 2011, which is hereby incorporated by reference in its entirety.

FIELD OF THE INVENTION

The present invention relates to organic compounds useful for therapy and/or prophylaxis in a mammal, and in particular to LFA-1 antagonists and dual LFA-1/MAC-1 antagonists useful for treating inflammatory diseases and disorders.

SUMMARY OF THE INVENTION

In an embodiment of the present invention, provided are compounds of general formula (I):

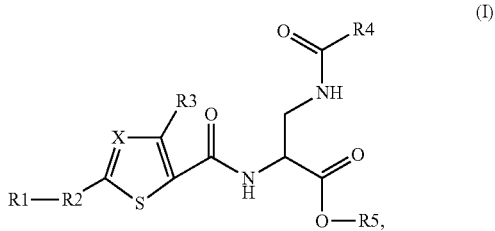

wherein:
X is N or CH;
R1 is indole, oxoindole, indazole or substituted phenyl, said substituted phenyl being mono- or bi-substituted independently with hydroxy, halogen, alkoxy or lower alkyl;
R2 is —(CH$_2$)$_n$C(O)NH—, —(CH$_2$)$_n$NHC(O)—, —(CH$_2$)$_n$NH—, —(CH$_2$)$_n$O— or —CH(CH$_3$)NHC(O)—;
R3 is hydrogen, methyl, trifluoromethyl, halogen or cyano;
R4 is indazole, benzimidazole, unsubstituted heteroaryl, heteroaryl mono- or bi-substituted independently with (=O), alkoxy or hydroxy, unsubstituted phenyl or phenyl mono- or bi-substituted independently with hydroxy, methyl, halogen or —COOH;
R5 is hydrogen, lower alkyl, alkoxy, cycloalkyl, heterocycloalkyl, lower alkyl-cycloalkyl, lower alkyl-heterocycloalkyl, —(CH$_2$)$_n$OR6, —CH(CH$_3$)O(O)R6 or —(CH$_2$)$_n$NR7R8;
R6, R7 and R8, independently of each other, are hydrogen, lower alkyl or alkoxy; and
n is 1, 2 or 3,
or a pharmaceutically acceptable salt thereof.

In a further embodiment of the invention, provided is a pharmaceutical composition comprising a therapeutically effective amount of a compound according to formula (I) and a therapeutically inert carrier.

In a still further embodiment of the invention, provided is a method for the treatment or prophylaxis of asthma or COPD, which method comprises the step of administering an effective amount of a compound according to formula (I) to a patient in need thereof.

All documents cited to or relied upon below are expressly incorporated herein by reference.

DETAILED DESCRIPTION OF THE INVENTION

Asthmatic and COPD symptoms such as restricted breathing and airway inflammation can be linked to the migration and activation of leukocytes into the lung. LFA-1 on neutrophils and MAC-1 on macrophages are major receptors that upon activation promote leukocyte infiltration and activation into the lung. Therefore, LFA-1 antagonists and dual LFA-1/MAC-1 antagonists are desirable therapeutics for the treatment of inflammatory diseases and disorders.

Provided herein are LFA-1 antagonist and dual LFA-1/MAC-1 antagonist compounds. The compounds of the invention are useful for the treatment of inflammatory diseases and disorders such as, for example, asthma and COPD.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further. Each substituent can independently be, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The alkyl, lower alkyl, aryl and heteroaryl groups described above may be substituted independently with one, two, or three substituents, with the understanding that said substituents are not, in turn, substituted further. These substituents may optionally form a ring with the heteroaryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

The present invention provides novel compounds of general formula (I):

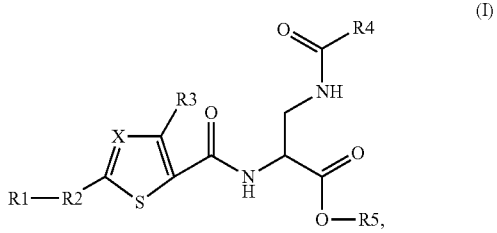

wherein:
X is N or CH;
R1 is indole, oxoindole, indazole or substituted phenyl, said substituted phenyl being mono- or bi-substituted independently with hydroxy, halogen, alkoxy or lower alkyl;
R2 is —(CH$_2$)$_n$C(O)NH—, —(CH$_2$)$_n$NHC(O)—, —(CH$_2$)$_n$NH—, —(CH$_2$)$_n$O— or —CH(CH$_3$)NHC(O)—;
R3 is hydrogen, methyl, trifluoromethyl, halogen or cyano;
R4 is indazole, benzimidazole, unsubstituted heteroaryl, heteroaryl mono- or bi-substituted independently with (=O), alkoxy or hydroxy, unsubstituted phenyl or phenyl mono- or bi-substituted independently with hydroxy, methyl, halogen or —COOH;
R5 is hydrogen, lower alkyl, alkoxy, cycloalkyl, heterocycloalkyl, lower alkyl-cycloalkyl, lower alkyl-heterocycloalkyl, —(CH$_2$)$_n$OR6, —CH(CH$_3$)O(O)R6 or —(CH$_2$)$_n$NR7R8;
R6, R7 and R8, independently of each other, are hydrogen, lower alkyl or alkoxy; and
n is 1, 2 or 3,
or a pharmaceutically acceptable salt thereof.

In another embodiment of the invention, provided is a compound according to formula (I) wherein X is N.

In another embodiment of the invention, provided is a compound according to formula (I) wherein X is CH.

In another embodiment of the invention, provided is a compound according to formula (I) wherein R1 is indole, oxoindole or indazole.

In another embodiment of the invention, provided is a compound according to formula (I) wherein R1 is phenyl mono- or bi-substituted independently with hydroxy, halogen, alkoxy or lower alkyl.

In another embodiment of the invention, provided is a compound according to formula (I) wherein R1 is hydroxyphenyl.

In another embodiment of the invention, provided is a compound according to formula (I) wherein R2 is —(CH$_2$)$_n$C(O)NH— or —(CH$_2$)$_n$NHC(O)—.

In another embodiment of the invention, provided is a compound according to formula (I) wherein R2 is —(CH$_2$)$_n$NH—, —(CH$_2$)$_n$O— or —CH(CH$_3$)NHC(O)—.

In another embodiment of the invention, provided is a compound according to formula (I) wherein R3 is methyl.

In another embodiment of the invention, provided is a compound according to formula (I) wherein R4 is indazole or benzimidazole.

In another embodiment of the invention, provided is a compound according to formula (I) wherein R4 is unsubstituted heteroaryl or heteroaryl mono- or bi-substituted independently with (=O), alkoxy or hydroxy.

In another embodiment of the invention, provided is a compound according to formula (I) wherein R4 is unsubstituted phenyl or phenyl mono- or bi-substituted independently with hydroxy, methyl, halogen or —COOH.

In another embodiment of the invention, provided is a compound according to formula (I) wherein R4 is thiophene, phenyl, hydroxyphenyl, dihydroxyphenyl or difluorophenyl.

In another embodiment of the invention, provided is a compound according to formula (I) wherein R5 is hydrogen, lower alkyl or alkoxy.

In another embodiment of the invention, provided is a compound according to formula (I) wherein R5 is cycloalkyl, heterocycloalkyl, lower alkyl-cycloalkyl or lower alkyl-heterocycloalkyl.

In another embodiment of the invention, provided is a compound according to formula (I) wherein R5 is —(CH$_2$)$_n$OR6, —CH(CH$_3$)O(O)R6 or —(CH$_2$)$_n$NR7R8.

In another embodiment of the invention, provided is a compound according to formula (I) wherein R5 is hydrogen.

In another embodiment of the invention, provided is a compound according to formula (I) wherein R6 is hydrogen or methyl.

In another embodiment of the invention, provided is a compound according to formula (I) wherein R7 and R8 independently of each other are hydrogen or methyl.

In another embodiment of the invention, provided is a compound according to formula (I) wherein n is 1.

Particular compounds of formula I include the following:
(S)-3-(3,5-Difluoro-benzoylamino)-2-({2-[2-(3-hydroxy-phenyl)-acetylamino]-4-methyl-thiazole-5-carbonyl}-amino)-propionic acid;
(S)-2-({2-[2-(3-Hydroxy-phenyl)-acetylamino]-4-methyl-thiazole-5-carbonyl}-amino)-3-[(thiophene-2-carbonyl)-amino]-propionic acid;
(S)-2-({2-[2-(3-Hydroxy-phenyl)-acetylamino]-thiazole-5-carbonyl}-amino)-3-[(thiophene-2-carbonyl)-amino]-propionic acid;
(S)-3-Benzoylamino-2-({2-[2-(3-hydroxy-phenyl)-acetylamino]-4-methyl-thiazole-5-carbonyl}-amino)-propionic acid;
(S)-3-(3-Hydroxy-benzoylamino)-2-({2-[2-(3-hydroxy-phenyl)-acetylamino]-4-methyl-thiazole-5-carbonyl}-amino)-propionic acid;
(S)-3-(3,5-Dihydroxy-benzoylamino)-2-({2-[2-(3-hydroxy-phenyl)-acetylamino]-4-methyl-thiazole-5-carbonyl}-amino)-propionic acid;
(S)-2-({2-[2-(3-Hydroxy-phenyl)-acetylamino]-4-methyl-thiazole-5-carbonyl}-amino)-3-[(thiophene-3-carbonyl)-amino]-propionic acid;
(S)-2-({4-Chloro-2-[2-(3-hydroxy-phenyl)-acetylamino]-thiazole-5-carbonyl}-amino)-3-[(thiophene-2-carbonyl)-amino]-propionic acid;

(S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid;

(S)-3-(3,5-Dihydroxy-benzoylamino)-2-({2-[3-(3-hydroxy-phenyl)-propionylamino]-4-methyl-thiazole-5-carbonyl}-amino)-propionic acid;

(S)-2-({2-[3-(3-Hydroxy-phenyl)-propionylamino]-4-methyl-thiazole-5-carbonyl}-amino)-3-[(thiophene-2-carbonyl)-amino]-propionic acid;

(S)-3-(3,5-Dihydroxy-benzoylamino)-2-({2-[2-(3-hydroxy-phenyl)-ethylamino]-4-methyl-thiazole-5-carbonyl}-amino)-propionic acid;

(S)-2-({2-[3-(3-Hydroxy-phenyl)-propoxy]-4-methyl-thiazole-5-carbonyl}-amino)-3-[(thiophene-2-carbonyl)-amino]-propionic acid;

(S)-2-{[2-(2-1H-Indazol-4-yl-acetylamino)-4-methyl-thiazole-5-carbonyl]-amino}-3-[(thiophene-2-carbonyl)-amino]-propionic acid;

(S)-3-(3,5-Dihydroxy-benzoylamino)-2-{[2-(2-1H-indazol-4-yl-acetylamino)-4-methyl-thiazole-5-carbonyl]-amino}-propionic acid;

(S)-2-{[2-(2-1H-Indazol-4-yl-acetylamino)-4-trifluoromethyl-thiazole-5-carbonyl]-amino}-3-[(thiophene-2-carbonyl)-amino]-propionic acid;

(S)-2-({2-[3-(1H-Indazol-4-yl)-propylamino]-4-methyl-thiazole-5-carbonyl}-amino)-3-[(thiophene-2-carbonyl)-amino]-propionic acid;

(S)-2-{[2-(2-1H-Indazol-4-yl-acetylamino)-4-methyl-thiazole-5-carbonyl]-amino}-3-[(thiophene-2-carbonyl)-amino]propionic acid 3,3-dimethyl-butyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid ethyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid isobutyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid butyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 1-ethyl-propyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid cyclopentyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 2,2-dimethyl-propyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid cyclopropylmethyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 3-ethoxy-propyl ester;

(S)-2-{[2-(2-1H-Indazol-4-yl-acetylamino)-4-trifluoromethyl-thiazole-5-carbonyl]-amino}-3-[(thiophene-2-carbonyl)-amino]-propionic acid 3-ethoxy-propyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid ethyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 2-morpholin-4-yl-ethyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 1-(2,2-dimethyl-propionyloxy)-ethyl ester;

(S)-2-{[2-(2-1H-Indazol-4-yl-acetylamino)-4-methyl-thiazole-5-carbonyl]-amino}-3-[(thiophene-2-carbonyl)-amino]-propionic acid 2-diethylamino-ethyl ester;

(S)-2-{[5-(3-hydroxy-benzylcarbamoyl)-3-methyl-thiophen-2-carbonyl]-amino}-3-[(thiophene-2-carbonyl)-amino]-propionic acid;

(S)-2-{[2-tert-butyl-5-(3-hydroxy-benzylcarbamoyl)-thiophen-2-carbonyl]-amino}-3-[(thiophene-2-carbonyl)-amino]-propionic acid;

(S)-2-({5-[(1H-indol-4-ylmethyl)carbamoyl]-3-methyl-thiophen-2-carbonyl}-amino)-3-[(thiophene-2-carbonyl)-amino]-propionic acid;

(S)-2-({3-methyl-5-[(2-oxo-2,3-dihydro-1H-indol-4-ylmethyl)carbamoyl]-thiophen-2-carbonyl}-amino)-3-[(thiophene-2-carbonyl)-amino]-propionic acid;

(S)-2-({5-[(1H-indazol-4-ylmethyl)-carbamoyl]-3-methyl-thiophen-2-carbonyl}-amino)-3-[(thiophene-2-carbonyl)-amino]-propionic acid;

(S)-2-({5-[1-(3-hydroxy-phenyl)-ethylcarbamoyl]-3-methyl-thiophen-2-carbonyl}-amino)-3-[(thiophene-2-carbonyl)-amino]-propionic acid;

(S)-3-(3,5-dihydroxy-benzoylamino)-2-{[5-(3-hydroxy-benzylcarbamoyl)-3-methyl-thiophen-2-carbonyl]-amino}-propionic acid;

(S)-3-[(2,6-dioxo-1,2,3,6-tetrahydro-pyrimidine-4-carbonyl)-amino]-2-{[5-(3-hydroxy-benzylcarbamoyl)-3-methyl-thiophene-2-carbonyl-amino]-propionic acid;

(S)-3-(3-hydroxy-benzoylamino)-2-{[5-(3-hydroxy-benzylcarbamoyl)-3-methyl-thiophene-2-carbonyl-amino]-propionic acid;

(S)-3-(3-hydroxy-benzoylamino)-2-{[5-(3-hydroxy-benzylcarbamoyl)-3-methyl-thiophene-2-carbonyl-amino]-propionic acid;

(S)-3-[(1H-benzoimidazole-5-carbonyl)-amino]-2-{[5-(3-hydroxy-benzylcarbamoyl)-3-methyl-thiophene-2-carbonyl-amino]-propionic acid (HCl salt);

(S)-3-[(2,6-dimethoxy-pyrimidine-4-carbonyl)-amino]-2-{[5-(3-hydroxy-benzylcarbamoyl)-3-methyl-thiophene-2-carbonyl]-amino}-propionic acid;

(S)-2-{[5-(3-hydroxy-benzylcarbamoyl)-3-methyl-thiophene-2-carbonyl]-amino}-3-[(1H-indazole-4-carbonyl)-amino]-propionic acid (HCl salt);

(S)-2-{[5-(3-hydroxy-benzylcarbamoyl)-3-methyl-thiophene-2-carbonyl]-amino}-3-[(5-hydroxy-pyrazine-2-carbonyl)-amino]-propionic acid;

(S)-3-[(1H-benzoimidazole-4-carbonyl)-amino]-2-{[5-(3-hydroxy-benzylcarbamoyl)-3-methyl-thiophene-2-carbonyl]-amino}-propionic acid (HCl salt);

(S)-3-[(benzoic acid-3-carbonyl)-amino]-2-{[5-(3-hydroxy-benzylcarbamoyl)-3-methyl-thiophene-2-carbonyl]-amino}-propionic acid;

(S)-2-({5-[2-(3-hydroxy-phenyl)ethyl-carbamoyl]-3-methyl-thiophen-2-carbonyl}-amino)-3-[(thiophene-2-carbonyl)-amino]-propionic acid;

(S)-3-(3,5-dihydroxy-benzoylamino)-2-({5-[2-(3-hydroxy-phenyl)-ethyl-carbamoyl]-3-methyl-thiophen-2-carbonyl}-amino)-propionic acid;

(S)-2-({5-[(1H-Indol-4-ylmethyl)-carbamoyl]-3-trifluoromethyl-thiophene-2-carbonyl}-amino)-3-[(thiophene-2-carbonyl)-amino]-propionic acid;

(S)-2-({5-[(2-Oxo-2,3-dihydro-1H-indol-4-ylmethyl)-carbamoyl]-3-trifluoromethyl-thiophene-2-carbonyl}-amino)-3-[(thiophene-2-carbonyl)-amino]-propionic acid;

(S)-2-{[5-(3-Hydroxy-benzylcarbamoyl)-3-trifluoromethyl-thiophene-2-carbonyl]-amino}-3-[(thiophene-2-carbonyl)-amino]-propionic acid;

(S)-2-{[5-(3-Hydroxy-benzylcarbamoyl)-3-phenyl-thiophene-2-carbonyl]-amino}-3-[(thiophene-2-carbonyl)-amino]-propionic acid;

(S)-2-{[3-Chloro-5-(3-hydroxy-benzylcarbamoyl)-thiophene-2-carbonyl]-amino}-3-[(thiophene-2-carbonyl)-amino]-propionic acid;

(S)-2-{[3-Chloro-5-(3-hydroxy-benzylcarbamoyl)-thiophene-2-carbonyl]-amino}-3-[(thiophene-2-carbonyl)-amino]-propionic acid isobutyl ester;

(S)-2-({3-Chloro-5-[(1H-indazol-4-ylmethyl)-carbamoyl]-thiophene-2-carbonyl}-amino)-3-[(thiophene-2-carbonyl)-amino]-propionic acid;

(S)-2-({3-Chloro-5-[(1H-indazol-4-ylmethyl)-carbamoyl]-thiophene-2-carbonyl}-amino)-3-[(thiophene-2-carbonyl)-amino]-propionic acid isobutyl ester;

(S)-2-({5-[(1H-Indazol-4-ylmethyl)-carbamoyl]-3-trifluoromethyl-thiophene-2-carbonyl}-amino)-3-[(thiophene-2-carbonyl)-amino]-propionic acid;

(S)-2-{[5-(3-Hydroxy-benzylcarbamoyl)-3-isopropyl-thiophene-2-carbonyl]-amino}-3-[(thiophene-2-carbonyl)-amino]-propionic acid;

(S)-2-({5-[(1H-Indazol-4-ylmethyl)-carbamoyl]-3-isopropyl-thiophene-2-carbonyl}-amino)-3-[(thiophene-2-carbonyl)-amino]-propionic acid;

(S)-2-{[3-Ethyl-5-(3-hydroxy-benzylcarbamoyl)-thiophene-2-carbonyl]-amino}-3-[(thiophene-2-carbonyl)-amino]-propionic acid;

(S)-2-({3-Ethyl-5-[(1H-indazol-4-ylmethyl)-carbamoyl]-thiophene-2-carbonyl}-amino)-3-[(thiophene-2-carbonyl)-amino]-propionic acid;

(S)-2-{[3-Bromo-5-(3-hydroxy-benzylcarbamoyl)-thiophene-2-carbonyl]-amino}-3-[(thiophene-2-carbonyl)-amino]-propionic acid;

(S)-2-{[5-(4-Fluoro-3-hydroxy-benzylcarbamoyl)-3-methyl-thiophene-2-carbonyl]-amino}-3-[(thiophene-2-carbonyl)-amino]-propionic acid;

(S)-2-{[3-Cyano-5-(3-hydroxy-benzylcarbamoyl)-thiophene-2-carbonyl]-amino}-3-[(thiophene-2-carbonyl)-amino]-propionic acid;

(S)-2-({3-Cyano-5-[(1H-indazol-4-ylmethyl)-carbamoyl]-thiophene-2-carbonyl}-amino)-3-(3,5-dihydroxy-benzoylamino)-propionic acid; or (S)-2-({5-[(1H-Indazol-4-ylmethyl)-carbamoyl]-3-methyl-thiophene-2-carbonyl}-amino)-3-[(thiophene-2-carbonyl)-amino]-propionic acid isobutyl ester.

In another embodiment of the invention, provided is a process for the preparation of a compound according to any formula I, comprising the steps of:

saponifying a compound of formula (II):

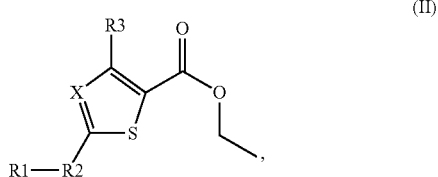

and forming a compound of formula (I):

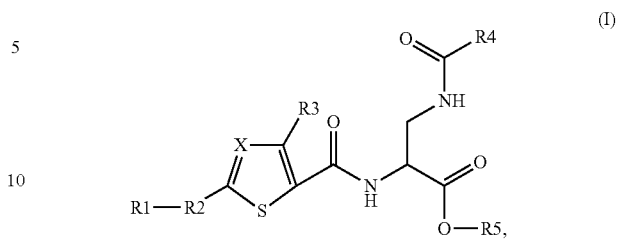

or a pharmaceutically acceptable salt thereof.

In another embodiment of the invention, provided is a compound according to formula (I) for use as a therapeutically active substance.

In another embodiment of the invention, provided is a pharmaceutical composition, comprising a therapeutically effective amount of a compound according to formula (I) and a therapeutically inert carrier.

In another embodiment of the invention, provided is the use of a compound according to formula (I) for the treatment or prophylaxis of asthma or COPD.

In another embodiment of the invention, provided is the use of a compound according to formula (I) for the preparation of a medicament for the treatment or prophylaxis of asthma or COPD.

In another embodiment of the invention, provided is a compound according formula (I) for the treatment or prophylaxis of asthma or COPD.

In another embodiment of the invention, provided is a compound of formula (I) when manufactured according to a process described herein.

In another embodiment of the invention, provided is a method for the treatment or prophylaxis of asthma or COPD, which method comprises the step of administering an effective amount of a compound according to formula (I) to a patient in need thereof.

In another embodiment of the invention, provided is an invention as hereinbefore described.

Compounds of the present invention can be prepared beginning with commercially available starting materials, or utilizing general synthetic techniques and procedures known to those skilled in the art. Chemicals may be purchased from companies such as for example Aldrich, Argonaut Technologies, VWR, Lancaster, Princeton, Alfa, Oakwood, TCI, Fluorochem, Apollo, Matrix, Maybridge or Meinoah. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography. Final compounds and intermediates were named using the AutoNom2000 feature in the MDL ISIS Draw application.

General Reaction Schemes

Compounds of formula (I) can be synthesized according to the general reaction schemes below. Starting materials are available from commercial sources or their preparation is described herein.

Scheme 1

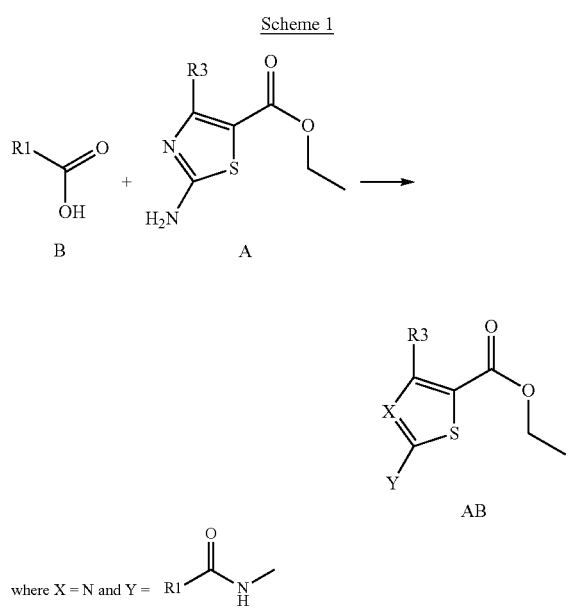

As shown in Scheme 1, compounds of Formula I can be prepared starting from appropriate substituted amino thiazoles A by coupling of appropriate substituted carboxylic acids B with 1-propanephosphonic acid cyclic anhydride in 50% ethyl acetate in an inert solvent such as THF in the presence of a suitable base such as Triethylamine to produce intermediates of formula AB.

Scheme 2

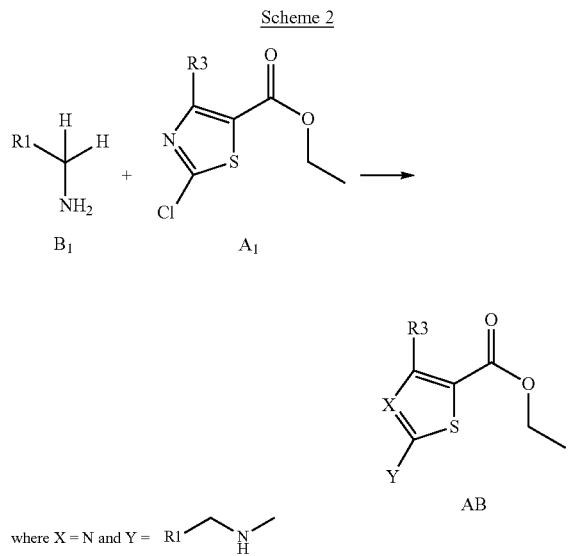

As shown in Scheme 2, compounds of Formula I can be prepared starting from appropriate substituted chloro thiazoles $A_1$ by nucleophilic substitution of the chloro atom of the appropriately substituted thiazoles with an appropriate substituted nucleophiles, such as an amine $B_1$ in the presence of a base such as potassium acetate and solvent such as ethanol at elevated temperatures such as 120-160° C., the rate of reaction often being enhanced by the use of a microwave reactor to produce intermediates of formula AB.

Scheme 3

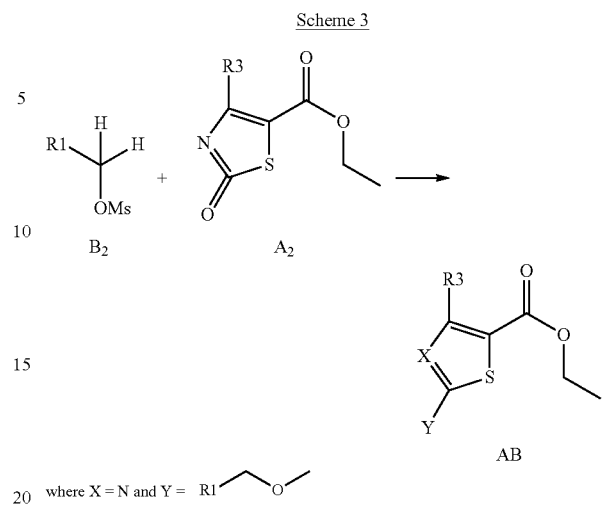

As shown in Scheme 3, compounds of Formula I can be prepared starting from appropriately substituted compound $B_2$ by nucleophilic substitution of the mesilylate atom with compounds appropriately substituted compounds like $A_2$ in the presence of a base such as cesium carbonate and inert solvent such as DMF at elevated temperatures such as 80-160° C., the rate of reaction often being enhanced by the use of a microwave reactor to produce intermediates of formula AB.

Scheme 4

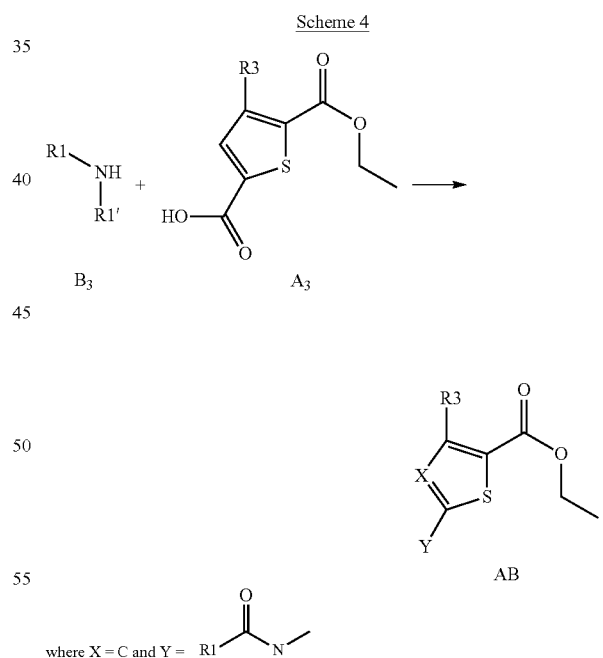

As shown in Scheme 4, compounds of Formula I can be prepared starting from Compounds of the general formula AB can be prepared by coupling of compounds using methods for the formation of peptide bonds such as activation of the carboxylic acid A3 with HBTU/HOBt and coupling with the amine B3 in an inert solvent such as DMF in the presence of a suitable base such as Triethylamine

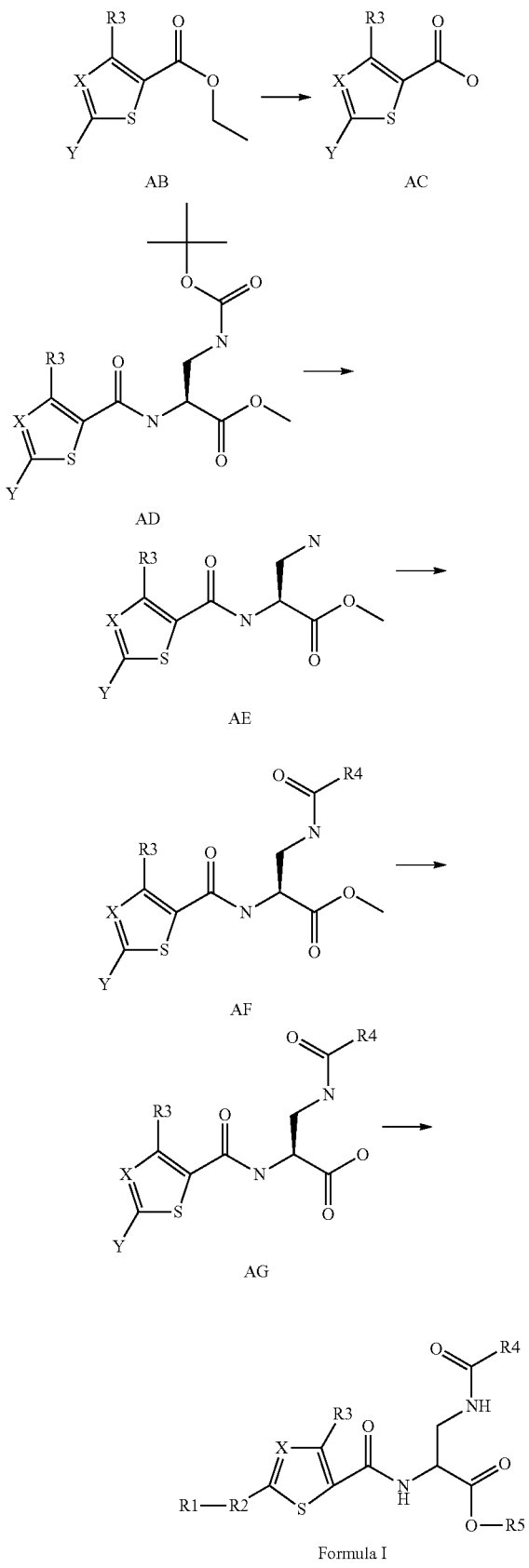

Scheme 5

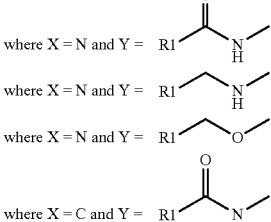

As shown in Scheme 5, saponification of compounds of the formula AB to compounds of the formula AC can be carried out with a suitable base such as a metal hydroxide, preferably lithium hydroxide in an appropriate solvent such as THF and mixtures thereof with water preferably at room temperature or higher as needed.

Compounds of the general formula AD can be prepared by coupling of compounds of the general formula AC with H-DAP-BOC-OMe using methods for the formation of peptide bonds such as activation of the carboxylic acid with HBTU/HOBt and coupling with the amine in an inert solvent such as DMF in the presence of a suitable base such as Triethylamine Compounds of the general formula AE can be prepared by deprotection of the amine of compounds of general formula AD by treatment with a mineral acid, preferably HCl in an inert solvent such as Dioxane or mixtures thereof with methanol.

Compounds of the general formula AF can be prepared by coupling of compounds of the general formula AE with a desired carboxylic acid using methods for the formation of peptide bonds such as activation of the carboxylic acid with HBTU/HOBt and coupling with the amine in an inert solvent such as DMF in the presence of a suitable base such as Triethylamine.

Saponification of compounds of the formula AF to compounds of the formula AG can be carried out with a suitable base such as a metal hydroxide, preferably lithium hydroxide in an appropriate solvent such as THF and mixtures thereof with water preferably at room temperature.

Compounds of Formula I can be prepared by alkylation of the carboxylic acid of compounds of the general formula AG with an alkyl halide, preferably an alkyl bromide or iodide in an inert solvent such as DMF, in the presence of a base such as potassium carbonate at room temperature or by reaction in a microwave reactor at temperatures between 100-160° C. Alternatively carboxylic acids of general formula AG can be treated with a chlorinating agent/brominating agents, such as thionyl chloride and then reacting with an appropriately chosen alcohol in the presence of an inert solvent such as Dioxane.

As shown in the reaction schemes above, R1 can be indole, oxoindole, indazole or substituted phenyl, said substituted phenyl being mono- or bi-substituted independently with hydroxy, halogen, alkoxy or lower alkyl; R2 can be —(CH$_2$)$_n$C(O)NH—, —(CH$_2$)$_n$NHC(O)—, —(CH$_2$)$_n$NH—, —(CH$_2$)$_n$O— or —CH(CH$_3$)NHC(O)—; R3 can be hydrogen, methyl, trifluoromethyl, halogen or cyano; R4 can be indazole, benzimidazole, unsubstituted heteroaryl, heteroaryl mono- or bi-substituted independently with (=O), alkoxy or hydroxy, unsubstituted phenyl or phenyl mono- or bi-substituted independently with hydroxy, methyl, halogen or —COOH; R5 can be hydrogen, lower alkyl, alkoxy, cycloalkyl, heterocycloalkyl, lower alkyl-cycloalkyl, lower alkyl-heterocycloalkyl, —(CH$_2$)$_n$OR6, —CH(CH$_3$)O(O)R6 or —(CH$_2$)$_n$NR7R8; R6, R7 and R8, independently of each other, can be hydrogen, lower alkyl or alkoxy; and n can be 1, 2 or 3.

The invention will now be further described in the Examples below, which are intended as an illustration only and do not limit the scope of the invention.

EXAMPLES

Part I: Preparation of Preferred Intermediates

Preparation of 2-{2-[3-(tert-Butyl-dimethyl-silanyloxy)-phenyl]-acetylamino}-4-methyl-thiazole-5-carboxylic acid ethyl ester

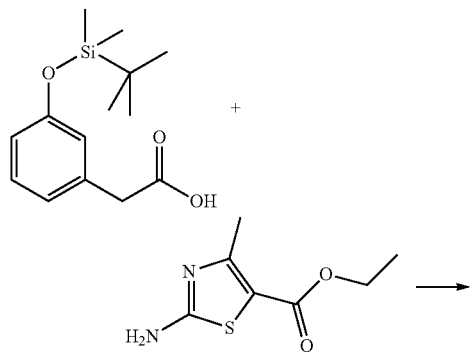

A solution of the 2-Amino-4-methyl-thiazole-5-carboxylic acid ethyl ester (1 g, 5.37 mmole), triethylamine (2.9 mL, 20.81 mmol), [3-(tert-Butyl-dimethyl-silanyloxy)-phenyl] acetic acid (0.55 g, 2.065 mmol), 1-propanephosphonic acid cyclic anhydride in 50% ethyl acetate (2.9 mL, 4.871 mmole) in anhydrous THF (50 mL) is heated at 60° C. for 1 h. The reaction was cooled, diluted with water, extracted with Methylene chloride (3×75 mL). The combined organic layers dried over MgSO$_4$, filtered and evaporated. The solid residue was purified by flash column (10-40% EtOAc in hexane to give 2-{2-[3-(tert-Butyl-dimethyl-silanyloxy)-phenyl]-acetylamino}-4-methyl-thiazole-5-carboxylic acid ethyl ester (1.21 g, 67.4%) as a white solid. MS m/e 435.2 (M+H$^+$).

In a similar manner the following intermediates were produced:

Preparation of 2-[2-{3-(tert-Butyl-dimethyl-silanyloxy)-phenyl]-acetylamino}-thiazole-5-carboxylic acid ethyl ester

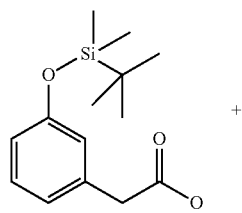

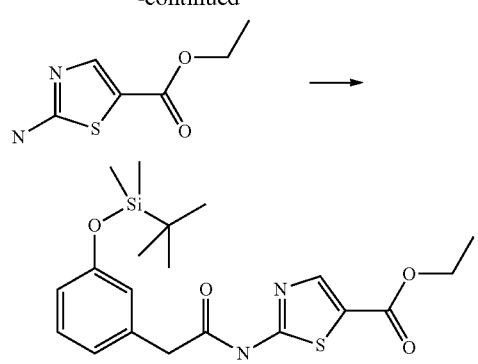

From 2-Amino-thiazole-5-carboxylic acid ethyl ester and [3-(tert-Butyl-dimethyl-silanyloxy)-phenyl]-acetic acid there was obtained 2-{2-[3-(tert-Butyl-dimethyl-silanyloxy)-phenyl]-acetylamino}-thiazole-5-carboxylic acid ethyl ester (78%) as an oil. MS m/e 421.6 (M+H$^+$).

Preparation of 2-[2-{3-(tert-Butyl-dimethyl-silanyloxy)-phenyl]-acetylamino}-4-trifluoromethyl-thiazole-5-carboxylic acid ethyl ester

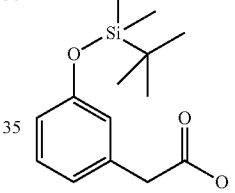

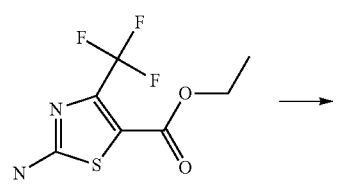

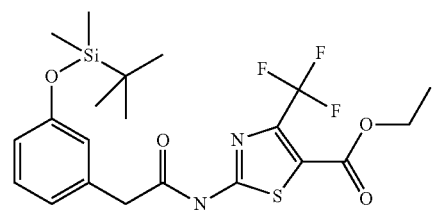

From 2-Amino-4-trifluoromethyl-thiazole-5-carboxylic acid ethyl ester and [3-(tert-Butyl-dimethyl-silanyloxy)-phenyl]-acetic acid there was obtained 2-{2-[3-(tert-Butyl-dimethyl-silanyloxy)-phenyl]-acetylamino}-4-trifluoromethyl-thiazole-5-carboxylic acid ethyl ester (68%) as an oil which solidified. MS m/e 489.2 (M+H$^+$).

Preparation of 2-[3-(tert-Butyl-dimethyl-silanyloxy)-phenyl]-N-(4-chloro-5-formyl-thiazol-2-yl)-acetamide

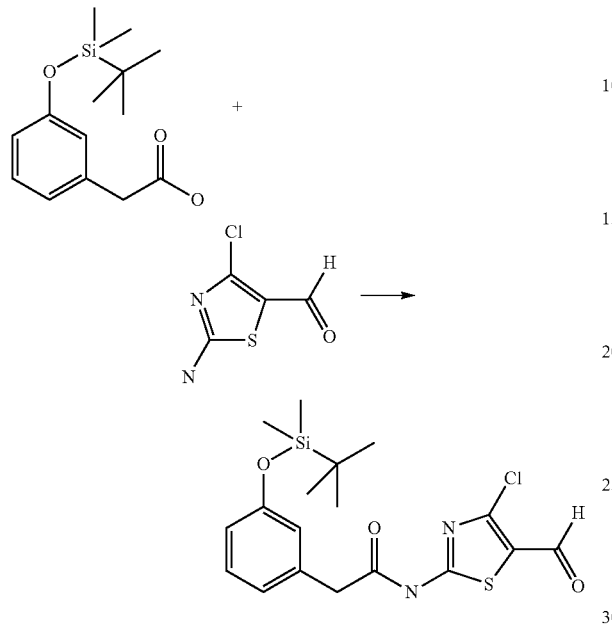

From 2-Amino-4-chloro-thiazole-5-carbaldehyde (prepared according to U.S. Pat. No. 5,206,376 procedure) and [3-(tert-Butyl-dimethyl-silanyloxy)-phenyl]-acetic acid there was obtained 2-[3-(tert-Butyl-dimethyl-silanyloxy)-phenyl]-N-(4-chloro-5-formyl-thiazol-2-yl)-acetamide (35%) as a yellow solid. MS m/e 411.2 (M+H$^+$).

Preparation of 2-[3-(3-Hydroxy-phenyl)-propionylamino]-4-methyl-thiazole-5-carboxylic acid ethyl ester

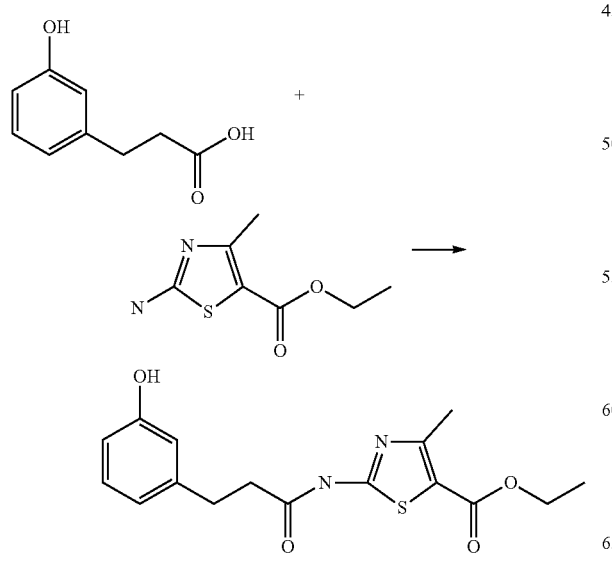

From 2-Amino-4-methyl-thiazole-5-carboxylic acid ethyl ester and 3-(3-Hydroxy-phenyl)-propionic acid there was obtained 2-[3-(3-Hydroxy-phenyl)-propionylamino]-4-methyl-thiazole-5-carboxylic acid ethyl ester (53.2%) as a pale yellow solid. MS m/e 335.4 (M+H$^+$).

Preparation of 2-[2-[3-(tert-Butyl-dimethyl-silanyloxy)-phenyl]-acetylamino]-4-chloro-thiazole-5-carboxylic acid

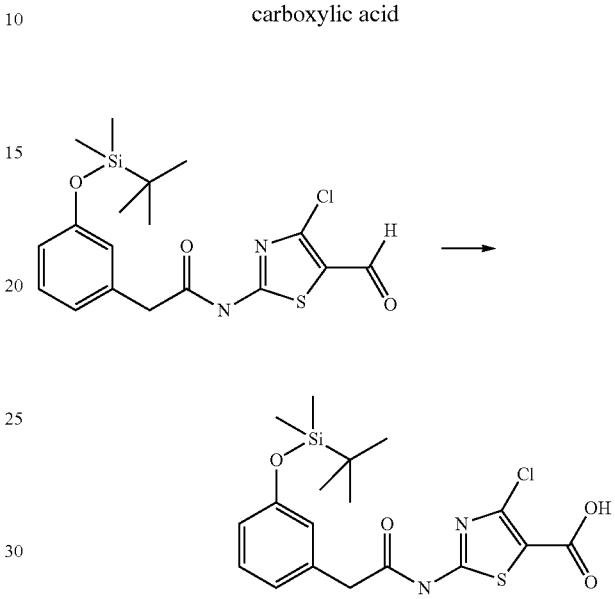

To a solution of 2-[3-(tert-Butyl-dimethyl-silanyloxy)-phenyl]-N-(4-chloro-5-formyl-thiazol-2-yl)-acetamide (590 mg, 1.436 mmol) in t-butanol (15 mL) stirred at 60° C. was added drop wise potassium permanganate (405 mg, 2.56 mmol) in water (5 mL) over 15 minutes. The resultant reaction mixture was heated at 80'C for 2 h. The reaction mixture was filtered hot through celite and washed with hot 1/1 t-butanol/water. The filtrate was acidified to pH 1 with aqueous 2N HCl and extracted with 9:1 Methylene chloride/methanol (3×75 mL). The organic layers were combined, washed with brine (50 mL), dried over MgSO$_4$, filtered, concentrated under reduced pressure and dried to give 2-{2-[3-(tert-Butyl-dimethyl-silanyloxy)-phenyl]-acetylamino}-4-chloro-thiazole-5-carboxylic acid (0.52 g, 84.8%) as a pale yellow solid. MS m/e 428.0 (M+H$^+$).

Preparation of 2-[3-(3-Hydroxy-phenyl)-propoxy]-4-methyl-thiazole-5-carboxylic acid ethyl ester

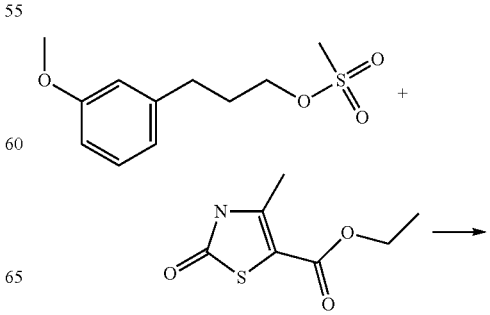

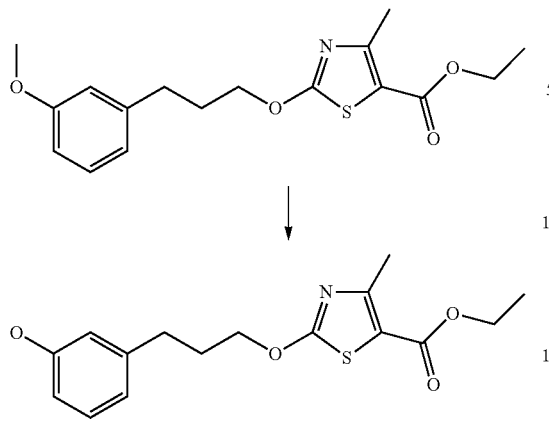

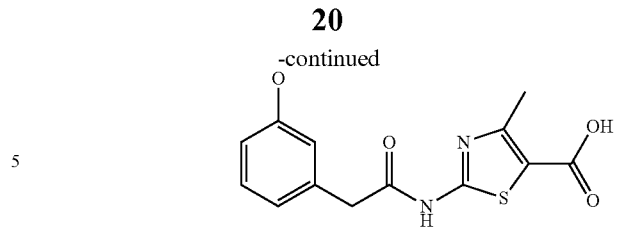

A mixture of methanesulfonic acid 3-(3-methoxy-phenyl)-propyl ester (1.20 g, 4.912 mmol), 4-Methyl-2-oxo-2,3-dihydro-thiazole-5-carboxylic acid ethyl ester (0.960 g, 5.128 mmol) and cesium carbonate (3.2 hm, 9.82 mmol) in anhydrous DMF was heated to oil bath at 75° C. for 2.5 h. The reaction mixture was cooled, concentrated and diluted with water (50 mL) and extracted with EtOAc (3×50 mL). The organic layers were washed with 2N HCl (30 mL), water ((30 mL), brine (30 mL), dried over magnesium sulphate, filtered and concentrated to give a brown oil. The crude product is purified by flash column chromatography (10%-30% EtOAc in hexane) to give 2-[3-(3-Methoxy-phenyl)-propoxy]-4-methyl-thiazole-5-carboxylic acid ethyl ester (0.84 g, 51%) as a yellow oil. MS m/e 336.4 (M+H⁺).

To a stirred and cooled solution of 2-[3-(3-Methoxy-phenyl)-propoxy]-4-methyl-thiazole-5-carboxylic acid ethyl ester (0.84 g, 2.5 mmol) in Methylene chloride (10 mL) at 0° C. was added 1M solution of boron tribromide in dichloromethane drop wise over a minute. The reaction was warmed gently to ambient temperature over 2 hrs. The resultant reaction is poured gently on ice water (25 mL) and extracted with Methylene chloride (3×75 mL). The organic layers are combined, washed with sodium bicarbonate (50 mL), brine (50 mL), dried over anhydrous MgSO₄, filtered and concentrated to give 2-[3-(3-Hydroxy-phenyl)-propoxy]-4-methyl-thiazole-5-carboxylic acid ethyl ester (0.63 g, 78.3%) as a light pink oil. MS m/e 322.4 (M+H⁺).

Preparation of 2-[2-(3-Hydroxy-phenyl)-acetylamino]-4-methyl-thiazole-5-carboxylic acid A mixture of 2-{2-[3-(tert-Butyl-dimethyl-silanyloxy)-phenyl]-acetylamino}-4-methyl-thiazole-5-carboxylic acid ethyl ester (1.02 g, 2.347 mmol) and lithium hydroxide monohydrate (1 g, 23.83 mmol) in THF (21 mL) and water (7 mL)) was stirred at 25° C. for 16 h. The reaction was quenched by addition of aqueous 2N HCl (25 mL) followed by addition of sodium chloride. The resultant biphasic solution was extracted with 7:3 ethyl acetate/THF (3×125 mL). The organic layers were combined, washed with brine (50 mL), dried over MgSO4, filtered and concentrated under reduced pressure to give 2-[2-(3-Hydroxy-phenyl)-acetylamino]-4-methyl-thiazole-5-carboxylic acid (0.62 g, 90.4%) as a white solid. MS m/e 293.3 (M+H⁺).

In a similar manner the following intermediates were produced:

Preparation of 2-[2-(3-Hydroxy-phenyl)-acetylamino]-thiazole-5-carboxylic acid

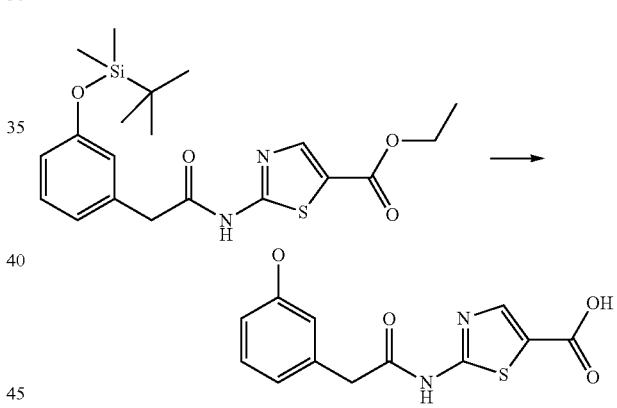

From 2-{2-[3-(tert-Butyl-dimethyl-silanyloxy)-phenyl]-acetylamino}-thiazole-5-carboxylic acid ethyl ester was obtained 2-[2-(3-Hydroxy-phenyl)-acetylamino]-thiazole-5-carboxylic acid (48%) as off white semisolid. MS m/e 279.3 (M+H⁺).

Preparation of 2-[2-(3-Hydroxy-phenyl)-acetylamino]-4-trifluoromethyl-thiazole-5-carboxylic acid

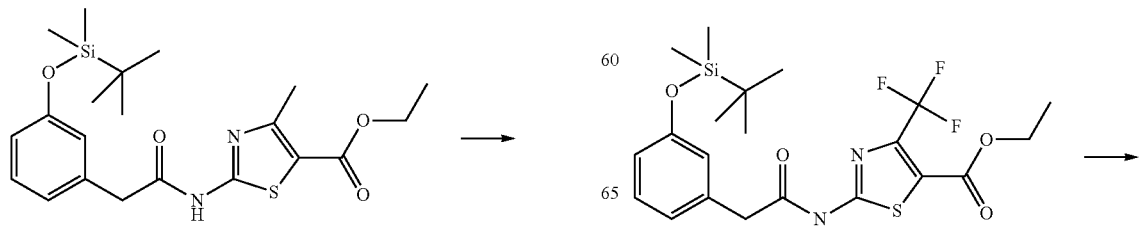

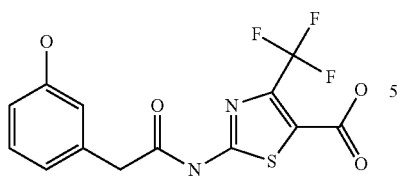

From 2-{2-[3-(tert-Butyl-dimethyl-silanyloxy)-phenyl]-acetylamino}-4-trifluoromethyl-thiazole-5-carboxylic acid ethyl ester was obtained 2-[2-(3-Hydroxy-phenyl)-acetylamino]-4-trifluoromethyl-thiazole-5-carboxylic acid (58%) as off white solid. MS m/e 347.3 (M+H$^+$).

Preparation of 2-[3-(3-Hydroxy-phenyl)-propionylamino]-4-methyl-thiazole-5-carboxylic acid

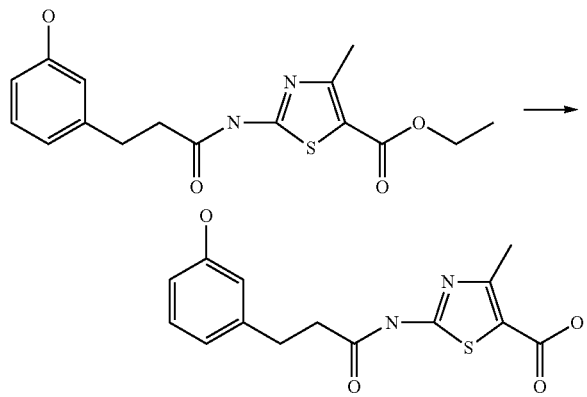

From 2-[3-(3-Hydroxy-phenyl)-propionylamino]-4-methyl-thiazole-5-carboxylic acid ethyl ester was obtained 2-[3-(3-Hydroxy-phenyl)-propionylamino]-4-methyl-thiazole-5-carboxylic acid (91%) as off white solid. MS m/e 307.3 (M+H$^+$).

Preparation of 2-[3-(3-Hydroxy-phenyl)-propionylamino]-4-methyl-thiazole-5-carboxylic acid

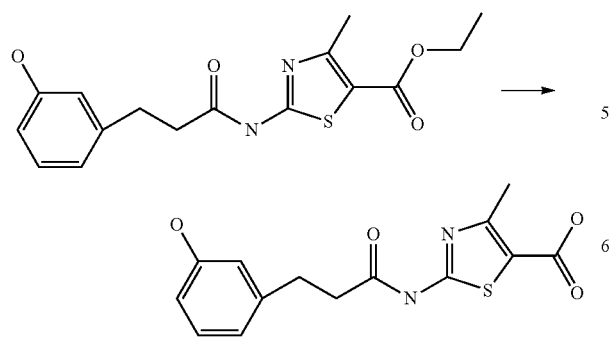

From 2-[3-(3-Hydroxy-phenyl)-propionylamino]-4-methyl-thiazole-5-carboxylic acid ethyl ester was obtained 2-[3-(3-Hydroxy-phenyl)-propionylamino]-4-methyl-thiazole-5-carboxylic acid (98%) as pink oil. MS m/e 294.3 (M+H$^+$).

Preparation of 2-[2-(3-Hydroxy-phenyl)-ethylamino]-4-methyl-thiazole-5-carboxylic acid

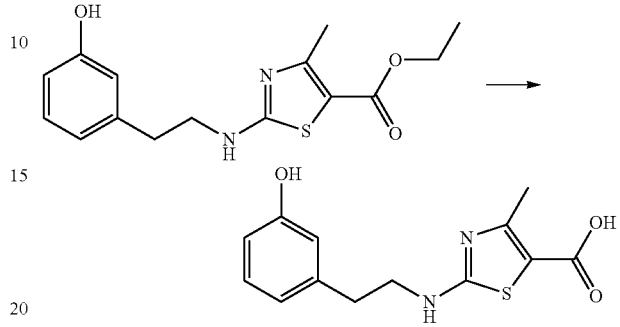

From 2-[2-(3-Hydroxy-phenyl)-ethylamino]-4-methyl-thiazole-5-carboxylic acid ethyl ester there was obtained 2-[2-(3-Hydroxy-phenyl)-ethylamino]-4-methyl-thiazole-5-carboxylic acid (85%) as an orange foam. MS m/e 279.3 (M+H$^+$).

Preparation of(S)-3-tert-Butoxycarbonylamino-2-({2-[2-(3-hydroxy-phenyl)-acetylamino]-4-methyl-thiazole-5-carbonyl}-amino)-propionic acid methyl ester

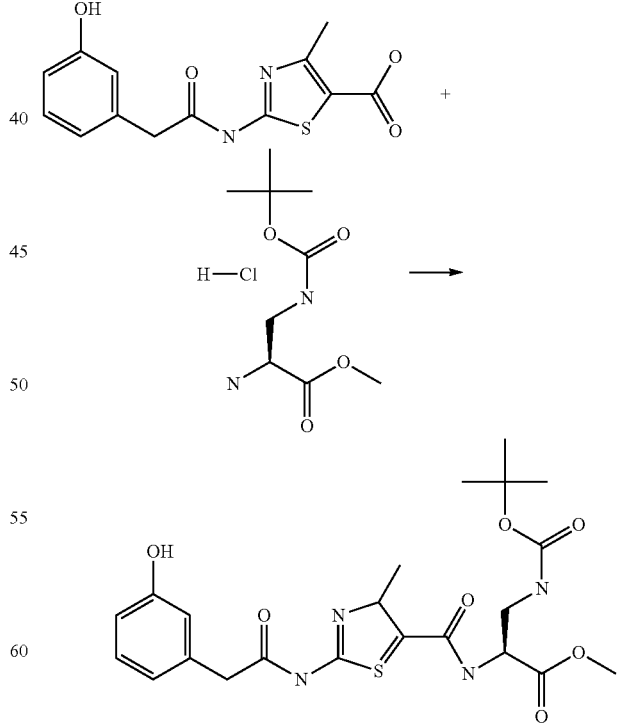

To a solution of 2-[2-(3-Hydroxy-phenyl)-acetylamino]-4-methyl-thiazole-5-carboxylic acid (620 mg, 2.121 mmol) in anhydrous DMF (25 mL) was added HBTU (980 mg, 2.584 mmol), HOBt (347 mg, 2.568 mmol), H-DAP(BOC)-OME HCl (810 mg, 3.18 mmol) and triethylamine (1.1 mL, 7.892 mmol). The solution was stirred at 25° C. for 1 h and concentrated at reduced pressure to remove most of the DMF. The reaction was then diluted with ethyl acetate (200 mL), washed with water (50 mL), aqueous 1N HCl (50 mL), and brine (50 mL), dried over MgSO₄, filtered and concentrated under reduced pressure. The resulting crude compound was purified by flash chromatography (40%-90% EtOAc in hexanes) to give (S)-3-tert-Butoxycarbonylamino-2-({2-[2-(3-hydroxy-phenyl)-acetylamino]-4-methyl-thiazole-5-carbonyl}-amino)-propionic acid methyl ester (902.1 mg, 77.7%) as a white foam. MS m/e 493.6 (M+H⁺).

In a similar manner the following intermediates were produced:

Preparation of (S)-3-tert-Butoxycarbonylamino-2-({2-[2-(3-hydroxy-phenyl)-acetylamino]-thiazole-5-carbonyl}-amino)-propionic acid methyl ester

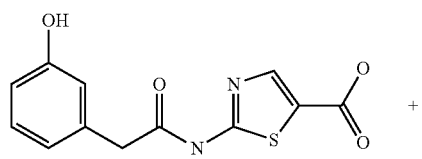

+

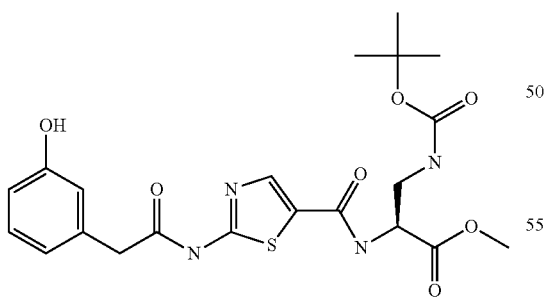

From 2-[2-(3-Hydroxy-phenyl)-acetylamino]-thiazole-5-carboxylic acid and H-DAP(BOC)-OME HCl was obtained (S)-3-tert-Butoxycarbonylamino-2-({2-[2-(3-hydroxy-phenyl)-acetylamino]-thiazole-5-carbonyl}-amino)-propionic acid methyl ester (48%) as white solid. MS m/e 479.6 (M+H⁺).

Preparation of (S)-3-tert-Butoxycarbonylamino-2-[(2-{2-[3-(tert)-butyl-dimethyl-silanyloxy)-phenyl]-acetylamino}-4-chloro-thiazole-5-carbonyl)-amino]-propionic acid methyl ester

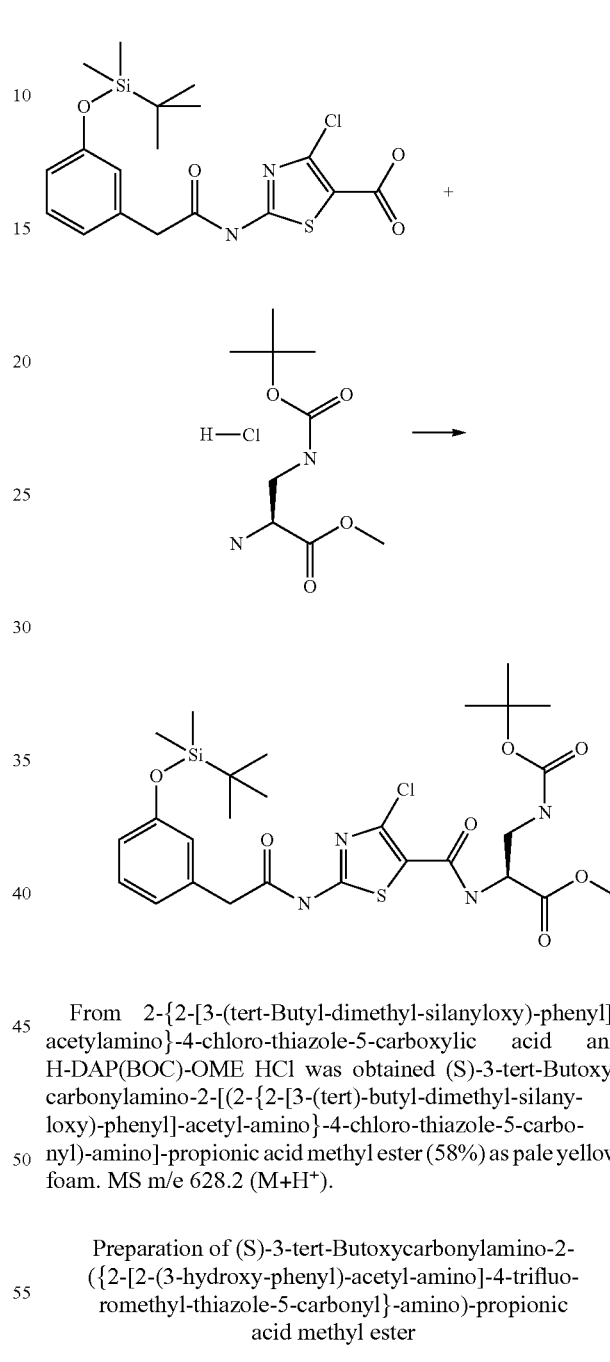

From 2-{2-[3-(tert-Butyl-dimethyl-silanyloxy)-phenyl]-acetylamino}-4-chloro-thiazole-5-carboxylic acid and H-DAP(BOC)-OME HCl was obtained (S)-3-tert-Butoxycarbonylamino-2-[(2-{2-[3-(tert)-butyl-dimethyl-silanyloxy)-phenyl]-acetyl-amino}-4-chloro-thiazole-5-carbonyl)-amino]-propionic acid methyl ester (58%) as pale yellow foam. MS m/e 628.2 (M+H⁺).

Preparation of (S)-3-tert-Butoxycarbonylamino-2-({2-[2-(3-hydroxy-phenyl)-acetyl-amino]-4-trifluoromethyl-thiazole-5-carbonyl}-amino)-propionic acid methyl ester

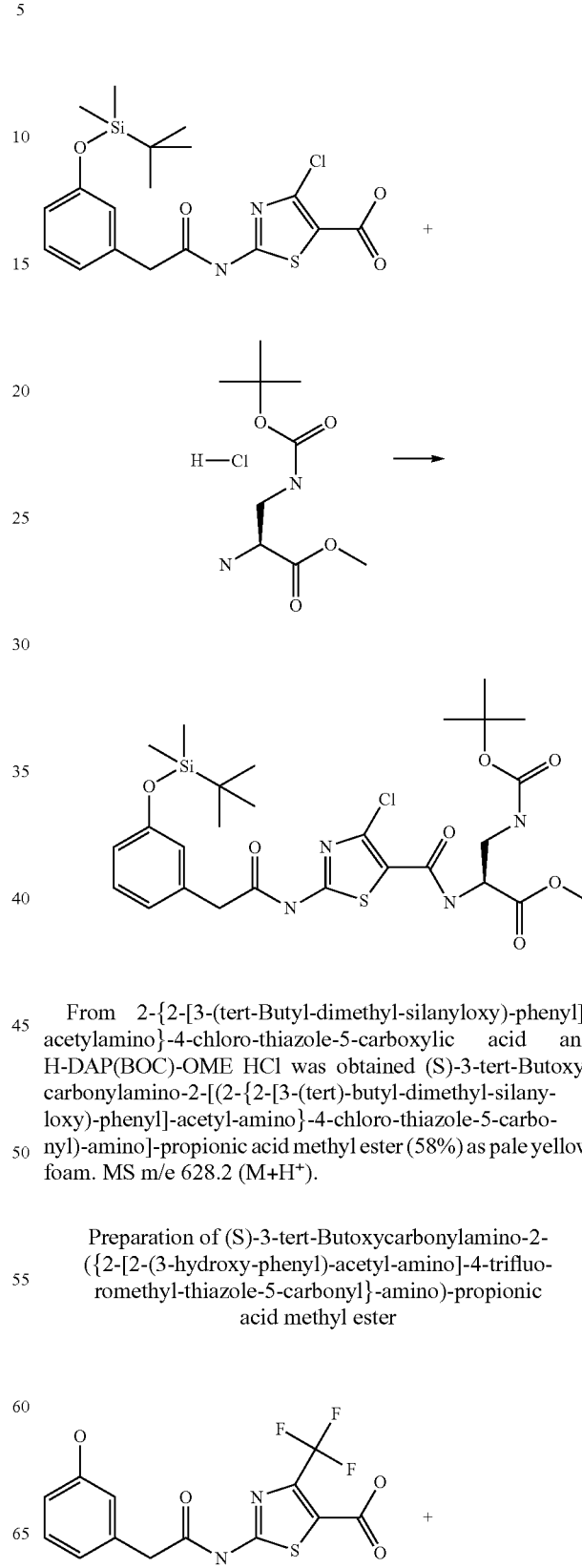

+

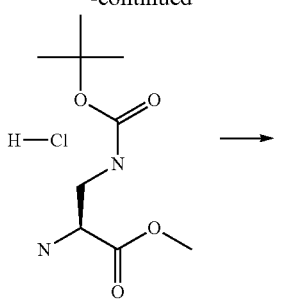

→

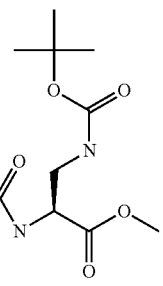

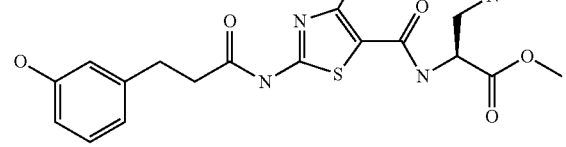

From 2-[3-(3-Hydroxy-phenyl)-propionylamino]-4-methyl-thiazole-5-carboxylic acid and H-DAP(BOC)-OME HCl was obtained (S)-3-tert-Butoxycarbonylamino-2-({2-[2-(3-hydroxy-phenyl)-acetylamino]-4-trifluoromethyl-thiazole-5-carbonyl}-amino)-propionic acid methyl ester (31%) as off white solid. MS m/e 507.6 (M+H⁺).

Preparation of (S)-3-tert-Butoxycarbonylamino-2-({2-[3-(3-hydroxy-phenyl)-propoxy]-4-methyl-thiazole-5-carbonyl}-amino)-propionic acid methyl ester

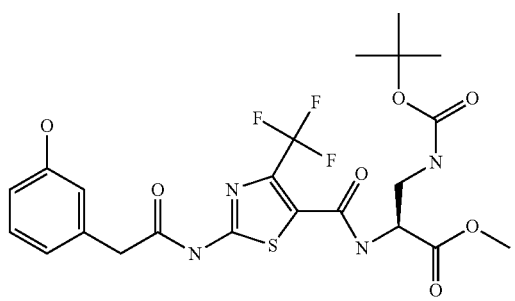

From 2-[2-(3-Hydroxy-phenyl)-acetylamino]-4-trifluoromethyl-thiazole-5-carboxylic acid and H-DAP(BOC)-OME HCl was obtained (S)-3-tert-Butoxycarbonylamino-2-({2-[2-(3-hydroxy-phenyl)-acetylamino]-4-trifluoromethyl-thiazole-5-carbonyl}-amino)-propionic acid methyl ester (39%) as white foam. MS m/e 547.5 (M+H⁺).

Preparation of (S)-3-tert-Butoxycarbonylamino-2-({2-[3-(3-hydroxy-phenyl)-propionylamino]-4-methyl-thiazole-5-carbonyl}-amino)-propionic acid methyl ester

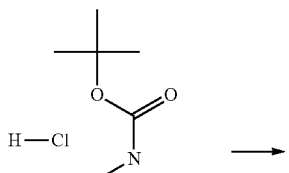

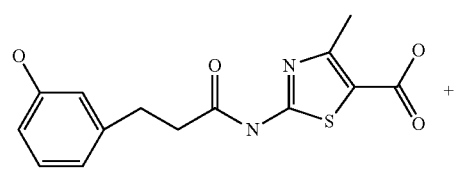 +

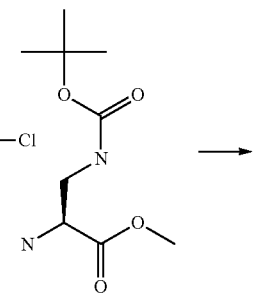 →

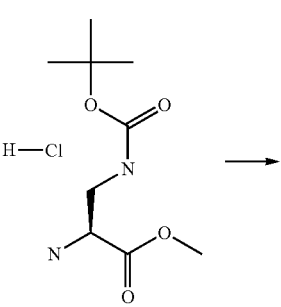

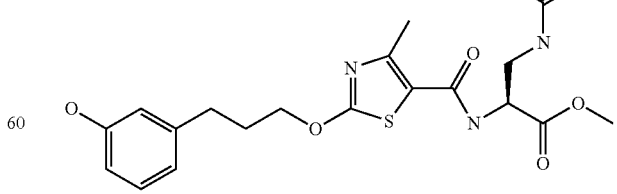

From 2-[3-(3-Hydroxy-phenyl)-propoxy]-4-methyl-thiazole-5-carboxylic acid and H-DAP(BOC)-OME HCl was obtained (S)-3-tert-Butoxycarbonylamino-2-({2-[3-(3-hydroxy-phenyl)-propoxy]-4-methyl-thiazole-5-carbonyl}-amino)-propionic acid methyl ester (95%) as off white solid. MS m/e 494.6 (M+H⁺).

Preparation of (S)-3-tert-Butoxycarbonylamino-2-({2-[2-(3-hydroxy-phenyl)-ethylamino]-4-methyl-thiazole-5-carbonyl}-amino)-propionic acid methyl ester

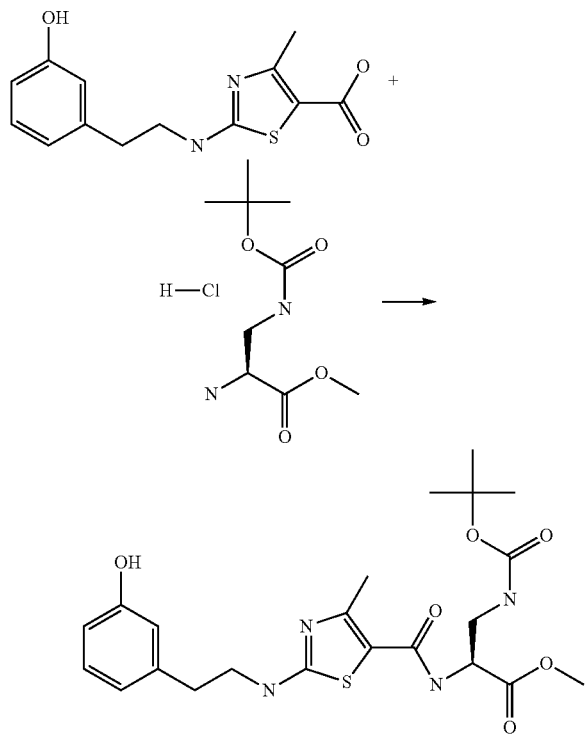

From 2-[2-(3-Hydroxy-phenyl)-ethylamino]-4-methyl-thiazole-5-carboxylic acid and H-DAP(BOC)-OME HCl there was obtained (S)-3-tert-Butoxycarbonylamino-2-({2-[2-(3-hydroxy-phenyl)-ethylamino]-4-methyl-thiazole-5-carbonyl}-amino)-propionic acid methyl ester (37%) as a tan solid. MS m/e 479.6 (M+H⁺).

Preparation of (S)-3-(3,5-Difluoro-benzoylamino)-2-({2-[2-(3-hydroxy-phenyl)-acetylamino]-4-methyl-thiazole-5-carbonyl}-amino)-propionic acid methyl ester

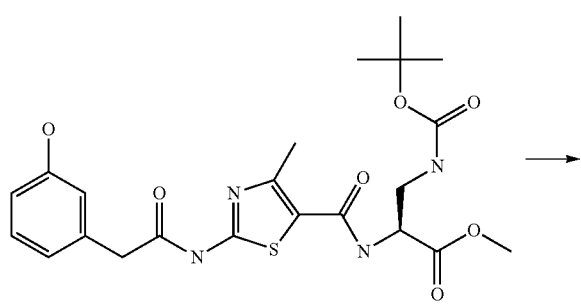

-continued

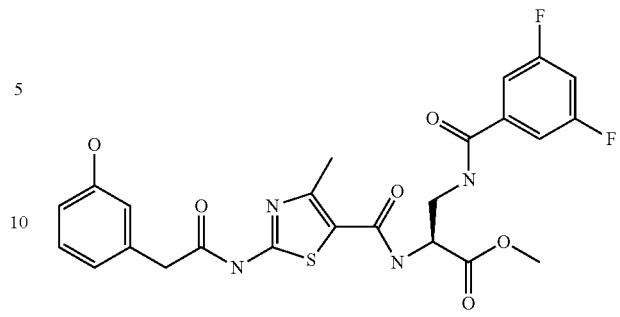

A solution of (S)-3-tert-Butoxycarbonylamino-2-({2-[2-(3-hydroxy-phenyl)-acetylamino]-4-methyl-thiazole-5-carbonyl}-amino)-propionic acid methyl ester (150 mg, 0.305 mmol) in 4M HCl in dioxane (6 mL, 24 mmol) was stirred at 25° C. for 2 h. The reaction mixture was concentrated under reduced pressure. To the reaction solid was added ethyl ether (2×50) followed by concentrating under reduced pressure to give a white solid, which was dissolved in the anhydrous DMF (6 mL). To this solution was added HBTU (174 mg, 0.459 mmol), HOBt (61 mg, 0.451 mmol), 3,5-difluorobenzoic acid (60 mg, 0.379 mmol) and triethylamine (0.16 mL, 1.148 mmol). The solution was allowed to stir at 25° C. for 2 h and concentrated under reduced pressure to remove most of the DMF. The reaction was then diluted with ethyl acetate (100 mL), washed with water (20 mL), followed by aqueous 1N HCl (20 mL) and then brine (20 mL). The organic layer was dried over MgSO₄, filtered and concentrated under reduced pressure. The resulting crude compound was purified by flash chromatography (40%-100% EtOAc in hexanes) to give (S)-3-(3,5-Difluoro-benzoylamino)-2-({2-[2-(3-hydroxy-phenyl)-acetylamino]-4-methyl-thiazole-5-carbonyl}-amino)-propionic acid methyl ester (92.5 mg, 57%) as a white foam. MS m/e 533.5 (M+H⁺).

In a similar manner the following compounds were produced:

Preparation of (S)-2-({2-[2-(3-Hydroxy-phenyl)-acetylamino]-4-methyl-thiazole-5-carbonyl}-amino)-3-[(thiophene-2-carbonyl)-amino]-propionic acid methyl ester

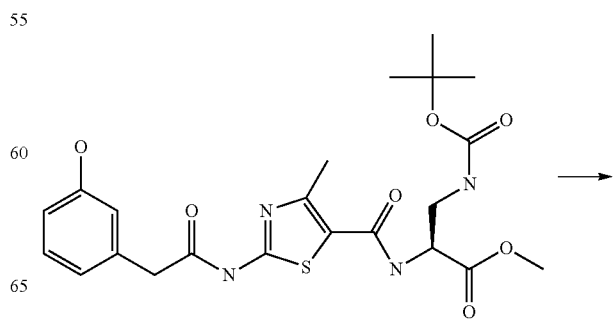

-continued

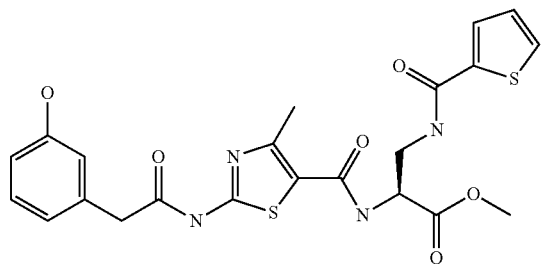

From (S)-3-tert-Butoxycarbonylamino-2-({2-[2-(3-hydroxy-phenyl)-acetylamino]-4-methyl-thiazole-5-carbonyl}-amino)-propionic acid methyl ester there was obtained (S)-2-({2-[2-(3-Hydroxy-phenyl)-acetylamino]-4-methyl-thiazole-5-carbonyl}-amino)-3-[(thiophene-2-carbonyl)-amino]-propionic acid methyl ester (53.6%) as a pale yellow semisolid. MS m/e 503.5 (M+H$^+$).

Preparation of (S)-2-({2-[2-(3-Hydroxy-phenyl)-acetylamino]-thiazole-5-carbonyl}-amino)-3-[(thiophene-2-carbonyl)-amino]-propionic acid methyl ester

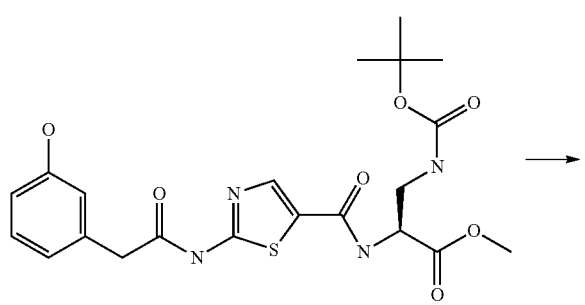

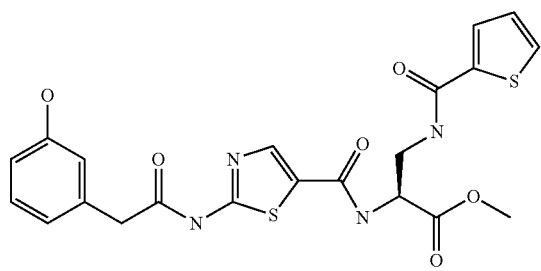

From (S)-3-tert-Butoxycarbonylamino-2-({2-[2-(3-hydroxy-phenyl)-acetylamino]-thiazole-5-carbonyl}-amino)-propionic acid methyl ester there was obtained (S)-2-({2-[2-(3-Hydroxy-phenyl)-acetylamino]thiazole-5-carbonyl}-amino)-3-[(thiophene-2-carbonyl)-amino]-propionic acid methyl ester (63.6%) as a pale yellow foam. MS m/e 489.5 (M+H$^+$).

Preparation of (S)-3-Benzoylamino-2-({2-[2-(3-hydroxy-phenyl)-acetylamino]-4-methyl-thiazole-5-carbonyl}-amino)-propionic acid methyl ester

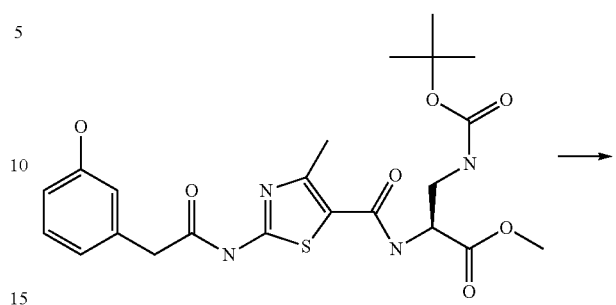

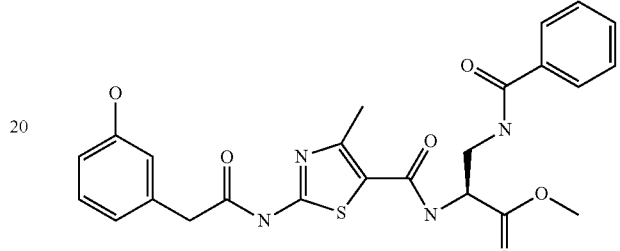

From (S)-3-tert-Butoxycarbonylamino-2-({2-[2-(3-hydroxy-phenyl)-acetylamino]-4-methyl-thiazole-5-carbonyl}-amino)-propionic acid methyl ester there was obtained (S)-3-Benzoylamino-2-({2-[2-(3-hydroxy-phenyl)-acetylamino]-4-methyl-thiazole-5-carbonyl}-amino)-propionic acid methyl ester (66%) as a white foam. MS m/e 497.5 (M+H$^+$).

Preparation of (S)-3-(3-Hydroxy-benzoylamino)-2-({2-[2-(3-hydroxy-phenyl)-acetylamino]-4-methyl-thiazole-5-carbonyl}-amino)-propionic acid methyl ester

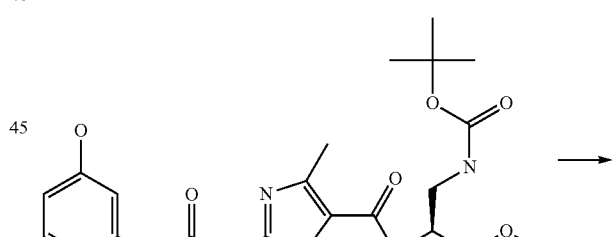

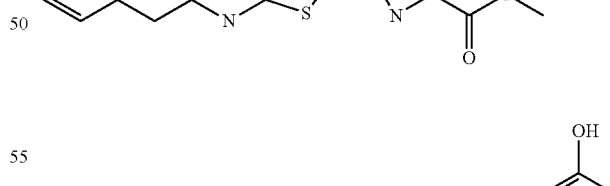

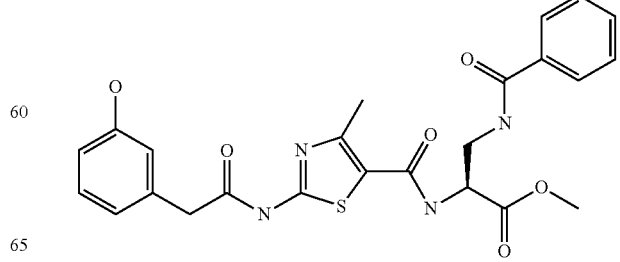

From (S)-3-tert-Butoxycarbonylamino-2-({2-[2-(3-hydroxy-phenyl)-acetylamino]-4-methyl-thiazole-5-carbonyl}-amino)-propionic acid methyl ester there was obtained (S)-3-(3-Hydroxy-benzoylamino)-2-({2-[2-(3-hydroxy-phenyl)-acetylamino]-4-methyl-thiazole-5-carbonyl}-amino)-propionic acid methyl ester (75%) as an off white foam. MS m/e 513.5 (M+H⁺).

Preparation of (S)-3-(3,5-Dihydroxy-benzoylamino)-2-({2-[2-(3-hydroxy-phenyl)-acetylamino]-4-methyl-thiazole-5-carbonyl}-amino)-propionic acid methyl ester

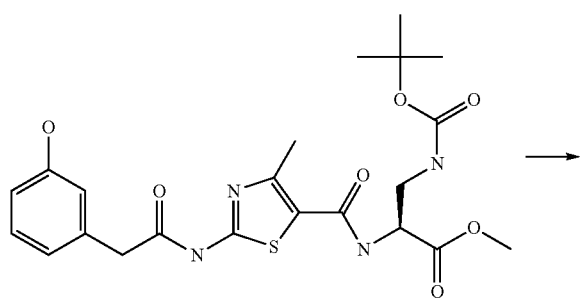

From (S)-3-tert-Butoxycarbonylamino-2-({2-[2-(3-hydroxy-phenyl)-acetylamino]-4-methyl-thiazole-5-carbonyl}-amino)-propionic acid methyl ester there was obtained (S)-3-(3,5-Dihydroxy-benzoylamino)-2-({2-[2-(3-hydroxy-phenyl)-acetylamino]-4-methyl-thiazole-5-carbonyl}-amino)-propionic acid methyl ester (62%) as a white foam. MS m/e 529.5 (M+H⁺).

Preparation of (S)-2-({2-[2-(3-Hydroxy-phenyl)-acetylamino]-4-methyl-thiazole-5-carbonyl}-amino)-3-[(thiophene-3-carbonyl)-amino]-propionic acid methyl ester

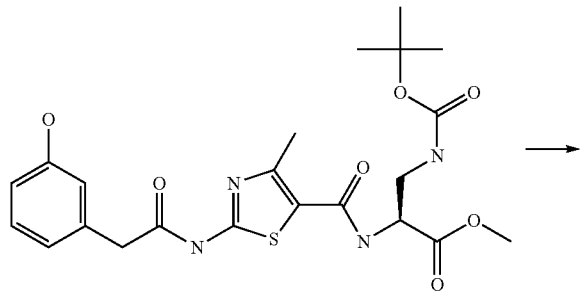

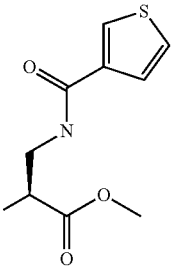

From (S)-3-tert-Butoxycarbonylamino-2-({2-[2-(3-hydroxy-phenyl)-acetylamino]-4-methyl-thiazole-5-carbonyl}-amino)-propionic acid methyl ester there was obtained (S)-2-({2-[2-(3-Hydroxy-phenyl)-acetylamino]-4-methyl-thiazole-5-carbonyl}-amino)-3-[(thiophene-3-carbonyl)-amino]-propionic acid methyl ester (62%) as a yellow semi-solid. MS m/e 503.5 (M+H⁺).

Preparation of (S)-2-({4-Chloro-2-[2-(3-hydroxy-phenyl)-acetylamino]-thiazole-5-carbonyl}-amino)-3-[(thiophene-2-carbonyl)-amino]-propionic acid methyl ester

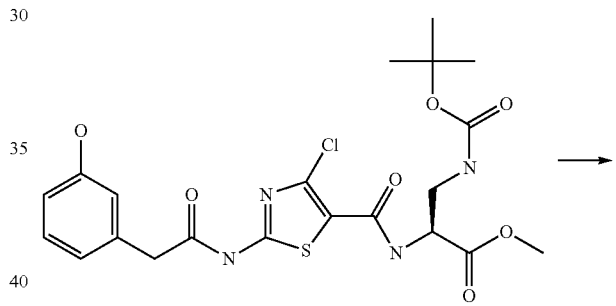

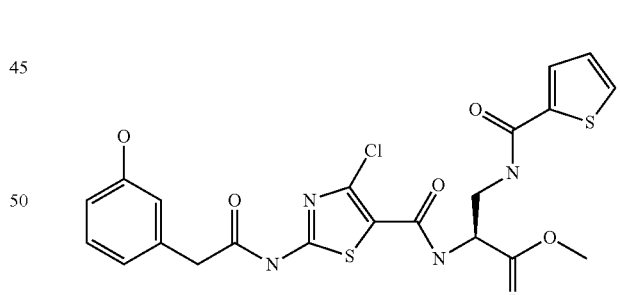

From (S)-3-tert-Butoxycarbonylamino-2-[(2-{2-[3-(tert-butyl-dimethyl-silanyloxy)-phenyl]-acetylamino}-4-chloro-thiazole-5-carbonyl)-amino]-propionic acid methyl ester there was obtained (S)-2-({4-Chloro-2-[2-(3-hydroxy-phenyl)-acetylamino]-thiazole-5-carbonyl}-amino)-3-[(thiophene-2-carbonyl)-amino]-propionic acid methyl ester (81%) as a pale yellow solid. MS m/e 523.9 (M+H⁺).

Preparation of (S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid methyl ester

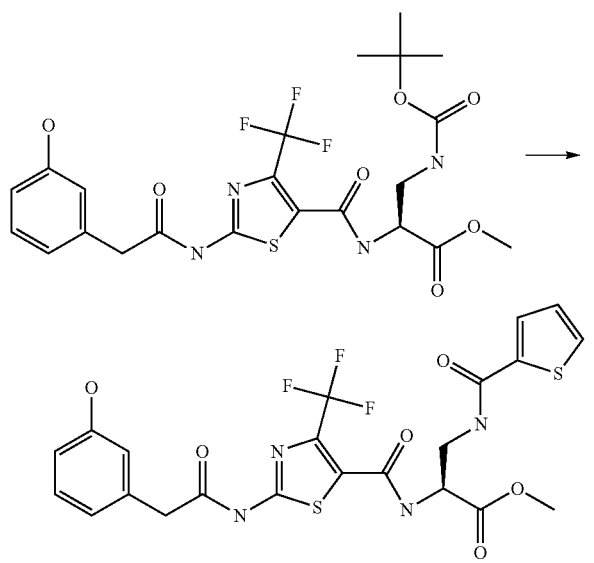

From (S)-3-tert-Butoxycarbonylamino-2-({2-[2-(3-hydroxy-phenyl)-acetylamino]-4-trifluoromethyl-thiazole-5-carbonyl}-amino)-propionic acid methyl ester there was obtained (S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid methyl ester (41%) as an off white solid. MS m/e 557.5 (M+H+).

Preparation of (S)-3-(3,5-Dihydroxy-benzoylamino)-2-({2-[3-(3-hydroxy-phenyl)-propionylamino]-4-methyl-thiazole-5-carbonyl}-amino)-propionic acid methyl ester

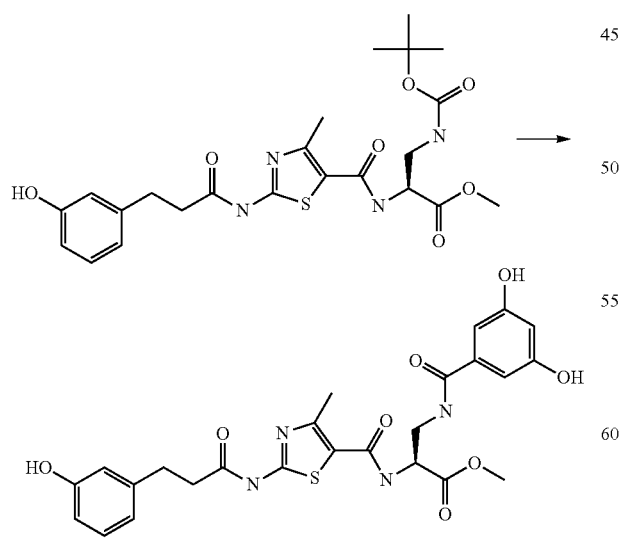

From (S)-3-tert-Butoxycarbonylamino-2-({2-[3-(3-hydroxy-phenyl)-propionylamino]-4-methyl-thiazole-5-carbo- nyl}-amino)-propionic acid methyl ester there was obtained (S)-3-(3,5-Dihydroxy-benzoylamino)-2-({2-[3-(3-hydroxy-phenyl)-propionylamino]-4-methyl-thiazole-5-carbonyl}-amino)-propionic acid methyl ester (46%) as a white solid. MS m/e 543.5 (M+H+).

Preparation of (S)-2-({2-[3-(3-Hydroxy-phenyl)-propionylamino]-4-methyl-thiazole-5-carbonyl}-amino)-3-[(thiophene-2-carbonyl)-amino]-propionic acid methyl ester

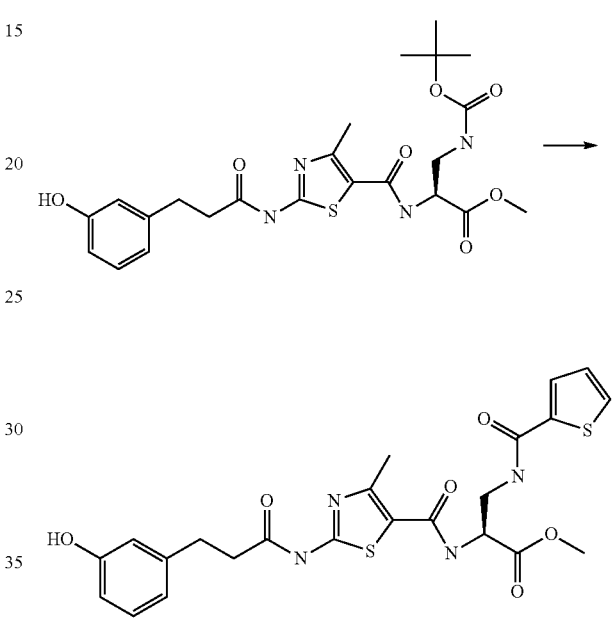

From (S)-3-tert-Butoxycarbonylamino-2-({2-[3-(3-hydroxy-phenyl)-propionylamino]-4-methyl-thiazole-5-carbonyl}-amino)-propionic acid methyl ester there was obtained (S)-2-({2-[3-(3-Hydroxy-phenyl)-propionylamino]-4-methyl-thiazole-5-carbonyl}-amino)-3-[(thiophene-2-carbonyl)-amino]-propionic acid methyl ester (39.3%) as a white solid. MS m/e 517.6 (M+H+).

Preparation of (S)-2-([2-[3-(3-Hydroxy-phenyl)-propoxy]-4-methyl-thiazole-5-carbonyl]-amino)-3-[(thiophene-2-carbonyl)-amino]-propionic acid methyl ester

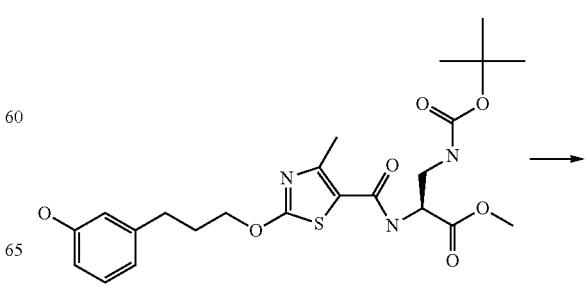

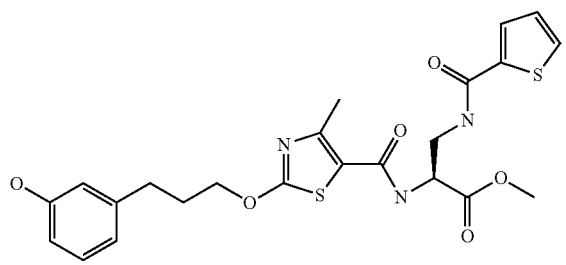

From (S)-3-tert-Butoxycarbonylamino-2-({2-[3-(3-hydroxy-phenyl)-propoxy]-4-methyl-thiazole-5-carbonyl}-amino)-propionic acid methyl ester there was obtained (S)-2-({2-[3-(3-Hydroxy-phenyl)-propoxy]-4-methyl-thiazole-5-carbonyl}-amino)-3-[(thiophene-2-carbonyl)-amino]-propionic acid methyl ester (27%) as white foam. MS m/e 504.6 (M+H$^+$).

Preparation of (S)-3-(3,5-Dihydroxy-benzoylamino)-2-({2-[2-(3-hydroxy-phenyl)-ethylamino]-4-methyl-thiazole-5-carbonyl}-amino)-propionic acid methyl ester

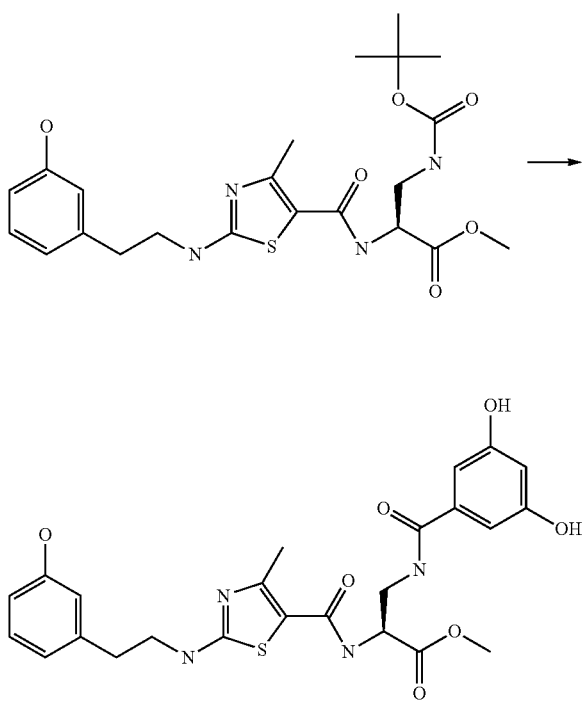

From (S)-3-tert-Butoxycarbonylamino-2-({2-[2-(3-hydroxy-phenyl)-ethylamino]-4-methyl-thiazole-5-carbonyl}-amino)-propionic acid methyl ester there was obtained (S)-3-(3,5-Dihydroxy-benzoylamino)-2-({2-[2-(3-hydroxy-phenyl)-ethylamino]-4-methyl-thiazole-5-carbonyl}-amino)-propionic acid methyl ester (47%) as an off white semi-solid. MS m/e 515.5 (M+H$^+$).

Preparation of 4-bromomethyl-1-(tetrahydro-pyran-2-yl)-1H-indazole

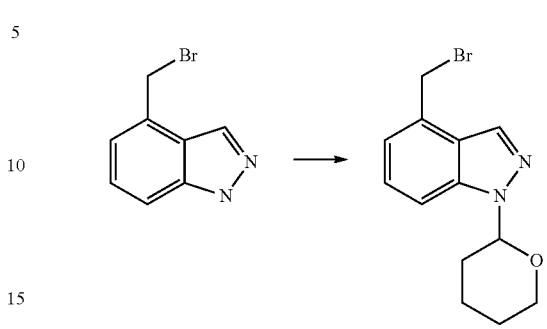

A solution of 4-bromomethyl-1H-indazole (2.0 g, 9.476 mmol), 3,4-dihyro-2H-pyran (4.0 mL, 43.84 mmol), p-toluenesulfonic acid monohydrate (2.0 g, 10.51 mmol) and anhydrous THF (20 mL) was heated at 60° C. for 1 h. The reaction mixture was cooled, added to aqueous saturated sodium carbonate solution (50 mL) and extracted with ethyl acetate (200 mL). The organic layer was washed with brine (50 mL), dried over MgSO$_4$, filtered and concentrated under reduced pressure. The resulting crude compound was purified by flash chromatography (20% EtOAc in hexanes) to give 4-bromomethyl-1-(tetrahydro-pyran-2-yl)-1H-indazole (2.43 g, 86.9%) as an off white solid. MS m/e 296.2 (M+H$^+$).

Preparation of [1-(Tetrahydro-pyran-2-yl)-1H-indazol-4-yl]-acetic acid

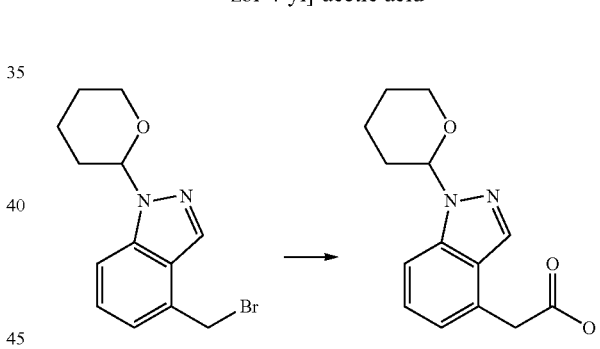

A mixture of 4-bromomethyl-1-(tetrahydro-pyran-2-yl)-1H-indazole (2.43 g, 8.232 mmol), dichlorobis(triphenylphosphine)palladium(II) (314 mg, 0.447 mmol), pulverized potassium carbonate (1.3 g, 9.406 mmol), THF (95 mL) and methanol (12 mL) was stirred at 25° C. in a sealed tube under 40 psi of carbon monoxide for 3 h. The reaction mixture was diluted with water (100 mL) and extracted with ethyl acetate (3×150 mL). The organic layers were combined, washed with brine (100 mL), dried over MgSO4, filtered and concentrated under reduced pressure. To the resulting brown oil was added THF (20 mL), water (12 mL) and lithium hydroxide monohydrate (3.4 g, 81.03 mmol) at 25° C. and heated at 80° C. for 90 min. The reaction mixture was cooled, diluted with water (100 mL) and washed with ether (2×50 mL). The aqueous layer was acidified with aqueous 6N HCl, saturated with sodium chloride and extracted with ethyl acetate (3×150 mL). The organic layers were combined, washed with brine (100 mL), dried over MgSO$_4$, filtered and concentrated under reduced pressure to give [1-(Tetrahydro-pyran-2-yl)-1H-indazol-4-yl]-acetic acid (1.85 g, 86.3%) as a yellow gum which solidified. MS m/e 261.3 (M+H$^+$).

Preparation of 2-[3-(1H-Indazol-4-yl)-propylamino]-4-methyl-thiazole-5-carboxylic acid methyl ester

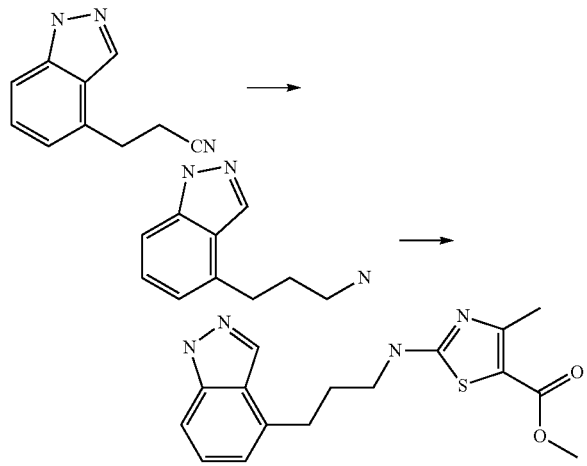

To a stirred solution of the 1.0M LAH in THF (8.3 mL, 8.30 mmol) at 0° C. was added drop wise a solution of 3-(1H-Indazol-4-yl)-propionitrile (0.94 g, 5.491 mmol) in anhydrous THF (20 mL) over 3 min. The resultant reaction mixture was gradually warmed and stirred at room temp for 2 h. The reaction was quenched by cooling in an ice bath followed by adding aq. 1N NaOH (1 mL). The suspension was filtered through celite, washed well with THF, concentrated and extracted with 3/1: EtOAc/THF. The organic layer were washed with brine (20 mL). The organic layer washed with brine (50 mL), dried over anhydrous magnesium sulfate, filtered, concentrated give 3-(1H-Indazol-4-yl)-propylamine (684.1 mg, 71.1%) as a pale yellow oil. MS m/e 173.3 (M+H$^+$). This was taken to next step.

A mixture of ethyl 2-chloro-4-methyl-1,3-thiazole-5-carboxylate (0.28 g, 1.361 mmol), 3-(1H-Indazol-4-yl)-propylamine (300 mg, 1.712 mmol), potassium acetate (180 mg, 1.834 mmol) and ethanol (3 mL) was microwaved for 90 min. at 160° C. The reaction is diluted with ethyl acetate (150 mL) and water (30 mL). and washed with brine (2×30 mL), dried over anhydrous magnesium sulfate, filtered, concentrated to give 2-[3-(1H-Indazol-4-yl)-propylamino]-4-methyl-thiazole-5-carboxylic acid methyl ester (0.230 g, 49%)) as a yellow solid. MS m/e 331.4 (M+H$^+$).

Preparation of 4-Methyl-2-[2-[1-(tetrahydro-pyran-2-yl)-1H-indazol-4-yl]-acetylamino]-thiazole-5-carboxylic acid ethyl ester

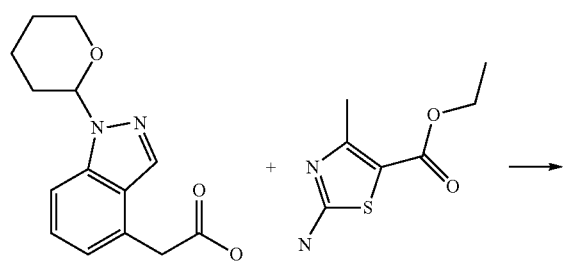

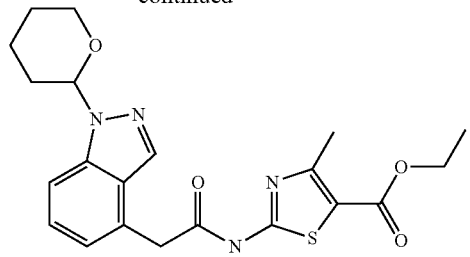

A solution of 2-Amino-4-methyl-thiazole-5-carboxylic acid ethyl ester (1.74 g, 9.343 mmol) and triethylamine (5.2 mL, 37.31 mol) in anhydrous THF (40 mL) was heated to 60° C. and [1-(Tetrahydro-pyran-2-yl)-1H-indazol-4-yl]acetic acid (1.85 g, 7.107 mmol) in anhydrous THF (20 mL) was added followed by the addition of 1-propanephosphonic acid cyclic anhydride, 50 wt. % solution in ethyl acetate (5.2 mL, 8.735 mmol) over 1 min. The reaction mixture was heated at 60° C. for 40 min, cooled, diluted with water (150 mL) and extracted with ethyl acetate (3×150 mL). The organic layers were combined, washed with 1/1 aqueous 2N HCl/brine (100 mL), brine (100 mL), dried over MgSO4, filtered and concentrated under reduced pressure. The resulting crude compound was purified by flash chromatography (33% EtOAc in hexanes) to give 4-Methyl-2-{2-[1-(tetrahydro-pyran-2-yl)-1H-indazol-4-yl]-acetylamino}-thiazole-5-carboxylic acid ethyl ester (2.23 g, 73%) as a yellow foam. MS m/e 429.5 (M+H$^+$).

Preparation of 4-Methyl-2-[2-[4-(tetrahydro-pyran-2-yl)-1H-indazol-4-yl]-acetylamino]-thiazole-5-carboxylic acid

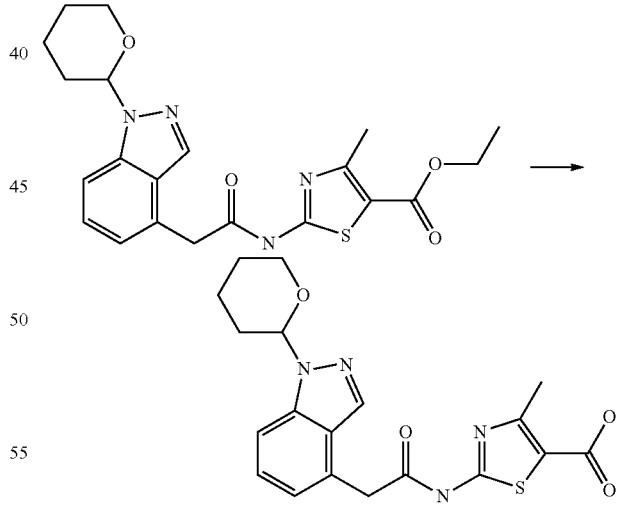

A mixture of 4-Methyl-2-{2-[1-(tetrahydro-pyran-2-yl)-1H-indazol-4-yl]-acetylamino}-thiazole-5-carboxylic acid ethyl ester (800 mg, 1.867 mmol), lithium hydroxide monohydrate (394 mg, 9.391 mmol), ethanol (8 mL) and water (24 mL) was placed in an oil bath preheated to 90° C. and the resulting solution was heated for 28 min. The reaction solution was diluted with water (20 mL), saturated with sodium chloride, acidified with aqueous 2N HCl and extracted with 4/1 ethyl acetate/THF (4×100 mL). The organic layers were combined, washed with brine (50 mL), dried over MgSO$_4$, filtered and concentrated under reduced pressure to give 4-Methyl-2-{2-[1-(tetrahydro-pyran-2-yl)-1H-indazol-4-yl]-acetylamino}-thiazole-5-carboxylic acid (0.54 g, 72.2%) as a yellow solid. MS m/e 401.4 (M+H$^+$).

In a similar manner the following compounds were produced:

Preparation of 2-[3-(1H-Indazol-4-yl)-propylamino]-4-methyl-thiazole-5-carboxylic acid

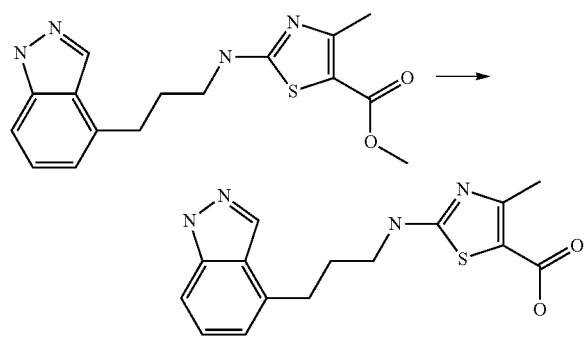

From 2-[3-(1H-Indazol-4-yl)-propylamino]-4-methyl-thiazole-5-carboxylic acid ethyl ester, there was obtained 2-[3-(1H-Indazol-4-yl)-propylamino]-4-methyl-thiazole-5-carboxylic acid (67.3%) as a yellow solid. MS m/e 317.4 (M+H$^+$).

Preparation of (S)-3-tert-Butoxycarbonylamino-2-[(4-methyl-2-[2-[4-(tetrahydro-pyran-2-yl)-1H-indazol-4-yl]-acetylamino]-thiazole-5-carbonyl)-amino]-propionic acid methyl ester

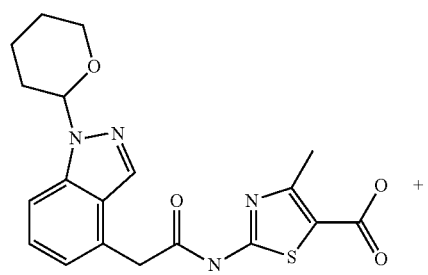

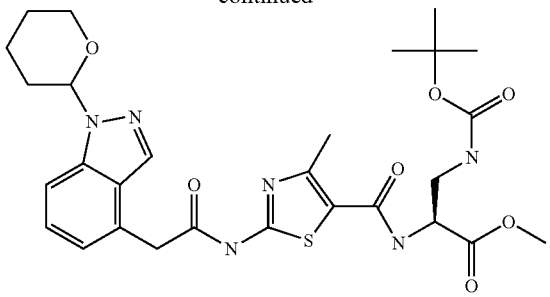

To a solution of 4-Methyl-2-{2-[1-(tetrahydro-pyran-2-yl)-1H-indazol-4-yl]-acetylamino}-thiazole-5-carboxylic acid (540 mg, 1.348 mmol) in anhydrous DMF (25 mL) was added HBTU (614 mg, 1.619 mmol), HOBt (219 mg, 1.621 mmol), H-DAP(BOC)-OME HCL (515 mg, 2.022 mmol) and triethylamine (0.9 mL, 6.457 mmol). The reaction mixture was stirred at 25° C. for 1 h and concentrated under reduced pressure to remove most of the DMF. The residue was diluted with ethyl acetate (200 mL), washed with 1/1 water/brine (40 mL), aqueous 1N HCl (40 mL), brine (40 mL), dried over MgSO$_4$, filtered and concentrated under reduced pressure. The resulting crude compound was purified by flash chromatography (40% to 100% EtOAc in hexanes) to give (S)-3-tert-Butoxycarbonylamino-2-[(4-methyl-2-{2-[1-(tetrahydropyran-2-yl)-1H-indazol-4-yl]-acetylamino}-thiazole-5-carbonyl)-amino]-propionic acid methyl ester (548.6 mg, 68%) as an off white foam. MS m/e 617.4 (M+H$^+$).

In a similar manner the following compound was produced:

Preparation of (S)-3-tert-Butoxycarbonylamino-2-({2-[3-(1H-indazol-4-yl)-propylamino]-4-methyl-thiazole-5-carbonyl}-amino)-propionic acid methyl ester

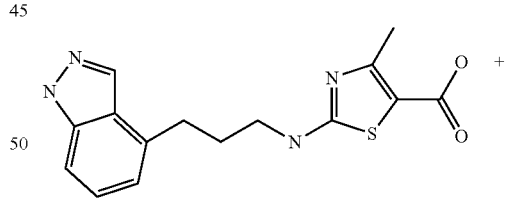

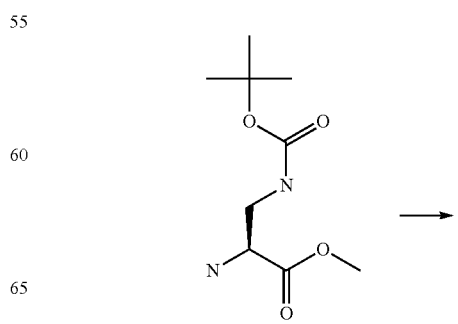

-continued

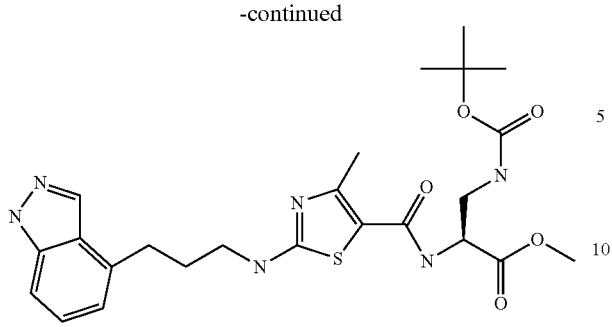

From 2-[3-(1H-Indazol-4-yl)-propylamino]-4-methyl-thiazole-5-carboxylic acid there was obtained (S)-3-tert-Butoxycarbonylamino-2-({2-[3-(1H-indazol-4-yl)-propylamino]-4-methyl-thiazole-5-carbonyl}-amino)-propionic acid methyl ester (43%) as a dark yellow solid. MS m/e 517.6 (M+H$^+$).

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid methyl ester

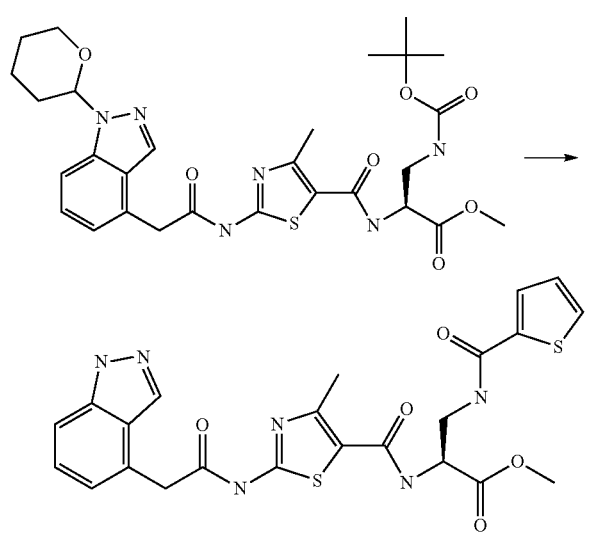

A solution of (S)-3-tert-Butoxycarbonylamino-2-[(4-methyl-2-{2-[1-(tetrahydro-pyran-2-yl)-1H-indazol-4-yl]-acetylamino}-thiazole-5-carbonyl)-amino]-propionic acid methyl ester (96.1 mg, 0.160 mmol) in 4M HCl in dioxane (4 mL, 16 mmol) was stirred at room temp for 40 min. Methanol (0.5 mL) was added to the gummy precipitate and the resulting solution was stirred at room temp for 5½ h. The reaction solution was concentrated under reduced pressure, added ether (2×) with concentrating under reduced pressure. To the resulting white solid dissolved in anhydrous DMF (3 mL) was added HBTU (91 mg, 0.240 mmol), HOBt (32 mg, 0.237 mmol), 2-thiophenecarboxylic acid (26 mg, 0.203 mmol) and triethylamine (0.12 mL, 0.861 mmol). The solution was allowed to stir at 25° C. for 1 h and concentrated under reduced pressure to remove most of the DMF. Ethyl acetate (80 mL) was added, washed with 3/1 water/brine (20 mL), aqueous 1N HCl (20 mL), brine (20 mL), dried over MgSO$_4$, filtered and concentrated under reduced pressure. The resulting crude compound was purified by flash chromatography (50% to 100% EtOAc in hexanes) to give (S)-2-{[2-(2-1H-Indazol-4-yl-acetylamino)-4-methyl-thiazole-5-carbonyl]-amino}-3-[(thiophene-2-carbonyl)-amino]-propionic acid methyl ester (36.1 mg, 42.9%) as a white solid. MS m/e 527.6 (M+H$^+$).

In a similar manner the following intermediate were produced:

(S)-3-(3,5-Dihydroxy-benzoylamino)-2-{[2-(2-1H-indazol-4-yl-acetylamino)-4-methyl-thiazole-5-carbonyl]-amino}-propionic acid methyl ester

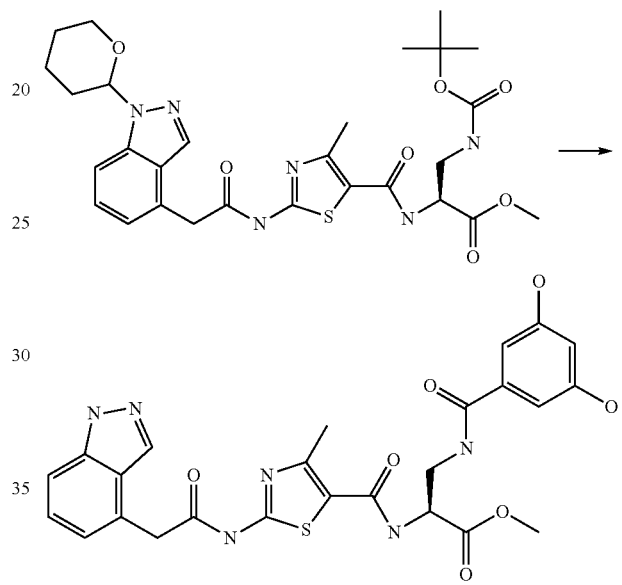

From (S)-3-tert-Butoxycarbonylamino-2-{[2-(2-1H-indazol-4-yl-acetylamino)-4-methyl-thiazole-5-carbonyl]-amino}-propionic acid methyl ester there was obtained (S)-3-(3,5-Dihydroxy-benzoylamino)-2-{[2-(2-1H-indazol-4-yl-acetylamino)-4-methyl-thiazole-5-carbonyl]-amino}-propionic acid methyl ester (18%) as a white solid MS m/e 552.5 (M+H$^+$).

Preparation of (S)-2-({2-[3-(1H-Indazol-4-yl)-propylamino]-4-methyl-thiazole-5-carbonyl}-amino)-3-[(thiophene-2-carbonyl)-amino]-propionic acid methyl ester

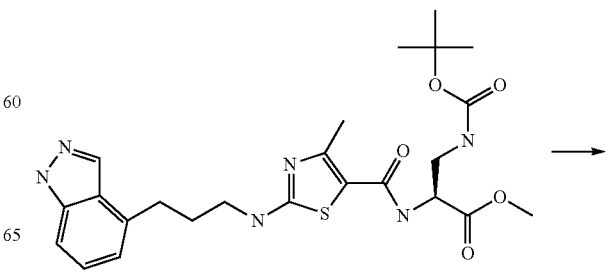

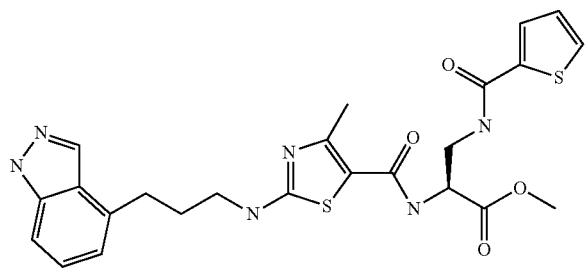

From (S)-3-tert-Butoxycarbonylamino-2-({2-[3-(1H-indazol-4-yl)-propylamino]-4-methyl-thiazole-5-carbonyl}-amino)-propionic acid methyl ester there was obtained (S)-2-({2-[3-(1H-Indazol-4-O-propylamino)-4-methyl-thiazole-5-carbonyl}-amino)-3-[(thiophene-2-carbonyl)-amino]-propionic acid methyl ester (34%) as a white solid. MS m/e 527.6 (M+H$^+$).

Preparation of 2-tert-Butoxycarbonylamino-4-trifluoromethyl-thiazole-5-carboxylic acid ethyl ester

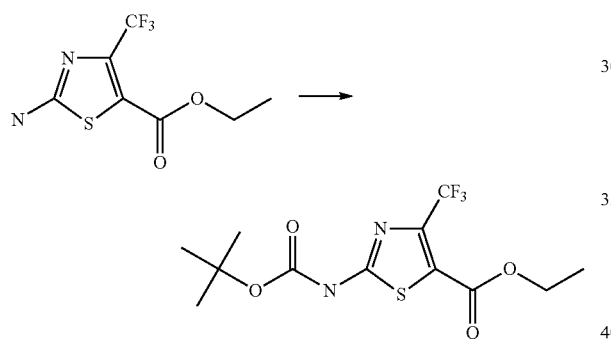

To a solution of 2-Amino-4-trifluoromethyl-thiazole-5-carboxylic acid ethyl ester (5.3 g, 22.06 mmol) in THF (65 mL) was added di-t-butyl dicarbonate (5.8 g, 26.58 mmol) and DMAP (0.27 g, 2.21 mmol). The reaction mixture was stirred at room temperature for 17 h, diluted with ethyl acetate (250 mL), washed with aqueous 1N HCl (75 mL), 1/1 water/brine (75 mL), dried over MgSO$_4$, filtered, concentrated under reduced pressure and triturated with hexane (25 mL) to give 2-tert-Butoxycarbonylamino-4-trifluoromethyl-thiazole-5-carboxylic acid ethyl ester (6.67 g, 88.8%) as an off white solid. MS m/e 341.3 (M+H$^+$).

Preparation of 2-tert-Butoxycarbonylamino-4-trifluoromethyl-thiazole-5-carboxylic acid

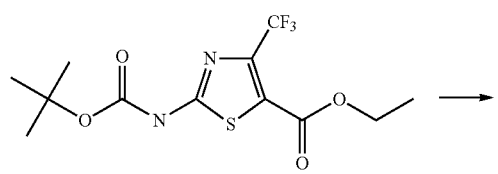

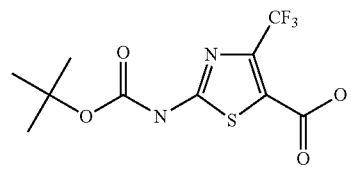

To a solution of 2-tert-Butoxycarbonylamino-4-trifluoromethyl-thiazole-5-carboxylic acid ethyl ester (6.67 g, 19.60 mmol) in THF (42 mL) and ethanol (63 mL) was added aqueous 6N potassium hydroxide (100 mL) cautiously at 25° C. and heated at 60° C. for 20 h. The reaction mixture was cooled to room temperature, added water (200 mL), cooled in an ice bath with stirring at 0° C., cautiously acidified to pH 1 with concentrated HCl and extracted with ethyl acetate (3×200 mL). The organic layers were combined, washed with brine (200 mL), dried over MgSO$_4$, filtered and concentrated under reduced pressure to give 2-tert-Butoxycarbonylamino-4-trifluoromethyl-thiazole-5-carboxylic acid (6.03 g, 100%) as a pale yellow solid.

Preparation of (S)-3-tert-Butoxycarbonylamino-2-[(2-tert-butoxycarbonylamino-4-trifluoromethyl-thiazole-5-carbonyl)-amino]-propionic acid methyl ester

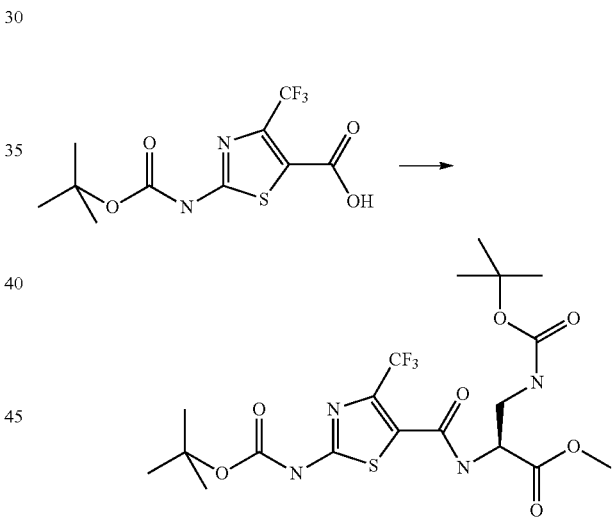

To a solution of 2-tert-Butoxycarbonylamino-4-trifluoromethyl-thiazole-5-carboxylic acid (6.23 g, 19.96) in anhydrous DMF (100 mL) was added HBTU (8.29 g, 24.97 mmol), HOBt (3.39 g, 19.96 mmol), H-DAP(BOC)-OME HCL (8.08 g, 31.02 mmol) and triethylamine (11.97 mL, 85.94 mmol). The reaction mixture was stirred at 25'C for 1 h and concentrated under reduced pressure to remove most of the DMF. The residue was diluted with ethyl acetate (200 mL), washed with 1:1 water/brine (40 mL), aqueous 1N HCl (40 mL), brine (40 mL), dried over MgSO$_4$, filtered and concentrated under reduced pressure. The resulting crude compound was purified by flash chromatography (40% to 100% EtOAc in hexanes) to give (S)-3-tert-Butoxycarbonylamino-2-[(2-tert-butoxycarbonylamino-4-trifluoromethyl-thiazole-5-carbonyl)-amino]-propionic acid methyl ester (8 g, 78%) as a pale yellow foam. MS m/e 513.5 (M+H$^+$).

Preparation of (S)-2-[(2-tert-Butoxycarbonylamino-4-trifluoromethyl-thiazole-5-carbonyl)-amino]-3-[(thiophene-2-carbonyl)-amino]-propionic acid methyl ester

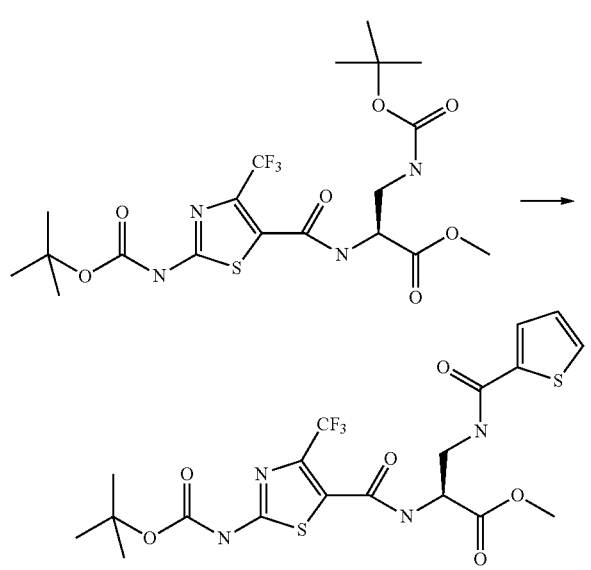

A stirred solution of (S)-3-tert-Butoxycarbonylamino-2-[(2-tert-butoxycarbonylamino-4-trifluoromethyl-thiazole-5-carbonyl)-amino]-propionic acid methyl ester (10.67 g, 20.82 mmol) in methanol (80 mL) was treated with the 4 M HCl in Dioxane (50 mL, 200 mmol) and reaction was heated at 40° C. for 45 min. The resultant intermediate was concentrated to give a pale yellow foam oil. A solution of this material in DMF (150 mL) was treated with the HBTU (9.6 g, 25.31 mmol), HOBt (3.5 g, 25.90 mmol), 2-thiophenecarboxylic acid (2.9 g, 22.63 mmol) and the triethylamine (19 mL, 136.3 mmol) and stirred at room temp for 2 h. The reaction was then concentrated to remove DMF, followed by dilution with water (300 mL), and extracted with ethyl acetate (1×300 mL, 1×100 mL). The combined organic layers washed with water (3×100 mL) followed by aq sat sodium bicarbonate solution (3×100 mL), water (2×100 mL), brine (100 mL), dried over magnesium sulfate, filtered, concentrated to give (9.41 g) as crude product. Column purification The solid residue was purified by flash column (20-80 EtOAc in hexane) to give 10.2 g (98%) of yellow oil. MS m/e 523.5 (M+H⁺).

Preparation of 4-Methyl-2-{2-[1-(tetrahydro-pyran-2-O-1H-indazol-4-yl]-acetylamino}-thiazole-5-carboxylic acid ethyl

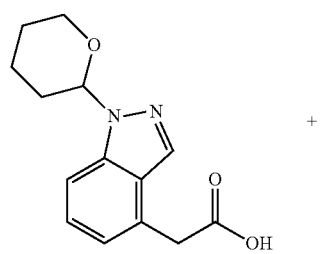

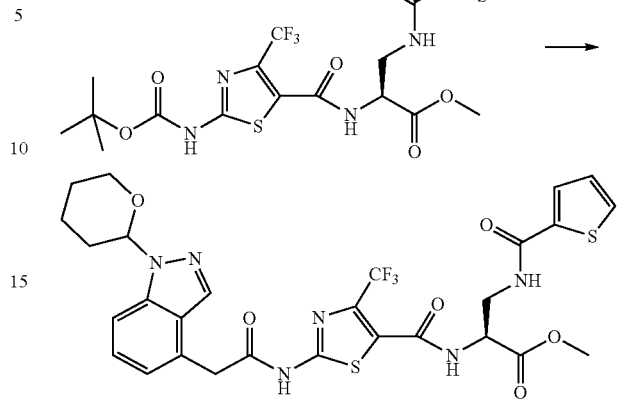

A solution of (S)-2-[(2-tert-Butoxycarbonylamino-4-trifluoromethyl-thiazole-5-carbon yl)-amino]-3-[(thiophene-2-carbonyl)-amino]-propionic acid methyl ester (1.2 g, 2.29 mmol) in methanol (8 mL), was treated with 4M HCl in dioxane (10 mL) and heated and at 45° C. for 35 minutes. The resultant reaction was concentrated to give a white solid which was dissolved in THF (10 mL) followed by addition of 1-(Tetrahydro-pyran-2-yl)-1H-indazol-4-yl]-acetic acid (0.720 g, 2.77 mmol), triethylamine (2.20 mL, 15.78 mol) in anhydrous THF (40 mL) and 1-propanephosphonic acid cyclic (50 wt. % solution in ethyl acetate) (5.2 mL, 8.735 mmol). The resultant mixture was heated to 60'C for 2 h. The reaction mixture is cooled, diluted with water (150 mL) and extracted with ethyl acetate (3×150 mL). The organic layers were combined, washed with 1/1 aqueous 2N HO/brine (100 mL), brine (100 mL), dried over MgSO₄, filtered and concentrated under reduced pressure. The resulting crude compound was purified by flash chromatography (33% EtOAc in hexanes) to give (S)-2-[(2-{2-[1-(Tetrahydro-pyran-2-yl)-1H-indazol-4-yl]-acetylamino}-4-trifluoromethyl-thiazole-5-carbonyl)-amino]-3-[(thiophene-2-carbonyl)-amino]-propionic acid methyl ester (1.04 g, 68.1%) as a pale yellow foam. MS m/e 655.7 (M+H⁺).

Preparation of 5,5-diethoxy-pent-3yne-2-one

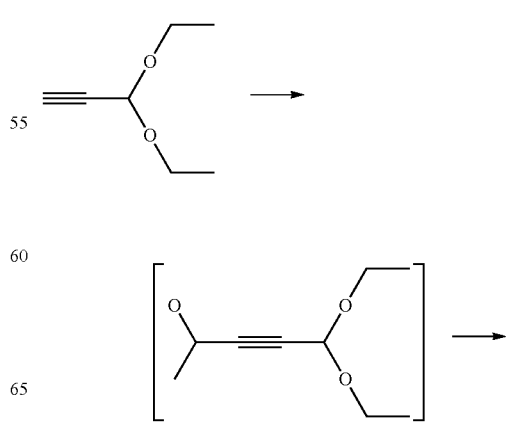

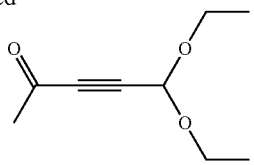

A solution of propargylaldehyde diethyl acetal (5 ml, 35 mmol) in THF (50 ml) was cooled to −78° C. (dry ice-acetone bath). 2.0M n-butyllithium in cyclohexane (26.2 ml, 52.4 mmol) was added dropwise with a dropping funnel at −78° C., and the mixture was stirred for 15 min. Acetaldehyde (3.52 ml, 62.8 mmol) was added in one portion and stirred at −78° C. for 15 min. The cooling bath was removed and the mixture was stirred at rt for 2 h. The reaction mixture was quenched by pouring into ice and 1M NaH$_2$PO$_4$ (100 ml) then extracted with EtOAC. The layers were separated. The organic layer was washed with brine, dried over Na$_2$SO$_4$ and concentrated under reduced pressure. The residue was purified by flash chromatography with 15-30% EtOAc in hexane to afford the desired alcohol intermediate (3.99 g). This intermediate was dissolved in dichloromethane (250 ml) and treated with activated MnO$_2$ (60 g) at rt for 2 h 45 min. The reaction mixture was filtered through a plug of celite and Na$_2$SO$_4$. The filtrated was concentrated under reduced pressure to afford the desired ketone (3.51 g, 59% yield).

Preparation of
5-diethoxymethyl-3-methyl-thiophene-2-carboxylic
acid methyl ester

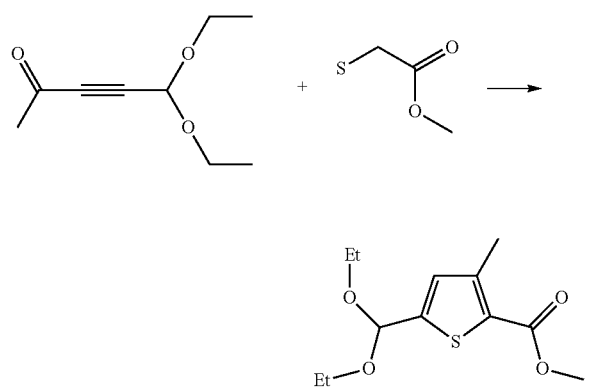

A solution of 5,5-diethoxy-pent-3yne-2-one (3.51 g, 20.6 mmol) in THF (30 ml) was cooled to 0° C. (ice bath). Methyl thioglycolate (1.84 ml, 20.6 mmol) was added in one portion and the mixture was stirred at 0° C. for 2 h. Methanol (10 ml) and Cs$_2$CO$_3$/MgSO$_4$ (7 g/14 g, pre-dried at 200° C. in vacuum) were added at 0° C. The mixture was stirred at 0° C. for 15 min and then at rt for 2.5 h. The reaction mixture was quenched by pouting into ice and 1M NaH$_2$PO$_4$ (100 ml), then extracted with EtOAc. The layers were separated. The organic layer was washed with brine, dried over Na$_2$SO$_4$ and concentrated under reduced pressure. The residue was purified by flash chromatography with 5-15% EtOAc in hexane to afford the desired product (4.41 g, 83% yield).

Preparation of
5-formyl-3-methyl-thiophene-2-carboxylic acid
methyl ester

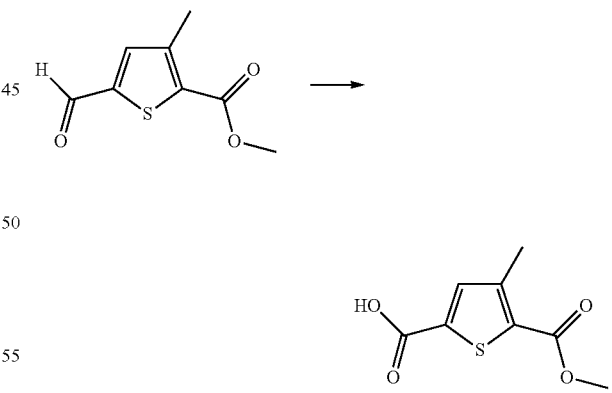

A solution of 5-diethoxymethyl-3-methyl-thiophene-2-carboxylic acid methyl ester (4.41 g, 17.1 mmol) in dioxane (20 ml) was cooled to 0° C. (ice bath). 88% formic acid (40 ml) was added in one portion and the mixture was stirred at 0° C. for 5 min and then at rt for 30 min. The mixture was concentrated under reduced pressure to afford the desired product which was not further purified (3.2 g, 100% yield).

Preparation of 3-methyl-thiophene-2,5-dicarboxylic
acid 2-methyl ester

To a solution of 5-formyl-3-methyl-thiophene-2-carboxylic acid methyl ester (3.2 g, 17.4 mmol) in dioxane (20 ml) was added 2-methyl-2-butene (15 ml) and a solution of Na$_2$ClO$_2$ (4.71 g, 52.1 mmol) and NaH$_2$PO$_4$ (4.71 g, 39.2 mmol) in water (15 ml). The mixture was stirred at rt for 1 h. The solution was saturated with sodium chloride, then successively extracted with EtOAc and dichloromethane. The combined organic layers were dried over Na₂SO₄ and concentrated under reduced pressure to afford the desired product (3.13 g, 90% yield)

Preparation of
6,6-diethoxy-2,2-dimethyl-hex-4-yne-3-one

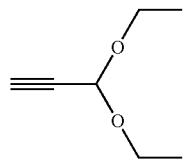

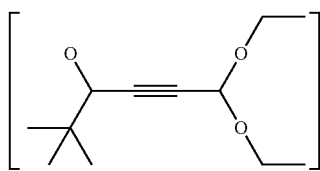

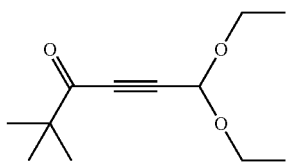

A solution of propargylaldehyde diethyl acetal (5 ml, 35 mmol) in THF (50 ml) was cooled to −78° C. (dry ice-acetone bath). 2.0M n-butyllithium in cyclohexane (26.2 ml, 52.4 mmol) was added dropwise with a dropping funnel at −78° C., and the mixture was stirred for 15 min. Trimethylacetaldehyde (6.82 ml, 62.8 mmol) was added in one portion and the mixture was stirred at −78° C. for 10 min. The cooling bath was removed and the mixture was stirred at rt for 2 h. The reaction mixture was quenched by pouring into ice and 1M NaH₂PO₄ (100 ml) then extracted with EtOAC. The layers were separated. The organic layer was washed with brine, dried over Na₂SO₄ and concentrated under reduced pressure. The residue was purified by flash chromatography with 15-30% EtOAc in hexane to afford the desired alcohol intermediate (7.00 g). This intermediate was dissolved in dichloromethane (400 ml) and treated with activated MnO₂ (105 g) at rt overnight. The reaction mixture was filtered through a plug of celite. The filtrated was concentrated under reduced pressure to afford the desired ketone (6.50 g, 87% yield).

Preparation of 5-diethoxymethyl-3-tert-butyl-thiophene-2-carboxylic acid methyl ester

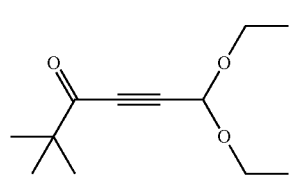 + 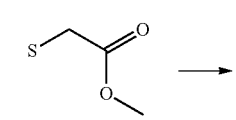 → 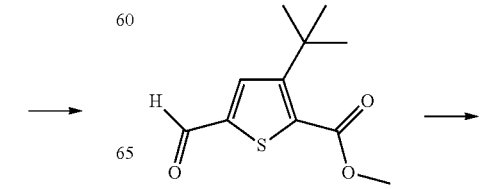

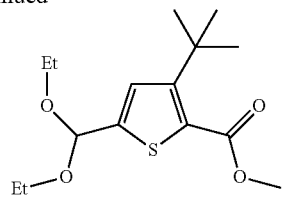

A solution of 6,6-diethoxy-2,2-dimethyl-hex-4-yne-2-one (6.50 g, 30.6 mmol) in THF (60 ml) was cooled to 0° C. (ice bath). Methyl thioglycolate (2.74 ml, 30.6 mmol) was added in one portion and the mixture was stirred at 0° C. for 2 h. Methanol (10 ml) and Cs₂CO₃/MgSO₄ (10 g/20 g, pre-dried at 200° C. in vacuum) were added at 0° C. The mixture was stirred at 0° C. for 15 min and then at rt for 2.5 h. The reaction mixture was quenched by pouting into ice and 1M NaH₂PO₄ (100 ml), then extracted with EtOAc. The layers were separated. The organic layer was washed with brine, dried over Na₂SO₄ and concentrated under reduced pressure. The residue was purified by flash chromatography with 5-20% EtOAc in hexane to afford the desired product (1.84 g, 20% yield).

Preparation of
5-formyl-3-tert-butyl-thiophene-2-carboxylic acid methyl ester

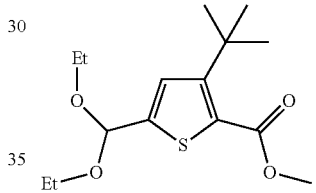

A solution of 5-diethoxymethyl-3-tert-butyl-thiophene-2-carboxylic acid methyl ester (1.84 g, 6.1 mmol) in dioxane (10 ml) was cooled to 0° C. (ice bath). 88% formic acid (20 ml) was added in one portion and the mixture was stirred at 0° C. for 5 min and then at rt for 2 h. The mixture was concentrated under reduced pressure to afford the desired product which was not further purified (1.57 g, 100% yield).

Preparation of
3-tert-butyl-thiophene-2,5-dicarboxylic acid 2-methyl ester

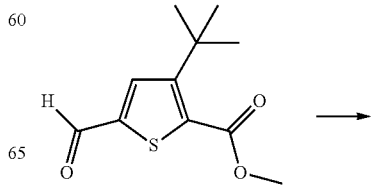

-continued

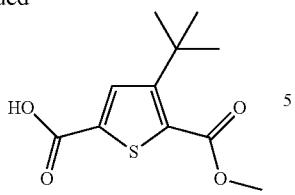

To a solution of 5-formyl-3-methyl-thiophene-2-carboxylic acid methyl ester (1.57 g, 6.9 mmol) in dioxane (25 ml) was added 2-methyl-2-butene (6.5 ml) and a solution of $Na_2ClO_2$ (1.88 g, 20.8 mmol) and $NaH_2PO_4$ (1.88 g, 15.7 mmol) in water (6.5 ml). The mixture was stirred at rt for 45 min. The solution was saturated with sodium chloride, then successively extracted with EtOAc and dichloromethane. The combined organic layers were dried over $Na_2SO_4$ and concentrated under reduced pressure to afford the desired product (1.55 g, 92% yield)

Preparation of 3-(tert-butyl-dimethyl-silyl)-oxy-benzylamine

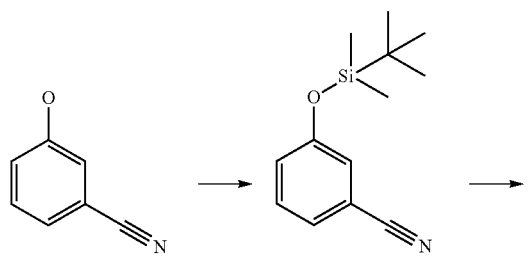

To a solution of 3-cyanophenol (5 g, 42 mmol) in DMF (85 ml) was added imidazole (6.3 g, 92.5 mmol) at rt. The mixture was cooled to 0° C. (ice bath) and t-butyl-dimethylsilyl chloride (7.6 g, 50.4 mmol) was added in one portion. The mixture was stirred at 0° C. for 10 min, then at rt overnight. The mixture was concentrated under reduced pressure and the residue was diluted with water and extracted with ether. The layers were separated. The organic layer was successively washed with water and brine, then dried over $Na_2SO_4$ and concentrated under reduced pressure to afford the intermediate silyl ether (9.46 g). This material was not purified and was dissolved in methanol (225 ml). This solution was hydrogenated for 4.5 h at rt in a Parr apparatus at 50 psi over 10% Pd/C (wet catalyst, 2.3 g). The mixture was filtered through celite. The cake of celite was washed with methanol and the filtrate was concentrated under reduced pressure to afford the desired amine (9.37 g, 94% yield).

Preparation of 5-[3-(tert-butyl-dimethyl-silyl)-oxy-benzylcarbamoyl]-3-methyl-thiophene-2-carboxylic acid methyl ester

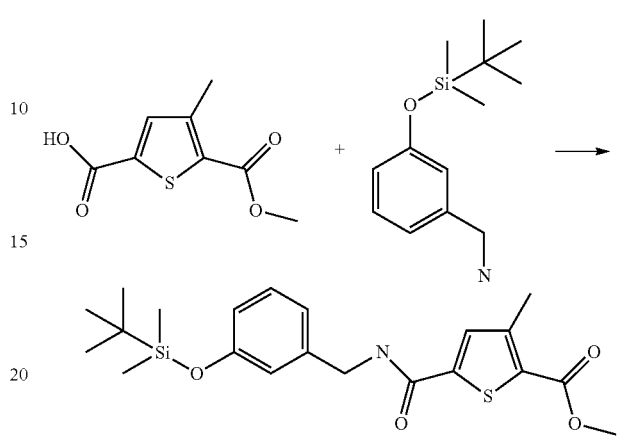

To a solution of 3-methyl-thiophene-2,5-dicarboxylic acid 2-methyl ester (1 g, 5 mmol) and 3-(tert-butyl-dimethyl-silyl)-oxy-benzylamine (1.42 g, 6.0 mmol) in DMF (15 ml) was added at rt triethylamine (1.4 ml, 10 mmol) and HBTU (3.8 g, 10 mmol). The mixture was stirred at rt for 1.5 h, then quenched with 1N HCl and extracted with EtOAc. The layers were separated. The organic layer was successively washed with water and brine, then dried over $Na_2SO_4$ and concentrated under reduced pressure. The residue was purified by flash chromatography with 10-25% EtOAc in hexane to afford the desired product (1.1 g, 52% yield).

Preparation of 5-[3-(tert-butyl-dimethyl-silyl)-oxy-benzylcarbamoyl]-3-tert-butyl-thiophene-2-carboxylic acid methyl ester

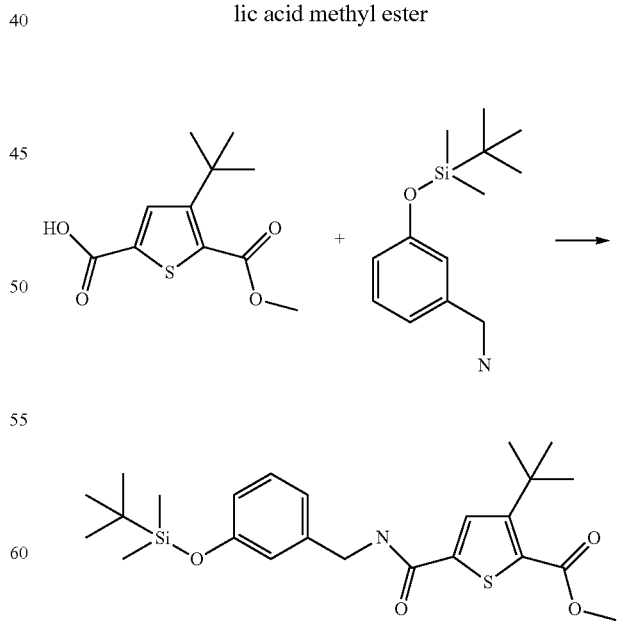

To a solution of 3-tert-butyl-thiophene-2,5-dicarboxylic acid 2-methyl ester (0.5 g, 2.1 mmol) and 3-(tert-butyl-dimethyl-silyl)-oxy-benzylamine (0.590 g, 2.5 mmol) in DMF (10 ml) was added at rt triethylamine (0.57 ml, 4.1 mmol) and HBTU (1.6 g, 4.2 mmol). The mixture was stirred at rt for 20 min, then quenched with 1NHCl and extracted with EtOAc. The layers were separated. The organic layer was successively washed with water and brine, then dried over $Na_2SO_4$ and concentrated under reduced pressure. The residue was purified by flash chromatography with 10-20% EtOAc in hexane to afford the desired product (0.44 g, 46% yield).

Preparation of 5-(3-hydroxy-benzylcarbamoyl]-3-methyl-thiophene-2-carboxylic acid

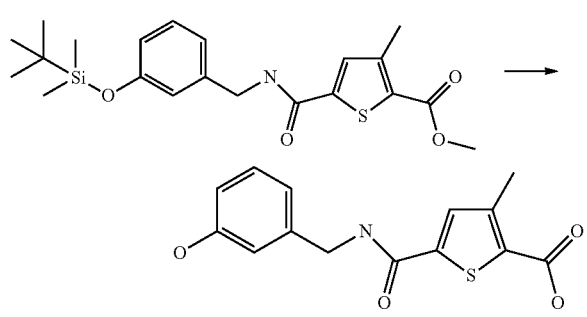

A solution of 5-[3-(tert-butyl-dimethyl-silyl)-oxy-benzyl-carbamoyl]-3-methyl-thiophene-2-carboxylic acid methyl ester (1.8 g, 2.6 mmol) in THF/water (12 ml/6 ml) was treated with $LiOH.H_2O$ (1.1 g, 26 mmol) at rt for 1.5 h. The reaction mixture was quenched with 1N HCl and extracted with EtOAc. The layers were separated. The organic layer was successively washed with water and brine, then dried over $Na_2SO_4$ and concentrated under reduced pressure to afford the desired product (0.8 g, 100% yield).

Preparation of 5-(3-hydroxy-benzylcarbamoyl]-3-tert-butyl-thiophene-2-carboxylic acid

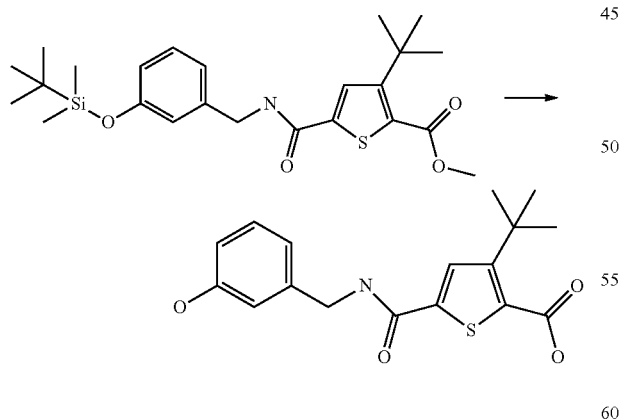

A solution of 5-[3-(tert-butyl-dimethyl-silyl)-oxy-benzyl-carbamoyl]-3-tert-butyl-thiophene-2-carboxylic acid methyl ester (0.26 g, 0.56 mmol) in THF/water (6 ml/3 ml) was treated with $LiOH.H_2O$ (0.24 g, 5.6 mmol) at rt overnight. The reaction mixture was quenched with 1N HCl and extracted with EtOAc. The layers were separated. The organic layer was successively washed with water and brine, then dried over $Na_2SO_4$ and concentrated under reduced pressure to afford the desired product (0.2 g, 100% yield).

Preparation of (S)-3-tert-butoxycarbamoylamino-2-{[5-(3-hydroxy-benzylcarbamoyl)-3-methyl-thiophene-2-carbonyl]-amino}-propionic acid methyl ester

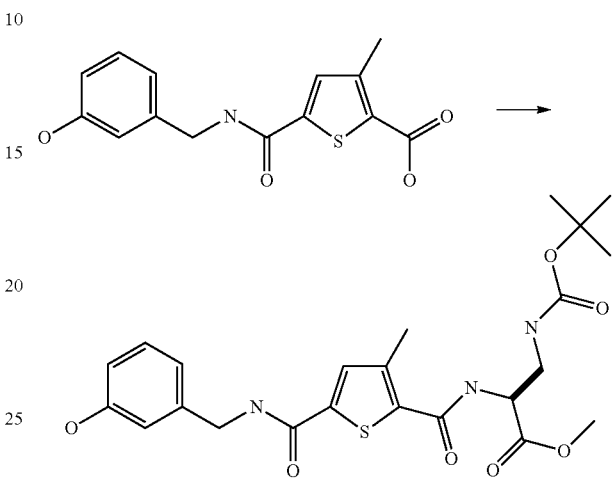

To a solution of 5-(3-hydroxy-benzylcarbamoyl]-3-methyl-thiophene-2-carboxylic acid (0.25 g, 0.85 mmol) and H-DAP(Boc)OMe hydrochloride (0.32 g, 1.2 mmol) in DMF (10 ml) was added at rt triethylamine (0.35 ml, 2.5 mmol), HOBT (0.14 g, 1.0 mmol) and HBTU (0.38 g, 1.0 mmol). The mixture was stirred at rt for 30 min, then quenched with 1NHCl and extracted with EtOAc. The layers were separated. The organic layer was successively washed with water and brine, then dried over $Na_2SO_4$ and concentrated under reduced pressure. The residue was purified by flash chromatography with 30-60% EtOAc in hexane to afford the desired product (0.38 g, 93% yield).

Preparation of (S)-3-amino-2-{[5-(3-hydroxy-benzylcarbamoyl)-3-methyl-thiophene-2-carbonyl]-amino}-propionic acid methyl ester, HCl salt

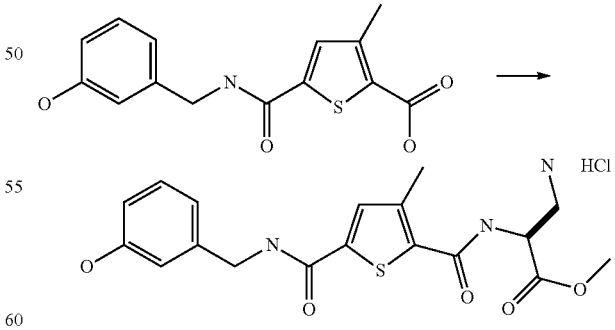

To a solution of 5-(3-hydroxy-benzylcarbamoyl]-3-methyl-thiophene-2-carboxylic acid (0.4 g, 1.4 mmol) and H-DAP(Boc)OMe hydrochloride (0.52 g, 2.1 mmol) in DMF (10 ml) was added at rt triethylamine (0.57 ml, 4.1 mmol), HOBT (0.22 g, 1.6 mmol) and HBTU (0.62 g, 1.6 mmol). The mixture was stirred at rt for 1 h, then quenched with 1NHCl and extracted with EtOAc. The layers were separated. The organic layer was successively washed with water and brine, then dried over Na$_2$SO$_4$ and concentrated under reduced pressure. The residue was purified by flash chromatography with 35-100% EtOAc in hexane to afford the BOC protected amine (0.7 g). This material was treated with 4NHCl in dioxane (15 ml) at rt for 2 h. The solution was concentrated under reduced pressure to afford the desired HCl salt as an hygroscopic solid (0.6 g, 100% yield).

Preparation of (S)-3-amino-2-{[5-(3-hydroxy-benzylcarbamoyl)-3-tert-butyl-thiophene-2-carbonyl]-amino}-propionic acid methyl ester, TFA salt

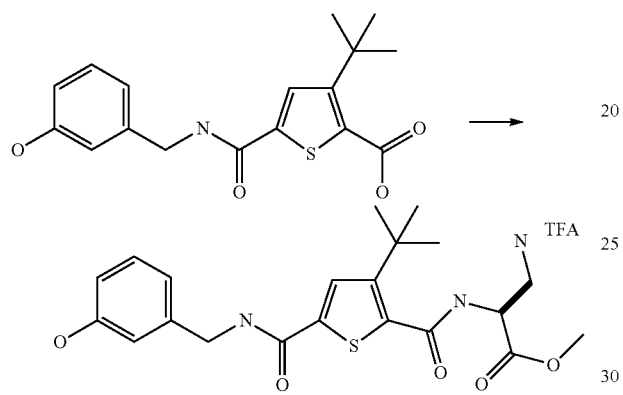

To a solution of 5-(3-hydroxy-benzylcarbamoyl]-3-tert-butyl-thiophene-2-carboxylic acid (30 mg, 0.09 mmol) and H-DAP(Boc)OMe hydrochloride (28 mg, 0.11 mmol) in THF (3 ml) was added at rt triethylamine (0.04 ml, 0.27 mmol), and DCC (22 mg, 0.11 mmol). The mixture was stirred at rt overnight, then quenched with 1NHCl and extracted with EtOAc. The layers were separated. The organic layer was successively washed with water and brine, then dried over Na$_2$SO$_4$ and concentrated under reduced pressure. The residue was purified by flash chromatography with 40-60% EtOAc in hexane to afford the BOC protected amine (47 mg, 98% yield). This procedure was repeated on a 73 mg scale to afford a second batch of BOC amine (95 mg, 82% yield). The two batches were combined, dissolved in dichloromethane (5 ml) and treated with TFA (5 ml) at rt for 30 min. The mixture was concentrated to dryness. The residue with triturated with ether. The supernatant was removed and the product was dried under vacuum at 45° C. (130 mg, 91% yield).

Preparation of C-(1H-indol-4-yl)-methylamine

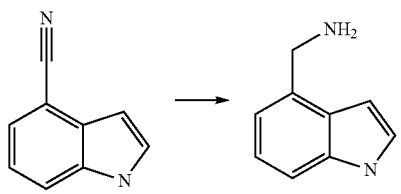 [SMILES: N#Cc1cccc2[nH]ccc12 ; NCc1cccc2[nH]ccc12]

To a solution of 4-cyanoindole (7.5 g, 53 mmol) in THF (100 ml) was added at rt a 1.0M solution of lithium aluminum hydride in THF (100 ml, 100 mmol). The mixture was refluxed for 30 min then cooled to rt. The reaction mixture was quenched with 1N NaOH and filtered. The filtrate was acidified with 1N HCl and stirred at rt for 10 min. The pH was adjusted to ~8 by adding sat NaHCO$_3$ and extracted with n-butanol. The layers were separated and the organic layer was concentrated to dryness. The residue was triturated with methanol. Insoluble materials were removed by filtration and the filtrate was concentrated under reduced pressure to afford the desired product as a solid that was further dried under high vacuum at 50° C. (7.27 g, 94% yield).

Preparation of 5-[(1H-indol-4-ylmethyl)-carbamoyl]-3-methyl-thiophene-2-carboxylic acid methyl ester

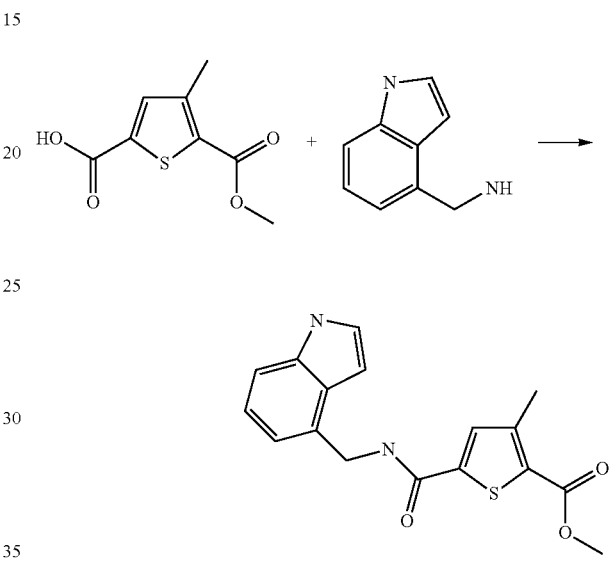

To a solution of 3-methyl-thiophene-2,5-dicarboxylic acid 2-methyl ester (200 mg,) mmol) and C-(1H-indol-4-yl)-methylam (219 mg, 1.5 mmol) in DMF (5 ml) was added at rt triethylamine (0.42 ml, 3 mmol), HOBT (162 mg, 1.2 mmol) and HBTU (455 mg, 1.2 mmol). The mixture was stirred at rt for 30 min, then quenched with 1NHCl and extracted with EtOAc. The layers were separated. The organic layer was successively washed with water and brine, then dried over Na$_2$SO$_4$ and concentrated under reduced pressure. The residue was purified by flash chromatography with 20-60% EtOAc in hexane to afford the desired product (119 mg, 36% yield).

Preparation of 5-[(1H-indol-4-ylmethyl)-carbamoyl]-3-methyl-thiophene-2-carboxylic acid

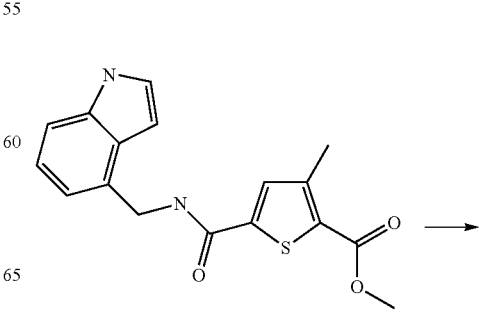

-continued

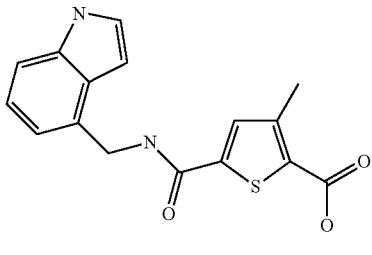

A solution of 5-[(1H-indol-4-ylmethyl)-carbamoyl]-3-methyl-thiophene-2-carboxylic acid methyl ester (115 mg, 0.35 mmol) in THF/water (6 ml/3 ml) was treated with LiOH.H₂O (157 mg, 3.5 mmol) at rt for 24 h. The reaction mixture was quenched with 1N HCl and extracted with EtOAc. The layers were separated. The organic layer was successively washed with water and brine, then dried over Na₂SO₄ and concentrated under reduced pressure to afford the desired product (126 mg, 100% yield).

Preparation of (S)-3-tert-butoxycarbamoylamino-2-([5-[(1H-indol-4-ylmethyl)-carbamoyl]-3-methyl-thiophene-2-carbonyl]-amino)-propionic acid methyl ester

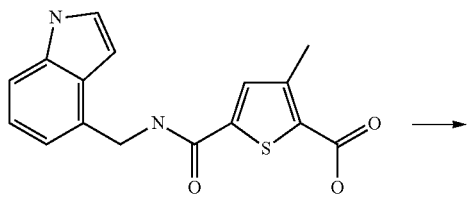

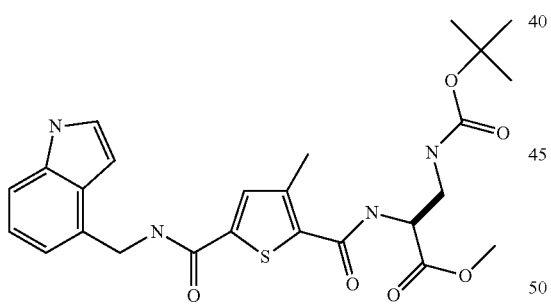

To a solution of 5-[(1H-indol-4-ylmethyl)-carbamoyl]-3-methyl-thiophene-2-carboxylic acid (126 mg, 0.4 mmol) and H-DAP(Boc)OMe hydrochloride (153 mg, 0.6 mmol) in DMF (5 ml) was added at rt triethylamine (0.17 ml, 1.2 mmol), HOBT (65 mg, 0.48 mmol) and HBTU (182 mg, 0.48 mmol). The mixture was stirred at rt for 1.5 h, then quenched with 1N HCl and extracted with EtOAc. The layers were separated. The organic layer was successively washed with water and brine, then dried over Na₂SO₄ and concentrated under reduced pressure. The residue was purified by flash chromatography with 30-60% EtOAc in hexane to afford the desired product (126 mg, 61% yield).

Preparation of 3-methyl-5-[(2-oxo-2,3-dihydro-1H-indol-4-ylmethyl)-carbamoyl]-thiophene-2-carboxylic acid methyl ester

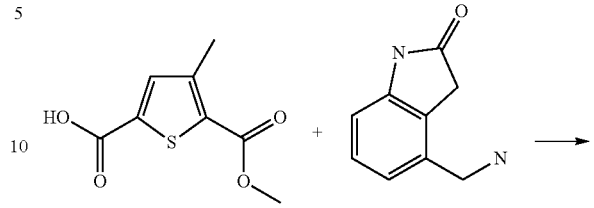

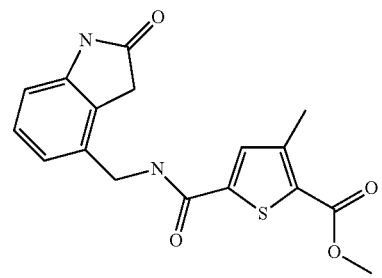

To a solution of 3-methyl-thiophene-2,5-dicarboxylic acid 2-methyl ester (200 mg, 1 mmol) and 4-aminomethyl-1,3-dihydro-indol-2-one (prepared as described in WO 2000021920) (298 mg, 1.5 mmol) in DMF (5 ml) was added at rt triethylamine (0.42 ml, 3 mmol), HOBT (162 mg, 1.2 mmol) and HBTU (455 mg, 1.2 mmol). The mixture was stirred at rt for 30 min, then quenched with 1NHCl and extracted with EtOAc. The layers were separated. The organic layer was successively washed with water and brine, then dried over Na₂SO₄ and concentrated under reduced pressure. The residue was purified by re-crystallization from hot methanol (161 mg, 46% yield).

Preparation of 3-methyl-5-[(2-oxo-2,3-dihydro-1H-indol-4-ylmethyl)-carbamoyl]-thiophene-2-carboxylic acid

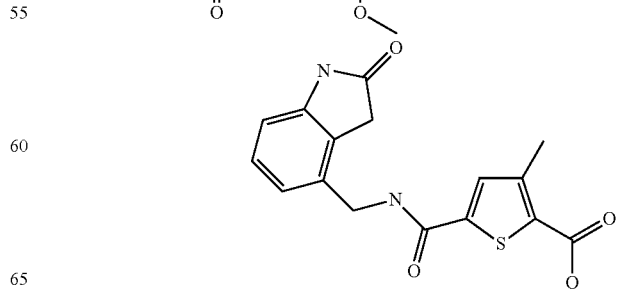

A solution of 3-methyl-5-[(2-oxo-2,3-dihydro-1H-indol-4-ylmethyl)-carbamoyl]-thiophene-2-carboxylic acid methyl ester (158 mg, 0.46 mmol) in THF/water (6 ml/3 ml) was treated with LiOH.H₂O (206 mg, 4.6 mmol) at rt for 1 h. The reaction mixture was quenched with 1N HCl and extracted with EtOAc. The layers were separated. The organic layer was successively washed with water and brine, then dried over Na₂SO₄ and concentrated under reduced pressure to afford the desired product (141 mg, 95% yield).

Preparation of (S)-3-tert-butoxycarbamoylamino-2-({3-methyl-5-[(2-oxo-2,3-dihydro-1H-indol-4-ylmethyl)-carbamoyl]-thiophene-2-carbonyl}-amino)-propionic acid methyl ester

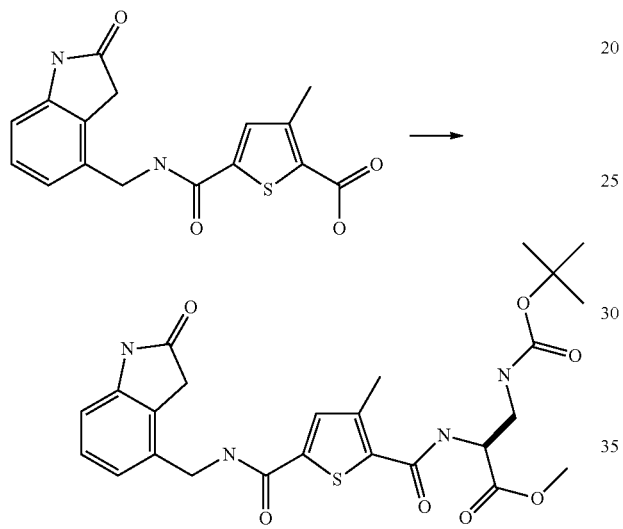

To a solution of 3-methyl-5-[(2-oxo-2,3-dihydro-1H-indol-4-ylmethyl)-carbamoyl]-thiophene-2-carboxylic acid (141 mg, 0.43 mmol) and H-DAP(Boc)OMe hydrochloride (163 mg, 0.64 mmol) in DMF (5 ml) was added at rt triethylamine (0.18 ml, 1.3 mmol), HOBT (69 mg, 0.51 mmol) and HBTU (194 mg, 0.51 mmol). The mixture was stirred at rt for 1.5 h, then quenched with 1NHCl and extracted with EtOAc. The layers were separated. The organic layer was successively washed with water and brine, then dried over Na₂SO₄ and concentrated under reduced pressure. The residue was purified by flash chromatography with 60-100% EtOAc in hexane to afford the desired product (94 mg, 42% yield).

Preparation of 5-[(1H-indazol-4-yilmethyl)-carbamoyl]-3-methyl-thiophene-2-carboxylic acid methyl ester

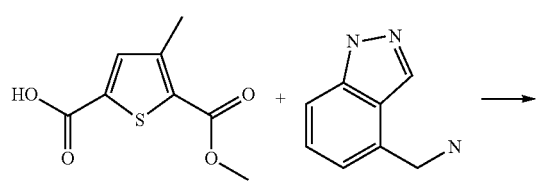

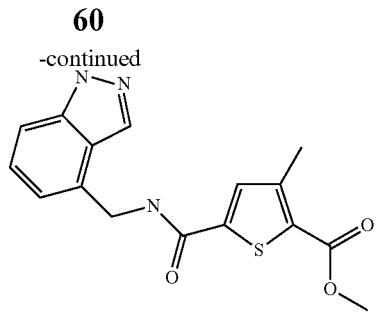

To a solution of 3-methyl-thiophene-2,5-dicarboxylic acid 2-methyl ester (89 mg, 0.45 mmol) and C-(1H-indazol-4-yl)-methylamine) (prepared as described in WO 2000021920) (98 mg, 0.67 mmol) in DMF (3 ml) was added at rt triethylamine (0.19 ml, 1.35 mmol), HOBT (73 mg, 0.54 mmol) and HBTU (205 mg, 0.54 mmol). The mixture was stirred at rt for 30 min, then quenched with 1NHCl and extracted with EtOAc. The layers were separated. The organic layer was successively washed with water and brine, then dried over Na₂SO₄ and concentrated under reduced pressure. The residue was purified by flash chromatography with 35-60% EtOAc in hexane to afford the desired product (72 mg, 49% yield).

Preparation of 5-[(1H-indazol-4-yilmethyl)-carbamoyl]-3-methyl-thiophene-2-carboxylic acid

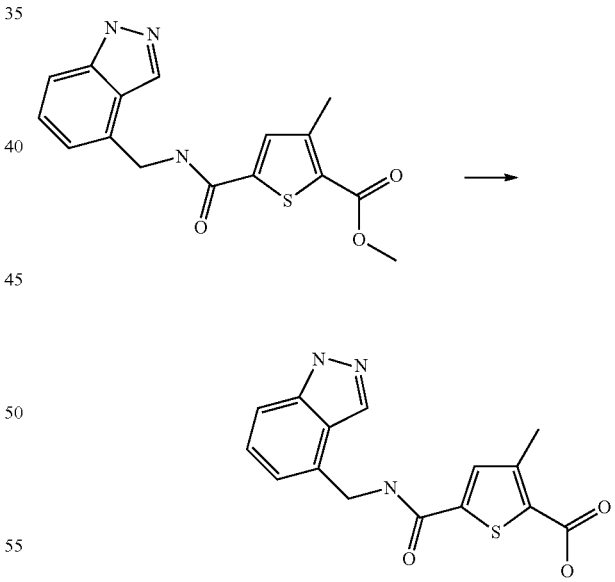

A solution of 5-[(1H-indazol-4-ylmethyl)-carbamoyl]-3-methyl-thiophene-2-carboxylic acid methyl ester (70 mg, 0.21 mmol) in THF/water (2 ml/1 ml) was treated with LiOH.H₂O (89 mg, 2.1 mmol) at rt overnight. The reaction mixture was quenched with 1N HCl and extracted with EtOAc. The layers were separated. The organic layer was successively washed with water and brine, then dried over Na₂SO₄ and concentrated under reduced pressure to afford the desired product (48 mg, 73% yield).

Preparation of (S)-3-tert-butoxycarbamoylamino-2-([5-[(1H-indazol-4-ylmethyl)-carbamoyl]-3-methyl-thiophene-2-carbonyl]-amino)-propionic acid methyl ester

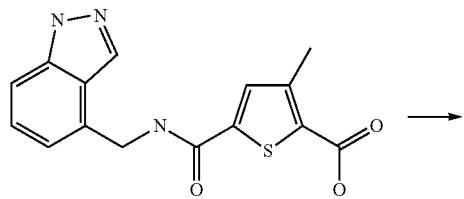

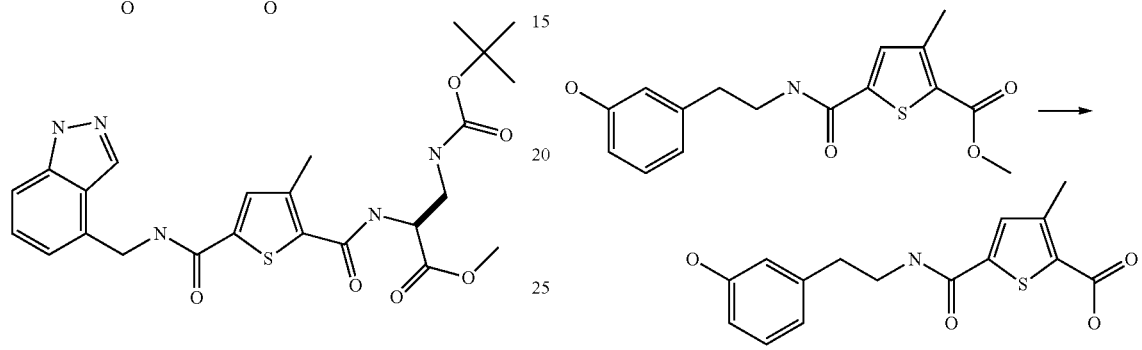

To a solution of 5-[(1H-indazol-4-yilmethyl)-carbamoyl]-3-methyl-thiophene-2-carboxylic acid (48 mg, 0.15 mmol) and H-DAP(Boc)OMe hydrochloride (58 mg, 0.23 mmol) in DMF (3 ml) was added at rt triethylamine (0.064 ml, 0.46 mmol), HOBT (25 mg, 0.18 mmol) and HBTU (69 mg, 0.18 mmol). The mixture was stirred at rt for 1.5 h, then quenched with 1NHCl and extracted with EtOAc. The layers were separated. The organic layer was successively washed with water and brine, then dried over Na₂SO₄ and concentrated under reduced pressure. The residue was purified by flash chromatography with 60-100% EtOAc in hexane to afford the desired product (59 mg, 77% yield).

Preparation of 5-[2-(3-hydroxy-phenyl)-ethyl-carbamoyl]-3-methyl-thiophene-2-carboxylic acid methyl ester

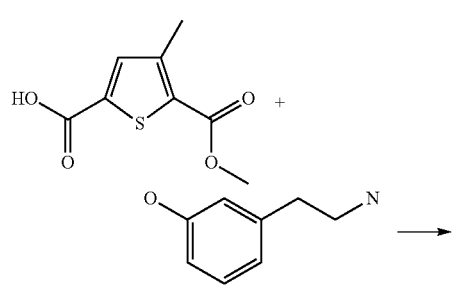

To a solution of 3-methyl-thiophene-2,5-dicarboxylic acid 2-methyl ester (0.1 g, 0.5 mmol) and 3-hydroxyphenethylamine hydrochloride (105 mg, 0.6 mmol) in DMF (5 ml) was added at rt triethylamine (0.21 ml, 1.5 mmol), HOBT (81 mg, 0.6 mmol) and HBTU (230 mg, 0.6 mmol). The mixture was stirred at rt for 1 h, then quenched with 1NHCl and extracted with EtOAc. The layers were separated. The organic layer was washed with brine, then dried over Na₂SO₄ and concentrated under reduced pressure. The residue was purified by flash chromatography with 15-65% EtOAc in hexane to afford the desired product (260 mg, 81% yield).

Preparation of 5-[2-(3-hydroxy-phenyl)-ethyl-carbamoyl]-3-methyl-thiophene-2-carboxylic acid

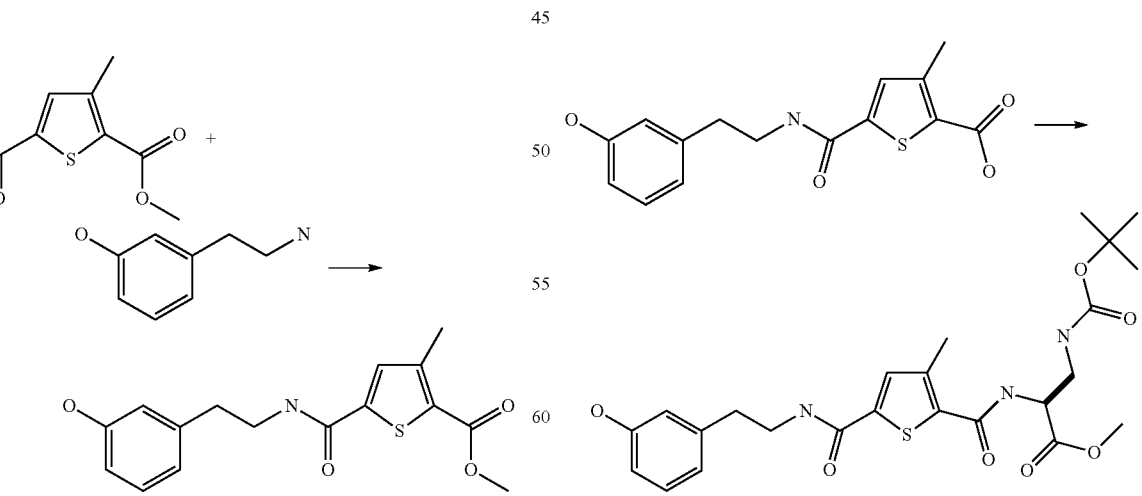

A solution of 5-[2-(3-hydroxy-phenyl)-ethyl-carbamoyl]-3-methyl-thiophene-2-carboxylic acid methyl ester (260 mg, 0.81 mmol) in THF/water (8 ml/4 ml) was treated with LiOH.H₂O (171 mg, 4.1 mmol) at 40° C. for 1.5 h. The reaction mixture was quenched with 1N HCl and extracted with EtOAc. The layers were separated. The organic layer was washed with brine, then dried over Na₂SO₄ and concentrated under reduced pressure to afford the desired product (172 mg, 70% yield).

Preparation of (S)-3-tert-butoxycarbamoylamino-2-([5-[2-(3-hydroxy-phenyl)-ethyl-carbamoyl]-3-methyl-thiophene-2-carbonyl]-amino)-propionic acid methyl ester To a solution of 5-[2-(3-hydroxy-phenyl)-ethyl-carbamoyl]-3-methyl-thiophene-2-carboxylic acid (172 mg, 0.56 mmol) and H-DAP(Boc)OMe hydrochloride (216 mg, 0.85 mmol) in DMF (5 ml) was added at rt triethylamine (0.24 ml, 1.7 mmol), HOBT (92 mg, 0.68 mmol) and HBTU (260 mg, 0.68 mmol). The mixture was stirred at rt for 1 h, then quenched with 1NHCl and extracted with EtOAc. The layers were separated. The organic layer was washed with brine, then dried over Na₂SO₄ and concentrated under reduced pressure. The residue was purified by flash chromatography with 50-100% EtOAc in hexane to afford the desired product (191 mg, 68% yield).

Preparation of 5-[1-(3-hydroxy-phenyl)-ethyl-carbamoyl]-3-methyl-thiophene-2-carboxylic acid methyl ester

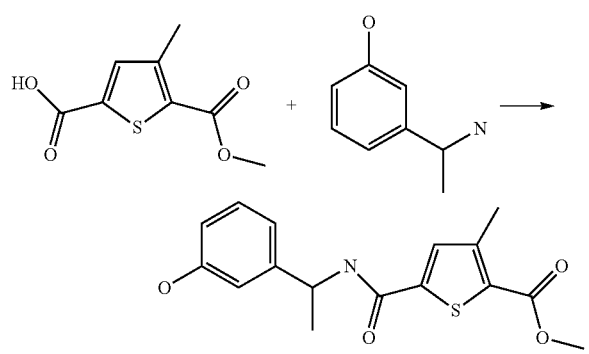

To a solution of 3-methyl-thiophene-2,5-dicarboxylic acid 2-methyl ester (0.1 g, 0.5 mmol) and 3-(1-amino-ethyl)-phenol (82 mg, 0.6 mmol) in DMF (4 ml) was added at rt triethylamine (0.1 ml, 0.75 mmol), HOBT (81 mg, 0.6 mmol) and HBTU (228 mg, 0.6 mmol). The mixture was stirred at rt for 30 min, then quenched with 1NHCl and extracted with EtOAc. The layers were separated. The organic layer was washed with brine, then dried over Na₂SO₄ and concentrated under reduced pressure. The residue was purified by flash chromatography with 30-70% EtOAc in hexane to afford the desired product (121 mg, 75% yield).

Preparation of 5-[1-(3-hydroxy-phenyl)-ethyl-carbamoyl]-3-methyl-thiophene-2-carboxylic acid

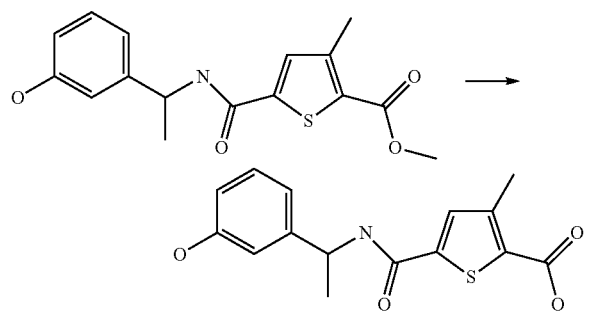

A solution of 5-[1-(3-hydroxy-phenyl)-ethyl-carbamoyl]-3-methyl-thiophene-2-carboxylic acid methyl ester (121 mg, 0.38 mmol) in THF/water (3 ml/1 ml) was treated with LiOH.H₂O (158 mg, 3.8 mmol) at rt overnight. The reaction mixture was quenched with 1N HCl and extracted with EtOAc. The layers were separated. The organic layer was washed with brine, then dried over Na₂SO₄ and concentrated under reduced pressure to afford the desired product (112 mg, 100% yield).

Preparation of (S)-3-tert-butoxycarbamoylamino-2-([5-[1-(3-hydroxy-phenyl)-ethylcarbamoyl]-3-methyl-thiophene-2-carbonyl]-amino)-propionic acid methyl ester

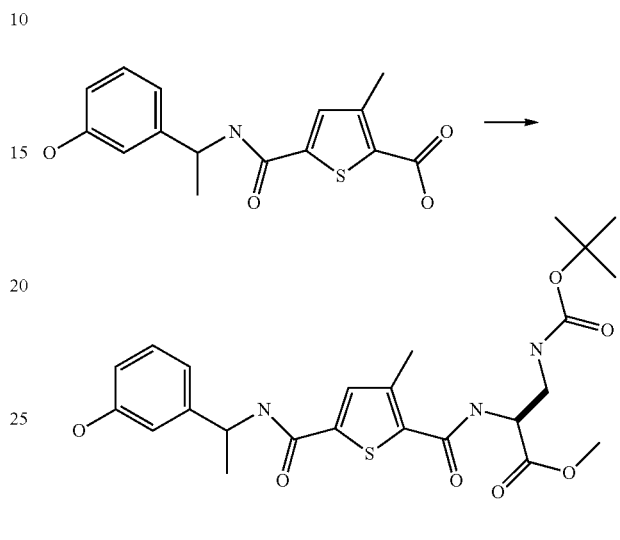

To a solution of 5-[1-(3-hydroxy-phenyl)-ethyl-carbamoyl]-3-methyl-thiophene-2-carboxylic acid (112 mg, 0.38 mmol) and H-DAP(Boc)OMe hydrochloride (145 mg, 0.57 mmol) in DMF (5 ml) was added at rt triethylamine (0.16 ml, 1.13 mmol), HOBT (92 mg, 0.68 mmol) and HBTU (258 mg, 0.68 mmol). The mixture was stirred at rt for 1.5 h, then quenched with 1NHCl and extracted with EtOAc. The layers were separated. The organic layer was washed with brine, then dried over Na₂SO₄ and concentrated under reduced pressure. The residue was purified by flash chromatography with 40-100% EtOAc in hexane to afford the desired product (180 mg, 97% yield).

Preparation of 5,5-Diethoxy-1,1,1-trifluoro-pent-3-yn-2-one

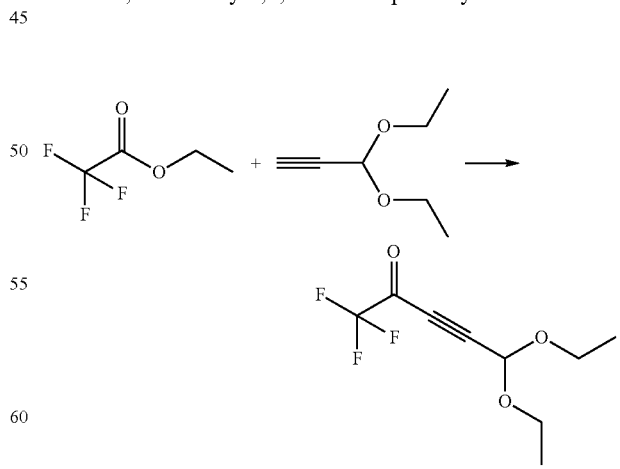

A mixture of 3,3-Diethoxy-propyne (0.98 g, 7.64 mmol) in THF (20 ml) was cooled to −78 C under Ar. A solution of n-BuLi (2.0M in cyclohexane, 4.2 ml, 8.40 mmol) was added. After 30 min., Trifluoroacetic acid ethyl ester (1.19 g, 8.40 mmol) was added. After 1 h, the reaction was quenched by dilution with 1N HCl, warmed to room temperature and extracted into EtOAc. The organic layer was washed with brine, dried over sodium sulfate, filtered and evaporated. The residue was purified by flash chromatography (0-40% EtOAc in Hexanes) to give product, 0.51 g (30%).

Preparation of 5-Diethoxymethyl-3-trifluoromethyl-thiophene-2-carboxylic acid methyl ester

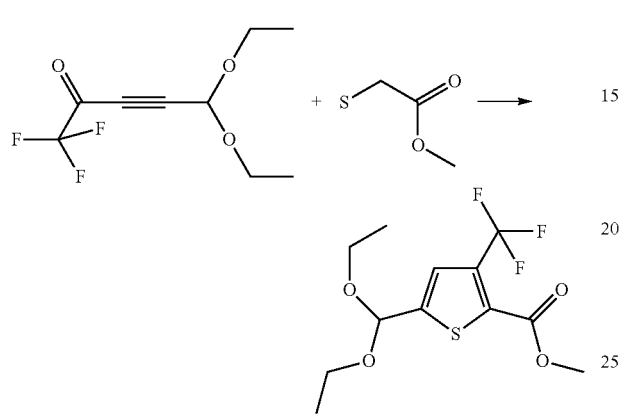

A solution of 5,5-Diethoxy-1,1,1-trifluoro-pent-3-yn-2-one (2.16 g, 9.64 mmol) in THF (30 ml) was cooled to 0° C. (ice bath). Methyl thioglycolate (0.88 ml, 9.64 mmol) was added in one portion and the mixture was stirred at 0° C. for 1.5 h. Methanol (6 ml) and Cs$_2$CO$_3$/MgSO$_4$ (2 g/4 g, pre-dried at 200° C. in vacuum) were added at 0° C. The mixture was stirred at 0° C. for 15 min and then at rt for 15 h. The reaction mixture was quenched by pouting into EtOAc. The organic layer was washed with brine, dried over Na$_2$SO$_4$ and concentrated under reduced pressure. The residue was purified by flash chromatography with 0-30% EtOAc in hexane to afford the desired product (1.90 g, 63% yield).

Preparation of 5-Formyl-3-trifluoromethyl-thiophene-2-carboxylic acid methyl ester

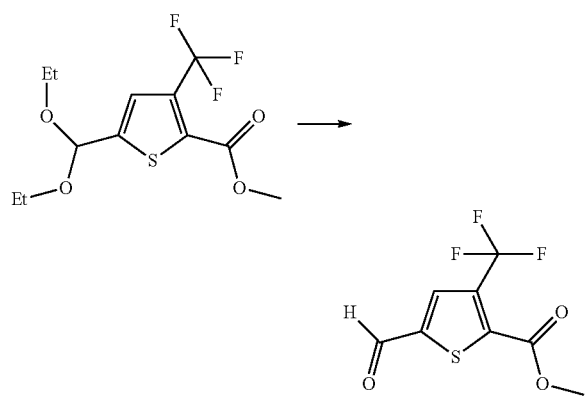

A solution of 5-Diethoxymethyl-3-trifluoromethyl-thiophene-2-carboxylic acid methyl ester (2.72 g, 8.71 mmol) in dioxane (20 ml) was cooled to 0° C. (ice bath). 88% formic acid (25 ml) was added in one portion and the mixture was stirred at 0° C. for 5 min and then at rt for 60 min The reaction mixture was quenched by pouring into EtOAc. The organic layer was washed with water, dried over Na$_2$SO$_4$ and concentrated under reduced pressure to afford the desired product (2.05 g, 99% yield).

Preparation of 3-Trifluoromethyl-thiophene-2,5-dicarboxylic acid 2-methyl ester

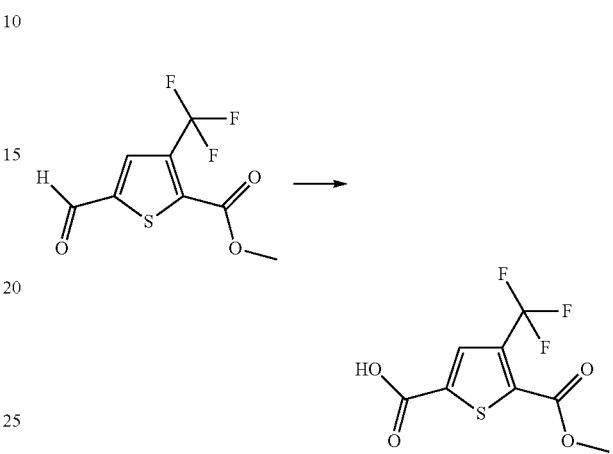

To a solution of 5-Formyl-3-trifluoromethyl-thiophene-2-carboxylic acid methyl ester (2.05 g, 8.61 mmol) in dioxane (40 ml) was added 2-methyl-2-butene (9 ml) and a solution of Na$_2$ClO$_2$ (2.34 g, 25.92 mmol) and NaH$_2$PO$_4$ (2.82 g) in water (9 ml). The mixture was stirred at rt for 1.5 h. The solution was saturated with sodium chloride, then successively extracted with EtOAc. The combined organic layers were dried over Na$_2$SO$_4$ and concentrated under reduced pressure to afford the desired product (2.61 g, 100% yield).

Preparation of 5-[(1H-Indol-4-ylmethyl)-carbamoyl]-3-trifluoromethyl-thiophene-2-carboxylic acid methyl ester

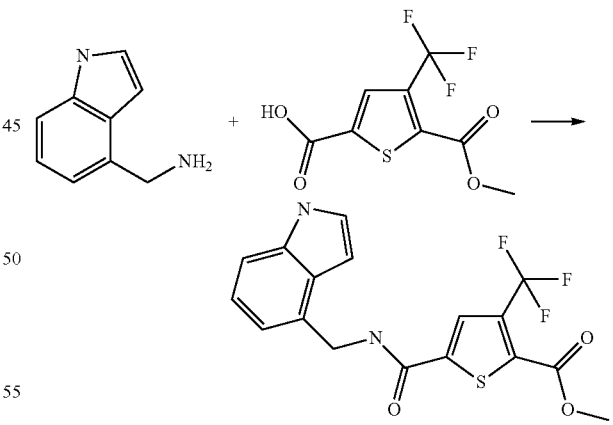

To a solution of 3-Trifluoromethyl-thiophene-2,5-dicarboxylic acid 2-methyl ester (570 mg, 2.24 mmol) in anhydrous DMF (10 mL) was added triethylamine (1.25 mL, 8.96 mmol), EDC (520 mg, 2.69 mmol), HOBT (360 mg, 2.69 mmol), and C-(1H-Indol-4-yl)-methylamine (390 mg, 2.69 mmol). The mixture was stirred at room temperature 3 h, then quenched by pouring into EtOAc. The organic layer was washed with brine, dried over Na$_2$SO$_4$ and concentrated under reduced pressure. The residue was purified by flash chromatography with 0-70% EtOAc in hexane to afford the desired product (0.27 g, 31% yield).

Preparation of 5-[(1H-Indol-4-ylmethyl)-carbamoyl]-3-trifluoromethyl-thiophene-2-carboxylic acid

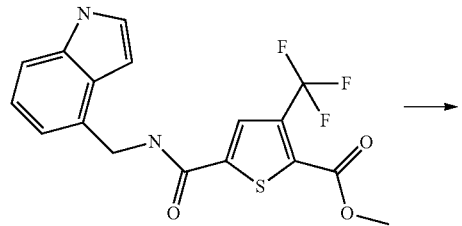

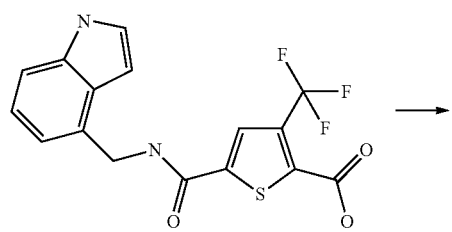

A mixture of 5-[(1H-Indol-4-ylmethyl)-carbamoyl]-3-trifluoromethyl-thiophene-2-carboxylic acid methyl ester (270 mg, 0.33 mmol), lithium hydroxide monohydrate (300, mg, 7.10 mmol), THF (5 mL) and water (5 mL) was stirred 15 h, acidified with 1N HCl and extracted with EtOAc (×3). The organic extracts were combined, washed with brine, dried over sodium sulfate, filtered and evaporated to give the title compound, 260 mg (99%). MS m/e 369.0 (M+H⁺).

Preparation of (S)-3-tert-Butoxycarbonylamino-2-({5-[(1H-indol-4-ylmethyl)-carbamoyl]-3-trifluoromethyl-thiophene-2-carbonyl}-amino)-propionic acid methyl ester

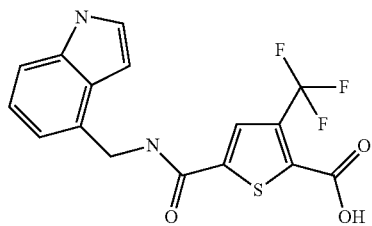

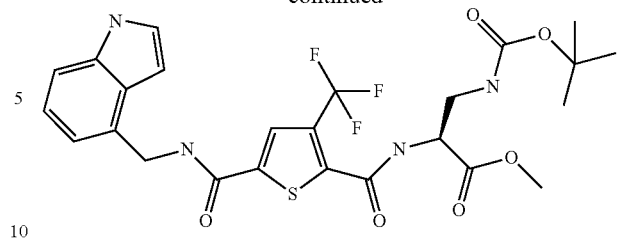

To a solution of 5-[(1H-Indol-4-ylmethyl)-carbamoyl]-3-trifluoromethyl-thiophene-2-carboxylic acid (0.26 g, 0.71 mmol) in anhydrous DMF (10 mL) was added triethylamine (0.3 mL, 2.13 mmol), HBTU (0.32 g, 0.85 mmol), HOBT (0.11 g, 0.85 mmol), and H-DAP(Boc)OMe hydrochloride (0.27 g, 1.06 mmol). The mixture was stirred at room temperature 1.5 h, treated with EtOAc (50 mL), washed with brine, dried over sodium sulfate, filtered and evaporated. The solid residue was purified by column (0-80% EtOAc in hexane) to give 0.278 g (69%) off-white solid product. MS m/e 567.0 (M+H⁺).

Preparation of (S)-3-Amino-2-({5-[(1H-indol-4-ylmethyl)-carbamoyl]-3-trifluoromethyl-thiophene-2-carbonyl}-amino)-propionic acid methyl ester trifluoro-acetic acid salt

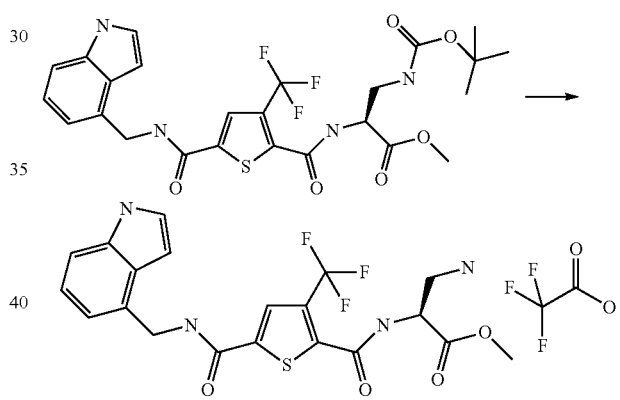

To a solution of (S)-3-tert-Butoxycarbonylamino-2-({5-[(1H-indol-4-ylmethyl)-carbamoyl]-3-trifluoromethyl-thiophene-2-carbonyl}-amino)-propionic acid methyl ester (0.278 g, 0.49 mmol) in DCM (5 mL) was added TFA (3.0 mL). The mixture was stirred at room temperature 1 h and evaporated. Isolate 0.32 g of crude product which was used without further purification.

Preparation of (S)-2-([5-[(1H-Indol-4-ylmethyl)-carbamoyl]-3-trifluoromethyl-thiophene-2-carbonyl]-amino)-3-[(thiophene-2-carbonyl)-amino]-propionic acid methyl ester

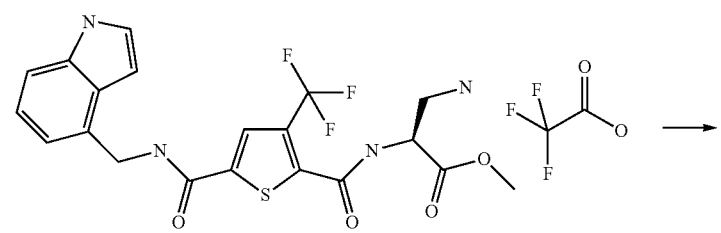

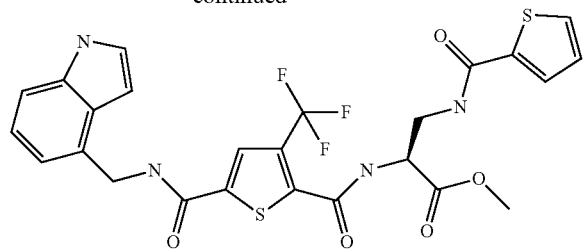

To a solution of (S)-3-Amino-2-({5-[(1H-indol-4-ylmethyl)-carbamoyl]-3-trifluoromethyl-thiophene-2-carbonyl}-amino)-propionic acid methyl ester trifluoro-acetic acid salt (0.32 g, 0.49 mmol) in anhydrous DMF (10 mL) was added triethylamine (0.20 mL, 1.47 mmol), HBTU (0.28 g, 0.74 mmol), HOBT (0.079 g, 0.59 mmol), and 2-Thiophenecarboxylic acid (0.069 g, 0.54 mmol). The mixture was stirred at room temperature 2 h, treated with EtOAc (100 mL), washed with brine, dried over sodium sulfate, filtered and evaporated. The solid residue was purified by column (0-80% EtOAc in hexane) to give 0.172 g (61%) colorless oil product. MS m/e 579.0 (M+H$^+$).

Preparation of 5-[3-(tert-Butyl-dimethyl-silanyloxy)-benzylcarbamoyl]-3-trifluoromethyl-thiophene-2-carboxylic acid methyl ester

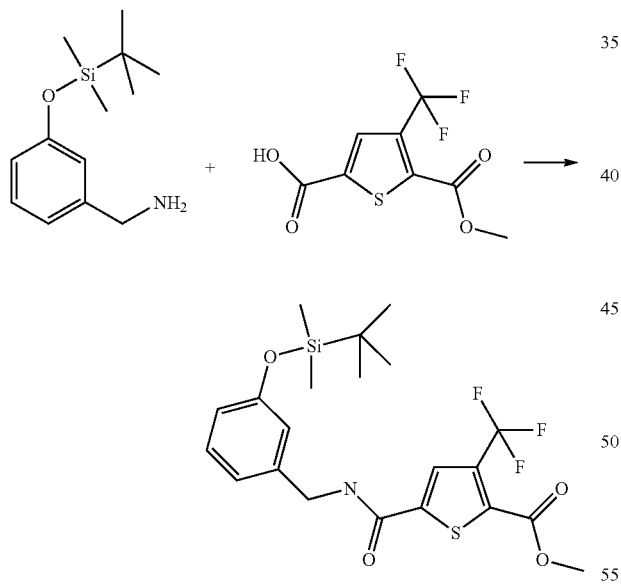

To a solution of 3-Trifluoromethyl-thiophene-2,5-dicarboxylic acid 2-methyl ester (560 mg, 2.20 mmol) in anhydrous DMF (10 mL) was added triethylamine (0.92 mL, 6.6 mmol), HBTU (1.0 g, 2.64 mmol), HOBT (360 mg, 2.64 mmol), and 3-(tert-Butyl-dimethyl-silanyloxy)-benzylamine (630 mg, 2.64 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-40% EtOAc in hexane to afford the desired product (0.21 g, 20% yield).

Preparation of 5-(3-Hydroxy-benzylcarbamoyl)-3-trifluoromethyl-thiophene-2-carboxylic acid

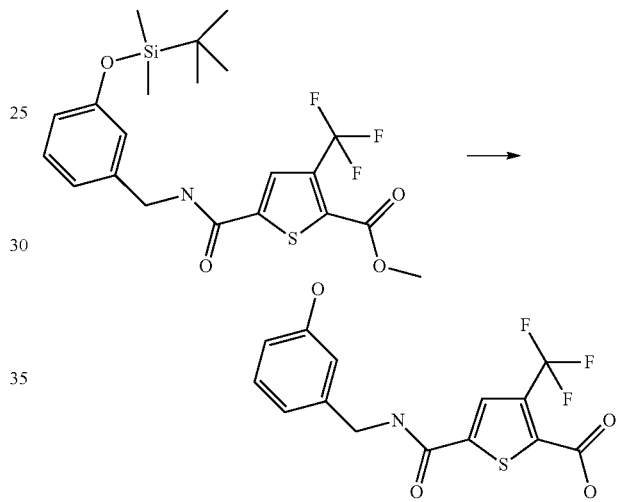

A mixture of 5-[3-(tert-Butyl-dimethyl-silanyloxy)-benzylcarbamoyl]-3-trifluoromethyl-thiophene-2-carboxylic acid methyl ester (210 mg, 0.44 mmol), lithium hydroxide monohydrate (370, mg, 8.87 mmol), THF (4 mL) and water (4 mL) was stirred over weekend, acidified with 1N HCl and extracted with EtOAc (×3). The organic extracts were combined, washed with brine, dried over sodium sulfate, filtered and evaporated to give the title compound, 120 mg (79%). MS m/e 346.0 (M+H$^+$).

Preparation of (S)-3-tert-Butoxycarbonylamino-2-{[5-(3-hydroxy-benzylcarbamoyl)-3-trifluoromethyl-thiophene-2-carbonyl]-amino}-propionic acid methyl ester

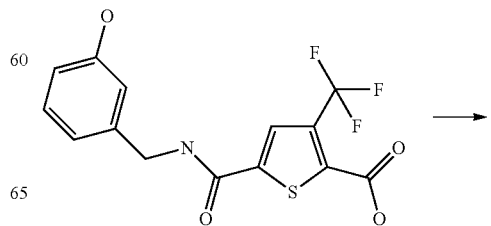

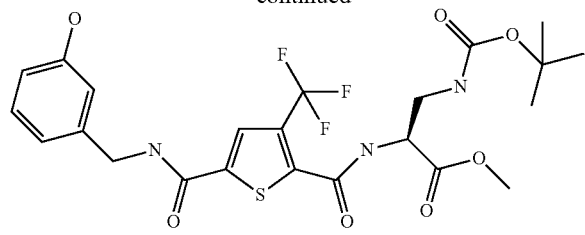

To a solution of 5-(3-Hydroxy-benzylcarbamoyl)-3-trifluoromethyl-thiophene-2-carboxylic acid (0.12 g, 0.35 mmol) in anhydrous DMF (10 mL) was added triethylamine (0.15 mL, 1.05 mmol), HBTU (0.16 g, 0.42 mmol), HOBT (0.057 g, 0.42 mmol), and H-DAP(Boc)OMe hydrochloride (0.13 g, 0.53 mmol). The mixture was stirred at room temperature 2 h, treated with EtOAc (75 mL), washed with brine, dried over sodium sulfate, filtered and evaporated. The solid residue was purified by column (0-60% EtOAc in hexane) to give 0.190 g (99%) white foam.

Preparation (S)-3-Amino-2-{[5-(3-hydroxy-benzylcarbamoyl)-3-trifluoromethyl-thiophene-2-carbonyl]-amino}-propionic acid methyl ester trifluoro-acetic acid salt

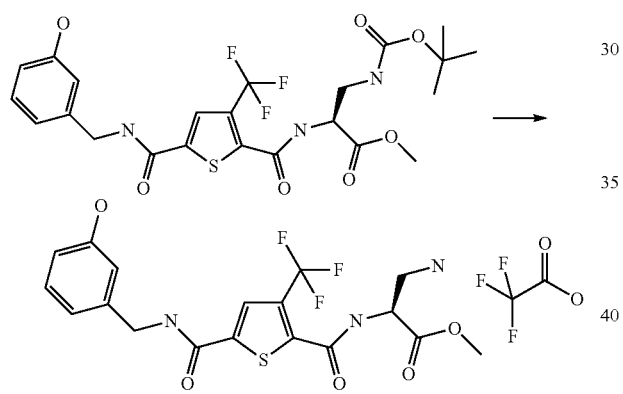

To a solution of (S)-3-tert-Butoxycarbonylamino-2-{[5-(3-hydroxy-benzylcarbamoyl)-3-trifluoromethyl-thiophene-2-carbonyl]-amino}-propionic acid methyl ester (0.19 g, 0.34 mmol) in DCM (6 mL) was added TFA (3.0 mL). The mixture was stirred at room temperature 1 h and evaporated. Isolate 0.23 g of crude product which was used without further purification.

Preparation of (S)-2-{[5-(3-Hydroxy-benzylcarbamoyl)-3-trifluoromethyl-thiophene-2-carbonyl]-amino}-3-[(thiophene-2-carbonyl)-amino]-propionic acid methyl ester

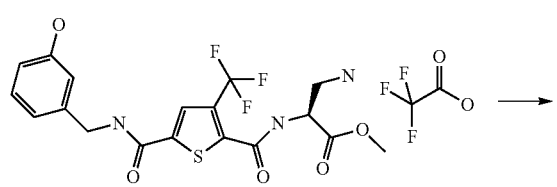

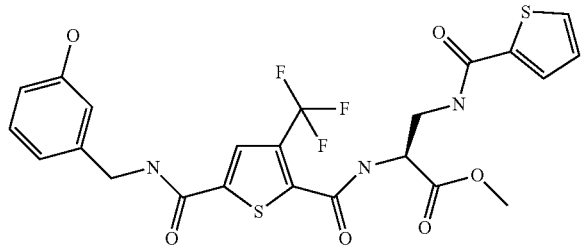

To a solution of S)-3-Amino-2-{[5-(3-hydroxy-benzylcarbamoyl)-3-trifluoromethylthiophene-2-carbonyl]-amino}-propionic acid methyl ester trifluoro-acetic acid salt (0.34 mmol) in anhydrous DMF (5 mL) was added triethylamine (0.14 mL, 1.02 mmol), HBTU (0.19 g, 0.51 mmol), HOBT (0.055 g, 0.41 mmol), and 2-Thiophenecarboxylic acid (0.048 g, 0.37 mmol). The mixture was stirred at room temperature 1.5 h, treated with EtOAc (50 mL), washed with brine, dried over sodium sulfate, filtered and evaporated. The solid residue was purified by column (50-80% EtOAc in hexane) to give 0.040 g (61%) colorless oil product. MS m/e 556.0 (M+H$^+$).

Preparation of 4,4-Diethoxy-1-phenyl-but-2-yn-1-ol

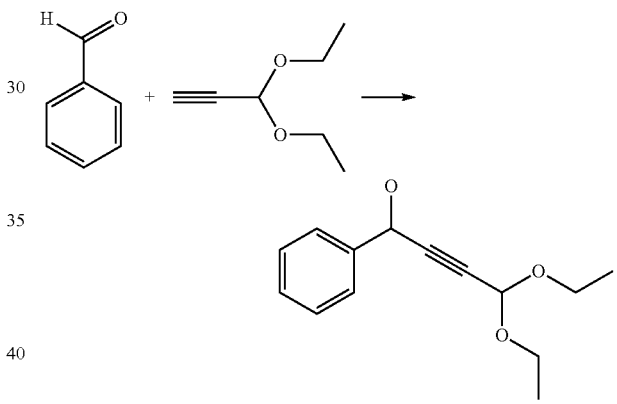

A mixture of 3,3-Diethoxy-propyne (4.55 g, 35.5 mmol) in THF (90 mL) was cooled to −78 C under N2. A solution of n-BuLi (2.0M in cyclohexane, 24 mL, 46 mmol) was added. After 30 min., Benzaldehyde (4.90 g, 46 mmol) was added. After 15 h, the reaction was quenched by dilution with 1N HCl, warmed to room temperature and extracted into EtOAc. The organic layer was washed with brine, dried over sodium sulfate, filtered and evaporated to give product, 9.46 g (88%).

Preparation of 4,4-Diethoxy-1-phenyl-but-2-yn-1-one

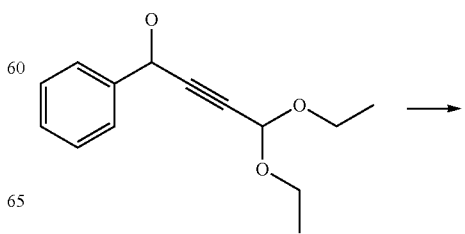

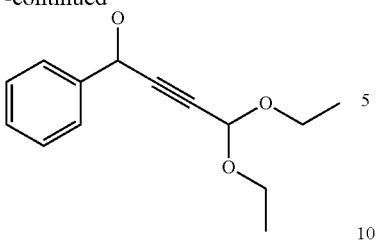

4,4-Diethoxy-1-phenyl-but-2-yn-1-ol (9.46 g, 40.38 mmol) was dissolved in dichloromethane (200 ml) and treated with activated MnO$_2$ (100 g) at rt for 15 h. The reaction mixture was filtered through a plug of celite and Na$_2$SO$_4$. The filtrated was concentrated under reduced pressure to afford the desired ketone (7.85 g, 84% yield).

Preparation of
5-Diethoxymethyl-3-phenyl-thiophene-2-carboxylic acid methyl ester

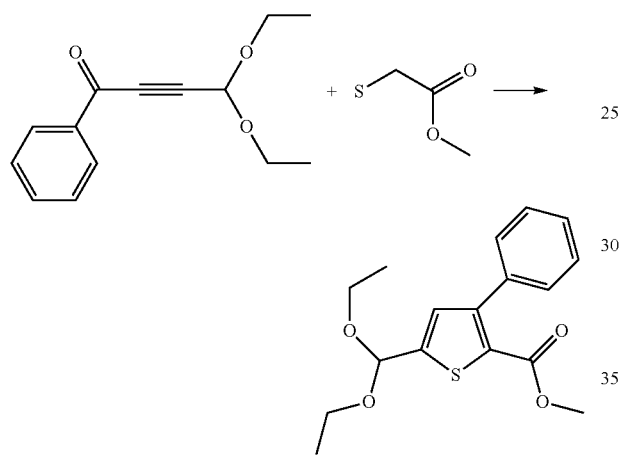

A solution of 4,4-Diethoxy-1-phenyl-but-2-yn-1-one (5.7 g, 24.54 mmol) in THF (75 ml) was cooled to 0° C. (ice bath). Methyl thioglycolate (2.2 ml, 24.54 mmol) was added in one portion and the mixture was stirred at 0° C. for 2 h. Methanol (25 ml) and Cs$_2$CO$_3$/MgSO$_4$ (8 g/16 g, pre-dried at 200° C. in vacuum) were added at 0° C. The mixture was stirred at 0° C. for 15 min and then at rt for 15 h. The reaction mixture was quenched by pouting into EtOAc. The organic layer was washed with brine, dried over Na$_2$SO$_4$ and concentrated under reduced pressure. The residue was purified by flash chromatography with 0-40% EtOAc in hexane to afford the desired product (5.07 g, 64% yield).

Preparation of
5-Formyl-3-phenyl-thiophene-2-carboxylic acid methyl ester

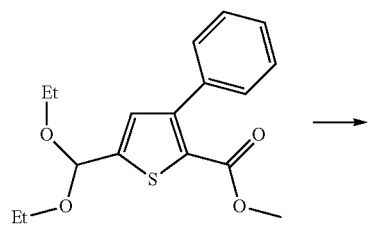

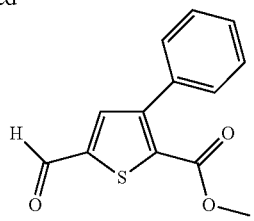

A solution of 5-Diethoxymethyl-3-phenyl-thiophene-2-carboxylic acid methyl ester (5.07 g, 15.82 mmol) in dioxane (25 ml) was cooled to 0° C. (ice bath). 95% formic acid (50 ml) was added dropwise and the mixture was stirred at 0° C. for 30 min and then at rt for 60 min. The reaction mixture was quenched by pouring into EtOAc. The organic layer was washed with water, dried over Na$_2$SO$_4$ and concentrated under reduced pressure to afford the desired product (3.50 g, 90% yield).

Preparation of 3-Phenyl-thiophene-2,5-dicarboxylic acid 2-methyl ester

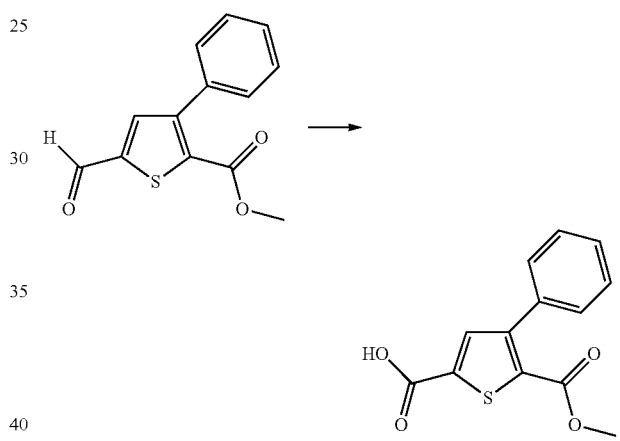

To a solution of 5-phenyl-thiophene-2-carboxylic acid methyl ester (3.50 g, 14.21 mmol) in dioxane (60 ml) was added 2-methyl-2-butene (15 ml) and a solution of Na$_2$ClO$_2$ (3.86 g, 42.63 mmol) and NaH$_2$PO$_4$ (4.7 g) in water (15 ml). The mixture was stirred at rt for 2 h. The solution was saturated with sodium chloride, then successively extracted with EtOAc. The combined organic layers were dried over Na$_2$SO$_4$ and concentrated under reduced pressure to afford the desired product (3.71 g, 99% yield).

Preparation of 5-[3-(tert-Butyl-dimethyl-silanyloxy)-benzylcarbamoyl]-3-phenyl-thiophene-2-carboxylic acid methyl ester

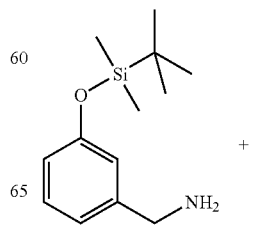

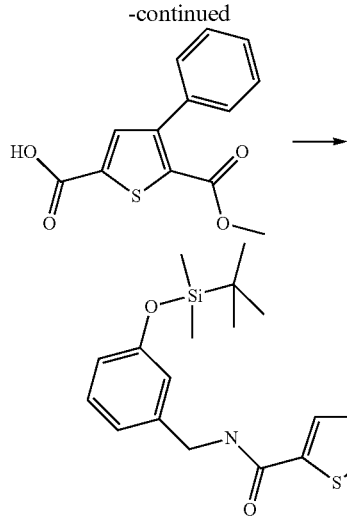

To a solution of 3-Phenyl-thiophene-2,5-dicarboxylic acid 2-methyl ester (500 mg, 1.91 mmol) in anhydrous DMF (10 mL) was added triethylamine (0.53 mL, 3.82 mmol), HBTU (1.45 g, 3.82 mmol), HOBT (390 mg, 3.82 mmol), and 3-(tert-Butyl-dimethyl-silanyloxy)-benzylamine (540 mg, 2.29 mmol). The mixture was stirred at room temperature 1 h, then quenched by pouring into EtOAc. The organic layer was washed with brine, dried over $Na_2SO_4$ and concentrated under reduced pressure. The residue was purified by flash chromatography with 0-30% EtOAc in hexane to afford the desired product (0.36 g, 39% yield).

Preparation of 5-(3-Hydroxy-benzylcarbamoyl)-3-phenyl-thiophene-2-carboxylic acid

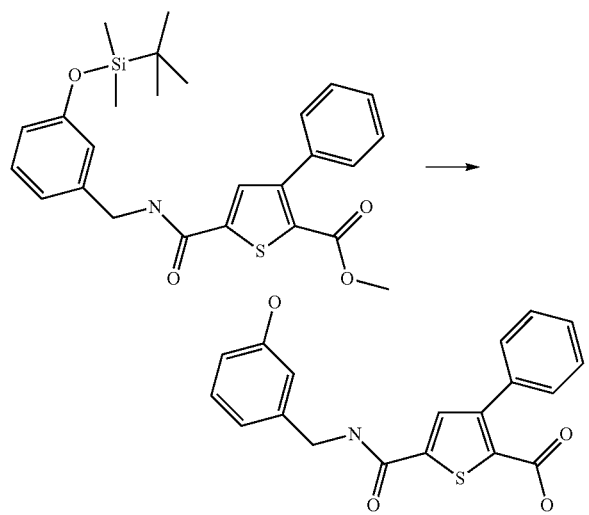

A mixture of 5-[3-(tert-Butyl-dimethyl-silanyloxy)-benzylcarbamoyl]-3-phenyl-thiophene-2-carboxylic acid methyl ester (180 mg, 0.37 mmol), lithium hydroxide monohydrate (310, mg, 7.47 mmol), THF (4 mL) and water (2 mL) was stirred 15 h, acidified with 1N HCl and extracted with EtOAc (×3). The organic extracts were combined, washed with brine, dried over sodium sulfate, filtered and evaporated to give the title compound, 140 mg (100%). MS m/e 354.0 $(M+H^+)$.

Preparation of (S)-3-tert-Butoxycarbonylamino-2-{[5-(3-hydroxy-benzylcarbamoyl)-3-phenyl-thiophene-2-carbonyl]-amino}-propionic acid methyl ester

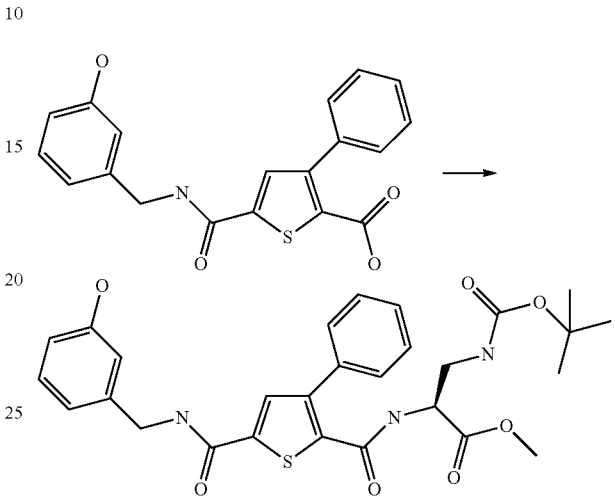

To a solution of 5-(3-Hydroxy-benzylcarbamoyl)-3-phenyl-thiophene-2-carboxylic acid (0.14 g, 0.40 mmol) in anhydrous DMF (10 mL) was added triethylamine (0.17 mL, 1.20 mmol), HBTU (0.18 g, 0.48 mmol), HOBT (0.065 g, 0.48 mmol), and H-DAP(Boc)OMe hydrochloride (0.15 g, 0.60 mmol). The mixture was stirred at room temperature 15 h, treated with EtOAc (100 mL), washed with brine, dried over sodium sulfate, filtered and evaporated. The solid residue was purified by column (0-60% EtOAc in hexane) to give 0.148 g (72%) white foam.

Preparation of (S)-3-Amino-2-{[5-(3-hydroxy-benzylcarbamoyl)-3-phenyl-thiophene-2-carbonyl]-amino}-propionic acid methyl ester trifluoro-acetic acid salt

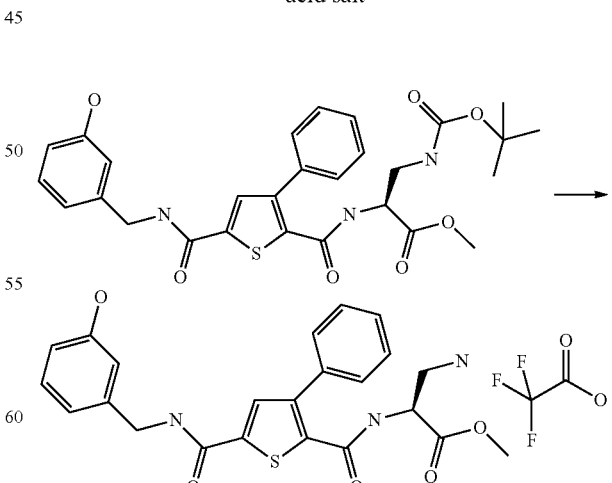

To a solution of (S)-3-tert-Butoxycarbonylamino-2-{[5-(3-hydroxy-benzylcarbamoyl)-3-phenyl-thiophene-2-carbonyl]-amino}-propionic acid methyl ester (0.148 g, 0.27 mmol) in DCM (5 mL) was added TFA (2.0 mL). The mixture was stirred at room temperature 1 h and evaporated. Isolate 0.23 g of crude product which was used without further purification.

Preparation of (S)-2-{[5-(3-Hydroxy-benzylcarbamoyl)-3-phenyl-thiophene-2-carbonyl]-amino}-3-[(thiophene-2-carbonyl)-amino]-propionic acid methyl ester

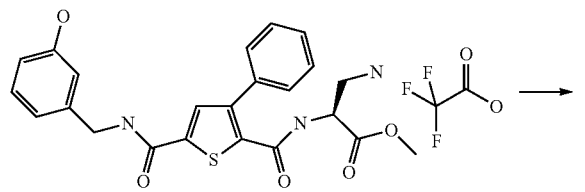

To a solution of (S)-3-Amino-2-{[5-(3-hydroxy-benzylcarbamoyl)-3-phenyl-thiophene-2-carbonyl]-amino}-propionic acid methyl ester trifluoro-acetic acid salt (0.27 mmol) in anhydrous DMF (5 mL) was added triethylamine (0.1 mL, 0.81 mmol), HBTU (0.15 g, 0.40 mmol), HOBT (0.044 g, 0.32 mmol), and 2-Thiophenecarboxylic acid (0.038 g, 0.30 mmol). The mixture was stirred at room temperature 1.25 h, treated with EtOAc (50 mL), washed with brine, dried over sodium sulfate, filtered and evaporated. The solid residue was purified by column (50-80% EtOAc in hexane) to give 0.040 g (26%) colorless oil product. MS m/e 564.0 (M+H$^+$).

Preparation of 3-Chloro-5-methyl-thiophene-2-carboxylic acid methyl ester

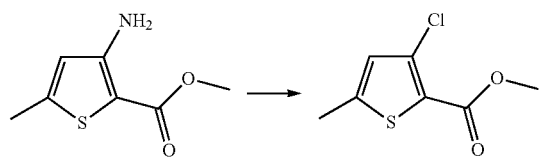

A mixture of 3-Amino-5-methyl-thiophene-2-carboxylic acid methyl ester (5.0 g, 29.2 mmol) in 6N HCl (25 ml) was cooled to 0° C. (ice bath). A solution of sodium nitrite (2.01 g, 29.2 mmol) in water (5 ml) was added dropwise and the mixture was stirred at 0° C. for 60 min This mixture was then added to a solution of copper(I)chloride (2.89 g, 29.2 mmol) in conc. HCl (25 ml) at 0° C. The reaction mixture was stirred at room temperature then warmed to 65° C. until gas evolution had ceased. The reaction mixture was diluted with water and extracted with EtOAc (2×150 mL), washed with water, brine, dried over sodium sulfate, filtered and evaporated. The residue was purified by column (0-30% EtOAc in hexane) to give 4.4 g (79%) yellow oil product.

Preparation of 5-Bromomethyl-3-chloro-thiophene-2-carboxylic acid methyl ester

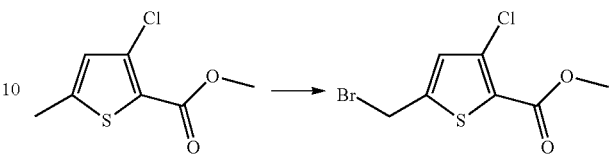

A mixture of 3-Chloro-5-methyl-thiophene-2-carboxylic acid methyl ester (4.4 g, 23.1 mmol), NBS (5.1 g, 28.85 mmol), and ACHN in CCl4 (40 ml) was refluxed in a pressure tube over the weekend. The reaction mixture was cooled and evaporated. The residue was purified by column (0-5% EtOAc in hexane) to give 3.8 g (61%) yellow solid product.

Preparation of 3-Chloro-5-hydroxymethyl-thiophene-2-carboxylic acid methyl ester

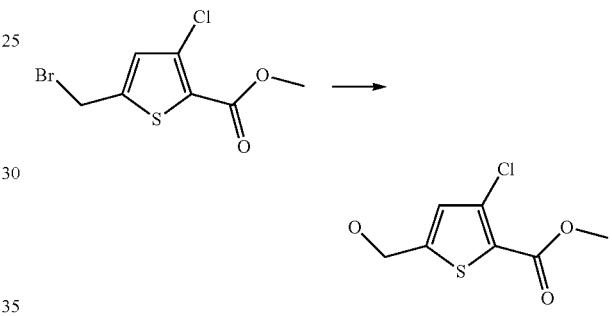

A mixture of 5-Bromomethyl-3-chloro-thiophene-2-carboxylic acid methyl ester (3.8 g, 14.1 mmol) and NaHCO3 (20 g, 238 mmol) in DMSO (100 ml) was heated at 115° C. for 4 h. The reaction mixture was cooled. The reaction mixture was diluted with water and extracted with DCM (3×100 mL), washed with brine, dried over sodium sulfate, filtered and evaporated. The residue was purified by column (0-30% EtOAc in hexane) to give 1.30 g (45%) product.

Preparation of 3-Chloro-thiophene-2,5-dicarboxylic acid 2-methyl ester

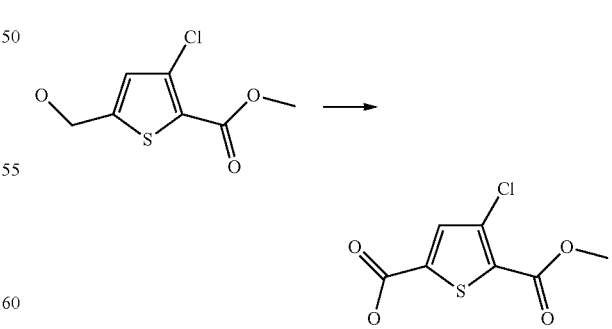

A mixture of 3-chloro-5-hydroxymethyl-thiophene-2-carboxylic acid methyl ester (1.3 g, 6.29 mmol) and Periodic Acid (3.15 g, 13.84 mmol) in MeCN (40 ml) was stirred for 30 min. A solution of PCC (0.027 g, 0.13 mmol) in MeCN (2 ml) was added. After 5 h, the reaction mixture was diluted with EtOAc (250 ml), washed with sodium sulfite, brine, dried over sodium sulfate, filtered and evaporated. Isolate 1.20 g (86%) of yellow solid product.

Preparation of 5-[3-(tert-Butyl-dimethyl-silanyloxy)-benzylcarbamoyl]-3-chloro-thiophene-2-carboxylic acid methyl ester

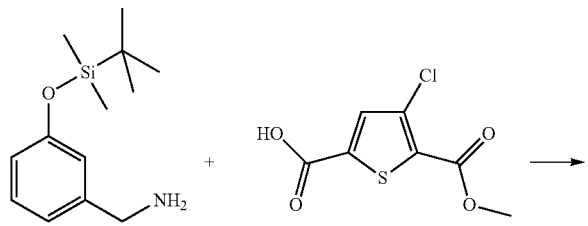

To a solution of 3-Chloro-thiophene-2,5-dicarboxylic acid 2-methyl ester (500 mg, 2.27 mmol) in anhydrous DMF (10 mL) was added triethylamine (1.0 mL, 6.81 mmol), HBTU (1.03 g, 2.72 mmol), HOBT (370 mg, 2.72 mmol), and 3-(tert-Butyl-dimethyl-silanyloxy)-benzylamine (650 mg, 2.72 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-30% EtOAc in hexane to afford the desired product (0.26 g, 26% yield).

Preparation of 3-Chloro-5-(3-hydroxy-benzylcarbamoyl)-thiophene-2-carboxylic acid

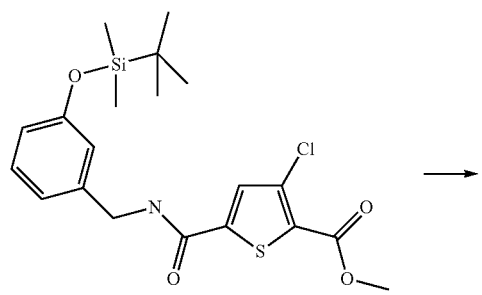

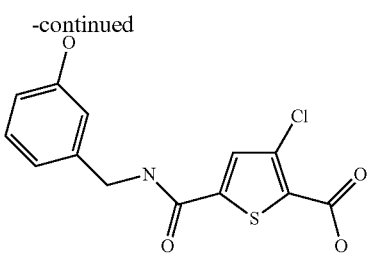

A mixture of 5-[3-(tert-Butyl-dimethyl-silanyloxy)-benzylcarbamoyl]-3-chloro-thiophene-2-carboxylic acid methyl ester (260 mg, 0.59 mmol), lithium hydroxide monohydrate (500, mg, 11.82 mmol), THF (5 mL) and water (5 mL) was stirred 15 h, acidified with 1N HCl and extracted with EtOAc (×3). The organic extracts were combined, washed with brine, dried over sodium sulfate, filtered and evaporated to give the title compound, 230 mg (100%). MS m/e 311.9 (M+H$^+$).

Preparation of (S)-3-tert-Butoxycarbonylamino-2-{[3-chloro-5-(3-hydroxy-benzylcarbamoyl)-thiophene-2-carbonyl]-amino}-propionic acid methyl ester

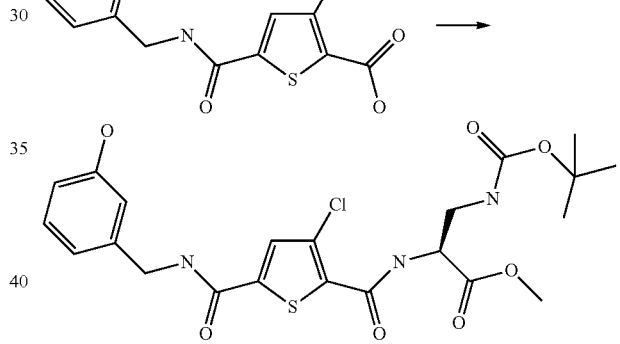

To a solution of 3-Chloro-5-(3-hydroxy-benzylcarbamoyl)-thiophene-2-carboxylic acid (0.23 g, 0.59 mmol) in anhydrous DMF (10 mL) was added triethylamine (0.25 mL, 1.77 mmol), HBTU (0.26 g, 0.71 mmol), HOBT (0.096 g, 0.71 mmol), and H-DAP(Boc)OMe hydrochloride (0.23 g, 0.89 mmol). The mixture was stirred at room temperature 2 h, treated with EtOAc (100 mL), washed with brine, dried over sodium sulfate, filtered and evaporated. The solid residue was purified by column (30-80% EtOAc in hexane) to give 0.31 g (100%) yellow oil.

Preparation of (S)-3-Amino-2-{[3-chloro-5-(3-hydroxy-benzylcarbamoyl)-thiophene-2-carbonyl]-amino}-propionic acid methylester trifluoro-acetic acid salt

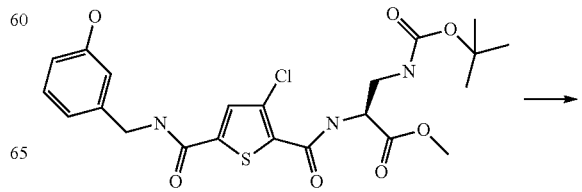

-continued

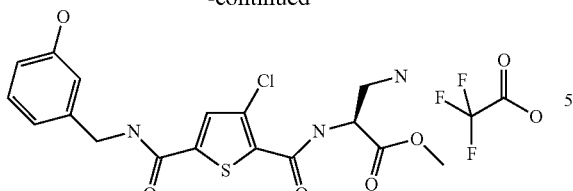

To a solution of (S)-3-tert-Butoxycarbonylamino-2-{[3-chloro-5-(3-hydroxy-benzylcarbamoyl)-thiophene-2-carbonyl]-amino}-propionic acid methyl ester (0.30 g, 0.59 mmol) in DCM (10 mL) was added TFA (3 mL). The mixture was stirred at room temperature 1 h and evaporated. Isolate 0.34 g of crude product which was used without further purification.

Preparation of (S)-2-{[3-Chloro-5-(3-hydroxy-benzylcarbamoyl)-thiophene-2-carbonyl]-amino}-3-[(thiophene-2-carbonyl)-amino]-propionic acid methyl ester

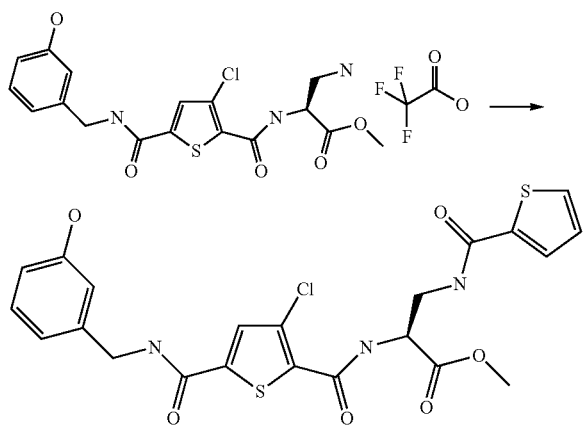

To a solution of (S)-3-Amino-2-{[3-chloro-5-(3-hydroxy-benzylcarbamoyl)-thiophene-2-carbonyl]-amino}-propionic acid methylester trifluoro-acetic acid salt (0.59 mmol) in anhydrous DMF (5 mL) was added triethylamine (0.2 mL, 1.18 mmol), DEPBT (0.35 g, 1.18 mmol), and 2-Thiophenecarboxylic acid (0.083 g, 0.65 mmol). The mixture was stirred at room temperature 15 h, treated with EtOAc (100 mL), washed with brine, dried over sodium sulfate, filtered and evaporated. The solid residue was purified by column (0-100% EtOAc in hexane) to give 0.15 g (49%) white foam. MS m/e 522.0 (M+H$^+$).

Preparation of 5-[(2-oxo-2,3-dihydro-1H-indol-4-ylmethyl)-carbamoyl]-3-trifluoromethyl-thiophene-2-carboxylic acid methyl ester

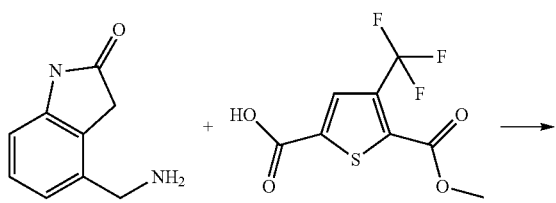

-continued

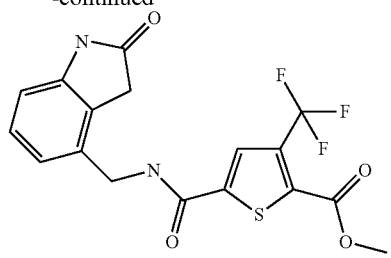

To a solution of 3-Trifluoromethyl-thiophene-2,5-dicarboxylic acid 2-methyl ester (590 mg, 2.32 mmol) in anhydrous DMF (10 mL) was added triethylamine (1.62 mL, 11.6 mmol), EDC (530 mg, 2.78 mmol), HOBT (380 mg, 2.78 mmol), and 4-Aminomethyl-1,3-dihydro-indol-2-one hydrochloride (550 mg, 2.78 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-90% EtOAc in hexane to afford the desired product (0.27 g, 29% yield).

Preparation of 5-[(2-oxo-2,3-dihydro-1H-indol-4-ylmethyl)-carbamoyl]-3-trifluoromethyl-thiophene-2-carboxylic acid

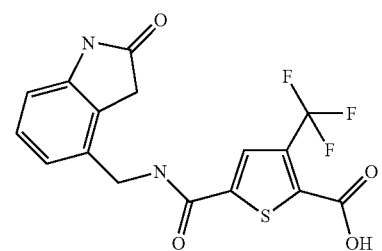

A mixture of 5-[(2-oxo-2,3-dihydro-1H-indol-4-ylmethyl)-carbamoyl]-3-trifluoromethyl-thiophene-2-carboxylic acid methyl ester (270 mg, 0.68 mmol), lithium hydroxide monohydrate (280 mg, 6.77 mmol), THF (5 mL) and water (5 mL) was stirred 15 h, acidified with 1N HCl and extracted with EtOAc (×3). The organic extracts were combined, washed with brine, dried over sodium sulfate, filtered and evaporated to give the title compound, 260 mg (99%). MS m/e 354.9 (M+H$^+$).

Preparation of (S)-3-tert-Butoxycarbonylamino-2-([5-[(2-oxo-2,3-dihydro-1H-indol-4-ylmethyl)-carbamoyl]-3-trifluoromethyl-thiophene-2-carbonyl]-amino)-propionic acid methyl ester

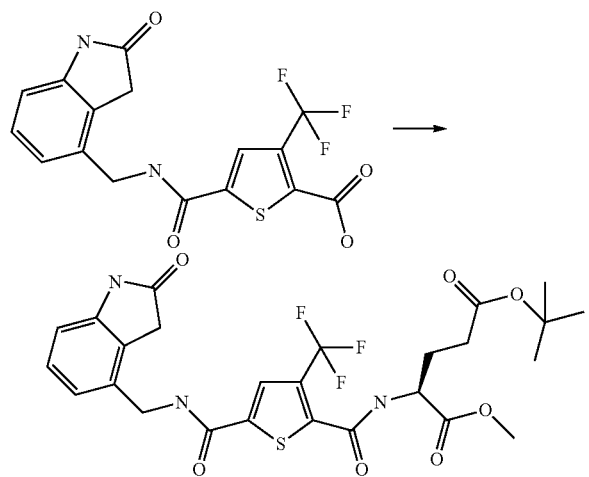

To a solution of 5-[(2-oxo-2,3-dihydro-1H-indol-4-ylmethyl)-carbamoyl]-3-trifluoromethyl-thiophene-2-carboxylic acid (0.26 g, 0.68 mmol) in anhydrous DMF (10 mL) was added triethylamine (0.28 mL, 2.04 mmol), HBTU (0.31 g, 0.82 mmol), HOBT (0.11 g, 0.82 mmol), and H-DAP(Boc)OMe hydrochloride (0.26 g, 1.01 mmol). The mixture was stirred at room temperature 3 h, treated with EtOAc (50 mL), washed with brine, dried over sodium sulfate, filtered and evaporated. The solid residue was purified by column (0-100% EtOAc in hexane) to give 0.10 g (25%) tan solid product. MS m/e 485.0 (M-Boc).

Preparation of (S)-3-Amino-2-({5-[(2-oxo-2,3-dihydro-1H-indol-4-ylmethyl)-carbamoyl}-3-trifluoromethyl-thiophene-2-carbonyl]-amino)-propionic acid methyl ester trifluoro-acetic acid salt

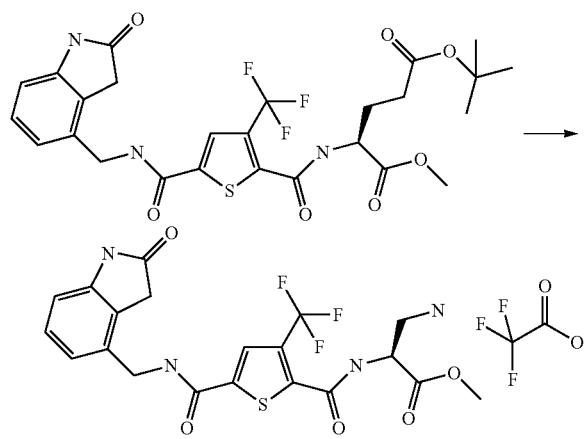

To a solution of (S)-3-tert-Butoxycarbonylamino-2-({5-[(2-oxo-2,3-dihydro-1H-indol-4-ylmethyl)-carbamoyl]-3-trifluoromethyl-thiophene-2-carbonyl}-amino)-propionic acid methyl ester (0.10 g, 0.17 mmol) in DCM (5 mL) was added TFA (1.5 mL). The mixture was stirred at room temperature 1 h and evaporated. Isolate 0.14 g of crude product which was used without further purification.

Preparation of (S)-2-([5-[(2-oxo-2,3-dihydro-1H-indol-4-ylmethyl)-carbamoyl]-3-trifluoromethyl-thiophene-2-carbonyl]-amino)-3-[(thiophene-2-carbonyl)-amino]-propionic acid methyl ester

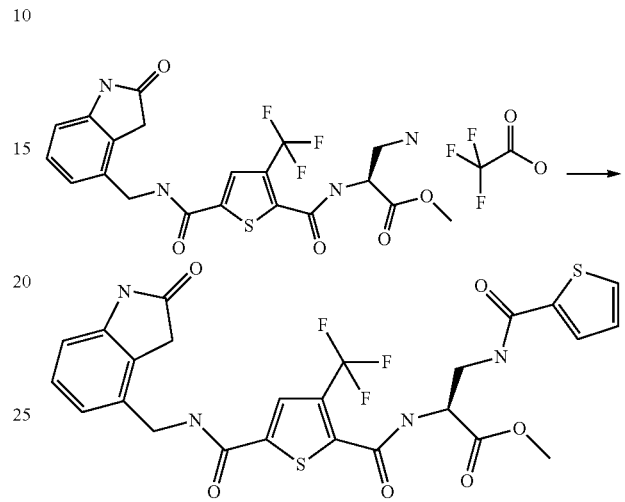

To a solution of (S)-3-Amino-2-β5-[(2-Oxo-2,3-dihydro-1H-indol-4-ylmethyl)-carbamoyl]-3-trifluoromethyl-thiophene-2-carbonyl}-amino)-propionic acid methyl ester trifluoro-acetic acid salt (0.14 g, 0.17 mmol) in anhydrous DMF (10 mL) was added triethylamine (0.07 mL, 0.51 mmol), HBTU (0.097 g, 0.26 mmol), HOBT (0.027 g, 0.20 mmol), and 2-Thiophenecarboxylic acid (0.024 g, 0.19 mmol). The mixture was stirred at room temperature 15 h, treated with EtOAc (50 mL), washed with brine, dried over sodium sulfate, filtered and evaporated. The solid residue was purified by column (0-100% EtOAc in hexane) to give 0.053 g (52%) colorless oil product. MS m/e 595.1 (M+H$^+$).

Preparation of 3-Chloro-5-[(1H-indazol-4-ylmethyl)-carbamoyl]-thiophene-2-carboxylic acid methyl ester

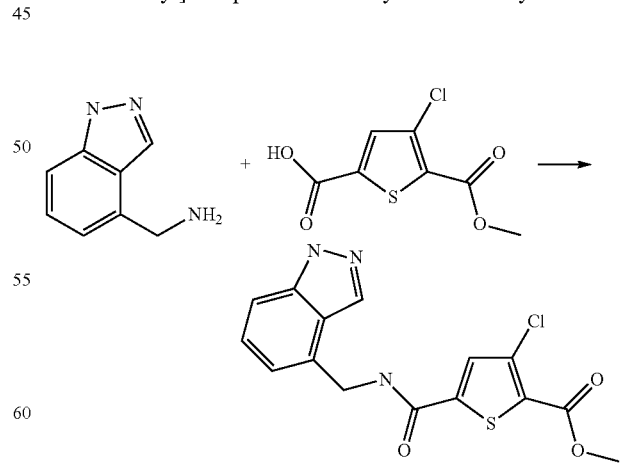

To a solution of 3-Chloro-thiophene-2,5-dicarboxylic acid 2-methyl ester (200 mg, 0.91 mmol) in anhydrous DMF (5 mL) was added triethylamine (0.38 mL, 2.73 mmol), HBTU (0.52 g, 1.37 mmol), HOBT (0.147 mg, 1.09 mmol), and C-(1H-Indazol-4-yl)-methylamine (146 mg, 1.0 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-70% EtOAc in hexane to afford the desired product (0.073 g, 23% yield).

Preparation of 3-Chloro-5-[(1H-indazol-4-ylmethyl)-carbamoyl]-thiophene-2-carboxylic acid

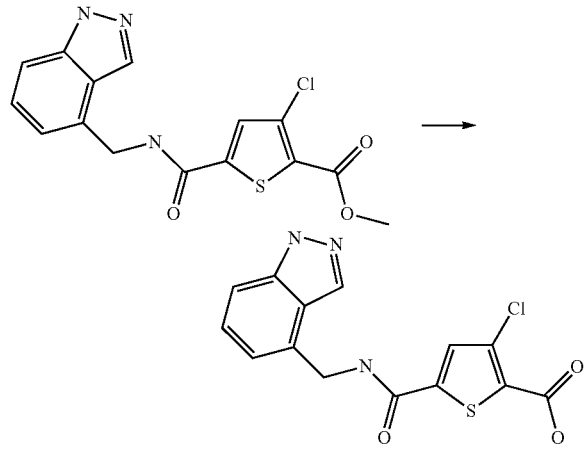

A mixture of 3-Chloro-5-[(1H-indazol-4-ylmethyl)-carbamoyl]-thiophene-2-carboxylic acid methyl ester (73 mg, 0.21 mmol), lithium hydroxide monohydrate (88 mg, 2.09 mmol), THF (6 mL) and water (6 mL) was stirred 15 h, acidified with 1N HCl and extracted with EtOAc (×3). The organic extracts were combined, washed with brine, dried over sodium sulfate, filtered and evaporated to give the title compound, 80 mg (100%). MS m/e 335.8 (M+H$^+$).

Preparation of (S)-3-tert-Butoxycarbonylamino-2-({3-chloro-5-[(1H-indazol-4-ylmethyl)-carbamoyl]-thiophene-2-carbonyl}-amino)-propionic acid methyl ester

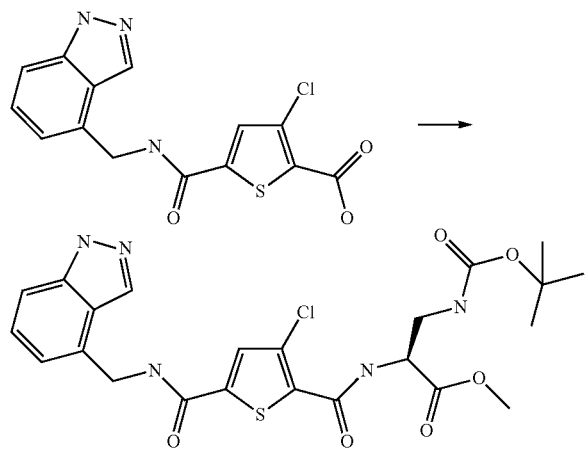

To a solution of 3-Chloro-5-[(1H-indazol-4-ylmethyl)-carbamoyl]-thiophene-2-carboxylic acid (0.080 g, 0.21 mmol) in anhydrous DMF (4 mL) was added triethylamine (0.09 mL, 0.63 mmol), HBTU (0.095 g, 0.25 mmol), HOBT (0.035 g, 0.25 mmol), and H-DAP(Boc)OMe hydrochloride (0.082 g, 0.32 mmol). The mixture was stirred at room temperature 15 h, treated with EtOAc (40 mL), washed with brine, dried over sodium sulfate, filtered and evaporated. The solid residue was purified by column (30-100% EtOAc in hexane) to give 0.1015 g (86%) colorless oil.

Preparation of (S)-3-Amino-2-({3-chloro-5-[(1H-indazol-4-ylmethyl)-carbamoyl]-thiophene-2-carbonyl}-amino)-propionic acid methyl ester trifluoro-acetic acid salt

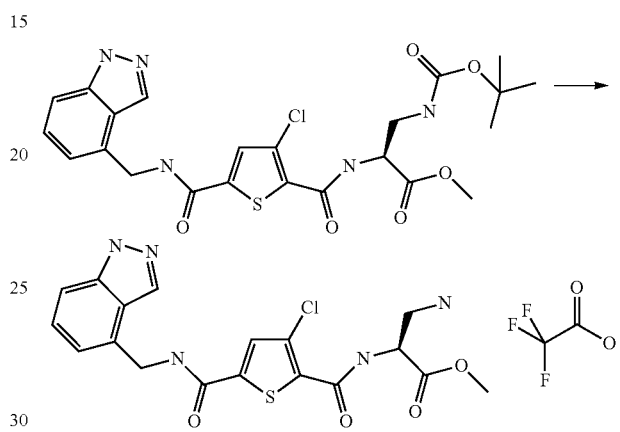

To a solution of (S)-3-tert-Butoxycarbonylamino-2-({3-chloro-5-[(1H-indazol-4-ylmethyl)-carbamoyl]-thiophene-2-carbonyl}-amino)-propionic acid methyl ester (0.1015 g, 0.19 mmol) in DCM (5 mL) was added TFA (1 mL). The mixture was stirred at room temperature 2 h and evaporated. Isolate 0.127 g of crude product which was used without further purification.

Preparation of (S)-2-({3-Chloro-5-[(1H-indazol-4-ylmethyl)-carbamoyl]-thiophene-2-carbonyl}-amino)-3-[(thiophene-2-carbonyl)-amino]-propionic acid methyl ester

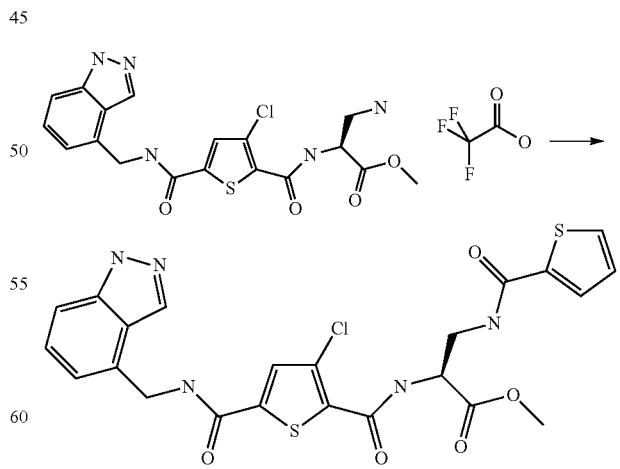

To a solution of (S)-3-Amino-2-({3-chloro-5-[(1H-indazol-4-ylmethyl)-carbamoyl]-thiophene-2-carbonyl}-amino)-propionic acid methyl ester trifluoro-acetic acid salt (0.19 mmol) in anhydrous DMF (5 mL) was added triethylamine (0.08 mL, 0.57 mmol), HBTU (0.108 g, 0.29 mmol), HOBt (0.031 g, 0.23 mmol), and 2-Thiophenecarboxylic acid (0.029 g, 0.23 mmol). The mixture was stirred at room temperature 2 h, treated with EtOAc (30 mL), washed with brine, dried over sodium sulfate, filtered and evaporated. The solid residue was purified by column (0-100% EtOAc in hexane) to give 0.0487 g (47%) colorless oil. MS m/e 545.9 (M+H$^+$).

Preparation of 5-[(1H-Indazol-4-ylmethyl)-carbamoyl]-3-trifluoromethyl-thiophene-2-carboxylic acid methyl ester

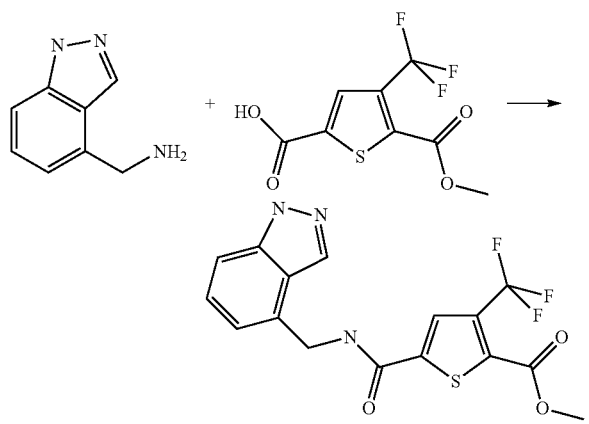

To a solution of 3-Trifluoromethyl-thiophene-2,5-dicarboxylic acid 2-methyl ester (630 mg, 2.47 mmol) in anhydrous DMF (12 mL) was added triethylamine (1.03 mL, 7.41 mmol), HBTU (1.41 g, 3.71 mmol), HOBT (0.40 mg, 2.96 mmol), and C-(1H-Indazol-4-yl)-methylamine (400 mg, 2.72 mmol). The mixture was stirred at room temperature 5 h, then quenched by pouring into EtOAc. The organic layer was washed with brine, dried over Na$_2$SO$_4$ and concentrated under reduced pressure. The residue was purified by flash chromatography with 0-80% EtOAc in hexane to afford the desired product (0.20 g, 21% yield).

Preparation of 5-[(1H-Indazol-4-ylmethyl)-carbamoyl]-3-trifluoromethyl-thiophene-2-carboxylic acid

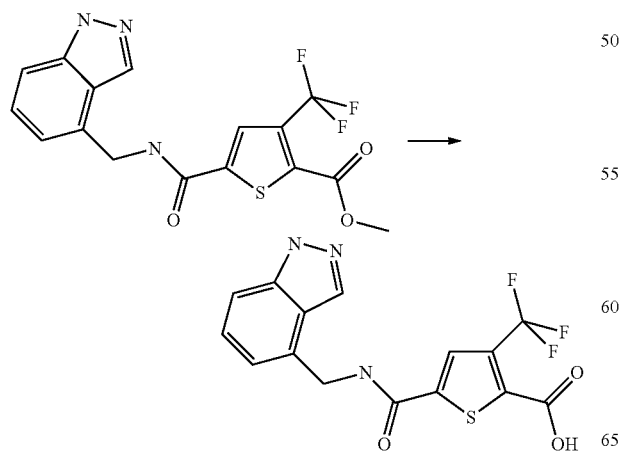

A mixture of 5-[(1H-Indazol-4-ylmethyl)-carbamoyl]-3-trifluoromethyl-thiophene-2-carboxylic acid methyl ester (200 mg, 0.52 mmol), lithium hydroxide monohydrate (220 mg, 5.22 mmol), THF (4 mL) and water (5 mL) was stirred 15 h, acidified with 1N HCl and extracted with EtOAc (×3). The organic extracts were combined, washed with brine, dried over sodium sulfate, filtered and evaporated to give the title compound, 160 mg (83%). MS m/e 370.0 (M+H$^+$).

Preparation of (S)-3-tert-Butoxycarbonylamino-2-({5-[(1H-indazol-4-ylmethyl)-carbamoyl]-3-trifluoromethyl-thiophene-2-carbonyl}-amino)-propionic acid methyl ester

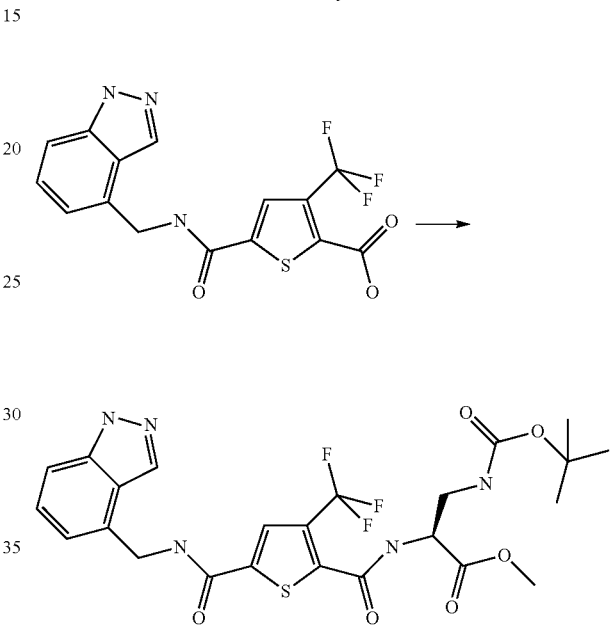

To a solution of 5-[(1H-Indazol-4-ylmethyl)-carbamoyl]-3-trifluoromethyl-thiophene-2-carboxylic acid (0.16 g, 0.43 mmol) in anhydrous DMF (10 mL) was added triethylamine (0.18 mL, 1.29 mmol), HBTU (0.20 g, 0.52 mmol), HOBT (0.070 g, 0.52 mmol), and H-DAP(Boc)OMe hydrochloride (0.17 g, 0.65 mmol). The mixture was stirred at room temperature 15 h, treated with EtOAc (50 mL), washed with brine, dried over sodium sulfate, filtered and evaporated. The solid residue was purified by column (0-100% EtOAc in hexane) to give 0.26 g (100%) colorless oil product.

Preparation of (S)-3-Amino-2-({5-[(1H-indazol-4-ylmethyl)-carbamoyl]-3-trifluoromethyl-thiophene-2-carbonyl}-amino)-propionic acid methyl ester trifluoro-acetic acid salt

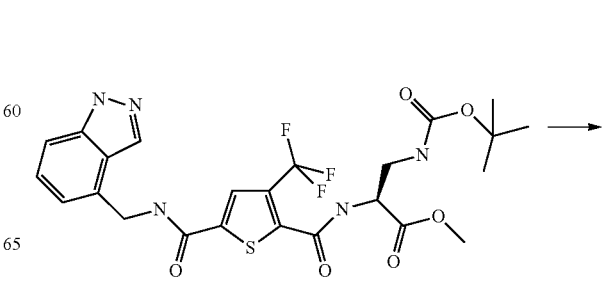

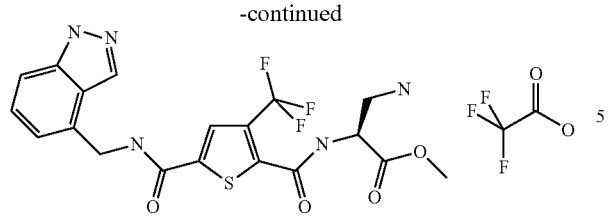

To a solution of (S)-3-tert-Butoxycarbonylamino-2-{5-[(1H-indazol-4-ylmethyl)-carbamoyl]-3-trifluoromethyl-thiophene-2-carbonyl}-amino)-propionic acid methyl ester (0.26 g, 0.46 mmol) in DCM (10 mL) was added TFA (2 mL). The mixture was stirred at room temperature 1.5 h and evaporated. Isolate 0.31 g of crude product which was used without further purification.

Preparation of (S)-2-([5-[(1H-Indazol-4-ylmethyl)-carbamoyl]-3-trifluoromethyl-thiophene-2-carbonyl]-amino)-3-[(thiophene-2-carbonyl)-amino]-propionic acid methyl ester

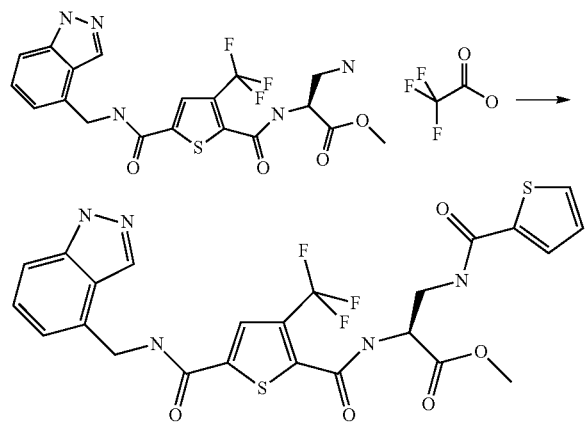

To a solution of (S)-3-Amino-2-({5-[(1H-indazol-4-ylmethyl)-carbamoyl]-3-trifluoromethyl-thiophene-2-carbonyl}-amino)-propionic acid methyl ester trifluoro-acetic acid salt (0.31 g, 0.46 mmol) in anhydrous DMF (10 mL) was added triethylamine (0.20 mL, 1.38 mmol), HBTU (0.26 g, 0.69 mmol), HOBT (0.074 g, 0.55 mmol), and 2-Thiophenecarboxylic acid (0.071 g, 0.55 mmol). The mixture was stirred at room temperature 2 d, treated with EtOAc (50 mL), washed with brine, dried over sodium sulfate, filtered and evaporated. The solid residue was purified by column (30-100% EtOAc in hexane) to give 0.13 g (49%) colorless oil product. MS m/e 579.9 (M+H$^+$).

Preparation of 6,6-Diethoxy-2-methyl-hex-4-yn-3-ol

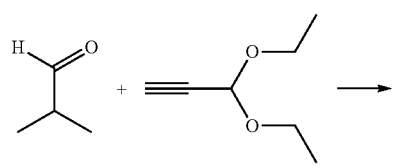

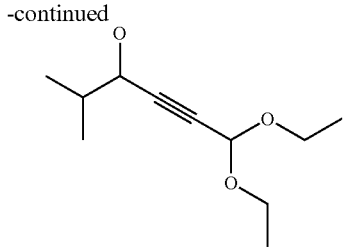

A mixture of 3,3-Diethoxy-propyne (1.82 g, 14.2 mmol) in THF (40 ml) was cooled to −78 C under N2. A solution of n-BuLi (2.0M in cyclohexane, 9.2 mL, 18.46 mmol) was added. After 30 min, Isobutyraldehyde (1.33 g, 18.46 mmol) in THF (10 ml) was added. After 3 h, the reaction was quenched by dilution with 1N HCl, warmed to room temperature and extracted into EtOAc. The organic layer was washed with brine, dried over sodium sulfate, filtered and evaporated to give product, 3.18 g (100%).

Preparation of 6,6-Diethoxy-2-methyl-hex-4-yn-3-one

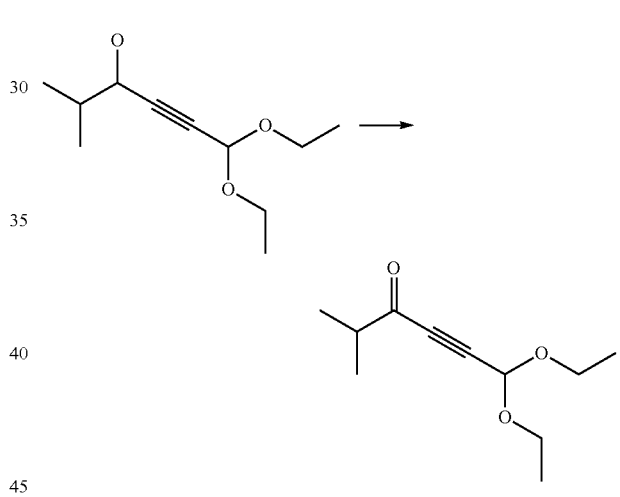

6,6-Diethoxy-2-methyl-hex-4-yn-3-ol (3.18 g, 18.46 mmol) was dissolved in dichloromethane (100 ml) and treated with activated MnO$_2$ (30 g) at rt for 15 h. The reaction mixture was filtered through a plug of celite and Na$_2$SO$_4$. The filtrated was concentrated under reduced pressure and purified by flash chromatography with 0-15% EtOAc in hexane to afford the desired product (1.32 g, 36% yield).

Preparation of 5-Diethoxymethyl-3-isopropyl-thiophene-2-carboxylic acid methyl ester

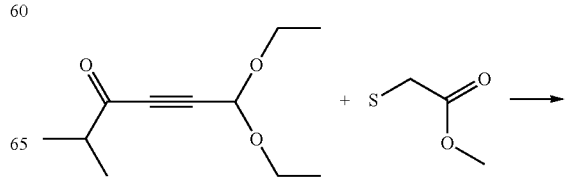

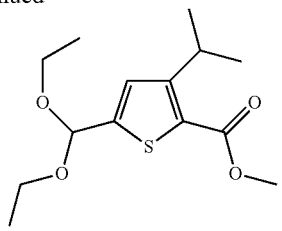

A solution of 6,6-Diethoxy-2-methyl-hex-4-yn-3-one (1.32 g, 6.66 mmol) in THF (20 ml) was cooled to 0° C. (ice bath). Methyl thioglycolate (0.6 ml, 6.66 mmol) was added in one portion and the mixture was stirred at 0° C. for 1 h. Methanol (3 ml) and Cs$_2$CO$_3$/MgSO$_4$ (1 g/2 g, pre-dried at 200° C. in vacuum) were added at 0° C. The mixture was stirred at 0° C. for 15 min and then at rt for 15 h. The reaction mixture was quenched by pouring into EtOAc. The organic layer was washed with brine, dried over Na$_2$SO$_4$ and concentrated under reduced pressure. The residue was purified by flash chromatography with 0-20% EtOAc in hexane to afford the desired product (0.58 g, 30% yield).

Preparation of
5-Formyl-3-isopropyl-thiophene-2-carboxylic acid
methyl ester

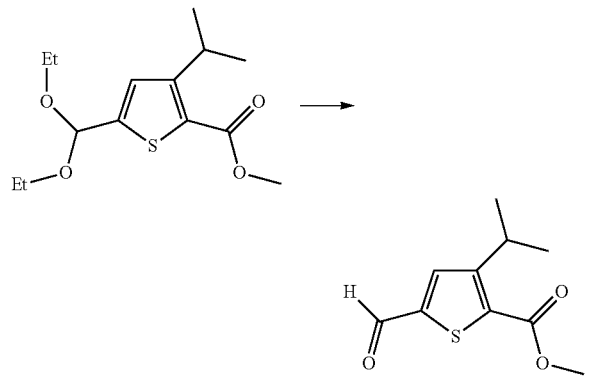

A solution of 5-Diethoxymethyl-3-isopropyl-thiophene-2-carboxylic acid methyl ester (0.58 g, 2.03 mmol) in dioxane (5 ml) was cooled to 0° C. (ice bath). 88% formic acid (6 ml) was added in one portion and the mixture was stirred at 0° C. for 5 min and then at rt for 60 min. The reaction mixture was quenched by pouring into EtOAc. The organic layer was washed with water, dried over Na$_2$SO$_4$ and concentrated under reduced pressure to afford the desired product (0.51 g, 99% yield).

Preparation of
3-Isopropyl-thiophene-2,5-dicarboxylic acid
2-methyl ester

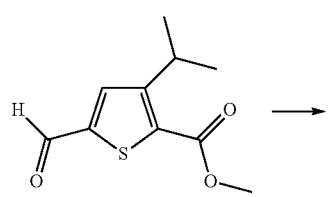

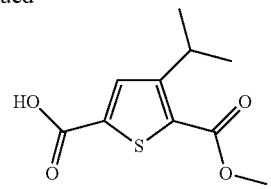

To a solution of 5-Formyl-3-isopropyl-thiophene-2-carboxylic acid methyl ester (0.51 g, 2.40 mmol) in dioxane (12 ml) was added 2-methyl-2-butene (3 ml) and a solution of Na$_2$ClO$_2$ (0.65 g, 7.21 mmol) and NaH$_2$PO$_4$ (0.79 g) in water (3 ml). The mixture was stirred at rt for 2 h. The solution was saturated with sodium chloride, then successively extracted with EtOAc. The combined organic layers were dried over Na$_2$SO$_4$ and concentrated under reduced pressure to afford the desired product (0.45 g, 82% yield).

Preparation of 5-(3-Hydroxy-benzylcarbamoyl)-3-isopropyl-thiophene-2-carboxylic acid methyl ester

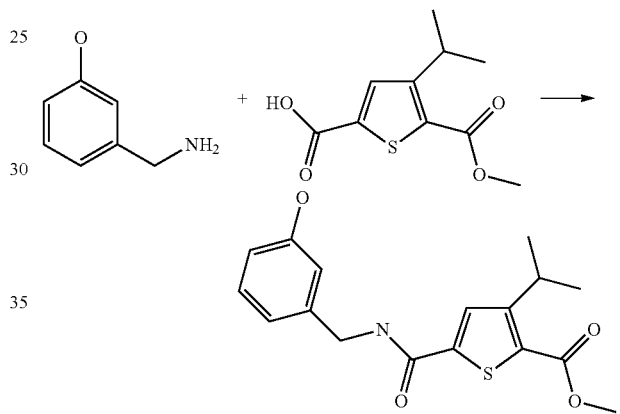

To a solution of 3-Isopropyl-thiophene-2,5-dicarboxylic acid 2-methyl ester (110 mg, 0.48 mmol) in anhydrous DMF (5 mL) was added triethylamine (0.20 mL, 1.45 mmol), HBTU (0.27 g, 0.72 mmol), HOBT (78 mg, 0.58 mmol), and 3-Aminomethyl phenol (65 mg, 0.53 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-60% EtOAc in hexane to afford the desired product (0.070 g, 44% yield).

Preparation of 5-(3-Hydroxy-benzylcarbamoyl)-3-isopropyl-thiophene-2-carboxylic acid

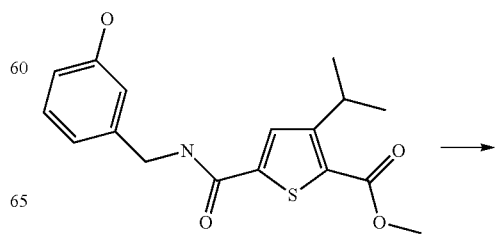

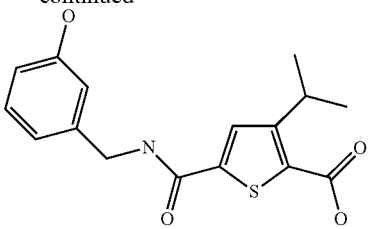

A mixture of 5-(3-Hydroxy-benzylcarbamoyl)-3-isopropyl-thiophene-2-carboxylic acid methyl ester (70 mg, 0.21 mmol), lithium hydroxide monohydrate (89 mg, 2.10 mmol), THF (5 mL) and water (5 mL) was stirred 15 h, acidified with 1N HCl and extracted with EtOAc (×3). The organic extracts were combined, washed with brine, dried over sodium sulfate, filtered and evaporated to give the title compound, 71.8 mg (100%). MS m/e 319.9 (M+H$^+$).

Preparation of (S)-3-tert-Butoxycarbonylamino-2-{[5-(3-hydroxy-benzylcarbamoyl)-3-isopropyl-thiophene-2-carbonyl]-amino}-propionic acid methyl ester

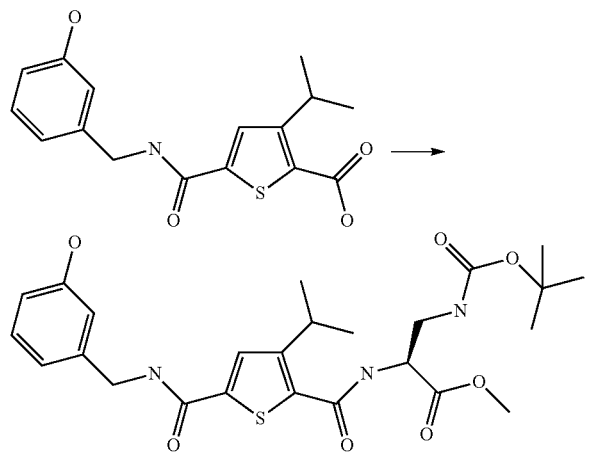

To a solution of 5-(3-Hydroxy-benzylcarbamoyl)-3-isopropyl-thiophene-2-carboxylic acid (0.0718 g, 0.21 mmol) in anhydrous DMF (4 mL) was added triethylamine (0.09 mL, 0.63 mmol), HBTU (0.095 g, 0.25 mmol), HOBT (0.035 g, 0.25 mmol), and H-DAP(Boc)OMe hydrochloride (0.082 g, 0.32 mmol). The mixture was stirred at room temperature 12 d, treated with EtOAc (25 mL), washed with brine, dried over sodium sulfate, filtered and evaporated. The solid residue was purified by column (30-100% EtOAc in hexane) to give 0.0850 g (78%) white foam.

Preparation of (S)-3-Amino-2-{[5-(3-hydroxy-benzylcarbamoyl)-3-isopropyl-thiophene-2-carbonyl]-amino}-propionic acid methyl ester trifluoro-acetic acid salt

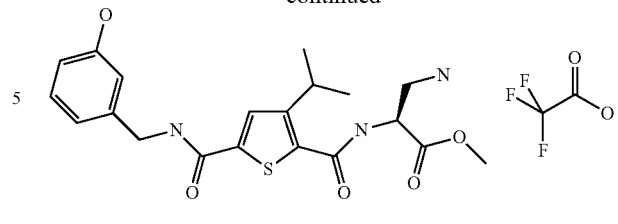

To a solution of (S)-3-tert-Butoxycarbonylamino-2-{[5-(3-hydroxy-benzylcarbamoyl)-3-isopropyl-thiophene-2-carbonyl]-amino}-propionic acid methyl ester (0.085 g, 0.16 mmol) in DCM (5 mL) was added TFA (1.0 mL). The mixture was stirred at room temperature 1 h and evaporated. Isolate 0.067 g of crude product which was used without further purification.

Preparation of (S)-2-{[5-(3-Hydroxy-benzylcarbamoyl)-3-isopropyl-thiophene-2-carbonyl]-amino}-3-[(thiophene-2-carbonyl)-amino]-propionic acid methyl ester

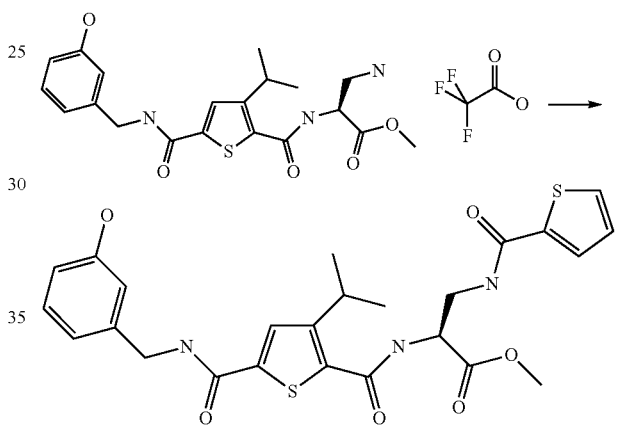

To a solution of (S)-3-Amino-2-{[5-(3-hydroxy-benzylcarbamoyl)-3-isopropyl-thiophene-2-carbonyl]-amino}-propionic acid methyl ester trifluoro-acetic acid salt (0.16 mmol) in anhydrous DMF (4 mL) was added triethylamine (0.07 mL, 0.48 mmol), HBTU (0.091 g, 0.24 mmol), HOBT (0.026 g, 0.19 mmol), and 2-Thiophenecarboxylic acid (0.025 g, 0.19 mmol). The mixture was stirred at room temperature 1.5 h, treated with EtOAc (30 mL), washed with brine, dried over sodium sulfate, filtered and evaporated. The solid residue was purified by column (0-100% EtOAc in hexane) to give 0.040 g (47%) white foam product. MS m/e 530.0 (M+H$^+$).

Preparation of 5-[(1H-Indazol-4-ylmethyl)-carbamoyl]-3-isopropyl-thiophene-2-carboxylic acid methyl ester

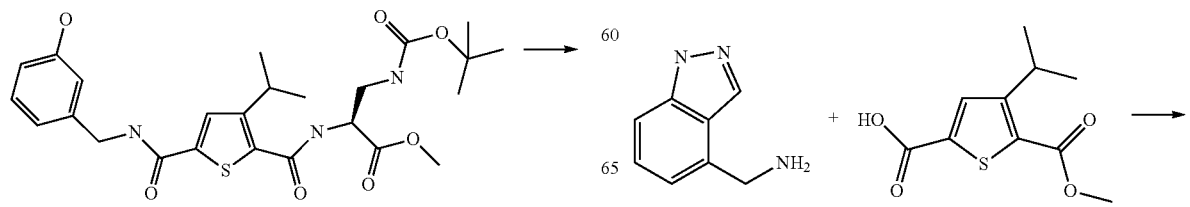

-continued

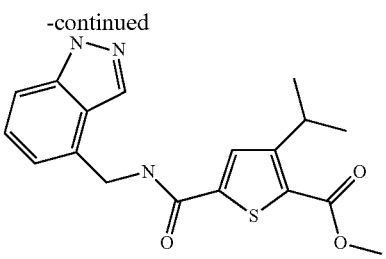

To a solution of 3-Isopropyl-thiophene-2,5-dicarboxylic acid 2-methyl ester (190 mg, 0.83 mmol) in anhydrous DMF (10 mL) was added triethylamine (0.35 mL, 2.49 mmol), HBTU (0.38 g, 1.0 mmol), HOBT (0.14 mg, 1.0 mmol), and C-(1H-Indazol-4-yl)-methylamine (180 mg, 1.25 mmol). The mixture was stirred at room temperature 15 h, then quenched by pouring into EtOAc. The organic layer was washed with brine, dried over $Na_2SO_4$ and concentrated under reduced pressure. The residue was purified by flash chromatography with 30-100% EtOAc in hexane to afford the desired product (0.1262 g, 42% yield).

Preparation of 5-[(1H-Indazol-4-ylmethyl)-carbamoyl]-3-isopropyl-thiophene-2-carboxylic acid

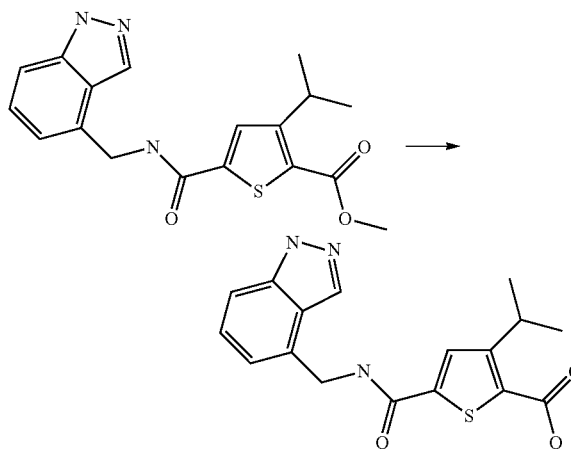

A mixture of 5-[(1H-Indazol-4-ylmethyl)-carbamoyl]-3-isopropyl-thiophene-2-carboxylic acid methyl ester (126 mg, 0.35 mmol), lithium hydroxide monohydrate (150 mg, 3.53 mmol), THF (4 mL) and water (5 mL) was stirred 15 h, acidified with 1N HCl and extracted with EtOAc (×3). The organic extracts were combined, washed with brine, dried over sodium sulfate, filtered and evaporated to give the title compound, 115.6 mg (96%). MS m/e 344.3 (M+H⁺).

Preparation of (S)-3-tert-Butoxycarbonylamino-2-([5-[(1H-indazol-4-ylmethyl)-carbamoyl]-3-isopropyl-thiophene-2-carbonyl]-amino)-propionic acid methyl ester

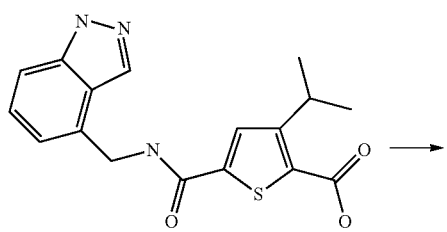

-continued

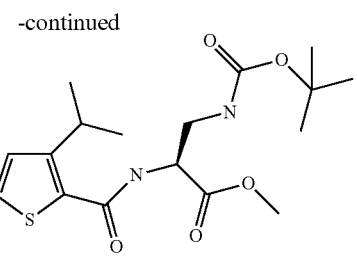

To a solution of 5-[(1H-Indazol-4-ylmethyl)-carbamoyl]-3-isopropyl-thiophene-2-carboxylic acid (0.1156 g, 0.34 mmol) in anhydrous DMF (8 mL) was added triethylamine (0.14 mL, 1.02 mmol), HBTU (0.155 g, 0.41 mmol), HOBT (0.055 g, 0.41 mmol), and H-DAP(Boc)OMe hydrochloride (0.129 g, 0.50 mmol). The mixture was stirred at room temperature 15 h, treated with EtOAc (50 mL), washed with brine, dried over sodium sulfate, filtered and evaporated. The solid residue was purified by column (30-100% EtOAc in hexane) to give 0.1779 g (96%) colorless oil.

Preparation of S)-3-Amino-2-([5-[(1H-indazol-4-ylmethyl)-carbamoyl]-3-isopropyl-thiophene-2-carbonyl]-amino)-propionic acid methyl ester trifluoroacetic acid salt

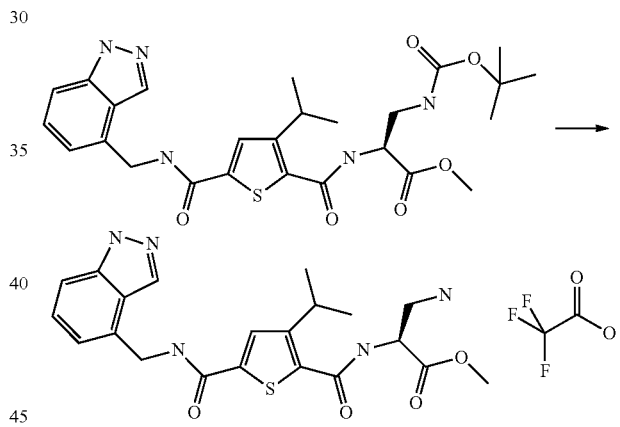

To a solution of (S)-3-tert-Butoxycarbonylamino-2-{5-[(1H-indazol-4-ylmethyl)-carbamoyl]-3-isopropyl-thiophene-2-carbonyl}-amino)-propionic acid methyl ester (0.1779 g, 0.33 mmol) in DCM (10 mL) was added TFA (1.5 mL). The mixture was stirred at room temperature 2 h and evaporated. Isolate 0.184 g of crude product which was used without further purification.

Preparation of (S)-2-({5-[(1H-Indazol-4-ylmethyl)-carbamoyl]-3-isopropyl-thiophene-2-carbonyl}-amino)-3-[(thiophene-2-carbonyl)-amino]-propionic acid methyl ester

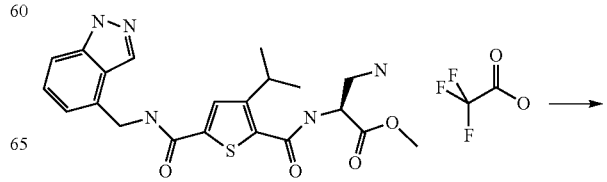

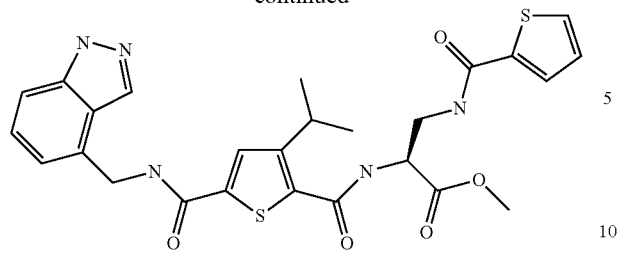

To a solution of (S)-3-Amino-2-({5-[(1H-indazol-4-ylmethyl)-carbamoyl]-3-isopropyl-thiophene-2-carbonyl}-amino)-propionic acid methyl ester trifluoro-acetic acid salt (0.33 mmol) in anhydrous DMF (8 mL) was added triethylamine (0.14 mL, 0.57 mmol), HBTU (0.188 g, 0.50 mmol), HOBt (0.054 g, 0.40 mmol), and 2-Thiophenecarboxylic acid (0.051 g, 0.40 mmol). The mixture was stirred at room temperature 15 h, treated with EtOAc (50 mL), washed with brine, dried over sodium sulfate, filtered and evaporated. The solid residue was purified by column (30-100% EtOAc in hexane) to give 0.1096 g (60%) white foam. MS m/e 554.0 (M+H$^+$).

Preparation of 6,6-Diethoxy-hex-4-yn-3-ol

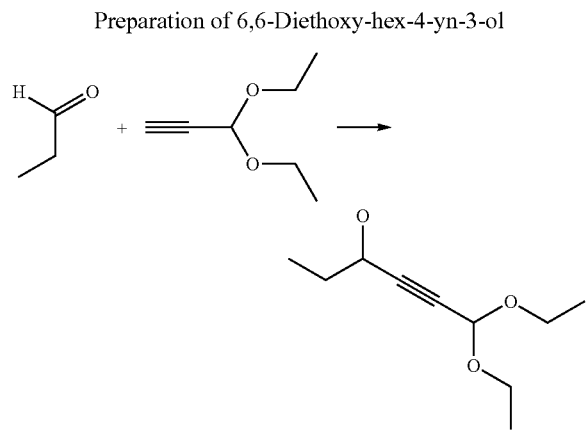

A mixture of 3,3-Diethoxy-propyne (2.73 g, 21.3 mmol) in THF (40 ml) was cooled to −78 C under N2. A solution of n-BuLi (2.0M in cyclohexane, 14 mL, 28 mmol) was added. After 30 min., Propionaldehyde (1.61 g, 27.7 mmol) in THF (10 ml) was added. After 15 h, the reaction was quenched by dilution with 1N HCl, warmed to room temperature and extracted into EtOAc. The organic layer was washed with brine, dried over sodium sulfate, filtered and evaporated to give product, 4.30 g (83%).

Preparation of 6,6-Diethoxy-hex-4-yn-3-one 6,6-Diethoxy-hex-4-yn-3-ol (4.30 g, 23.1 mmol) was dissolved in dichloromethane (200 ml) and treated with activated MnO$_2$ (50 g) at rt for 15 h. The reaction mixture was filtered through a plug of celite and Na$_2$SO$_4$. The filtrated was concentrated under reduced pressure and purified by flash chromatography with 0-20% EtOAc in hexane to afford the desired product (1.46 g, 34% yield).

Preparation of 5-Diethoxymethyl-3-ethyl-thiophene-2-carboxylic acid methyl ester

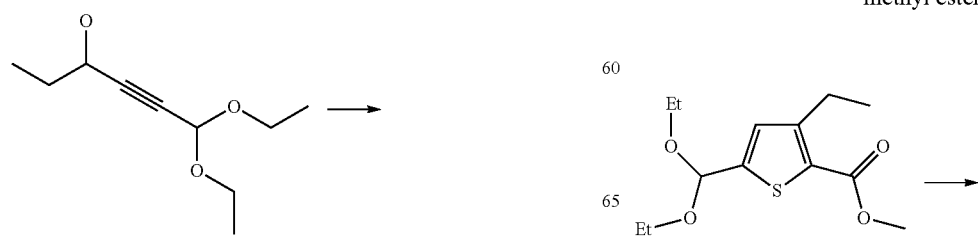

A solution of 6,6-Diethoxy-hex-4-yn-3-one (1.46 g, 6.66 mmol) in THF (25 ml) was cooled to 0° C. (ice bath). Methyl thioglycolate (0.71 ml, 6.66 mmol) was added in one portion and the mixture was stirred at 0° C. for 1 h. Methanol (4 ml) and Cs$_2$CO$_3$/MgSO$_4$ (1.5 g/3 g, pre-dried at 200° C. in vacuum) were added at 0° C. The mixture was stirred at 0° C. for 15 min and then at rt for 15 h. The reaction mixture was quenched by pouring into EtOAc. The organic layer was washed with brine, dried over Na$_2$SO$_4$ and concentrated under reduced pressure. The residue was purified by flash chromatography with 0-10% EtOAc in hexane to afford the desired product (1.76 g, 82% yield).

Preparation of 3-Ethyl-5-formyl-thiophene-2-carboxylic acid methyl ester

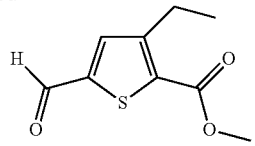

A solution of 5-Diethoxymethyl-3-ethyl-thiophene-2-carboxylic acid methyl ester (1.76 g, 6.46 mmol) in dioxane (16 ml) was cooled to 0° C. (ice bath). 88% formic acid (20 ml) was added in one portion and the mixture was stirred at 0° C. for 5 min and then at rt for 90 min. The reaction mixture was quenched by pouring into EtOAc. The organic layer was washed with water, dried over $Na_2SO_4$ and concentrated under reduced pressure to afford the desired product (1.22 g, 95% yield).

Preparation of 3-Ethyl-thiophene-2,5-dicarboxylic acid 2-methyl ester

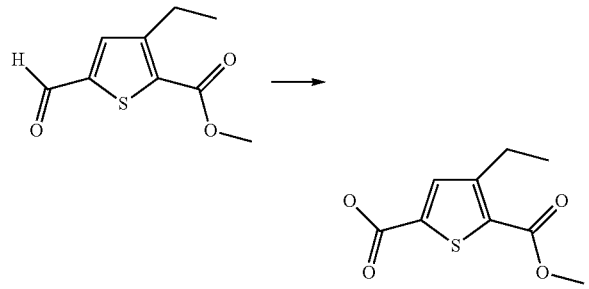

To a solution of 3-Ethyl-5-formyl-thiophene-2-carboxylic acid methyl ester (1.22 g, 6.15 mmol) in dioxane (30 ml) was added 2-methyl-2-butene (8 ml) and a solution of $Na_2ClO_2$ (3.42 g, 37.8 mmol) and $NaH_2PO_4$ (3.25 g) in water (8 ml). The mixture was stirred at rt for 2 h. The solution was saturated with sodium chloride, then successively extracted with EtOAc. The combined organic layers were dried over $Na_2SO_4$ and concentrated under reduced pressure to afford the desired product (1.48 g, 100% yield).

Preparation of 3-Ethyl-5-(3-hydroxy-benzylcarbamoyl)-thiophene-2-carboxylic acid methyl ester

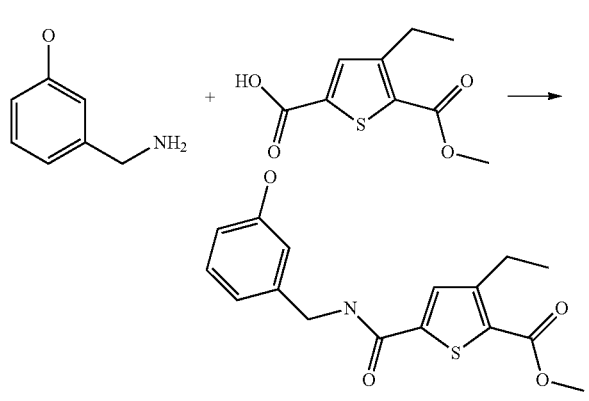

To a solution of 3-Ethyl-thiophene-2,5-dicarboxylic acid 2-methyl ester (250 mg, 1.17 mmol) in anhydrous DMF (10 mL) was added triethylamine (0.50 mL, 3.51 mmol), HBTU (0.67 g, 1.76 mmol), HOBT (190 mg, 1.40 mmol), and 3-Aminomethyl phenol (160 mg, 1.29 mmol). The mixture was stirred at room temperature 2 d, then quenched by pouring into EtOAc. The organic layer was washed with brine, dried over $Na_2SO_4$ and concentrated under reduced pressure. The residue was purified by flash chromatography with 0-50% EtOAc in hexane to afford the desired product (0.140 g, 38% yield).

Preparation of 3-Ethyl-5-(3-hydroxy-benzylcarbamoyl)-thiophene-2-carboxylic acid

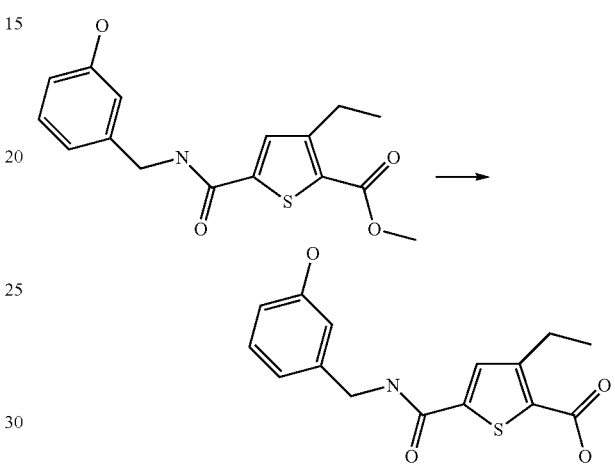

A mixture of 3-Ethyl-5-(3-hydroxy-benzylcarbamoyl)-thiophene-2-carboxylic acid methyl ester (140 mg, 0.44 mmol), lithium hydroxide monohydrate (180 mg, 4.38 mmol), THF (4 mL) and water (5 mL) was stirred 15 h, acidified with 1N HCl and extracted with EtOAc (×3). The organic extracts were combined, washed with brine, dried over sodium sulfate, filtered and evaporated to give the title compound, 145.4 (100%). MS m/e 305.9 (M+H$^+$).

Preparation of (S)-3-tert-Butoxycarbonylamino-2-{[3-ethyl-5-(3-hydroxy-benzylcarbamoyl)-thiophene-2-carbonyl]-amino}-propionic acid methyl ester

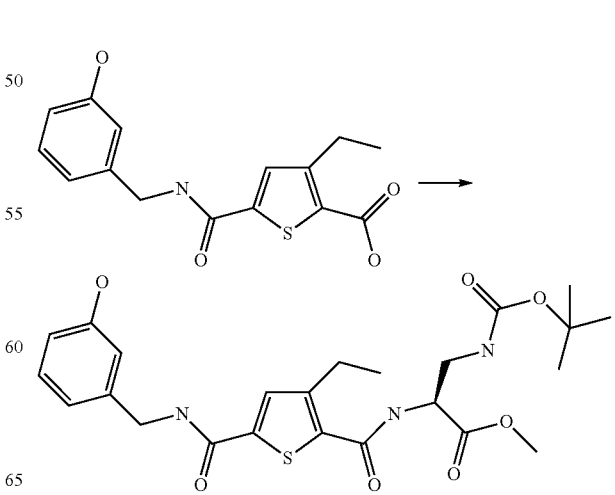

To a solution of 3-Ethyl-5-(3-hydroxy-benzylcarbamoyl)-thiophene-2-carboxylic acid (0.14 g, 0.46 mmol) in anhydrous DMF (8 mL) was added triethylamine (0.2 mL, 1.38 mmol), HBTU (0.21 g, 0.55 mmol), HOBT (0.074 g, 0.55 mmol), and H-DAP(Boc)OMe hydrochloride (0.175 g, 0.69 mmol). The mixture was stirred at room temperature 15 h, treated with EtOAc (50 mL), washed with brine, dried over sodium sulfate, filtered and evaporated. The solid residue was purified by column (30-70% EtOAc in hexane) to give 0.24 g (100%) yellow oil.

Preparation (S)-3-Amino-2-{[3-ethyl-5-(3-hydroxy-benzylcarbamoyl)-thiophene-2-carbonyl]-amino}-propionic acid methyl ester trifluoro-acetic acid salt

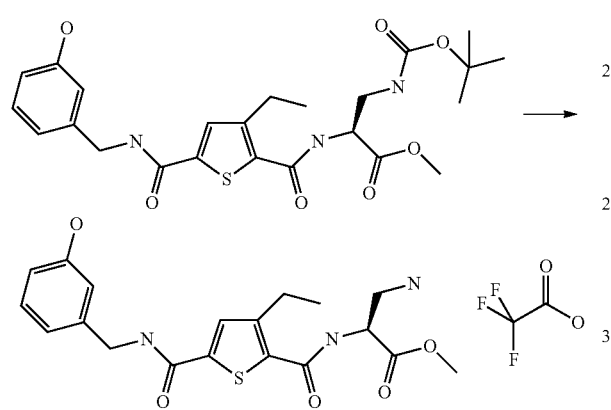

To a solution of (S)-3-tert-Butoxycarbonylamino-2-{[3-ethyl-5-(3-hydroxy-benzylcarbamoyl)-thiophene-2-carbonyl]-amino}-propionic acid methyl ester (0.24 g, 0.46 mmol) in DCM (5 mL) was added TFA (1.0 mL). The mixture was stirred at room temperature 1 h and evaporated to give crude product which was used without further purification.

Preparation (S)-2-{[3-Ethyl-5-(3-hydroxy-benzylcarbamoyl)-thiophene-2-carbonyl]-amino}-3-[(thiophene-2-carbonyl)-amino]-propionic acid methyl ester

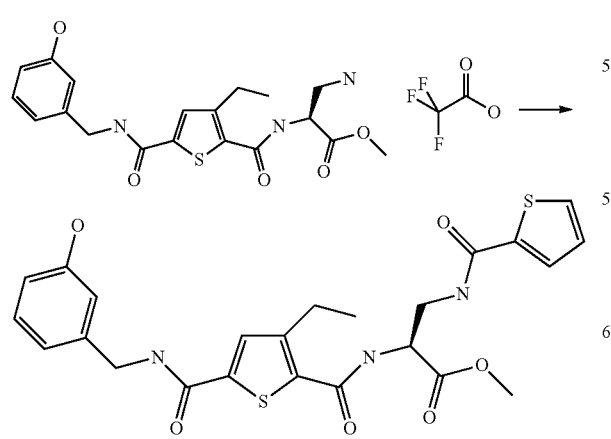

To a solution of (S)-3-Amino-2-{[3-ethyl-5-(3-hydroxy-benzylcarbamoyl)-thiophene-2-carbonyl]-amino}-propionic acid methyl ester trifluoro-acetic acid salt (0.46 mmol) in anhydrous DMF (10 mL) was added triethylamine (0.19 mL, 1.38 mmol), HBTU (0.26 g, 0.69 mmol), HOBT (0.074 g, 0.55 mmol), and 2-Thiophenecarboxylic acid (0.071 g, 0.55 mmol). The mixture was stirred at room temperature 15 h, treated with EtOAc (30 mL), washed with brine, dried over sodium sulfate, filtered and evaporated. The solid residue was purified by column (30-60% EtOAc in hexane) to give 0.0747 g (31%) white foam product. MS m/e 516.0 (M+H$^+$).

Preparation of 3-Ethyl-5-[(1H-indazol-4-ylmethyl)-carbamoyl]-thiophene-2-carboxylic acid methyl ester

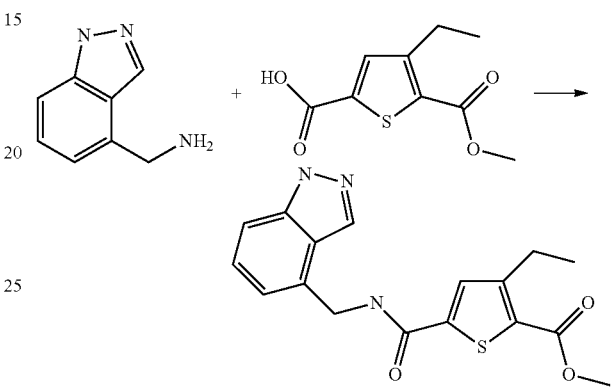

To a solution of 3-Ethyl-thiophene-2,5-dicarboxylic acid 2-methyl ester (130 mg, 0.61 mmol) in anhydrous DMF (5 mL) was added triethylamine (0.26 mL, 1.83 mmol), HBTU (0.35 g, 0.92 mmol), HOBT (0.099 g, 0.73 mmol), and C-(1H-Indazol-4-yl)-methylamine (100 mg, 0.67 mmol). The mixture was stirred at room temperature 2 d, then quenched by pouring into EtOAc. The organic layer was washed with brine, dried over Na$_2$SO$_4$ and concentrated under reduced pressure. The residue was purified by flash chromatography with 0-80% EtOAc in hexane to afford the desired product (0.095 g, 46% yield).

Preparation 3-Ethyl-5-[(1H-indazol-4-ylmethyl)-carbamoyl]-thiophene-2-carboxylic acid

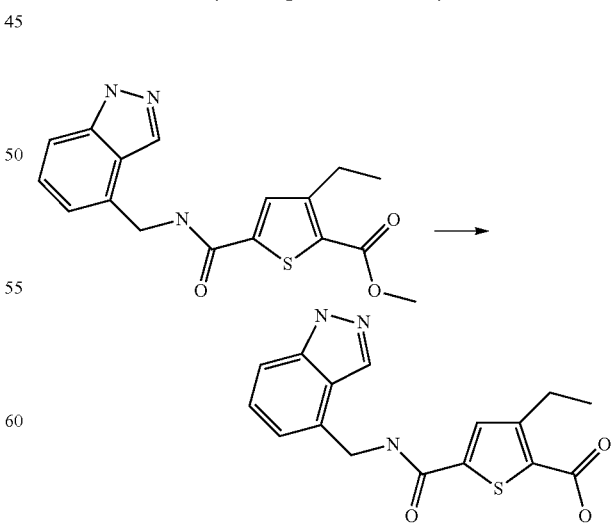

A mixture of 3-Ethyl-5-[(1H-indazol-4-ylmethyl)-carbamoyl]-thiophene-2-carboxylic acid methyl ester (95 mg, 0.35 mmol), lithium hydroxide monohydrate (120 mg, 2.77 mmol), THF (4 mL) and water (5 mL) was stirred 15 h, acidified with 1N HCl and extracted with EtOAc (×3). The organic extracts were combined, washed with brine, dried over sodium sulfate, filtered and evaporated to give the title compound, 67.8 mg (74%). MS m/e 329.9 (M+H⁺).

Preparation of (S)-3-tert-Butoxycarbonylamino-2-({3-ethyl-5-[(1H-indazol-4-ylmethyl)-carbamoyl]-thiophene-2-carbonyl}-amino)-propionic acid methyl ester

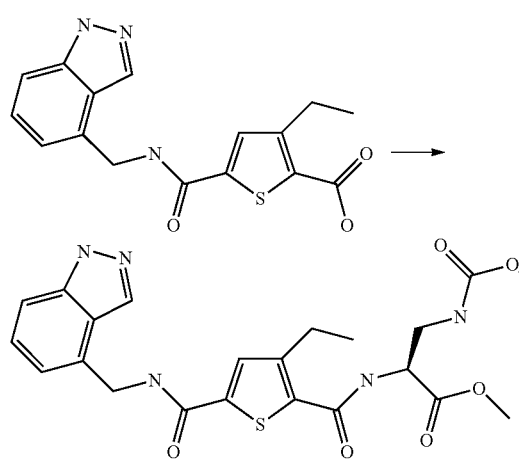

To a solution of 3-Ethyl-5-[(1H-indazol-4-ylmethyl)-carbamoyl]-thiophene-2-carboxylic acid (0.0678 g, 0.21 mmol) in anhydrous DMF (5 mL) was added triethylamine (0.09 mL, 0.63 mmol), HBTU (0.096 g, 0.25 mmol), HOBT (0.034 g, 0.25 mmol), and H-DAP(Boc)OMe hydrochloride (0.079 g, 0.31 mmol). The mixture was stirred at room temperature 15 h, treated with EtOAc (40 mL), washed with brine, dried over sodium sulfate, filtered and evaporated. The solid residue was purified by column (30-100% EtOAc in hexane) to give 0.0760 g (68%) colorless oil.

Preparation of (S)-3-Amino-2-({3-ethyl-5-[(1H-indazol-4-ylmethyl)-carbamoyl]-thiophene-2-carbonyl}-amino)-propionic acid methyl ester trifluoroacetic acid salt

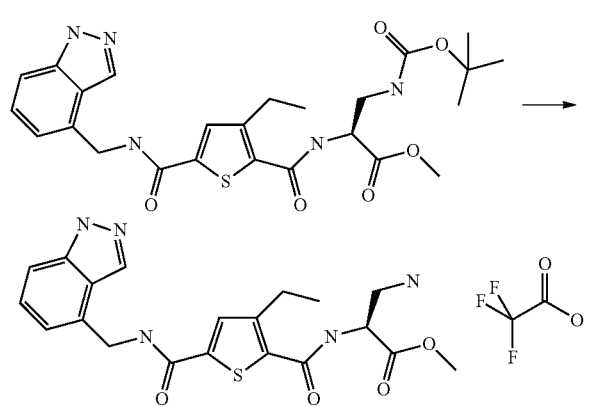

To a solution of (S)-3-tert-Butoxycarbonylamino-2-({3-ethyl-5-[(1H-indazol-4-ylmethyl)-carbamoyl]-thiophene-2-carbonyl}-amino)-propionic acid methyl ester (0.076 g, 0.14 mmol) in DCM (5 mL) was added TFA (1 mL). The mixture was stirred at room temperature 1 h and evaporated to give crude product which was used without further purification.

Preparation of (S)-2-({3-Ethyl-5-[(1H-indazol-4-ylmethyl)-carbamoyl]-thiophene-2-carbonyl}-amino)-3-[(thiophene-2-carbonyl)-amino]-propionic acid methyl ester

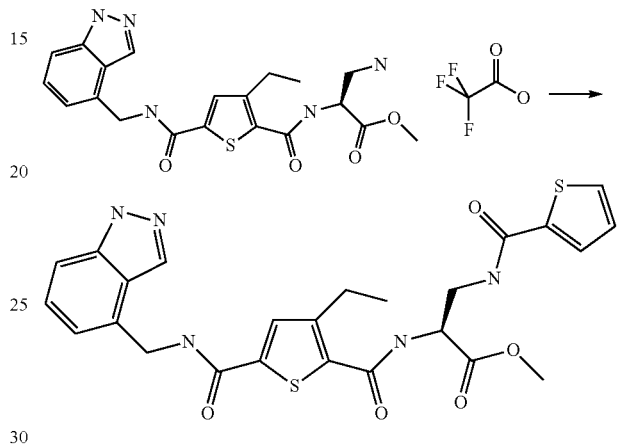

To a solution of (S)-3-Amino-2-({3-ethyl-5-[(1H-indazol-4-ylmethyl)-carbamoyl]-thiophene-2-carbonyl}-amino)-propionic acid methyl ester trifluoro-acetic acid salt (0.14 mmol) in anhydrous DMF (5 mL) was added triethylamine (0.06 ml, 0.42 mmol), HBTU (0.080 g, 0.21 mmol), HOBt (0.023 g, 0.17 mmol), and 2-Thiophenecarboxylic acid (0.022 g, 0.17 mmol). The mixture was stirred at room temperature 15 h, treated with EtOAc (30 mL), washed with brine, dried over sodium sulfate, filtered and evaporated. The solid residue was purified by column (30-100% EtOAc in hexane) to give 0.0280 g (37%) white foam. MS m/e 540.0 (M+H⁺).

Preparation of 3-Bromo-5-methyl-thiophene-2-carboxylic acid methyl ester

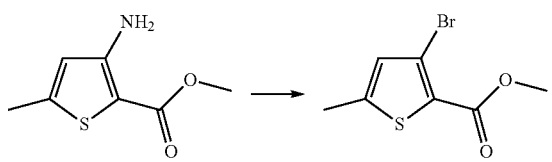

A mixture of Copper(II) bromide (2.68 g, 12 mmol) and t-Butylnitrite (1.55 g, 15 mmol) in MeCN (40 ml) was cooled to 0° C. (ice bath). A solution of 3-Amino-5-methyl-thiophene-2-carboxylic acid methyl ester (1.71 g, 10 mmol) in MeCN (2 ml) was added dropwise by syringe. The reaction mixture was stirred at room temperature for 1.5 h. The reaction mixture was diluted with 1N HCl and extracted with EtOAc (2×100 mL), washed with water, brine, dried over sodium sulfate, filtered and evaporated. The residue was purified by column (0-15% EtOAc in hexane) to give 1.66 g (71%) colorless oil product.

Preparation of 3-Bromo-5-bromomethyl-thiophene-2-carboxylic acid methyl ester

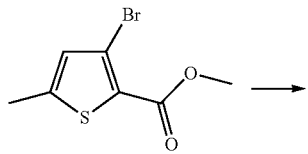

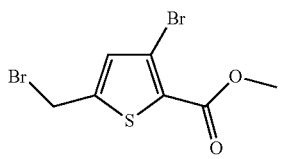

A mixture of 3-Bromo-5-methyl-thiophene-2-carboxylic acid methyl ester (1.66 g, 7.06 mmol), NBS (1.63 g, 9.18 mmol), and Benzoyl peroxide (0.085 g, 0.35 mmol) in CCl4 (15 ml) was refluxed in a pressure tube 15 h. The reaction mixture was cooled and evaporated. The residue was purified by column (0-15% EtOAc in hexane) to give 0.99 g (45%) yellow oil product.

Preparation of 3-Bromo-5-hydroxymethyl-thiophene-2-carboxylic acid methyl ester

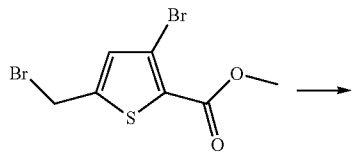

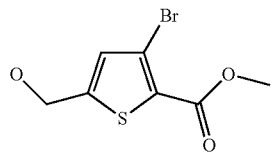

A mixture of 3-Bromo-5-bromomethyl-thiophene-2-carboxylic acid methyl ester (0.99 g, 3.15 mmol) and NaHCO3 (4.5 g, 53.6 mmol) in DMSO (25 ml) was heated at 115° C. for 3 h. The reaction mixture was cooled. The reaction mixture was EtOAc (250 ml), washed with brine, dried over sodium sulfate, filtered and evaporated. The residue was purified by column (0-30% EtOAc in hexane) to give 0.19 g (24%) yellow solid product.

Preparation of 3-Bromo-thiophene-2,5-dicarboxylic acid 2-methyl ester

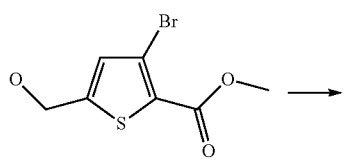

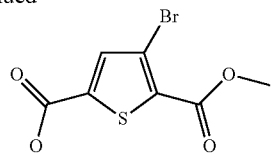

A mixture of 3-Bromo-5-hydroxymethyl-thiophene-2-carboxylic acid methyl ester (0.19 g, 0.76 mmol) and Periodic Acid (0.38 g, 1.66 mmol) in MeCN (10 ml) was stirred for 30 min A solution of PCC (0.010 g, 0.015 mmol) in MeCN (0.2 ml) was added. After 2 h, the reaction mixture was diluted with EtOAc (50 ml), washed with sodium sulfite, brine, dried over sodium sulfate, filtered and evaporated. Isolate 0.204 g (100%) of yellow solid product.

Preparation of 3-Bromo-5-(3-hydroxy-benzylcarbamoyl)-thiophene-2-carboxylic acid methyl ester

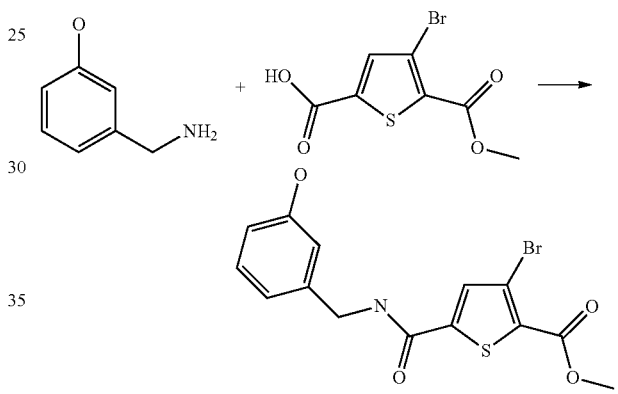

To a solution of 3-Bromo-thiophene-2,5-dicarboxylic acid 2-methyl ester (204 mg, 0.76 mmol) in anhydrous DMF (7 mL) was added triethylamine (0.32 mL, 2.28 mmol), HBTU (0.43 g, 1.14 mmol), HOBT (123 mg, 0.91 mmol), and 3-Aminomethyl-phenol (110 mg, 0.91 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 0-50% EtOAc in hexane to afford the desired product (0.1647 g, 59% yield).

Preparation of 3-Bromo-5-(3-hydroxy-benzylcarbamoyl)-thiophene-2-carboxylic acid

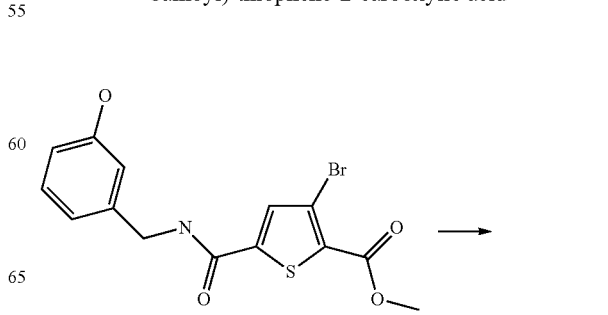

-continued

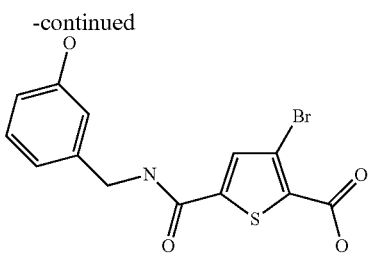

A mixture of 3-Bromo-5-(3-hydroxy-benzylcarbamoyl)-thiophene-2-carboxylic acid methyl ester (160 mg, 0.43 mmol), lithium hydroxide monohydrate (180, mg, 4.32 mmol), THF (5 mL) and water (6 mL) was stirred 15 h, acidified with 1N HCl and extracted with EtOAc (×3). The organic extracts were combined, washed with brine, dried over sodium sulfate, filtered and evaporated to give the title compound, 110 mg (70%). MS m/e 357.7 (M+H$^+$).

Preparation of (S)-2-{[3-Bromo-5-(3-hydroxy-benzylcarbamoyl)-thiophene-2-carbonyl]-amino}-3-tert-butoxycarbonylamino-propionic acid methyl ester

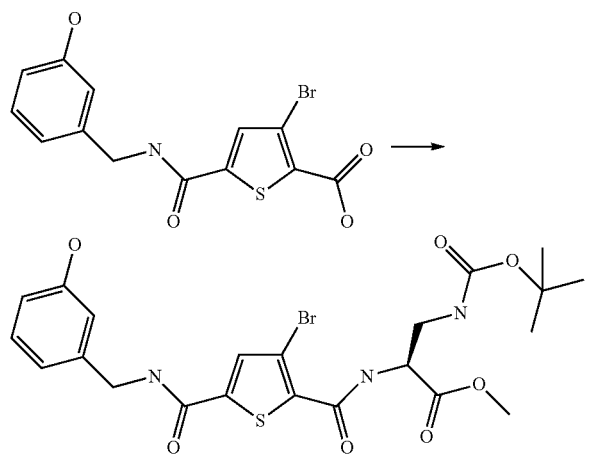

To a solution of 3-Bromo-5-(3-hydroxy-benzylcarbamoyl)-thiophene-2-carboxylic acid (0.11 g, 0.31 mmol) in anhydrous DMF (6 mL) was added triethylamine (0.13 mL, 0.94 mmol), HBTU (0.141 g, 0.37 mmol), HOBT (0.050 g, 0.37 mmol), and H-DAP(Boc)OMe hydrochloride (0.118 g, 0.46 mmol). The mixture was stirred at room temperature 15 h, treated with EtOAc (30 mL), washed with brine, dried over sodium sulfate, filtered and evaporated. The solid residue was purified by column (30-60% EtOAc in hexane) to give 0.142 g (82%) yellow oil.

Preparation (S)-3-Amino-2-{[3-bromo-5-(3-hydroxy-benzylcarbamoyl)-thiophene-2-carbonyl]-amino}-propionic acid methyl ester trifluoro-acetic acid salt

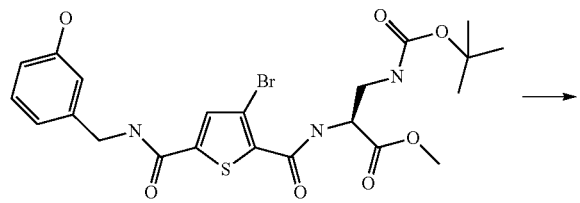

-continued

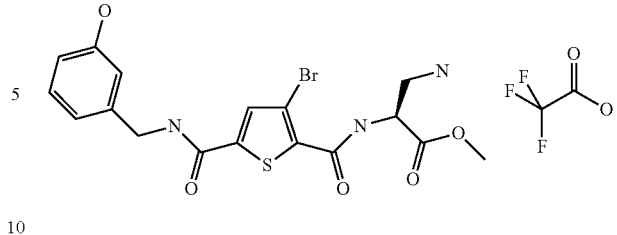

To a solution of (S)-2-{[3-Bromo-5-(3-hydroxy-benzylcarbamoyl)-thiophene-2-carbonyl]-amino}-3-tert-butoxycarbonylamino-propionic acid methyl ester (0.142 g, 0.26 mmol) in DCM (5 mL) was added TFA (0.5 mL). The mixture was stirred at room temperature 1 h and evaporated to give crude product which was used without further purification.

Preparation of (S)-2-{[3-Bromo-5-(3-hydroxy-benzylcarbamoyl)-thiophene-2-carbonyl]-amino}-3-[(thiophene-2-carbonyl)-amino]-propionic acid methyl ester

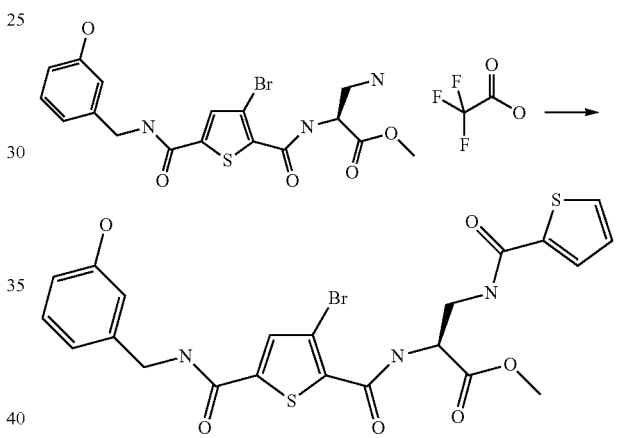

To a solution of (S)-3-Amino-2-{[3-bromo-5-(3-hydroxy-benzylcarbamoyl)-thiophene-2-carbonyl]-amino}-propionic acid methyl ester trifluoro-acetic acid salt (0.26 mmol) in anhydrous DMF (7 mL) was added triethylamine (0.11 mL, 0.78 mmol), HBTU (0.15 g, 0.39 mmol), HOBt (0.042 g, 0.31 mmol), and 2-Thiophenecarboxylic acid (0.050 g, 0.39 mmol). The mixture was stirred at room temperature 15 h, treated with EtOAc (50 mL), washed with brine, dried over sodium sulfate, filtered and evaporated. The solid residue was purified by column (30-50% EtOAc in hexane) to give 0.0242 g (16%) colorless oil. MS m/e 567.8 (M+H$^+$).

Preparation of 5-(4-Fluoro-3-hydroxy-benzylcarbamoyl)-3-methyl-thiophene-2-carboxylic acid methyl ester

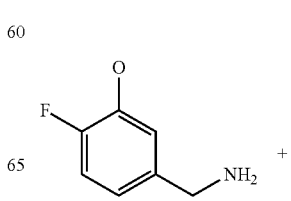

-continued

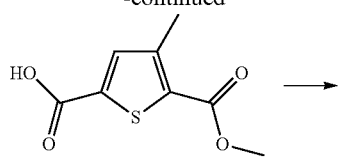

over sodium sulfate, filtered and evaporated to give the title compound, 320 mg (84%). MS m/e 309.8 (M+H⁺).

Preparation of (S)-3-tert-Butoxycarbonylamino-2-{[5-(4-fluoro-3-hydroxy-benzylcarbamoyl)-3-methyl-thiophene-2-carbonyl]-amino}-propionic acid methyl ester

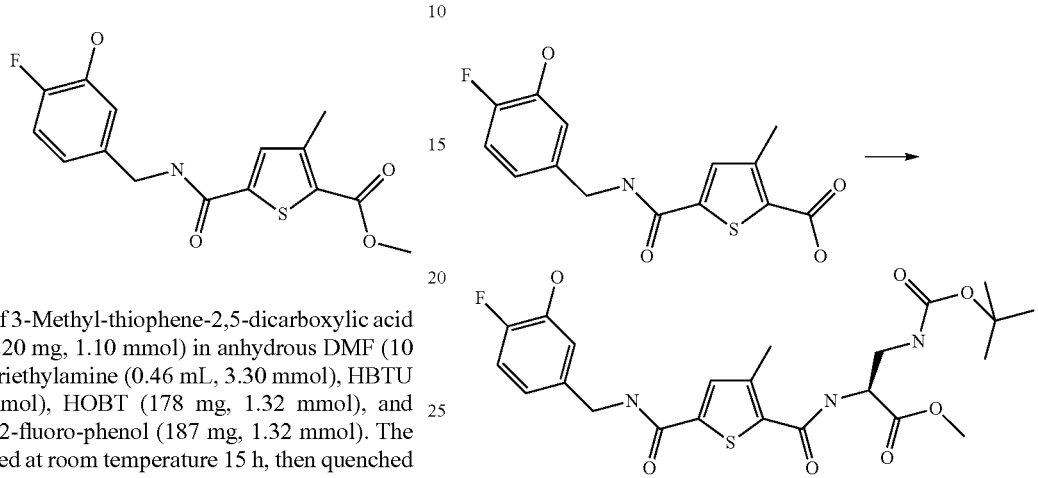

To a solution of 3-Methyl-thiophene-2,5-dicarboxylic acid 2-methyl ester (220 mg, 1.10 mmol) in anhydrous DMF (10 mL) was added triethylamine (0.46 mL, 3.30 mmol), HBTU (0.63 g, 1.65 mmol), HOBT (178 mg, 1.32 mmol), and 5-Aminomethyl-2-fluoro-phenol (187 mg, 1.32 mmol). The mixture was stirred at room temperature 15 h, then quenched by pouring into EtOAc. The organic layer was washed with brine, dried over Na₂SO₄ and concentrated under reduced pressure. The residue was purified by flash chromatography with 60-80% EtOAc in hexane to afford the desired product (0.3472 g, 98% yield).

Preparation of 3-Bromo-5-(4-fluoro-3-hydroxy-benzylcarbamoyl)-thiophene-2-carboxylic acid

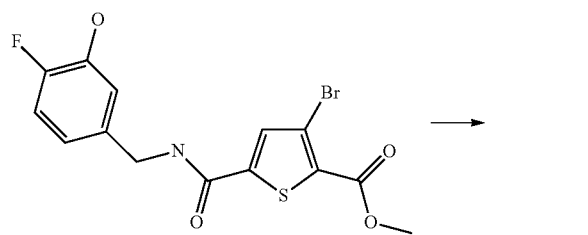

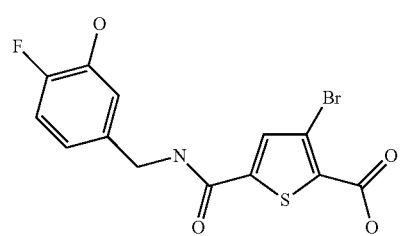

A mixture of 5-(4-Fluoro-3-hydroxy-benzylcarbamoyl)-3-methyl-thiophene-2-carboxylic acid methyl ester (398 mg, 1.23 mmol), lithium hydroxide monohydrate (520, mg, 12.31 mmol), THF (10 mL) and water (12 mL) was stirred 15 h, acidified with 1N HCl and extracted with EtOAc (×3). The organic extracts were combined, washed with brine, dried To a solution of 5-(4-Fluoro-3-hydroxy-benzylcarbamoyl)-3-methyl-thiophene-2-carboxylic acid (0.32 g, 0.99 mmol) in anhydrous DMF (10 mL) was added triethylamine (0.41 mL, 2.97 mmol), HBTU (0.45 g, 1.19 mmol), HOBT (0.16 g, 1.19 mmol), and H-DAP(Boc)OMe hydrochloride (0.38 g, 1.48 mmol). The mixture was stirred at room temperature 2 d, treated with EtOAc (100 mL), washed with brine, dried over sodium sulfate, filtered and evaporated. The solid residue was purified by column (30-70% EtOAc in hexane) to give 0.370 g (73%) white foam.

Preparation of (S)-3-Amino-2-{[5-(4-fluoro-3-hydroxy-benzylcarbamoyl)-3-methyl-thiophene-2-carbonyl]-amino}-propionic acid methyl ester trifluoroacetic acid salt

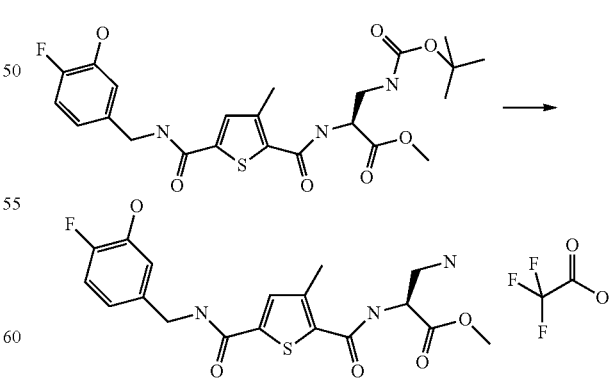

To a solution of (S)-3-tert-Butoxycarbonylamino-2-{[5-(4-fluoro-3-hydroxy-benzylcarbamoyl)-3-methyl-thiophene-2-carbonyl]-amino}-propionic acid methyl ester (0.370 g, 0.73 mmol) in DCM (10 mL) was added TFA (5 mL). The mixture was stirred at room temperature 2 h and evaporated to give crude product which was used without further purification.

Preparation of (S)-2-{[5-(4-Fluoro-3-hydroxy-benzylcarbamoyl)-3-methyl-thiophene-2-carbonyl]-amino}-3-[(thiophene-2-carbonyl)-amino]-propionic acid methyl ester

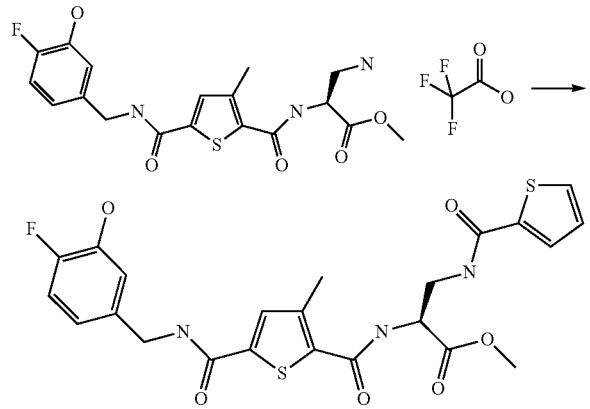

To a solution of (S)-3-Amino-2-{[5-(4-fluoro-3-hydroxy-benzylcarbamoyl)-3-methyl-thiophene-2-carbonyl]-amino}-propionic acid methyl ester trifluoro-acetic acid salt (0.73 mmol) in anhydrous DMF (15 mL) was added triethylamine (0.31 mL, 2.19 mmol), HBTU (0.33 g, 0.88 mmol), HOBt (0.12 g, 0.88 mmol), and 2-Thiophenecarboxylic acid (0.098 g, 0.77 mmol). The mixture was stirred at room temperature 15 h, treated with EtOAc (50 mL), washed with brine, dried over sodium sulfate, filtered and evaporated. The solid residue was purified by column (30-100% EtOAc in hexane). Material off the column was determined to be the mixed ester. It was refluxed in MeOH (20 ml) containing a catalytic amount of pTsOH for 15 h, purified by column (60-75% EtOAc in hexane). to give 0.014 g (4%) colorless oil. MS m/e 519.9 (M+H$^+$).

Preparation of 3-Cyano-5-methyl-thiophene-2-carboxylic acid methyl ester

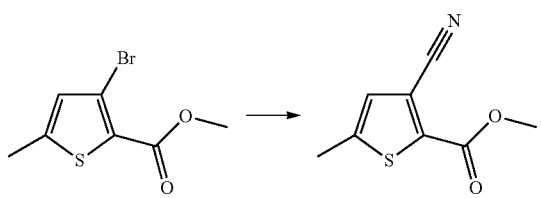

A mixture of 3-Bromo-5-methyl-thiophene-2-carboxylic acid methyl ester (0.54 g, 2.3 mmol), and Copper cyanide (0.27 g, 2.99 mmol) in NMP (3 ml) was heated in a microwave at 220° C. for 30 min. The reaction mixture was cooled and diluted with EtOAc. The organic layer was washed with aqueous NH4OH, and brine, dried over sodium sulfate, filtered and evaporated. The solid residue was purified by column (0-20% EtOAc in hexane) to give 0.31 g (74%) white solid.

Preparation of 5-Bromomethyl-3-cyano-thiophene-2-carboxylic acid methyl ester

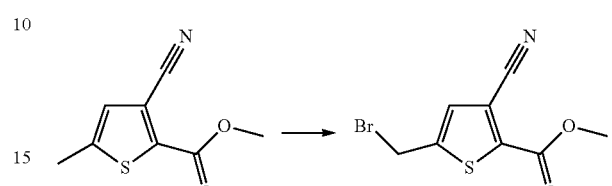

A mixture of 3-Cyano-5-methyl-thiophene-2-carboxylic acid methyl ester (0.51 g, 2.81 mmol), NBS (1.05 g, 5.91 mmol), and ACHN (0.032 g, 0.14 mmol) in CCl$_4$ (4 ml) was refluxed in a pressure tube 15 h. The reaction mixture was cooled and evaporated. The residue was purified by column (0-15% EtOAc in hexane) to give 0.16 g (22%) yellow solid.

Preparation of 3-Cyano-5-hydroxymethyl-thiophene-2-carboxylic acid methyl ester

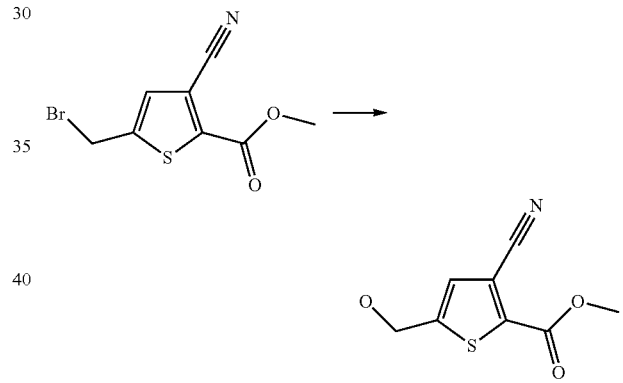

A mixture of 5-Bromomethyl-3-cyano-thiophene-2-carboxylic acid methyl ester (0.89 g, 3.42 mmol) and water (15 ml) in THF (2 ml) was heated at 70° C. for 2 d. The reaction mixture was cooled. The reaction mixture was poured into EtOAc (50 ml), washed with brine, dried over sodium sulfate, filtered and evaporated. The residue was purified by column (0-40% EtOAc in hexane) to give 0.1114 g (17%) yellow solid product.

Preparation of 3-Cyano-thiophene-2,5-dicarboxylic acid 2-methyl ester

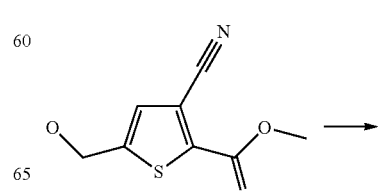

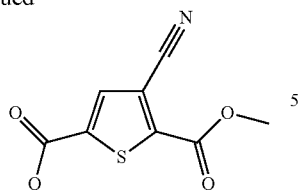

A mixture of 3-Cyano-5-hydroxymethyl-thiophene-2-carboxylic acid methyl ester (0.1342 g, 0.68 mmol) and Periodic Acid (0.34 g, 1.50 mmol) in MeCN (9.5 ml) was stirred for 30 min. A solution of PCC (0.010 g, 0.015 mmol) in MeCN (0.5 ml) was added. After 1 h, the reaction mixture was diluted with EtOAc (50 ml), washed with sodium sulfite, brine, dried over sodium sulfate, filtered and evaporated. Isolate 0.13 g (90%) of beige solid.

Preparation of 3-Cyano-5-(3-hydroxy-benzylcarbamoyl)-thiophene-2-carboxylic acid methyl ester

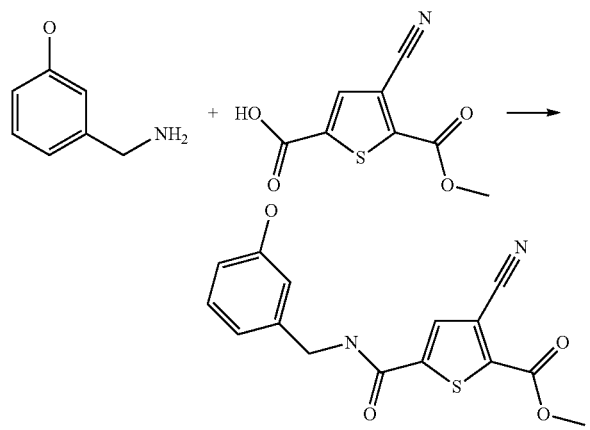

To a solution of 3-Cyano-thiophene-2,5-dicarboxylic acid 2-methyl ester (130 mg, 0.62 mmol) in anhydrous DMF (8 mL) was added triethylamine (0.26 mL, 1.86 mmol), HBTU (0.28 g, 0.74 mmol), HOBT (100 mg, 0.74 mmol), and 3-Aminomethyl-phenol (114 mg, 0.92 mmol). The mixture was stirred at room temperature 15 h, then quenched by pouring into EtOAc. The organic layer was washed with brine, dried over $Na_2SO_4$ and concentrated under reduced pressure. The residue was purified by flash chromatography with 0-50% EtOAc in hexane to afford the desired product (0.033 g, 17% yield).

Preparation of 3-Cyano-5-(3-hydroxy-benzylcarbamoyl)-thiophene-2-carboxylic acid

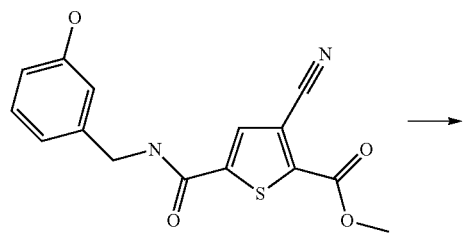

A mixture of 3-Cyano-5-(3-hydroxy-benzylcarbamoyl)-thiophene-2-carboxylic acid methyl ester (33 mg, 0.104 mmol), lithium hydroxide monohydrate (44 mg, 1.04 mmol), THF (2 mL) and water (3 mL) was stirred 15 h, acidified with 1N HCl and extracted with EtOAc (×3). The organic extracts were combined, washed with brine, dried over sodium sulfate, filtered and evaporated to give the title compound, 31.4 mg (100%). MS m/e 302.8 ($M+H^+$).

Preparation of (S)-3-tert-Butoxycarbonylamino-2-{[3-cyano-5-(3-hydroxy-benzylcarbamoyl)-thiophene-2-carbonyl]-amino}-propionic acid methyl ester

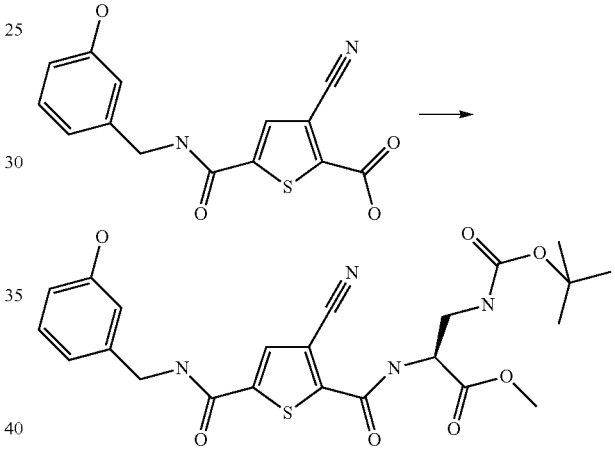

To a solution of 3-Cyano-5-(3-hydroxy-benzylcarbamoyl)-thiophene-2-carboxylic acid (0.031 g, 0.104 mmol) in anhydrous DMF (3 mL) was added triethylamine (0.043 mL, 0.312 mmol), HBTU (0.047 g, 0.125 mmol), HOBT (0.017 g, 0.125 mmol), and H-DAP(Boc)OMe hydrochloride (0.040 g, 0.156 mmol). The mixture was stirred at room temperature 3 h, treated with EtOAc (25 mL), washed with brine, dried over sodium sulfate, filtered and evaporated. The solid residue was purified by column (30-70% EtOAc in hexane) to give 0.0330 g (63%) colorless oil.

Preparation (S)-3-Amino-2-{[3-cyano-5-(3-hydroxy-benzylcarbamoyl)-thiophene-2-carbonyl]-amino}-propionic acid methyl ester hydrochloride

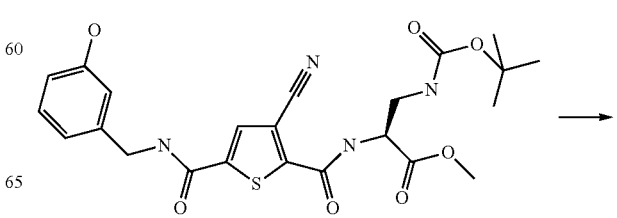

-continued

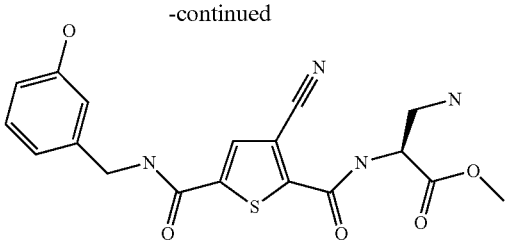

A solution of (S)-3-tert-Butoxycarbonylamino-2-{[3-cyano-5-(3-hydroxy-benzylcarbamoyl)-thiophene-2-carbonyl]-amino}-propionic acid methyl ester (0.033 g, 0.066 mmol)) and 4.0M Hydrogen Chloride in Dioxane (5 mL) was stirred at room temperature 1 h and evaporated to give crude product which was used without further purification.

Preparation of (S)-2-{[3-Cyano-5-(3-hydroxy-benzylcarbamoyl)-thiophene-2-carbonyl]-amino}-3-[(thiophene-2-carbonyl)-amino]-propionic acid methyl ester

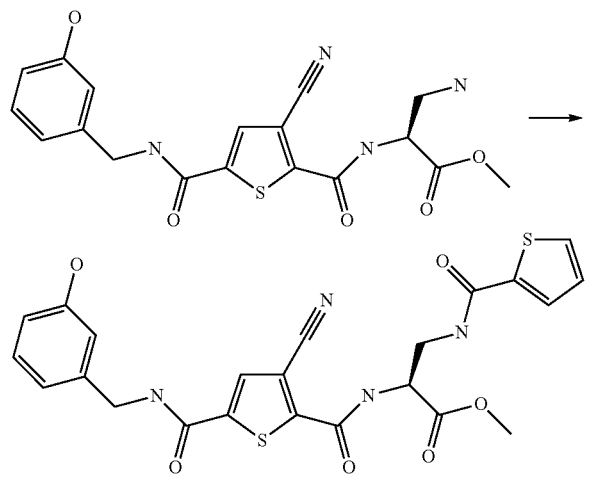

To a solution of (S)-3-Amino-2-{[3-cyano-5-(3-hydroxy-benzylcarbamoyl)-thiophene-2-carbonyl]-amino}-propionic acid methyl ester hydrochloride (0.066 mmol) in anhydrous DMF (5 mL) was added triethylamine (0.03 mL, 0.20 mmol), HBTU (0.030 g, 0.079 mmol), HOBt (0.011 g, 0.079 mmol), and 2-Thiophenecarboxylic acid (0.009 g, 0.069 mmol). The mixture was stirred at room temperature 1.5 h, treated with EtOAc (20 mL), washed with brine, dried over sodium sulfate, filtered and evaporated. The solid residue was purified by column (30-60% EtOAc in hexane) to give 0.0162 g (16%) colorless oil. MS m/e 512.9 (M+H$^+$).

Preparation of 3-Cyano-5-[(1H-indazol-4-ylmethyl)-carbamoyl]-thiophene-2-carboxylic acid methyl ester

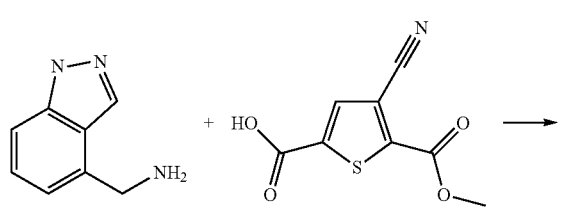

-continued

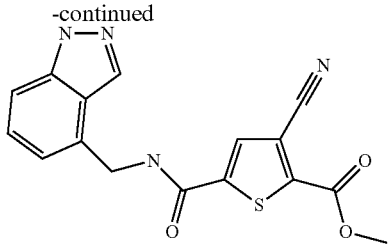

To a solution of 3-Cyano-thiophene-2,5-dicarboxylic acid 2-methyl ester (240 mg, 1.14 mmol) in anhydrous DMF (6 mL) was added triethylamine (0.64 mL, 4.56 mmol), HBTU (0.52 g, 1.36 mmol), HOBT (0.180 mg, 1.36 mmol), and C-(1H-Indazol-4-yl)-methylamine dihydrochloride (300 mg, 1.36 mmol). The mixture was stirred at room temperature 15 h, then quenched by pouring into EtOAc. The organic layer was washed with brine, dried over Na$_2$SO$_4$ and concentrated under reduced pressure. The residue was purified by flash chromatography with 30-100% EtOAc in hexane to afford the desired product (0.2627 g, 67% yield).

Preparation of 3-Cyano-5-[(1H-indazol-4-ylmethyl)-carbamoyl]-thiophene-2-carboxylic acid

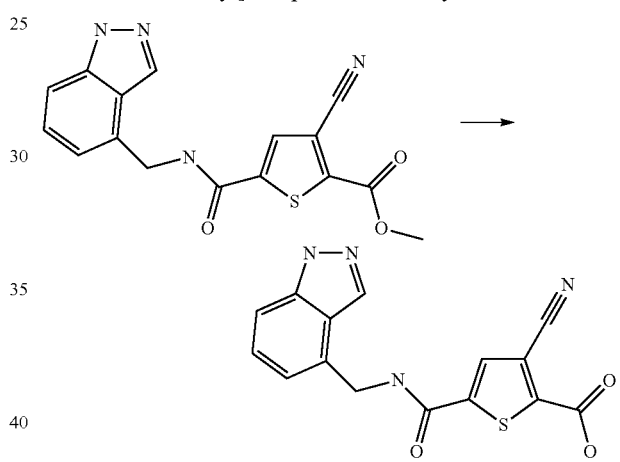

A mixture of 3-Cyano-5-[(1H-indazol-4-ylmethyl)-carbamoyl]-thiophene-2-carboxylic acid methyl ester (262.7 mg, 0.77 mmol), lithium hydroxide monohydrate (250 mg, 6.17 mmol), THF (8 mL) and water (10 mL) was stirred 4 h, acidified with 1N HCl and extracted with EtOAc (×3). The organic extracts were combined, washed with brine, dried over sodium sulfate, filtered and evaporated to give the title compound, 0.1369 g (54%). MS m/e 327.0 (M+H$^+$).

Preparation of (S)-3-tert-Butoxycarbonylamino-2-({3-cyano-5-[(1H-indazol-4-ylmethyl)-carbamoyl]-thiophene-2-carbonyl}-amino)-propionic acid methyl ester

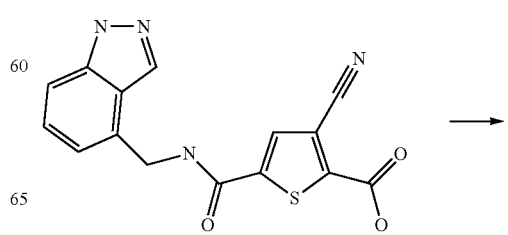

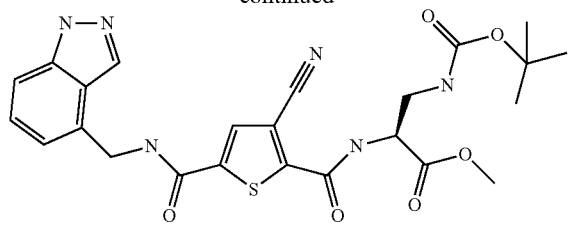

To a solution of 3-Cyano-5-[(1H-indazol-4-ylmethyl)-carbamoyl]-thiophene-2-carboxylic acid (0.1369 g, 0.42 mmol) in anhydrous DMF (10 mL) was added triethylamine (0.18 mL, 1.26 mmol), HBTU (0.19 g, 0.50 mmol), HOBT (0.068 g, 0.50 mmol), and H-DAP(Boc)OMe hydrochloride (0.13 g, 0.50 mmol). The mixture was stirred at room temperature 15 h, treated with EtOAc (40 mL), washed with brine, dried over sodium sulfate, filtered and evaporated. The solid residue was purified by column (30-100% EtOAc in hexane) to give 0.2008 g (91%) colorless oil.

Preparation of (S)-3-Amino-2-({3-cyano-5-[(1H-indazol-4-ylmethyl)-carbamoyl]-thiophene-2-carbonyl}-amino)-propionic acid methyl ester hydrochloride

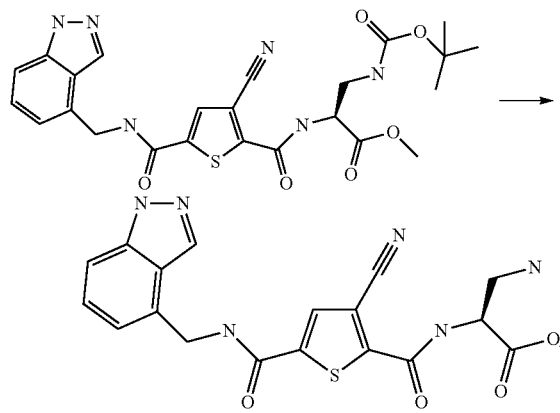

A solution of (S)-3-tert-Butoxycarbonylamino-2-({3-cyano-5-[(1H-indazol-4-ylmethyl)-carbamoyl]-thiophene-2-carbonyl}-amino)-propionic acid methyl ester (0.2008 g, 0.38 mmol)) and 4.0M Hydrogen Chloride in Dioxane (10 mL) and MeOH (3 ml) was stirred at room temperature 1.5 h and evaporated to give crude product which was used without further purification.

Preparation of (S)-2-({3-Cyano-5-[(1H-indazol-4-ylmethyl)-carbamoyl]-thiophene-2-carbonyl}-amino)-3-(3,5-dihydroxy-benzoylamino)-propionic acid methyl ester

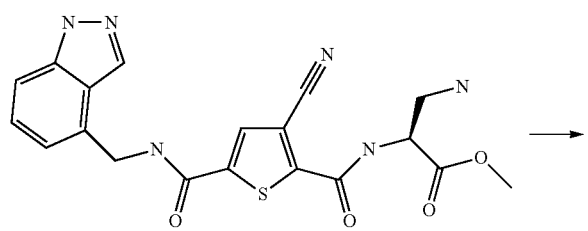

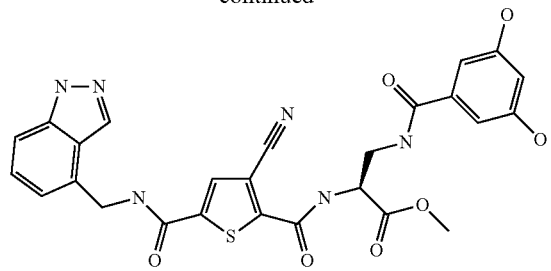

To a solution of (S)-3-Amino-2-({3-cyano-5-[(1H-indazol-4-ylmethyl)-carbamoyl]-thiophene-2-carbonyl}-amino)-propionic acid methyl ester hydrochloride (0.40 mmol) in anhydrous DMF (10 mL) was added triethylamine (0.17 mL, 1.20 mmol), HBTU (0.18 g, 0.048 mmol), HOBt (0.065 g, 0.048 mmol), and 3,5-Dimethoxybenzoic acid (0.062 g, 0.40 mmol). The mixture was stirred at room temperature 1 h, treated with EtOAc (40 mL), washed with brine, dried over sodium sulfate, filtered and evaporated. The solid residue was purified by column (50-100% EtOAc in hexane) to give 0.1241 g (55%) colorless oil. MS m/e 563.0 (M+H$^+$).

Part II: Preparation of Preferred Compounds of the Invention

Example 1

Preparation of (S)-3-(3,5-Difluoro-benzoylamino)-2-({2-[2-(3-hydroxy-phenyl)-acetylamino]-4-methyl-thiazole-5-carbonyl}-amino)-propionic acid

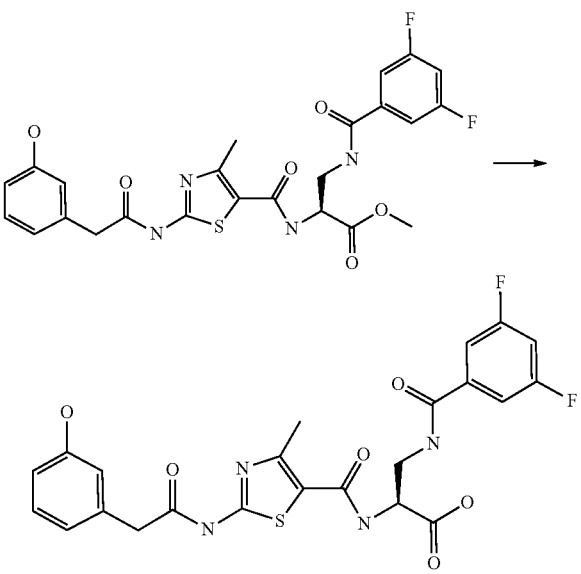

To a mixture of (S)-3-(3,5-Difluoro-benzoylamino)-2-({2-[2-(3-hydroxy-phenyl)-acetylamino]-4-methyl-thiazole-5-carbonyl}-amino)-propionic acid methyl ester (89.9 mg, 0.169 mmol) in THF (4 mL) and water (2 mL) was added lithium hydroxide monohydrate (80 mg, 1.91 mmol) The reaction was stirred at 25° C. for 1.5 h. The reaction mixture was acidified with concentrated HCl and concentrated under reduced pressure. The resulting crude compound was purified by HPLC to give (S)-3-(3,5-Difluoro-benzoylamino)-2-({2-

[2-(3-hydroxy-phenyl)-acetylamino]-4-methyl-thiazole-5-carbonyl}-amino)-propionic acid (51.7 mg, 59%) as a white solid. MS m/e 519.5 (M+H$^+$)

In a similar manner the following compounds were produced:

Example 2

Preparation of (S)-2-({2-[2-(3-Hydroxy-phenyl)-acetylamino]-4-methyl-thiazole-5-carbonyl}-amino)-3-[(thiophene-2-carbonyl)-amino]-propionic acid

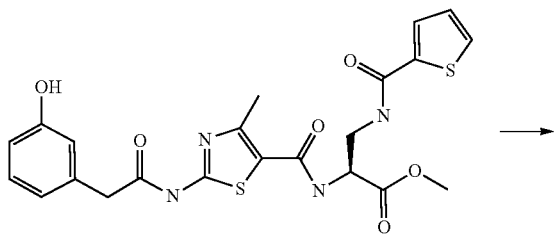

From (S)-2-({2-[2-(3-Hydroxy-phenyl)-acetylamino]-4-methyl-thiazole-5-carbonyl}-amino)-3-[(thiophene-2-carbonyl)-amino]-propionic acid methyl ester there was obtained (S)-2-({2-[2-(3-Hydroxy-phenyl)-acetylamino]-4-methyl-thiazole-5-carbonyl}-amino)-3-[(thiophene-2-carbonyl)-amino]-propionic acid (43%) as a white solid. MS m/e 489.5 (M+H$^+$)

Example 3

Preparation of (S)-2-({2-[2-(3-Hydroxy-phenyl)-acetylamino]-thiazole-5-carbonyl}-amino)-3-[(thiophene-2-carbonyl)-amino]-propionic acid

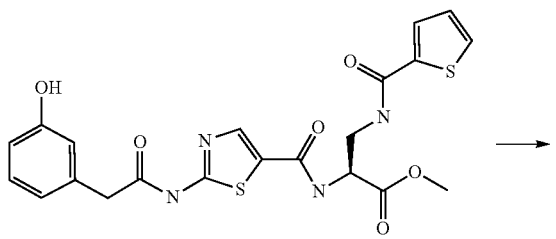

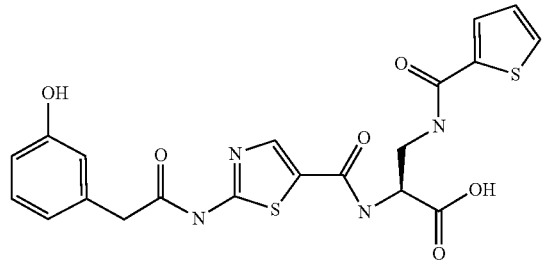

From (S)-2-({2-[2-(3-Hydroxy-phenyl)-acetylamino]-thiazole-5-carbonyl}-amino)-3-[(thiophene-2-carbonyl)-amino]-propionic acid methyl ester there was obtained (S)-2-({2-[2-(3-Hydroxy-phenyl)-acetylamino]-thiazole-5-carbonyl}-amino)-3-[(thiophene-2-carbonyl)-amino]-propionic acid (43%) as a white solid. MS m/e 474.5 (M+H$^+$)

Example 4

Preparation of (S)-3-Benzoylamino-2-([2-[2-(3-hydroxy-phenyl)-acetylamino]-4-methyl-thiazole-5-carbonyl]-amino)-propionic acid

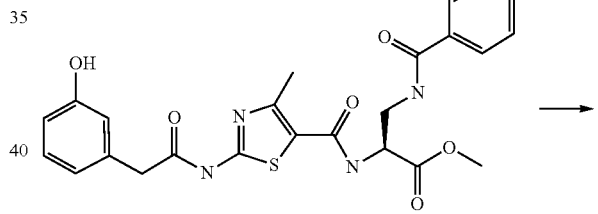

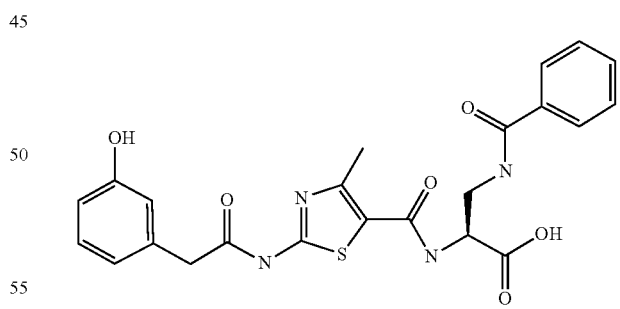

From S)-3-Benzoylamino-2-({2-[2-(3-hydroxy-phenyl)-acetylamino]-4-methyl-thiazole-5-carbonyl}-amino)-propionic acid methyl ester there was obtained (S)-3-Benzoylamino-2-({2-[2-(3-hydroxy-phenyl)-acetylamino]-4-methyl-thiazole-5-carbonyl}-amino)-propionic acid (61%) as a white solid. MS m/e 483.5 (M+H$^+$)

Example 5

Preparation of (S)-3-(3-Hydroxy-benzoylamino)-2-({2-[2-(3-hydroxy-phenyl)-acetylamino]-4-methyl-thiazole-5-carbonyl}-amino)-propionic acid

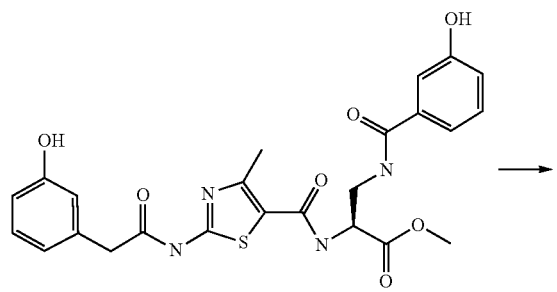

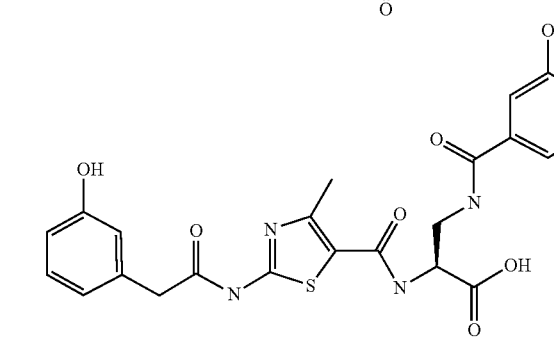

From (S)-3-(3-Hydroxy-benzoylamino)-2-({2-[2-(3-hydroxy-phenyl)-acetylamino]-4-methyl-thiazole-5-carbonyl}-amino)-propionic acid methyl ester there was obtained (S)-3-(3-Hydroxy-benzoylamino)-2-({2-[2-(3-hydroxy-phenyl)-acetylamino]-4-methyl-thiazole-5-carbonyl}-amino)-propionic acid (40.2%) as a white solid. MS m/e 499.5 (M+H$^+$).

Example 6

Preparation of (S)-3-(3,5-Dihydroxy-benzoylamino)-2-({2-[2-(3-hydroxy-phenyl)-acetylamino]-4-methyl-thiazole-5-carbonyl}-amino)-propionic acid

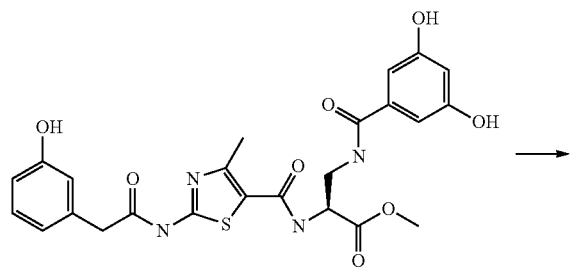

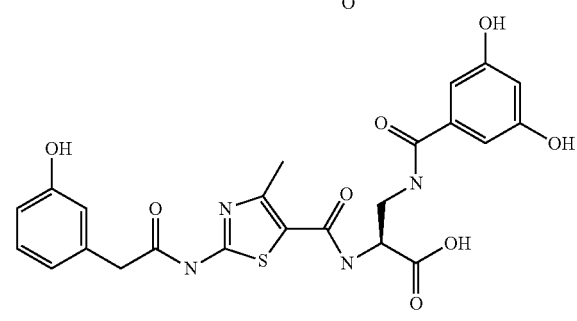

From (S)-3-(3,5-Dihydroxy-benzoylamino)-2-({2-[2-(3-hydroxy-phenyl)-acetylamino]-4-methyl-thiazole-5-carbonyl}-amino)-propionic acid methyl ester there was obtained (S)-3-(3,5-Dihydroxy-benzoylamino)-2-({2-[2-(3-hydroxy-phenyl)-acetylamino]-4-methyl-thiazole-5-carbonyl}-amino)-propionic acid (33%) as a white solid. MS m/e 515.5 (M+H$^+$).

Example 7

Preparation of (S)-2-({2-[2-(3-Hydroxy-phenyl)-acetylamino]-4-methyl-thiazole-5-carbonyl}-amino)-3-[(thiophene-3-carbonyl)-amino]-propionic acid

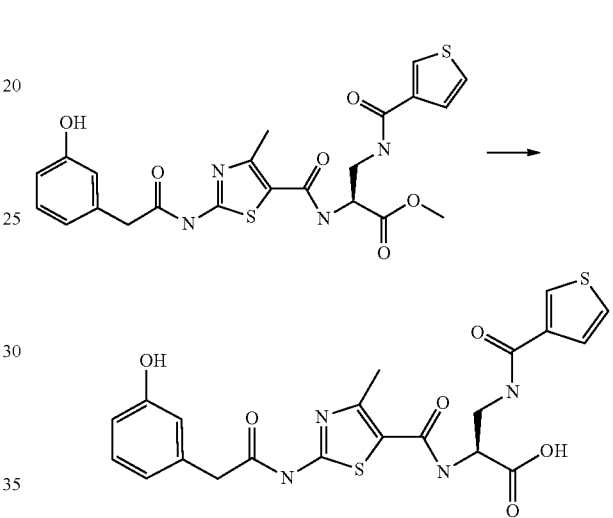

From (S)-2-({2-[2-(3-Hydroxy-phenyl)-acetylamino]-4-methyl-thiazole-5-carbonyl}-amino)-3-[(thiophene-3-carbonyl)-amino]-propionic acid methyl ester was obtained (S)-2-({2-[2-(3-Hydroxy-phenyl)-acetylamino]-4-methyl-thiazole-5-carbonyl}-amino)-3-[(thiophene-3-carbonyl)-amino]-propionic acid (31%) as an off white solid. MS m/e 489.5 (M+H$^+$).

Example 8

Preparation of (S)-2-({4-Chloro-2-[2-(3-hydroxy-phenyl)-acetylamino]-thiazole-5-carbonyl}-amino)-3-[(thiophene-2-carbonyl)-amino]-propionic acid

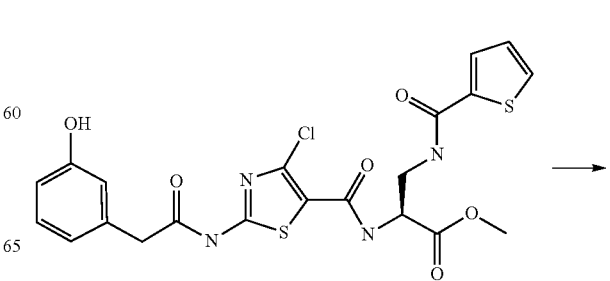

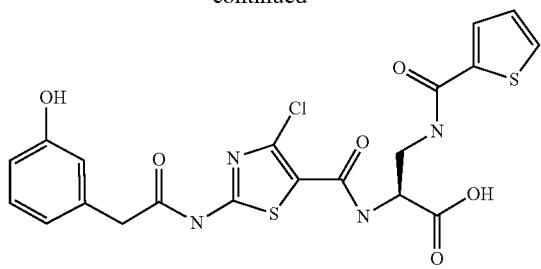

From (S)-2-({4-Chloro-2-[2-(3-hydroxy-phenyl)-acetylamino]-thiazole-5-carbonyl}-amino)-3-[(thiophene-2-carbonyl)-amino]-propionic acid methyl ester there was obtained (S)-2-({4-Chloro-2-[2-(3-hydroxy-phenyl)-acetylamino]-thiazole-5-carbonyl}-amino)-3-[(thiophene-2-carbonyl)-amino]-propionic acid as an off white solid. (42%) as an off white solid. MS m/e 509.9 (M+H$^+$).

Example 9

(S)-2-([2-[2-(3-Hydroxy-phenyl)-acetylamino]-4-trifluoromethyl-thiazole-5-carbonyl]-amino)-3-[(thiophene-2-carbonyl)-amino]-propionic acid

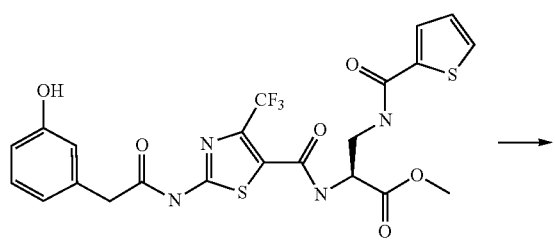

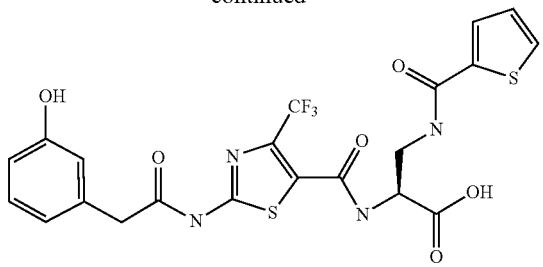

From (S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid methyl ester there was obtained (S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid (23%) as a white solid. MS m/e 543.5 (M+H$^+$).

Example 10

Preparation of (S)-3-(3,5-Dihydroxy-benzoylamino)-2-({2-[3-(3-hydroxy-phenyl)-propionylamino]-4-methyl-thiazole-5-carbonyl}-amino)-propionic acid

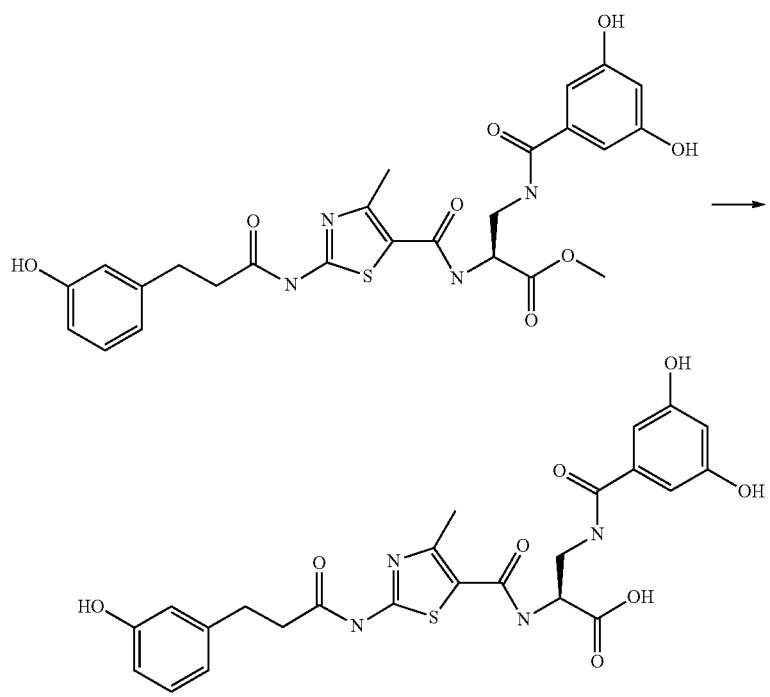

From (S)-3-(3,5-Dihydroxy-benzoylamino)-2-({2-[3-(3-hydroxy-phenyl)-propionyl-amino]-4-methyl-thiazole-5-carbonyl}-amino)-propionic acid methyl ester there was obtained(S)-3-(3,5-Dihydroxy-benzoylamino)-2-({2-[3-(3-hydroxy-phenyl)-propionyl-amino]-4-methyl-thiazole-5-carbonyl}-amino)-propionic acid (73%) as a white solid. MS m/e 529.5 (M+H⁺).

Example 11

Preparation of (S)-2-([2-[3-(3-Hydroxy-phenyl)-propionylamino]-4-methyl-thiazole-5-carbonyl]-amino)-3-[(thiophene-2-carbonyl)-amino]-propionic acid

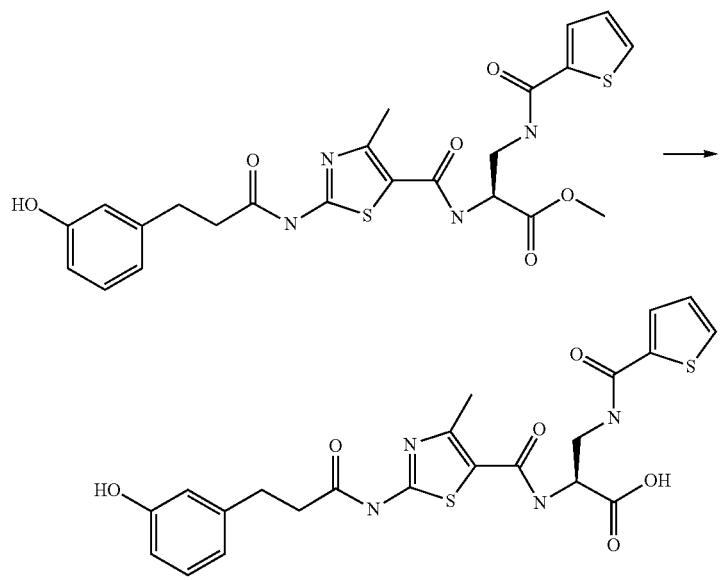

From (S)-2-({2-[3-(3-Hydroxy-phenyl)-propionylamino]-4-methyl-thiazole-5-carbonyl}-amino)-3-[(thiophene-2-carbonyl)-amino]-propionic acid methyl ester there was obtained (S)-2-({2-[3-(3-Hydroxy-phenyl)-propionylamino]-4-methyl-thiazole-5-carbonyl}-amino)-3-[(thiophene-2-carbonyl)-amino]-propionic acid (80.6%) as a white solid. MS m/e 503.5 (M+H⁺).

Example 12

Preparation of (S)-3-(3,5-Dihydroxy-benzoylamino)-2-({2-[2-(3-hydroxy-phenyl)-ethylamino]-4-methyl-thiazole-5-carbonyl}-amino)-propionic acid

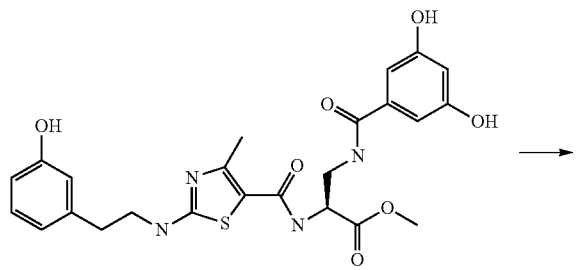

-continued

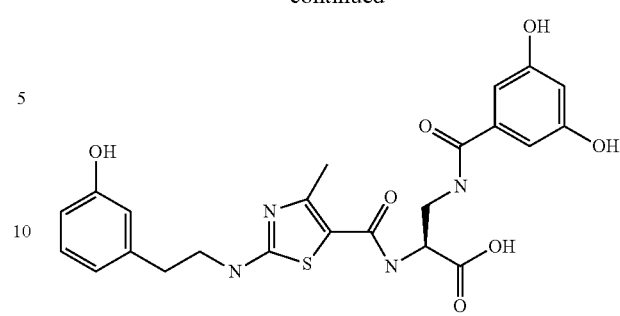

From (S)-3-(3,5-Dihydroxy-benzoylamino)-2-({2-[2-(3-hydroxy-phenyl)-ethylamino]-4-methyl-thiazole-5-carbonyl}-amino)-propionic acid methyl ester there was obtained (S)-3-(3,5-Dihydroxy-benzoylamino)-2-({2-[2-(3-hydroxy-phenyl)-ethylamino]-4-methyl-thiazole-5-carbonyl}-amino)-propionic acid (34%) as an off white solid. MS m/e 501.5 (M+H⁺).

Example 13

Preparation of (S)-2-({2-[3-(3-Hydroxy-phenyl)-propoxy]-4-methyl-thiazole-5-carbonyl}-amino)-3-[(thiophene-2-carbonyl)-amino]-propionic acid

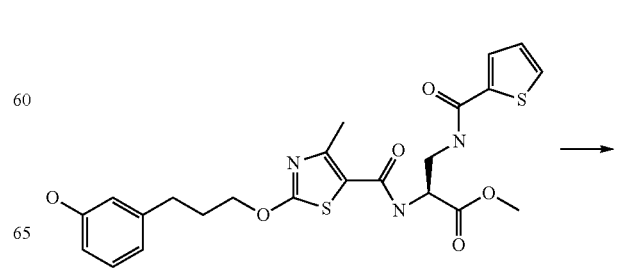

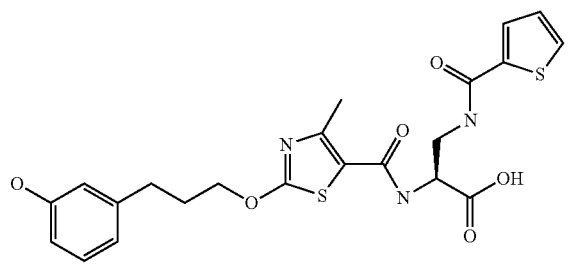

From (S)-2-({2-[3-(3-Hydroxy-phenyl)-propoxy]-4-methyl-thiazole-5-carbonyl}-amino)-3-[(thiophene-2-carbonyl)-amino]-propionic acid methyl ester there was obtained (S)-2-({2-[3-(3-Hydroxy-phenyl)-propoxy]-4-methyl-thiazole-5-carbonyl}-amino)-3-[(thiophene-2-carbonyl)-amino]-propionic acid (72%) as white solid. MS m/e 490.5 (M+H⁺).

Example 14

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid

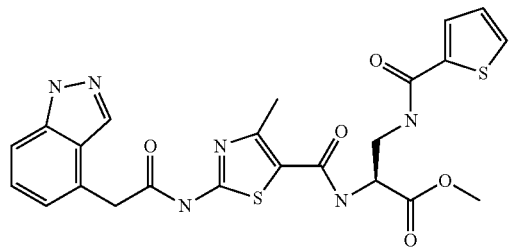

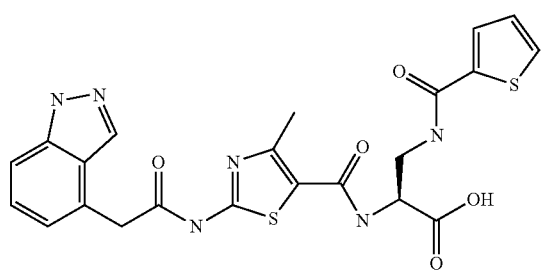

A mixture of the (S)-2-{[2-(2-1H-Indazol-4-yl-acetylamino)-4-methyl-thiazole-5-carbonyl]-amino}-3-[(thiophene-2-carbonyl)-amino]-propionic acid methyl ester (34 mg, 0.0646 mmol), lithium hydroxide monohydrate (32 mg, 0.763 mmol), THF (2 mL) and water (1 mL) was stirred at 25° C. for 1½ h. Aqueous 2N HCl was added and the reaction mixture was stirred for 2 hrs and then concentrated under reduced pressure. The resulting crude product was purified by HPLC to give (S)-2-{[2-(2-1H-Indazol-4-yl-acetylamino)-4-methyl-thiazole-5-carbonyl]-amino}-3-[(thiophene-2-carbonyl)-amino]-propionic acid (21 mg, 63.5%) as a white solid. MS m/e 513.5 (M+H⁺).

In a similar manner the following compounds were produced:

Example 15

Preparation of (S)-3-(3,5-Dihydroxy-benzoylamino)-2-{[2-(2-1H-indazol-4-yl-acetylamino)-4-methyl-thiazole-5-carbonyl}-amino]-propionic acid

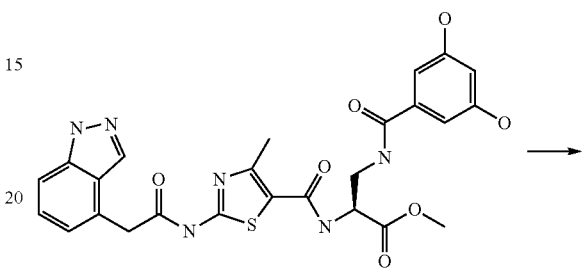

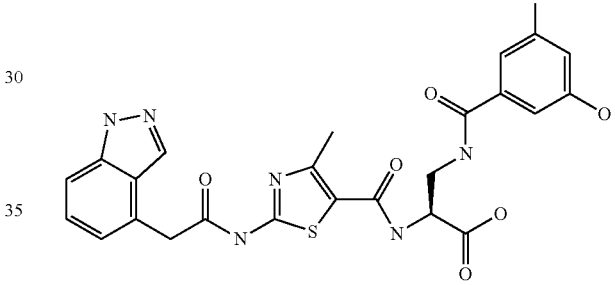

From (S)-3-(3,5-Dihydroxy-benzoylamino)-2-{[2-(2-1H-indazol-4-yl-acetylamino)-4-methyl-thiazole-5-carbonyl]-amino}-propionic acid methyl ester there was obtained (S)-3-(3,5-Dihydroxy-benzoylamino)-2-{[2-(2-1H-indazol-4-yl-acetylamino)-4-methyl-thiazole-5-carbonyl]-amino}-propionic acid (97.1%) as a white solid. MS m/e 539.5 (M+H+).

Example 16

Preparation of (S)-2-{[2-(2-1H-Indazol-4-yl-acetylamino)-4-trifluoromethyl-thiazole-5-carbonyl]-amino}-3-[(thiophene-2-carbonyl)-amino]-propionic acid

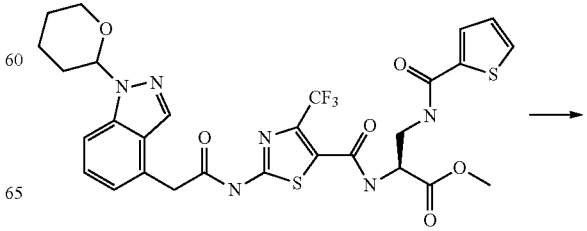

129

-continued

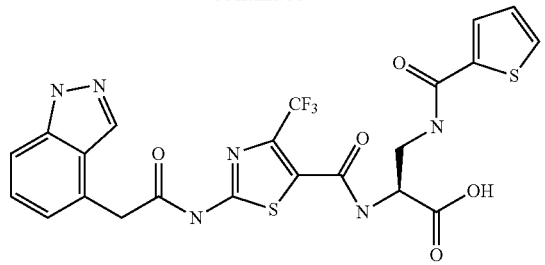

From (S)-2-{[2-(2-1H-Indazol-4-yl-acetylamino)-4-trifluoromethyl-thiazole-5-carbonyl]-amino}-3-[(thiophene-2-carbonyl)-amino]-propionic acid methyl ester there was obtained (S)-2-{[2-(2-1H-Indazol-4-yl-acetylamino)-4-trifluoromethyl-thiazole-5-carbonyl]-amino}-3-[(thiophene-2-carbonyl)-amino]-propionic acid (74.8%) as a white solid. MS m/e 567.5 (M+H+).

Example 17

Preparation of (S)-2-([2-[3-(1H-Indazol-4-yl)-propylamino]-4-methyl-thiazole-5-carbonyl]-amino)-3-[(thiophene-2-carbonyl)-amino]-propionic acid

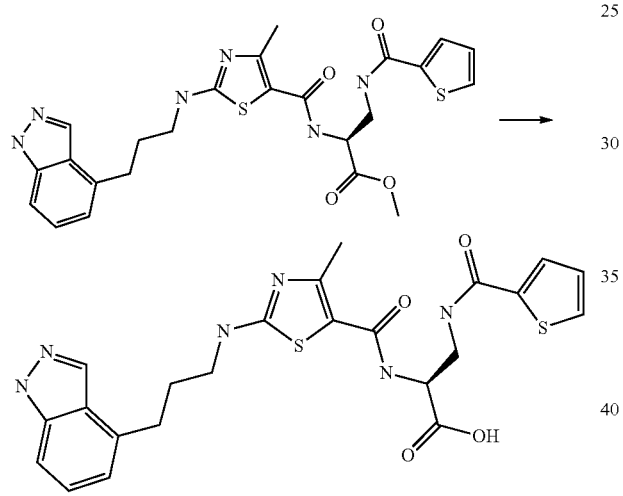

From (S)-2-({2-[3-(1H-Indazol-4-yl)-propylamino]-4-methyl-thiazole-5-carbonyl}-amino)-3-[(thiophene-2-carbonyl)-amino]-propionic acid methyl ester there was obtained (S)-2-({2-[3-(1H-Indazol-4-yl)-propylamino]-4-methyl-thiazole-5-carbonyl}-amino)-3-[(thiophene-2-carbonyl)-amino]-propionic acid (17%) as a white solid. MS m/e 513.6 (M+H$^+$).

Example 18

Preparation of (S)-2-{[2-(2-1H-Indazol-4-yl-acetylamino)-4-methyl-thiazole-5-carbonyl]-amino}-3-[(thiophene-2-carbonyl)-amino]propionic acid 3,3-dimethyl-butyl ester

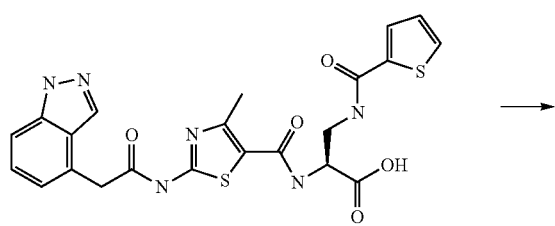

130

-continued

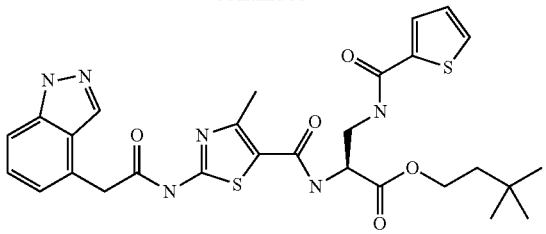

A mixture of the (S)-2-{[2-(2-1H-Indazol-4-yl-acetylamino)-4-methyl-thiazole-5-carbonyl]-amino}-3-[(thiophene-2-carbonyl)-amino]-propionic acid (75.3 mg, 0.147 mmole), 3,3-dimethyl-1-butanol (1 mL, 8.054 mmol) and p-toluenesulfonic acid monohydrate (14.1 mg, 0.0741 mmol) was heated at 100° C. for 2½ hours. The reaction is cooled, neutralized and extracted with ethyl acetate (3×15 mL). The organic layers were combined, washed with brine (50 mL), dried over MgSO$_4$, filtered and concentrated under reduced pressure. The resulting crude compound was purified by flash chromatography (80% EtOAc in hexanes) to give (S)-2-{[2-(2-1H-Indazol-4-yl-acetylamino)-4-methyl-thiazole-5-carbonyl]-amino}-3-[(thiophene-2-carbonyl)-amino] propionic acid 3,3-dimethyl-butyl ester (31.5 mg, 35.9%) as a white solid. MS m/e 597.7 (M+H$^+$).

In a similar manner, the following compounds were prepared:

Example 19

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid ethyl ester

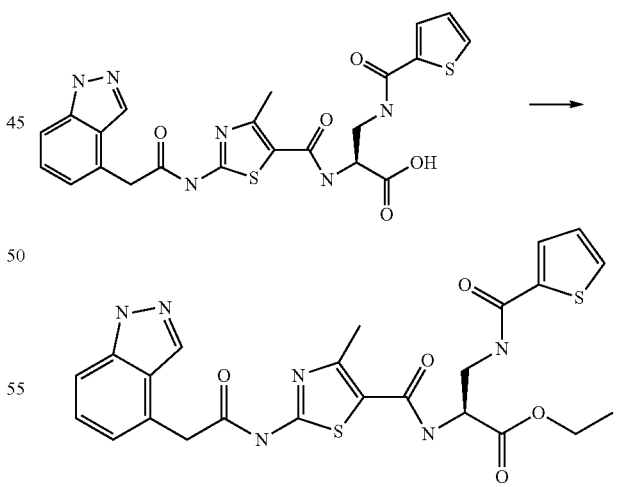

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid ethyl ester (58.6%) as a white solid. MS m/e 541.6 (M+H$^+$).

Example 20

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid isobutyl ester

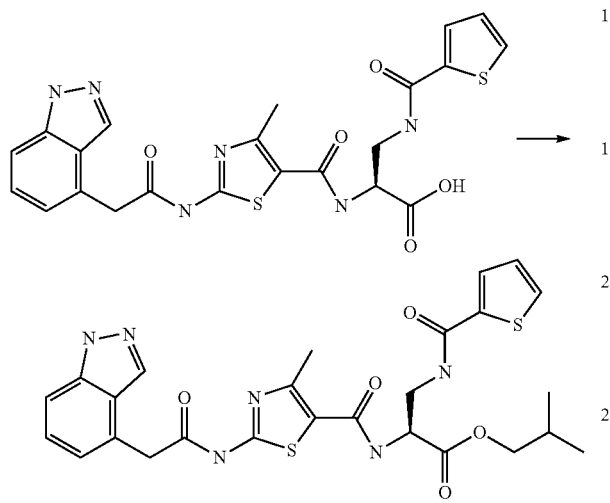

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid isobutyl ester (16.6%) as a white solid. MS m/e 569.7 (M+H$^+$).

Example 21

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid butyl ester

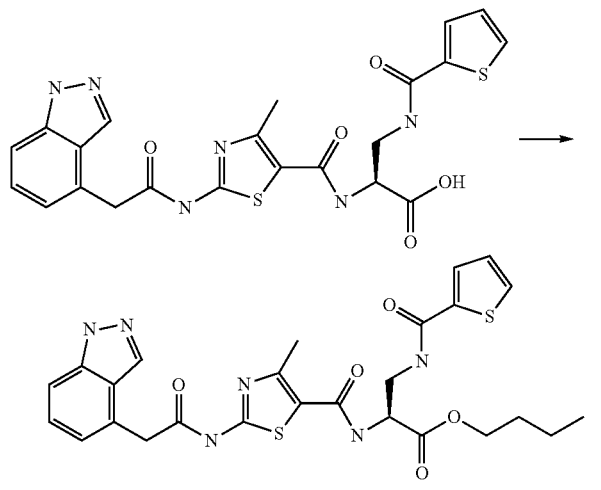

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid butyl ester (68.6%) as a white solid. MS m/e 569.7 (M+H$^+$).

Example 22

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid 1-ethyl-propyl ester

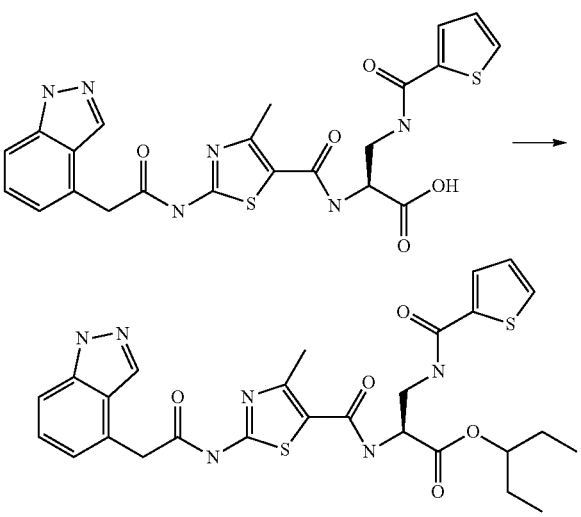

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid 1-ethyl-propyl ester (39.7%) as a white solid. MS m/e 583.7 (M+H$^+$).

Example 23

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid cyclopentyl ester

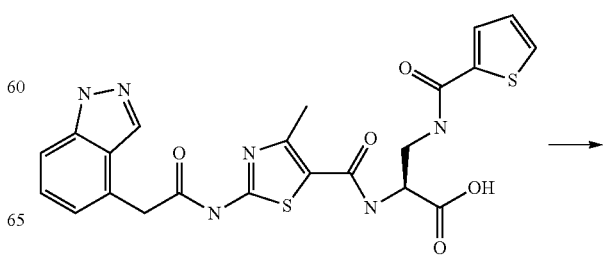

-continued

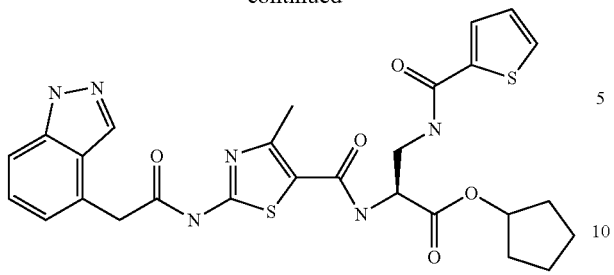

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid cyclopentyl ester (33.2%) as a white solid. MS m/e 581.7 (M+H$^+$).

Example 24

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid 2,2-dimethyl-propyl ester

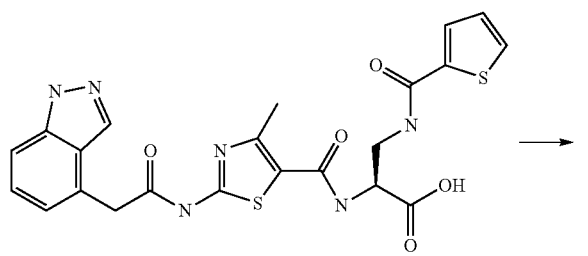

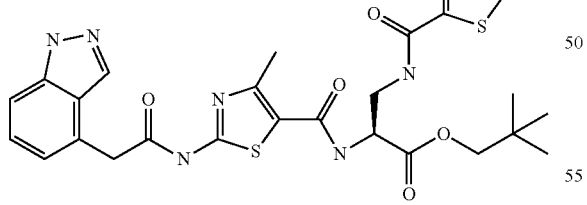

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid 2,2-dimethyl-propyl ester (36.3%) as a white solid. MS m/e 583.7 (M+H$^+$).

Example 25

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid cyclopropylmethyl ester

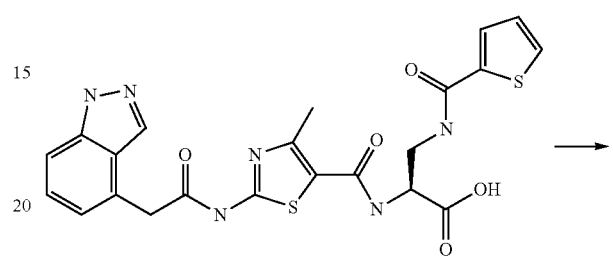

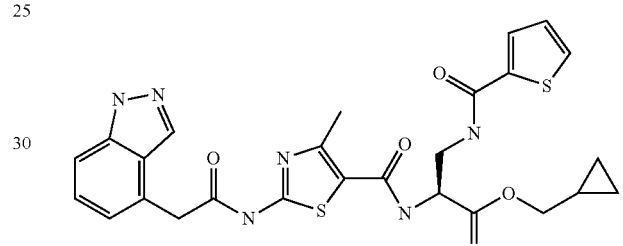

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid cyclopropylmethyl ester (25%) as a white solid. MS m/e 567.6 (M+H$^+$).

Example 26

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid 3-ethoxy-propyl ester

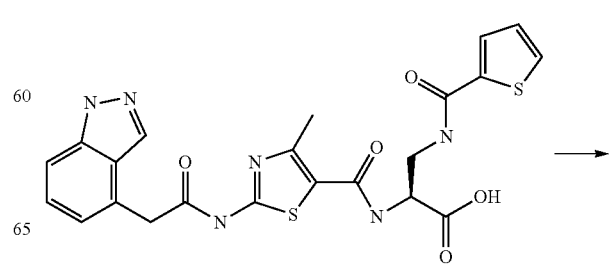

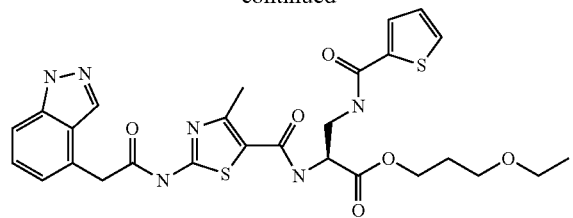

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid 3-ethoxy-propyl ester (54.4%) as a white solid. MS m/e 599.7 (M+H$^+$).

Example 27

Preparation of (S)-2-{[2-(2-1H-Indazol-4-yl-acetylamino)-4-trifluoromethyl-thiazole-5-carbonyl]-amino}-3-[(thiophene-2-carbonyl)-amino]-propionic acid 3-ethoxy-propyl ester

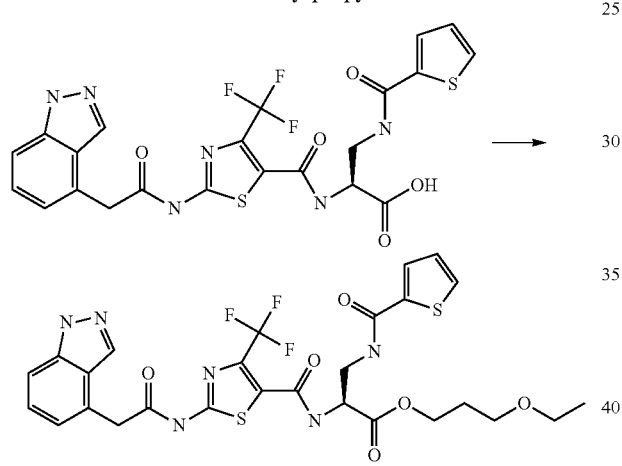

From (S)-2-{[2-(2-1H-Indazol-4-yl-acetylamino)-4-trifluoromethyl-thiazole-5-carbonyl]-amino}-3-[(thiophene-2-carbonyl)-amino]-propionic acid there was obtained (S)-2-{[2-(2-1H-Indazol-4-yl-acetylamino)-4-trifluoromethyl-thiazole-5-carbonyl]-amino}-3-[(thiophene-2-carbonyl)-amino]-propionic acid 3-ethoxy-propyl ester (30.9%) as a white solid. MS m/e 653.7 (M+H$^+$).

Example 28

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid ethyl ester

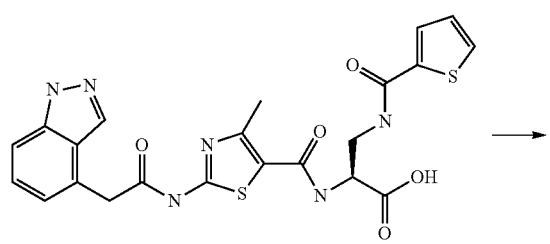

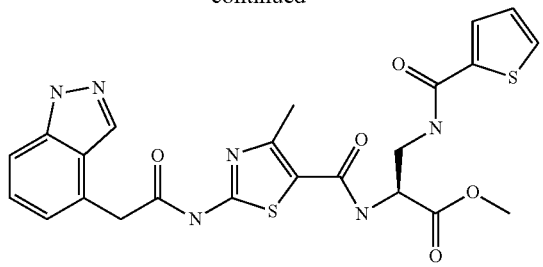

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid ethyl ester (58.6%) as a white solid. MS m/e 527.6 (M+H$^+$).

Example 29

Preparation of (S)-2-{[2-(2-1H-Indazol-4-O-acetylamino)-4-methyl-thiazole-5-carbonyl]-amino}-3-[(thiophene-2-carbonyl)-amino]-propionic acid 2-morpholin-4-yl-ethyl ester

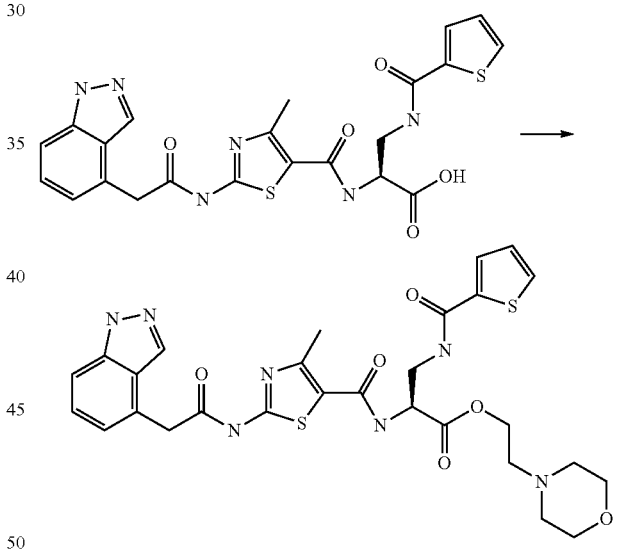

A mixture of (S)-2-{[2-(2-1H-Indazol-4-yl-acetylamino)-4-methyl-thiazole-5-carbonyl]-amino}-3-[(thiophene-2-carbonyl)-amino]-propionic acid (50 mg, 0.0975 mmol), 4-morpholineethanol (1.06 mL, 8.751 mmol) and 1-propanephosphonic acid cyclic anhydride, 50 wt. % solution in ethyl acetate (0.4 mL, 0.672 mmol) in THF (2 mL) was heated at 60°C for 25 h. The reaction mixture was cooled, diluted with 2/1 ethyl acetate/THF (100 mL), water (10 mL), brine (10 mL) and aqueous 1N KHSO$_4$ (10 mL), mixed and separated the layers. The aqueous layer was extracted with 2/1 ethyl acetate/THF (2×50 mL). The organic layers were combined, washed with aqueous saturated sodium bicarbonate solution (30 mL), brine (30 mL), dried over MgSO$_4$, filtered and concentrated under reduced pressure. The resulting crude compound was purified by flash chromatography (ethyl acetate to 10% methanol/ethyl acetate) followed by an ether trituration to give (S)-2-{[2-(2-1H-Indazol-4-yl-acetylamino)-4-methyl-thiazole-5-carbonyl]-amino}-3-[(thiophene-2-carbonyl)-amino]-propionic acid 2-morpholin-4-yl-ethyl ester (11.1 mg, 18.2%) as a white solid. MS m/e 626.7 (M+H⁺).

Example 30

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid 1-(2,2-dimethyl-propionyloxy)-ethyl ester

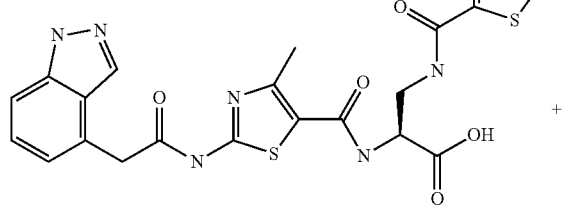

+

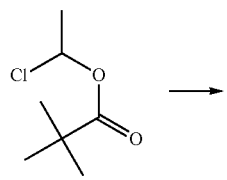

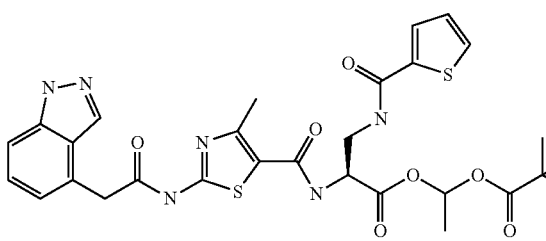

A solution of (S)-2-{[2-(2-1H-Indazol-4-yl-acetylamino)-4-methyl-thiazole-5-carbonyl]-amino}-3-[(thiophene-2-carbonyl)-amino]-propionic acid (70.2 mg, 0.137 mmol), 2,2-Dimethyl-propionic acid 1-chloro-ethyl ester (51 mg, 0.310 mmol), triethylamine (22 mg, 0.217 mmol) and sodium iodide (15 mg, 0.10 mmol) in anhydrous DMF (2.5 mL) was microwaved at 150° C. for 10 min and then concentrated at reduced pressure to remove most of the DMF. The residue was diluted with ethyl acetate (40 mL), washed with water (10 mL), brine (10 mL), dried over MgSO₄, filtered and concentrated under reduced pressure. The resulting crude compound was purified by flash chromatography (50% to 80% EtOAc in hexanes) to give(S)-2-{[2-(2-1H-Indazol-4-yl-acetylamino)-4-methyl-thiazole-5-carbonyl]-amino}-3-[(thiophene-2-carbonyl)-amino]-propionic acid 1-(2,2-dimethyl-propionyloxy)-ethyl ester (25.4 mg, 28.9%) as a yellow solid. MS m/e 641.7 (M+H⁺).

In a similar manner the following prodrug were produced:

Example 31

Preparation of (S)-2-{[2-(2-1H-Indazol-4-yl-acetylamino)-4-methyl-thiazole-5-carbonyl]-amino}-3-[(thiophene-2-carbonyl)-amino]-propionic acid 2-diethylamino-ethyl ester

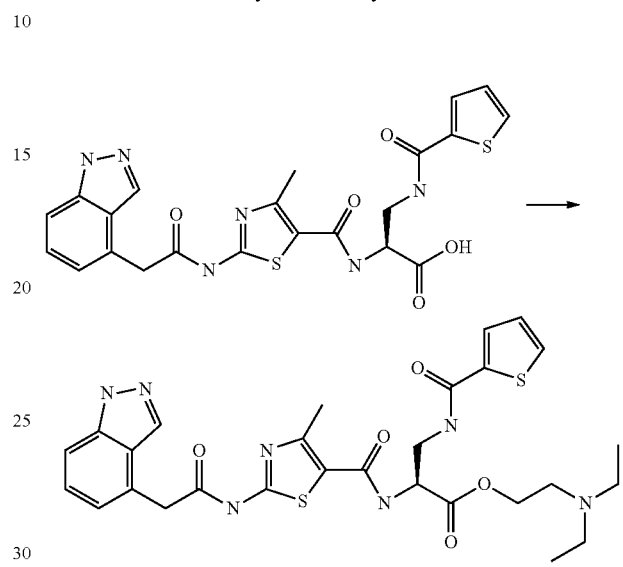

From (S)-2-{[2-(2-1H-Indazol-4-yl-acetylamino)-4-methyl-thiazole-5-carbonyl]-amino}-3-[(thiophene-2-carbonyl)-amino]-propionic acid there was obtained (S)-2-{[2-(2-1H-Indazol-4-yl-acetylamino)-4-methyl-thiazole-5-carbonyl]-amino}-3-[(thiophene-2-carbonyl)-amino]-propionic acid 2-diethylamino-ethyl ester (26.6%) as a pale yellow solid. MS m/e 612.7 (M+H⁺)

Example 32

Preparation of (S)-2-{[5-(3-hydroxy-benzylcarbamoyl)-3-methyl-thiophen-2-carbonyl]-amino}-3-[(thiophene-2-carbonyl)-amino]-propionic acid

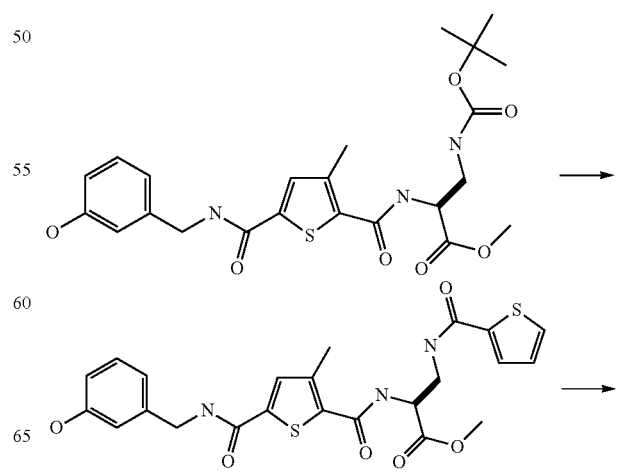

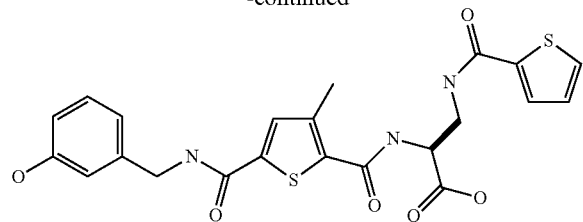

(S)-3-tert-butoxycarbamoylamino-2-{[5-(3-hydroxy-benzylcarbamoyl)-3-methyl-thiophen-2-carbonyl]-amino}-propionic acid methyl ester (0.38 g, 0.77 mmol) was dissolved in dichloromethane (10 ml) and treated with TFA (10 ml) at rt for 20 min. The reaction mixture was concentrated to dryness. The residue was dissolved in DMF (10 ml) and the following reagents were successively added at rt: thiophene-2-carboxylic acid (105 mg, 0.82 mmol), triethylamine (0.33 ml, 2.3 mmol), HOBT (126 mg, 0.93 mmol), and HBTU (442 mg, 1.16 mmol). The mixture was stirred at rt for 20 min, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 50-80% EtOAc in hexane to afford the desired methyl ester (294 mg, 76% yield). This ester was dissolved in THF/water (5 ml/2.5 ml) and treated with LiOH.H$_2$O (244 mg, 5.8 mmol) for 40 min at rt. The mixture was quenched with 1N HCl and extracted with EtOAc. The layers were separated. The organic layer was washed with brine, dried over Na$_2$SO$_4$ and concentrated under reduced pressure to afford the desired product (280 mg, 95% yield). MS m/e 487.9 (M+H$^+$).

Example 33

Preparation of (S)-2-{[2-tert-butyl-5-(3-hydroxy-benzylcarbamoyl)-thiophen-2-carbonyl]-amino}-3-[(thiophene-2-carbonyl)-amino]-propionic acid

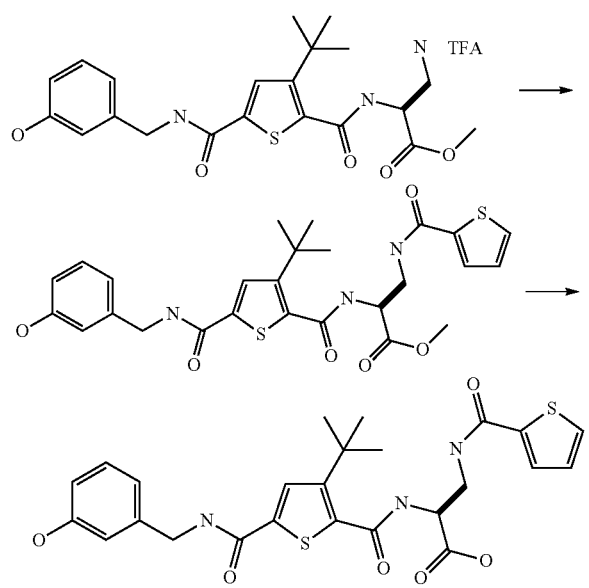

The TFA salt of (S)-3-amino-2-{[5-(3-hydroxy-benzylcarbamoyl)-3-tert-butyl-thiophene-2-carbonyl]-amino}-propionic acid methyl ester (125 mg, 0.23 mmol) was dissolved in DMF (5 ml) and the following reagents were successively added at rt: thiophene-2-carboxylic acid (3.1 mg, 0.24 mmol), triethylamine (0.95 ml, 0.68 mmol), HOBT (37 mg, 0.27 mmol), and HBTU (130 mg, 0.34 mmol). The mixture was stirred at rt for 30 min, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 50-80% EtOAc in hexane to afford the desired methyl ester (113 mg, 92% yield). This ester was dissolved in THF/water (4 ml/2. ml) and treated with LiOH.H$_2$O (85 mg, 2.0 mmol) for 30 min at rt. The mixture was quenched with 1N HCl and extracted with EtOAc. The layers were separated. The organic layer was washed with brine, dried over Na$_2$SO$_4$ and concentrated under reduced pressure to afford the desired product (89 mg, 95% yield). MS m/e 530.0 (M+H$^+$).

Example 34

Preparation of (S)-2-({5-[(1H-indol-4-ylmethyl)carbamoyl]-3-methyl-thiophen-2-carbonyl}-amino)-3-[(thiophene-2-carbonyl)-amino]-propionic acid

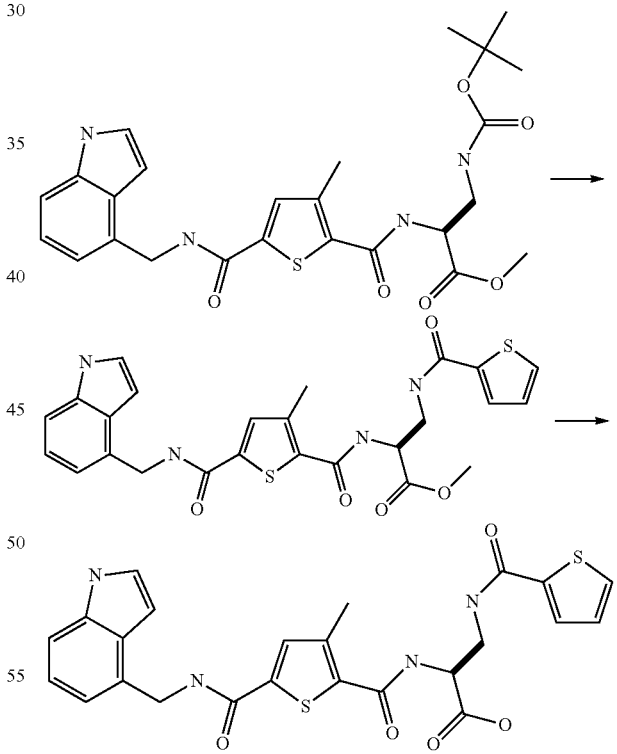

(S)-3-tert-butoxycarbamoylamino-2-({5-[(1H-indol-4-yl-methyl)-carbamoyl]-3-methyl-thiophene-2-carbonyl}-amino)-propionic acid methyl ester (125 mg, 0.24 mmol) was dissolved in dichloromethane (4 ml) and treated with TFA (4 ml) at rt for 30 min. The reaction mixture was concentrated to dryness. The residue was dissolved in DMF (5 ml) and the following reagents were successively added at rt: thiophene-2-carboxylic acid (33 mg, 0.25 mmol), triethylamine (0.10 ml, 0.73 mmol), HOBT (39 mg, 0.29 mmol), and HBTU (138 mg, 0.36 mmol). The mixture was stirred at rt for 30 min, then quenched with 1N HCl and extracted with EtOAc. The layers were separated. The organic layer was successively washed with water and brine, then dried over $Na_2SO_4$ and concentrated under reduced pressure. The residue was purified by flash chromatography with 40-60% EtOAc in hexane to afford the desired methyl ester (45 mg, 36% yield). This ester was dissolved in THF/water (3 ml/1.5 ml) and treated with $LiOH \cdot H_2O$ (36 mg, 0.86 mmol) for 2 h at rt. The mixture was quenched with 1N HCl and extracted with EtOAc. The layers were separated. The organic layer was washed with water and brine, dried over $Na_2SO_4$ then concentrated under reduced pressure to afford the desired product (43 mg, 97% yield). MS m/e M+H=511.0 (M+H$^+$).

Example 35

Preparation of (S)-2-({3-methyl-5-[(2-oxo-2,3-dihydro-1'1-indol-4-ylmethyl)carbamoyl]-thiophen-2-carbonyl}-amino)-3-[(thiophene-2-carbonyl)-amino]-propionic acid

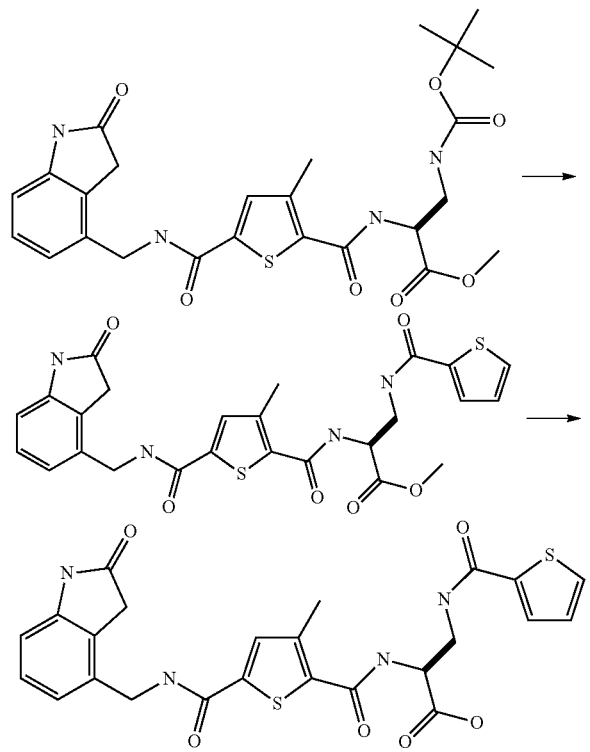

(S)-3-tert-butoxycarbamoylamino-2-({3-methyl-5-[(2-oxo-2,3-dihydro-1H-indol-4-ylmethyl)-carbamoyl]-thiophene-2-carbonyl}-amino)-propionic acid methyl ester (90 mg, 0.17 mmol) was dissolved in dichloromethane (4 ml) and treated with TFA (4 ml) at rt for 30 min. The reaction mixture was concentrated to dryness. The residue was dissolved in DMF (5 ml) and the following reagents were successively added at rt: thiophene-2-carboxylic acid (23 mg, 0.18 mmol), triethylamine (0.07 ml, 0.51 mmol), HOBT (27 mg, 0.20 mmol), and HBTU (96 mg, 0.25 mmol). The mixture was stirred at rt for 30 min, quenched with 1N HCl and extracted with EtOAc. The layers were separated. The organic layer was successively washed with water and brine, then dried over $Na_2SO_4$ and concentrated under reduced pressure. The residue was purified by flash chromatography with 80-100% EtOAc in hexane to afford the desired methyl ester (59 mg, 64% yield). This ester was dissolved in THF/water (3 ml/1.5 ml) and treated with $LiOH \cdot H_2O$ (46 mg, 1.1 mmol) for 2 h at rt. The mixture was quenched with 1N HCl and extracted with EtOAc. The layers were separated. The organic layer was washed with water and brine, dried over $Na_2SO_4$ then concentrated under reduced pressure to afford the desired product (35 mg, 62% yield). MS m/e M+H=527.0 (M+H$^+$).

Example 36

Preparation of (S)-2-({5-[(1H-indazol-4-ylmethyl)-carbamoyl]-3-methyl-thiophen-2-carbonyl}-amino)-3-[(thiophene-2-carbonyl)-amino]-propionic acid

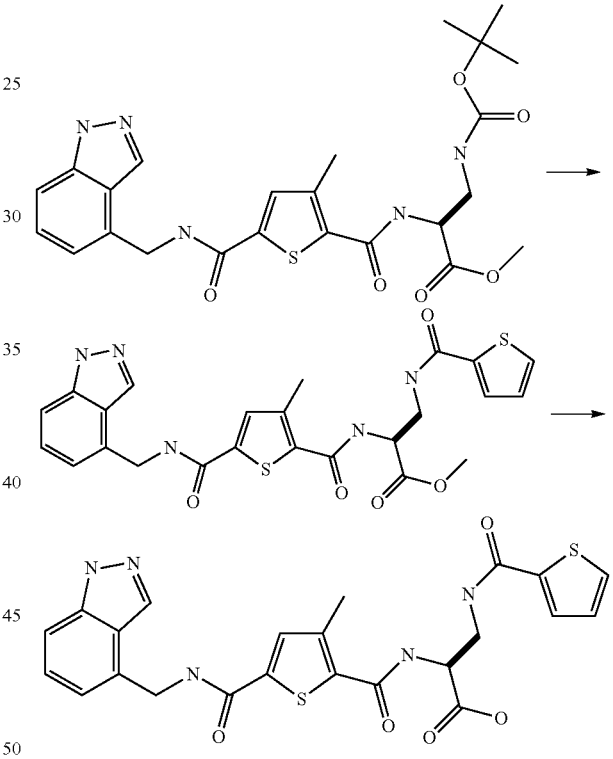

(S)-3-tert-butoxycarbamoylamino-2-({5-[(1H-indazol-4-ylmethyl)-carbamoyl]-3-methyl-thiophene-2-carbonyl}-amino)-propionic acid methyl ester (59 mg, 0.11 mmol) was dissolved in dichloromethane (2.5 ml) and treated with TFA (2.5 ml) at rt for 30 min. The reaction mixture was concentrated to dryness. The residue was triturated with ether. The supernatant was removed and the solid was dried under vacuum at 45° C. The solid was dissolved in DMF (3 ml) and the following reagents were successively added at rt: thiophene-2-carboxylic acid (15 mg, 0.12 mmol), triethylamine (0.05 ml, 0.34 mmol), HOBT (19 mg, 0.14 mmol), and HBTU (65 mg, 0.17 mmol). The mixture was stirred at rt for 45 min, then quenched with 1N HCl and extracted with EtOAc. The layers were separated. The organic layer was successively washed with water and brine, then dried over $Na_2SO_4$ and concentrated under reduced pressure. The residue was purified by flash chromatography with 60-100% EtOAc in hexane to afford the desired methyl ester (31 mg, 52% yield). This ester was dissolved in THF/water (2 ml/1 ml) and treated with LiOH.H$_2$O (25 mg, 0.59 mmol) at rt overnight. The mixture was quenched with 1N HCl and extracted with EtOAc. The layers were separated. The organic layer was washed with water and brine, dried over Na$_2$SO$_4$ then concentrated under reduced pressure to afford the desired product (22 mg, 73% yield). MS m/e M+H=512.0 (M+H$^+$).

Example 37

Preparation of (S)-2-({5-[1-(3-hydroxy-phenyl)-ethylcarbamoyl]-3-methyl-thiophen-2-carbonyl}-amino)-3-[(thiophene-2-carbonyl)-amino]-propionic acid

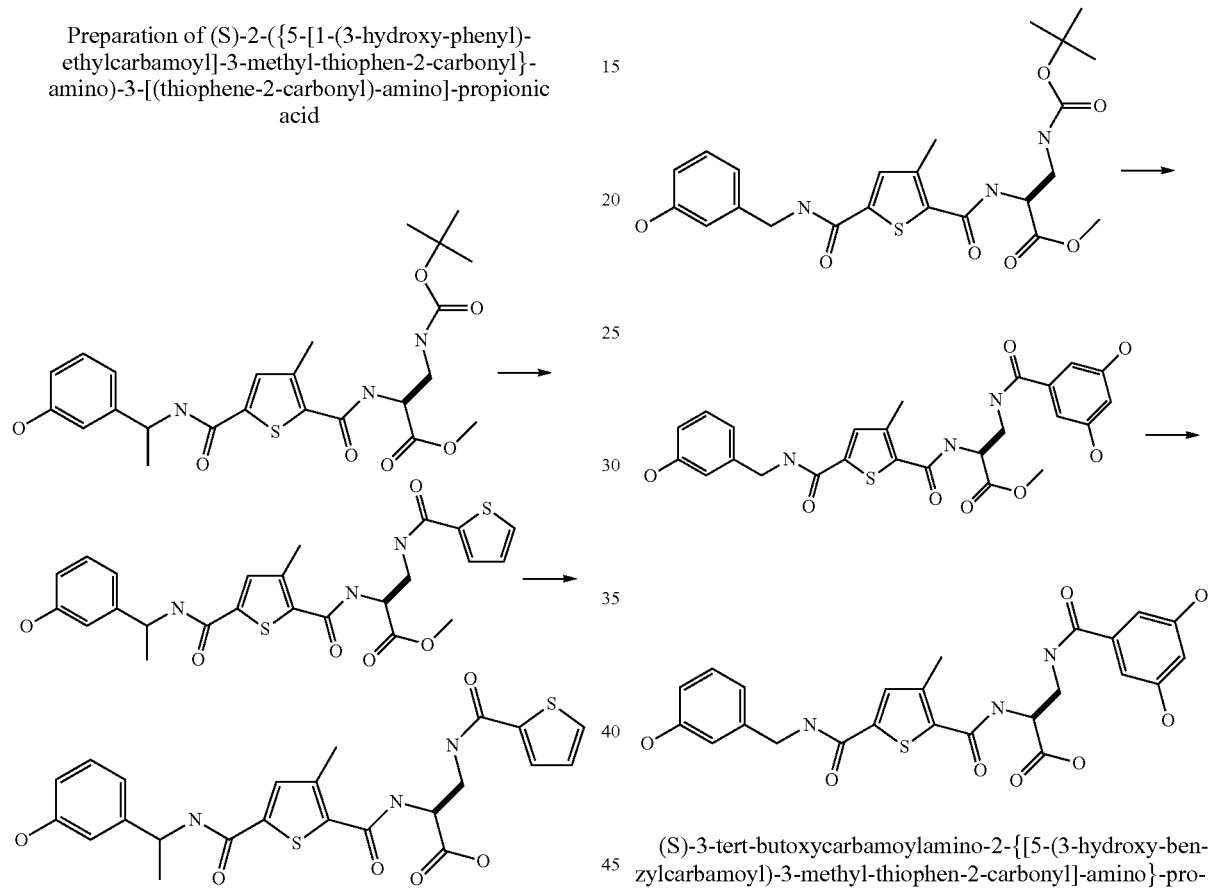

(S)-3-tert-butoxycarbamoylamino-2-({5-[1-(3-hydroxy-phenyl)-ethylcarbamoyl]-3-methyl-thiophene-2-carbonyl}-amino)-propionic acid methyl ester (186 mg, 0.38 mmol) was dissolved in dichloromethane (5 ml) and treated with TFA (5 ml) at rt for 45 min. The reaction mixture was concentrated to dryness. The residue was dissolved in DMF (4 ml) and the following reagents were successively added at rt: thiophene-2-carboxylic acid (52 mg, 0.40 mmol), triethylamine (0.16 ml, 1.14 mmol), HOBT (76 mg, 0.57 mmol), and HBTU (215 mg, 0.57 mmol). The mixture was stirred at rt for 20 min, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 50-80% EtOAc in hexane to afford the desired methyl ester (118 mg, 62% yield). This ester was dissolved in THF/water (4 ml/2 ml) and treated with LiOH.H$_2$O (96 mg, 2.3 mmol) at 40° C. for 1 h. The mixture was quenched with 1N HCl and extracted with EtOAc. The layers were separated. The organic layer was washed with brine, dried over Na$_2$SO$_4$ and concentrated under reduced pressure to afford the desired product (103 mg, 90% yield). MS m/e 502.0 (M+H$^+$).

Example 38

Preparation of (S)-3-(3,5-dihydroxy-benzoylamino)-2-{[5-(3-hydroxy-benzylcarbamoyl)-3-methyl-thiophen-2-carbonyl]-amino}-propionic acid

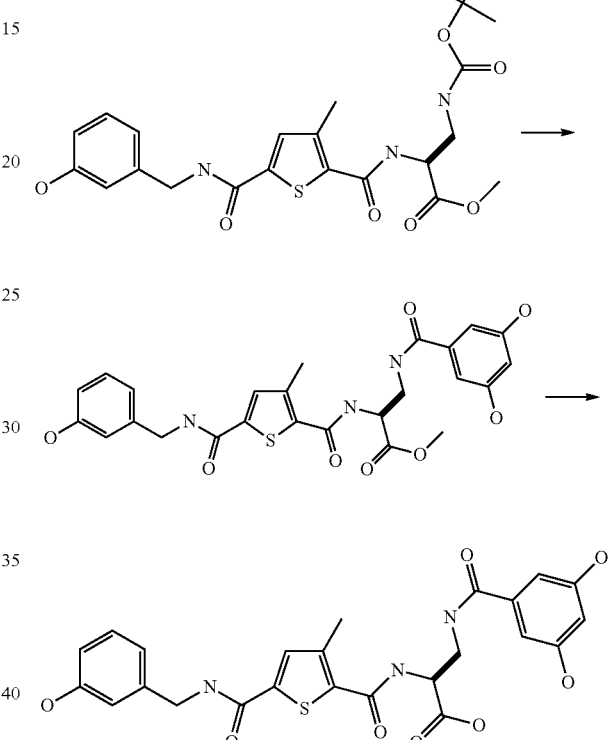

(S)-3-tert-butoxycarbamoylamino-2-{[5-(3-hydroxy-benzylcarbamoyl)-3-methyl-thiophen-2-carbonyl]-amino}-propionic acid methyl ester (78 mg, 0.16 mmol) was treated with 4NHCl in dioxane (1.5 ml) at rt for 2 h. The reaction mixture was concentrated to dryness. The residue was dissolved in DMF (1.5 ml) and the following reagents were successively added at rt: 3,5-dihydroxy benzoic acid (27 mg, 0.17 mmol), triethylamine (0.07 ml, 0.48 mmol), HOBT (28 mg, 0.21 mmol), and HBTU (80 mg, 0.21 mmol). The mixture was stirred at rt for 30 min, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 50-100% EtOAc in hexane to afford the desired methyl ester (40 mg, 48% yield). This ester was dissolved in THF/water (2 ml/1 ml) and treated with LiOH.H$_2$O (30 mg, 0.72 mmol) at 40° C. for 1 h. The mixture was quenched with 1N HCl and extracted with EtOAc. The layers were separated. The organic layer was washed with brine, dried over Na$_2$SO$_4$ and concentrated under reduced pressure. The crude was purified by reverse phase HPLC to afford the desired product (25 mg, 68% yield). MS m/e 513.9 (M+H$^+$).

Example 39

Preparation of (S)-3-[(2,6-dioxo-1,2,3,6-tetrahydro-pyrimidine-4-carbonyl)-amino]-2-{[5-(3-hydroxy-benzylcarbamoyl)-3-methyl-thiophene-2-carbonyl-amino]-propionic acid

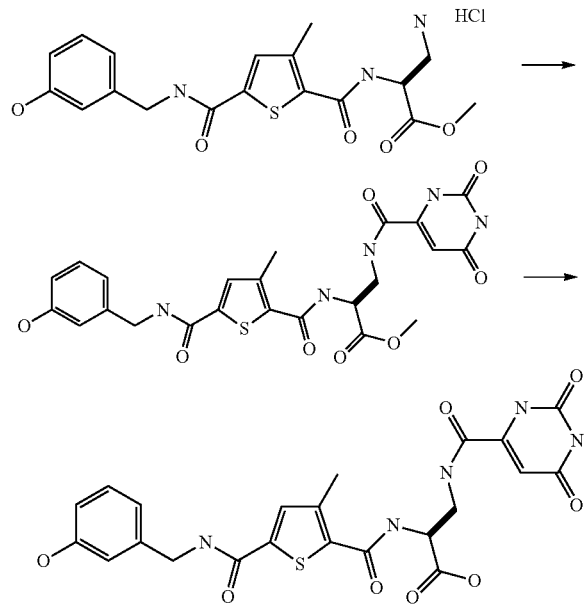

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: orotic acid (4.1 mg, 0.26 mmol), triethylamine (0.10 ml, 0.70 mmol), HOBT (38 mg, 0.28 mmol), and HBTU (110 mg, 0.28 mmol). The mixture was stirred at rt for 1 h, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 100% EtOAc to afford the desired methyl ester (20 mg, 17% yield). This ester was dissolved in THF/water (1 ml/0.5 ml) and treated with LiOH.H$_2$O (15 mg, 0.38 mmol) at 40° C. for 1 h. The mixture was quenched with 1N HCl and extracted with EtOAc. The layers were separated. The organic layer was washed with brine, dried over Na$_2$SO$_4$ and concentrated under reduced pressure. The crude was purified by reverse phase HPLC to afford the desired product (9 mg, 47% yield). MS m/e 515.9 (M+H$^+$).

Example 40

Preparation of (S)-3-(3-hydroxy-benzoylamino)-2-{[5-(3-hydroxy-benzylcarbamoyl)-3-methyl-thiophene-2-carbonyl-amino]-propionic acid

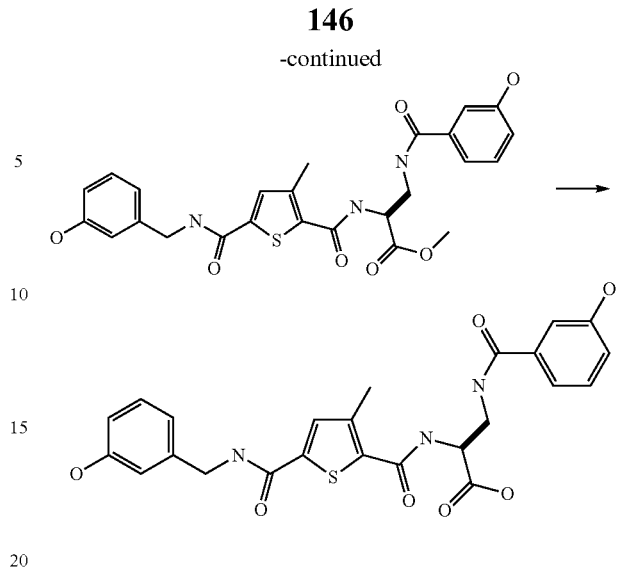

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: 3-hydroxy benzoic acid (36 mg, 0.26 mmol), triethylamine (0.10 ml, 0.70 mmol), HOBT (38 mg, 0.28 mmol), and HBTU (110 mg, 0.28 mmol). The mixture was stirred at rt for 1 h, then quenched with 1N HCl and extracted with EtOAc. The layers were separated. The organic layer was successively washed with water and brine, then dried over Na$_2$SO$_4$ and concentrated under reduced pressure. The residue was purified by flash chromatography with 50-100% EtOAc in hexane to afford the desired methyl ester (60 mg, 50% yield). This ester was dissolved in THF/water (2 ml/1 ml) and treated with LiOH.H$_2$O (50 mg, 1.17 mmol) at 40° C. for 1 h. The mixture was quenched with 1N HCl and extracted with EtOAc. The layers were separated. The organic layer was washed with brine, dried over Na$_2$SO$_4$ and concentrated under reduced pressure to afford the desired product (46 mg, 79% yield). MS m/e 497.9 (M+H$^+$).

Example 41

Preparation of (S)-3-(3-hydroxy-benzoylamino)-2-{[5-(3-hydroxy-benzylcarbamoyl)-3-methyl-thiophene-2-carbonyl-amino]-propionic acid

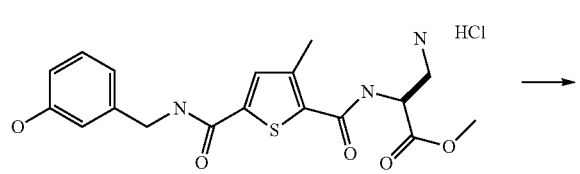

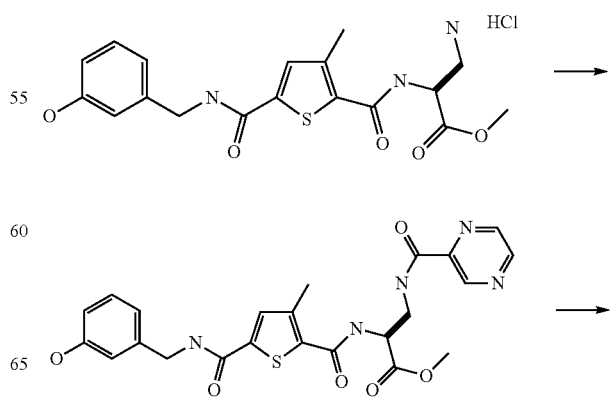

-continued

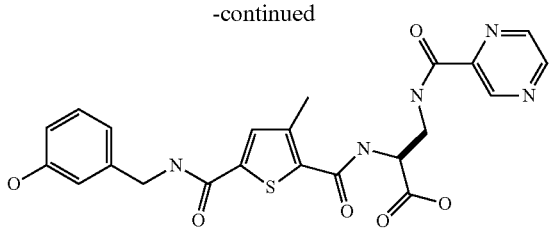

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: 2-pyrazine carboxylic acid (32 mg, 0.26 mmol), triethylamine (0.10 ml, 0.70 mmol), HOBT (38 mg, 0.28 mmol), and HBTU (110 mg, 0.28 mmol). The mixture was stirred at rt for 1 h, then quenched with 1N HCl and extracted with EtOAc. The layers were separated. The organic layer was successively washed with water and brine, then dried over $Na_2SO_4$ and concentrated under reduced pressure. The residue was purified by flash chromatography with 70-100% EtOAc in hexane to afford the desired methyl ester (55 mg, 48% yield). This ester was dissolved in THF/water (2 ml/1 ml) and treated with $LiOH.H_2O$ (46 mg, 1.1 mmol) at 40° C. for 1 h. The mixture was quenched with 1N HCl and extracted with EtOAc. The layers were separated. The organic layer was washed with brine, dried over $Na_2SO_4$ and concentrated under reduced pressure to afford the desired product (17 mg, 32% yield). MS m/e 484.0 (M+H$^+$).

Example 42

Preparation of (S)-3-[(1H-benzoimidazole-5-carbonyl)-amino]-2-{[5-(3-hydroxy-benzylcarbamoyl)-3-methyl-thiophene-2-carbonyl-amino]-propionic acid (HCl salt)

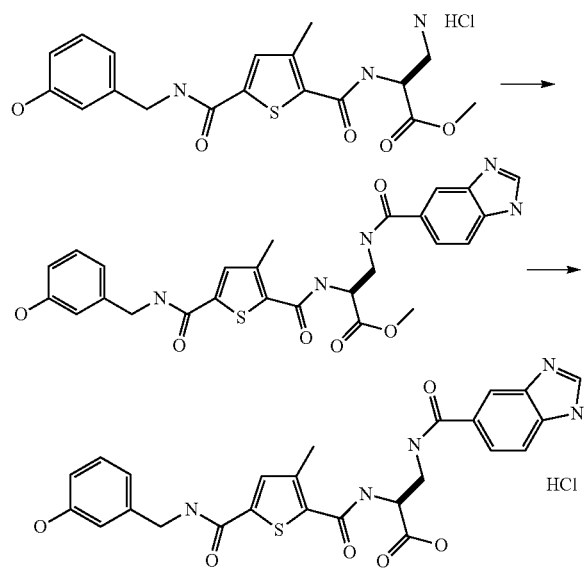

(S)-3-amino-2-{[5-(3-hydroxy-benzylcarbamoyl)-3-methyl-thiophene-2-carbonyl]-amino}-propionic acid methyl ester (HCl salt) (84 mg, 0.20 mmol) was dissolved in DMF (2 ml) and the following reagents were successively added at rt: 5-benzimidazole carboxylic acid (35 mg, 0.22 mmol), triethylamine (0.085 ml, 0.59 mmol), HOBT (32 mg, 0.24 mmol), and HBTU (92 mg, 0.24 mmol). The mixture was stirred at rt for 1 h, then quenched with 1N HCl and extracted with EtOAc. The layers were separated. The organic layer was discarded. The aqueous layer was neutralized with pH 7 buffer and extracted with EtOAc. The layers were separated. The organic layer was washed with brine, then dried over $Na_2SO_4$ and concentrated under reduced pressure to afford crude methyl ester (48 mg, 46% yield). This ester which was not purified was dissolved in THF/water (1 ml/0.5 ml) and treated with $LiOH.H_2O$ (48 mg, 0.9 mmol) at 40° C. for 1 h. The mixture was quenched with 1N HCl and concentrated. The crude was purified by reverse phase HPLC to afford the desired product as the HCl salt. (11 mg, 22% yield). MS m/e 522.0 (M+H$^+$).

Example 43

Preparation of (S)-3-[(2,6-dimethoxy-pyrimidine-4-carbonyl)-amino]-2-{[5-(3-hydroxy-benzylcarbamoyl)-3-methyl-thiophene-2-carbonyl]-amino}-propionic acid

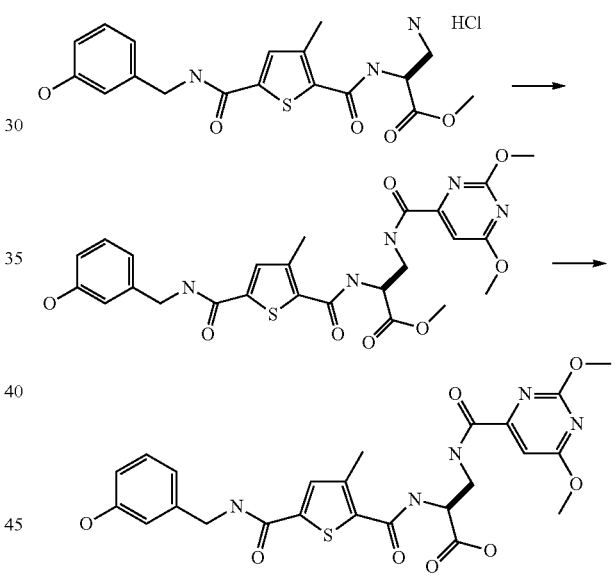

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: 2,6-dimetoxy-pyrimidine-4-carboxylic acid (47 mg, 0.26 mmol), triethylamine (0.10 ml, 0.70 mmol), HOBT (38 mg, 0.28 mmol), and HBTU (110 mg, 0.28 mmol). The mixture was stirred at rt for 1 h, then quenched with 1N HCl and extracted with EtOAc. The layers were separated. The organic layer was successively washed with water and brine, then dried over $Na_2SO_4$ and concentrated under reduced pressure. The residue was purified by flash chromatography with 50-100% EtOAc in hexane to afford the desired methyl ester (60 mg, 46% yield). This ester was dissolved in THF/water (2 ml/1 ml) and treated with $LiOH.H_2O$ (44 mg, 1.0 mmol) at 40° C. for 40 min. The mixture was quenched with 1N HCl and concentrated. The crude was purified by reverse phase HPLC to afford the desired product (39 mg, 72% yield). MS m/e 544.0 (M+H$^+$).

Example 44

Preparation of (S)-2-{[5-(3-hydroxy-benzylcarbamoyl)-3-methyl-thiophene-2-carbonyl]-amino}-3-[(1H-indazole-4-carbonyl)-amino]-propionic acid (HCl salt)

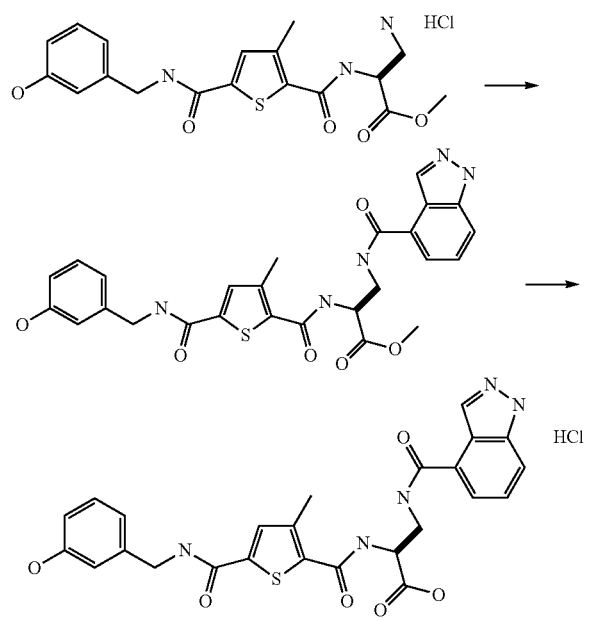

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: 1H-indazole-4-carboxylic acid (38 mg, 0.23 mmol), triethylamine (0.10 ml, 0.70 mmol), HOBT (38 mg, 0.28 mmol), and HBTU (110 mg, 0.28 mmol). The mixture was stirred at rt for 1 h, then quenched with pH 7 buffer and extracted with EtOAc. The layers were separated. The organic layer was successively washed with water and brine, then dried over $Na_2SO_4$ and concentrated under reduced pressure. The residue was purified by flash chromatography with 50-100% EtOAc in hexane to afford the desired methyl ester (48 mg, 38% yield). This ester was dissolved in THF/water (2 ml/1 ml) and treated with $LiOH.H_2O$ (38 mg, 0.9 mmol) at 40° C. for 1 h. The mixture was quenched with 1N HCl and concentrated. The crude was purified by reverse phase HPLC to afford the desired product (HCl salt) (25 mg, 50% yield). MS m/e 522.0 (M+H$^+$).

Example 45

Preparation of (S)-2-{[5-(3-hydroxy-benzylcarbamoyl)-3-methyl-thiophene-2-carbonyl]-amino}-3-[(5-hydroxy-pyrazine-2-carbonyl)-amino]-propionic acid

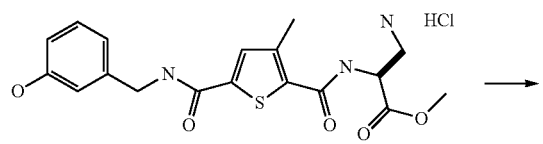

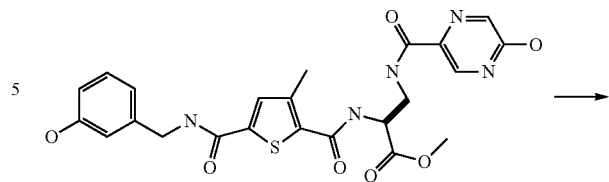

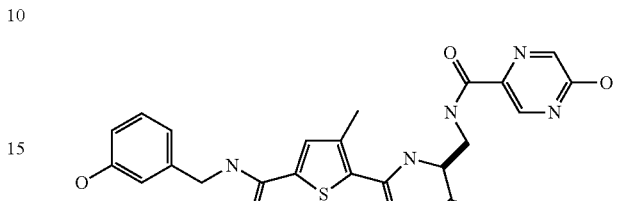

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: 5-hydroxy-pyrazine-2-carboxylic acid (33 mg, 0.23 mmol), triethylamine (0.10 ml, 0.70 mmol), HOBT (38 mg, 0.28 mmol), and HBTU (110 mg, 0.28 mmol). The mixture was stirred at rt for 0.5 h, then quenched with pH 7 buffer and extracted with EtOAc. The layers were separated. The organic layer was successively washed with water and brine, then dried over $Na_2SO_4$ and concentrated under reduced pressure. The residue was purified by flash chromatography with 100% EtOAc and then 10% MeOH in EtOAc to afford the desired methyl ester (32 mg, 27% yield), This ester was dissolved in THF/water (2 ml/1 ml) and treated with $LiOH.H_2O$ (26 mg, 0.6 mmol) at 40° C. for 1.5 h. The mixture was quenched with 1N HCl and concentrated. The crude was purified by reverse phase HPLC to afford the desired product (5 mg, 17% yield). MS m/e 499.9 (M+H$^+$).

Example 46

Preparation of (S)-3-[(1H-benzoimidazole-4-carbonyl)-amino]-2-{[5-(3-hydroxy-benzylcarbamoyl)-3-methyl-thiophene-2-carbonyl]-amino}-propionic acid (HCl salt)

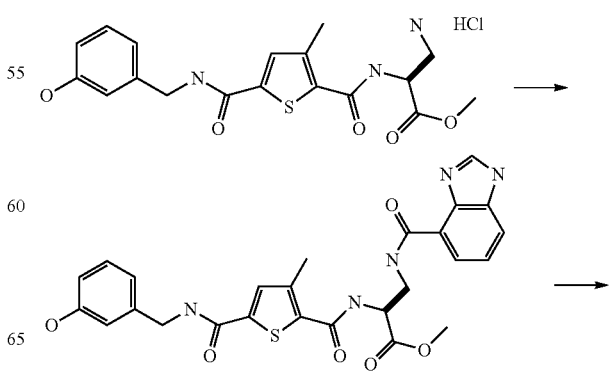

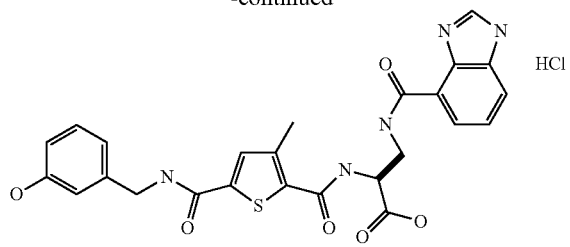

(S)-3-amino-2-{[5-(3-hydroxy-benzylcarbamoyl)-3-methyl-thiophene-2-carbonyl]-amino}-propionic acid methyl ester (HCl salt) (100 mg, 0.23 mmol) was dissolved in DMF (2.5 ml) and the following reagents were successively added at rt: benzimidazole-4-carboxylic acid (38 mg, 0.23 mmol), triethylamine (0.10 ml, 0.70 mmol), HOBT (38 mg, 0.28 mmol), and HBTU (110 mg, 0.28 mmol). The mixture was stirred at rt for 1 h, then quenched with pH 7 buffer and extracted with EtOAc. The layers were separated. The organic layer was successively washed with water and brine, then dried over $Na_2SO_4$ and concentrated under reduced pressure to afford the desired methyl ester as crude material which was not purified (55 mg). This crude ester was dissolved in THF/water (2 ml/1 ml) and treated with $LiOH.H_2O$ (42 mg, 1 mmol) at 40° C. for 50 min. The mixture was quenched with 1N HCl and concentrated. The crude was purified by reverse phase HPLC to afford the desired product (HCl salt) (35 mg, 27% overall yield). MS m/e 522.0 (M+H+).

Example 47

Preparation of (S)-3-[(benzoic acid-3-carbonyl)-amino]-2-{[5-(3-hydroxy-benzylcarbamoyl)-3-methyl-thiophene-2-carbonyl]-amino}-propionic acid

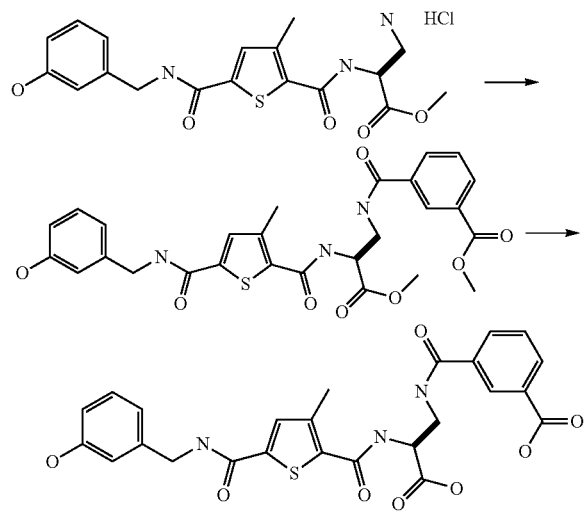

(S)-3-amino-2-{[5-(3-hydroxy-benzylcarbamoyl)-3-methyl-thiophene-2-carbonyl]-amino}-propionic acid methyl ester (HCl salt) (110 mg, 0.26 mmol) was dissolved in DMF (2.5 ml) and the following reagents were successively added at rt: mono-methyl-isophthalate (51 mg, 0.28 mmol), triethylamine (0.11 ml, 0.77 mmol), HOBT (42 mg, 0.31 mmol), and HBTU (121 mg, 0.31 mmol). The mixture was stirred at rt for 45 min, then quenched with 1N HCl and extracted with EtOAc. The layers were separated. The organic layer was successively washed with water and brine, then dried over $Na_2SO_4$ and concentrated under reduced pressure. The residue was purified by flash chromatography with 50-100% EtOAc in hexane to afford the desired methyl ester (71 mg, 51% yield). This ester was dissolved in THF/water (2 ml/1 ml) and treated with $LiOH.H_2O$ (30 mg, 0.63 mmol) at 40° C. for 50 min. The mixture was quenched with 1N HCl and extracted with EtOAc. The layers were separated. The organic layer was washed with brine, dried over $Na_2SO_4$ and concentrated. The residues was triturated with EtOAC and insoluble material were removed by filtration. The filtrate was concentrated under reduced pressure to afford the desired product (30 mg, 48% yield). MS m/e 526.0 (M+H+).

Example 48

Preparation of (S)-2-({5-[2-(3-hydroxy-phenyl)ethylcarbamoyl]-3-methyl-thiophen-2-carbonyl}-amino)-3-[(thiophene-2-carbonyl)-amino]-propionic acid

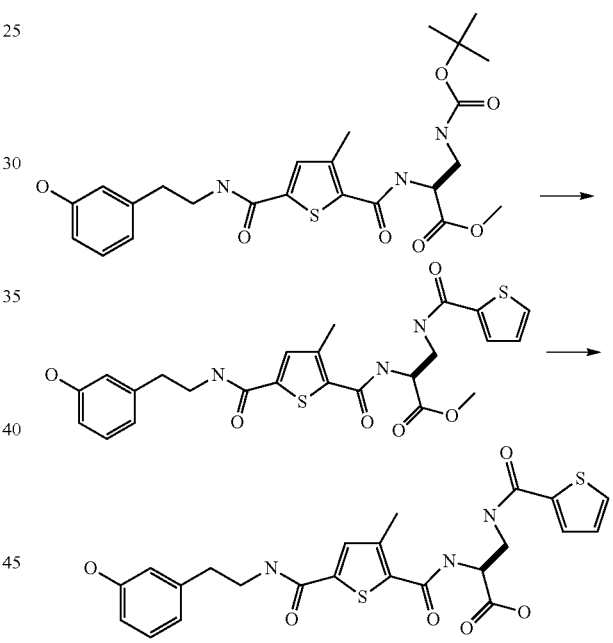

(S)-3-tert-butoxycarbamoylamino-2-({5-[2-(3-hydroxyphenyl)-ethyl-carbamoyl]-3-methyl-thiophene-2-carbonyl}-amino)-propionic acid methyl ester (190 mg, 0.38 mmol) was treated with 4NHCl indioxane (6 mL) at rt for 1.5 h. The reaction mixture was concentrated to dryness. A portion of this residue (50 mg) was dissolved in DMF (2 ml) and the following reagents were successively added at rt: thiophene-2-carboxylic acid (16 mg, 0.12 mmol), triethylamine (0.05 ml, 0.34 mmol), HOBT (20 mg, 0.14 mmol), and HBTU (52 mg, 0.14 mmol). The mixture was stirred at rt for 20 min, then quenched with 1N HCl and extracted with EtOAc. The layers were separated. The organic layer was successively washed with water and brine, then dried over $Na_2SO_4$ and concentrated under reduced pressure. The residue was purified by flash chromatography with 50-100% EtOAc in hexane to afford the desired methyl ester (30 mg). This ester was dissolved in THF/water (2 ml/1 ml) and treated with $LiOH.H_2O$ (15 mg, 0.29 mmol) at 40° C. for 1.5 h. The mixture was quenched with 1N HCl and extracted with EtOAc. The layers were separated. The organic layer was washed with brine, dried over Na₂SO₄ and concentrated under reduced pressure to afford the desired product (30 mg) MS m/e 501.9 (M+H⁺).

Example 49

Preparation of (S)-3-(3,5-dihydroxy-benzoylamino)-2-([5-[2-(3-hydroxy-phenyl)-ethyl-carbamoyl]-3-methyl-thiophen-2-carbonyl]-amino)-propionic acid

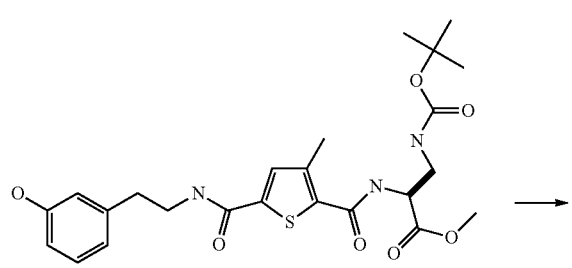

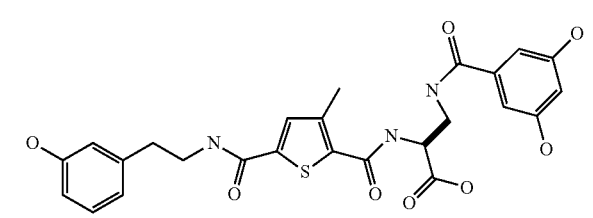

(S)-3-tert-butoxycarbamoylamino-2-({5-[2-(3-hydroxy-phenyl)-ethyl-carbamoyl]-3-methyl-thiophene-2-carbonyl}-amino)-propionic acid methyl ester (190 mg, 0.38 mmol) was treated with 4NHCl indioxane (6 ml) at rt for 1.5 h. The reaction mixture was concentrated to dryness. A portion of this residue (50 mg) was dissolved in DMF (2 ml) and the following reagents were successively added at rt: 3,5-dihydroxy benzoic acid (20 mg, 0.12 mmol), triethylamine (0.05 ml, 0.34 mmol), HOBT (20 mg, 0.14 mmol), and HBTU (52 mg, 0.14 mmol). The mixture was stirred at rt for 1 h 20 min, then quenched with 1N HCl and extracted with EtOAc. The layers were separated. The organic layer was successively washed with water and brine, then dried over Na₂SO₄ and concentrated under reduced pressure. The residue was purified by flash chromatography with 50-100% EtOAc in hexane to afford the desired methyl ester (34 mg). This ester was dissolved in THF/water (2 ml/1 ml) and treated with LiOH.H₂O (16 mg, 0.29 mmol) at 40° C. for 1.5 h. The mixture was quenched with 1N HCl and extracted with EtOAc. The layers were separated. The organic layer was washed with brine, dried over Na₂SO₄ and concentrated under reduced pressure to afford the desired product (22 mg) MS m/e 528 (M+H⁺).

Example 50

(S)-2-({5-[(1H-Indol-4-ylmethyl)-carbamoyl]-3-trifluoromethyl-thiophene-2-carbonyl}-amino)-3-[(thiophene-2-carbonyl)-amino]-propionic acid

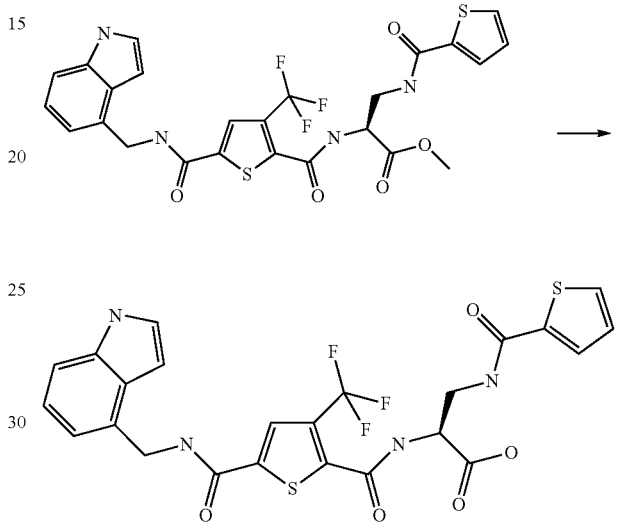

To a solution of (S)-2-({5-[(1H-Indol-4-ylmethyl)-carbamoyl]-3-trifluoromethyl-thiophene-2-carbonyl}-amino)-3-[(thiophene-2-carbonyl)-amino]-propionic acid methyl ester (170 mg, 0.29 mmol) in THF (6 mL) was added a solution of lithium hydroxide monohydrate (120 mg, 2.94 mmol) in water (8 mL). The mixture was then stirred at room temperature overnight. The mixture was then acidified with 1N HCl and extracted with EtOAc (×3). The extracts were combined, washed with water and brine, dried over sodium sulfate, filtered, and evaporated to pure product, 0.1089 g (67%). MS m/e 564.9 (M+H⁺).

Example 51

(S)-2-({5-[(2-oxo-2,3-dihydro-1H-indol-4-ylmethyl)-carbamoyl]-3-trifluoromethyl-thiophene-2-carbonyl}-amino)-3-[(thiophene-2-carbonyl)-amino]-propionic acid

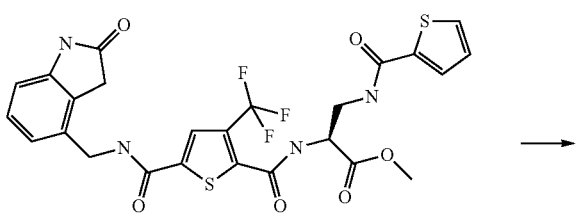

-continued

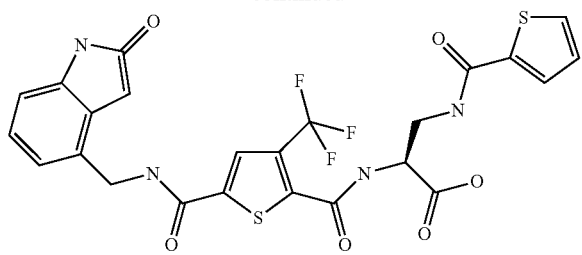

To a solution of (S)-2-({5-[(2-oxo-2,3-dihydro-1H-indol-4-ylmethyl)-carbamoyl]-3-trifluoromethyl-thiophene-2-carbonyl}-amino)-3-[(thiophene-2-carbonyl)-amino]-propionic acid methyl ester (53 mg, 0.089 mmol) in THF (5 mL) was added a solution of lithium hydroxide monohydrate (37 mg, 0.89 mmol) in water (6 mL). The mixture was then stirred at room temperature 5 h. The mixture was then acidified with 1N HCl and extracted with EtOAc (×3). The extracts were combined, washed with water and brine, dried over sodium sulfate, filtered, and evaporated to pure product, 0.0466 g (90%). MS m/e 581.0 (M+H$^+$).

Example 52

(S)-2-{[5-(3-Hydroxy-benzylcarbamoyl)-3-trifluoromethyl-thiophene-2-carbonyl]-amino}-3-[(thiophene-2-carbonyl)-amino]-propionic acid

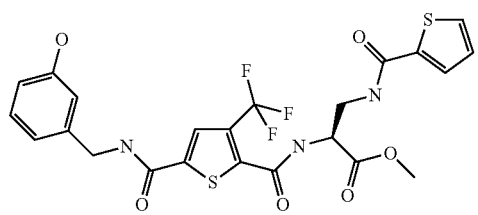

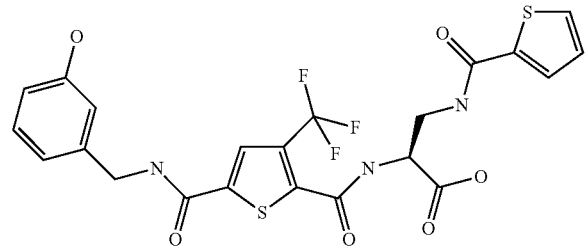

To a solution of (S)-2-{[5-(3-Hydroxy-benzylcarbamoyl)-3-trifluoromethyl-thiophene-2-carbonyl]-amino}-3-[(thiophene-2-carbonyl)-amino]-propionic acid methyl ester (40 mg, 0.072 mmol) in THF (5 mL) was added a solution of lithium hydroxide monohydrate (30 mg, 0.71 mmol) in water (6 mL). The mixture was then stirred at room temperature 4 h. The mixture was then acidified with 1N HCl and extracted with EtOAc (×3). The extracts were combined, washed with water and brine, dried over sodium sulfate, filtered, and evaporated to pure product, 26.7 mg (68%). MS m/e 542.0 (M+H$^+$).

Example 53

(S)-2-{[5-(3-Hydroxy-benzylcarbamoyl)-3-phenyl-thiophene-2-carbonyl]-amino}-3-[(thiophene-2-carbonyl)-amino]-propionic acid

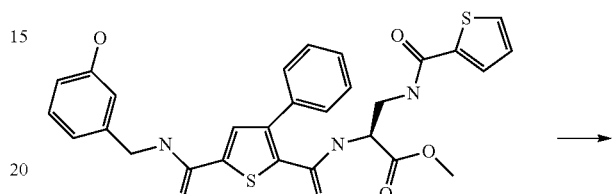

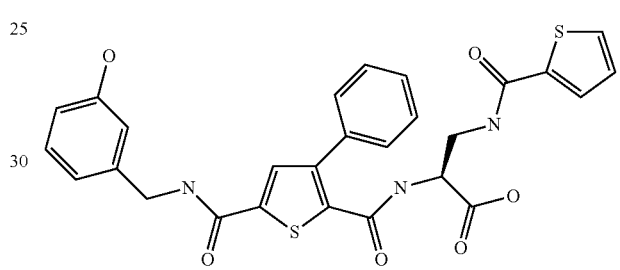

To a solution of (S)-2-{[5-(3-Hydroxy-benzylcarbamoyl)-3-phenyl-thiophene-2-carbonyl]-amino}-3-[(thiophene-2-carbonyl)-amino]-propionic acid methyl ester (40 mg, 0.07 mmol) in THF (2 mL) was added a solution of lithium hydroxide monohydrate (30 mg, 0.71 mmol) in water (3 mL). The mixture was then stirred at room temperature 4 h. The mixture was then acidified with 1N HCl and extracted with EtOAc (×3). The extracts were combined, washed with water and brine, dried over sodium sulfate, filtered, and evaporated to pure product, 20.9 mg (68%). MS m/e 549.1 (M+H$^+$).

Example 54

(S)-2-{[3-Chloro-5-(3-hydroxy-benzylcarbamoyl)-thiophene-2-carbonyl]-amino}-3-[(thiophene-2-carbonyl)-amino]-propionic acid

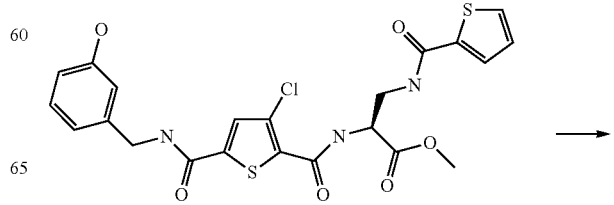

-continued

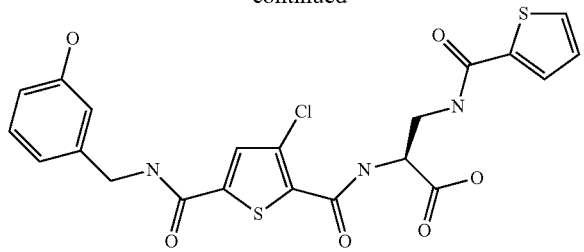

To a solution of 5(S)-2-{[3-Chloro-5-(3-hydroxy-benzyl-carbamoyl)-thiophene-2-carbonyl]-amino}-3-[(thiophene-2-carbonyl)-amino]-propionic acid methyl ester (150 mg, 0.29 mmol) in THF (6 mL) was added a solution of lithium hydroxide monohydrate (120 mg, 2.87 mmol) in water (6 mL). The mixture was then stirred at room temperature for 15 h. The mixture was then acidified with 1N HCl and extracted with EtOAc (×3). The extracts were combined, washed with water and brine, dried over sodium sulfate, filtered, and evaporated to pure product, 131.3 mg (89%). MS m/e 507.9 (M+H$^+$).

Example 55

(S)-2-{[3-Chloro-5-(3-hydroxy-benzylcarbamoyl)-thiophene-2-carbonyl]-amino}-3-[(thiophene-2-carbonyl)-amino]-propionic acid isobutyl ester

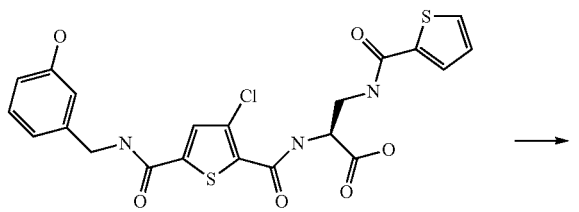

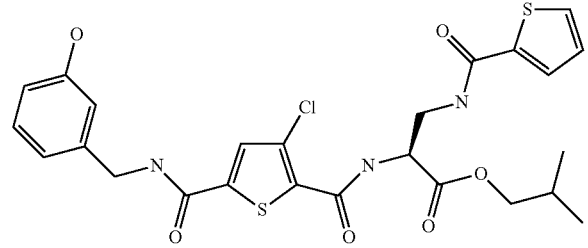

A solution of 5(S)-2-{[3-Chloro-5-(3-hydroxy-benzylcarbamoyl)-thiophene-2-carbonyl]-amino}-3-[(thiophene-2-carbonyl)-amino]-propionic acid (110 mg, 0.22 mmol), 1-Iodo-2-methylpropane (120 mg, 0.65 mmol), and triethylamine (0.09 ml, 0.65 mmol) in DMF (3 mL) was heated in a microwave at 100° C. for 30 min. The mixture was cooled to room temperature, treated with EtOAc (50 mL), washed with brine, dried over sodium sulfate, filtered and evaporated. The residue was purified by column (0-100% EtOAc in hexane) to give 0.0790 g (64%) white solid. MS m/e 563.8 (M+H$^+$).

Example 56

(S)-2-({3-Chloro-5-[(1H-indazol-4-ylmethyl)-carbamoyl]-thiophene-2-carbonyl}-amino)-3-[(thiophene-2-carbonyl)-amino]-propionic acid

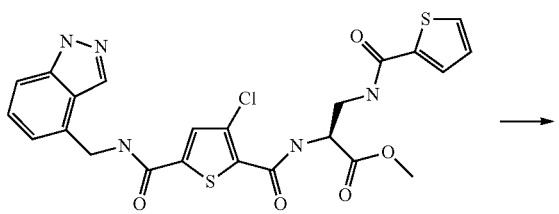

To a solution of (S)-2-({3-Chloro-5-[(1H-indazol-4-ylmethyl)-carbamoyl]-thiophene-2-carbonyl}-amino)-3-[(thiophene-2-carbonyl)-amino]-propionic acid methyl ester (48.7 mg, 0.089 mmol) in THF (2 mL) was added a solution of lithium hydroxide monohydrate (37 mg, 0.89 mmol) in water (3 mL). The mixture was then stirred at room temperature 15 h. The mixture was then acidified with 1N HCl and extracted with EtOAc (×3). The extracts were combined, washed with water and brine, dried over sodium sulfate, filtered, and evaporated to pure product, 34.8 mg (73%). MS m/e 531.9 (M+H$^+$).

Example 57

(S)-2-({3-Chloro-5-[(1H-indazol-4-ylmethyl)-carbamoyl]-thiophene-2-carbonyl}-amino)-3-[thiophene-2-carbonyl)-amino]-propionic acid isobutyl ester

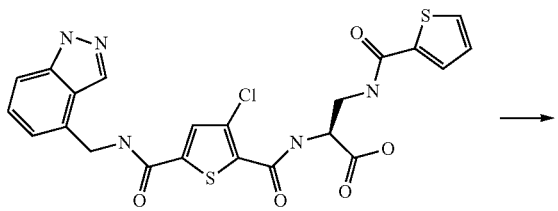

-continued

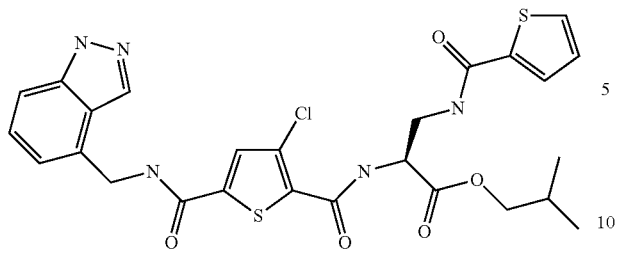

A solution of (S)-2-({3-Chloro-5-[(1H-indazol-4-ylmethyl)-carbamoyl]-thiophene-2-carbonyl}-amino)-3-[(thiophene-2-carbonyl)-amino]-propionic acid (160 mg, 0.30 mmol), 1-Iodo-2-methylpropane (160 mg, 0.90 mmol), and triethylamine (0.13 ml, 0.90 mmol) in DMF (4 mL) was heated in a microwave at 100° C. for 30 min. The mixture was cooled to room temperature, treated with EtOAc (50 mL), washed with brine, dried over sodium sulfate, filtered and evaporated. The residue was purified by column (30-100% EtOAc in hexane) to give 0.0998 g (57%) white solid. MS m/e 587.8 (M+H$^+$).

Example 58

(S)-2-({5-[(1H-Indazol-4-ylmethyl)-carbamoyl]-3-trifluoromethyl-thiophene-2-carbonyl}-amino)-3-[(thiophene-2-carbonyl)-amino]-propionic acid

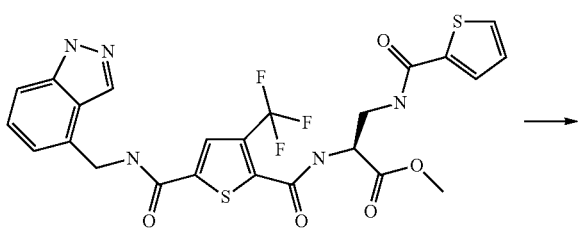

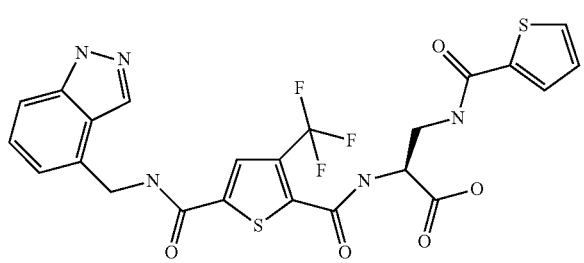

To a solution of (S)-2-({5-[(1H-Indazol-4-ylmethyl)-carbamoyl]-3-trifluoromethyl-thiophene-2-carbonyl}-amino)-3-[(thiophene-2-carbonyl)-amino]-propionic acid methyl ester (130 mg, 0.22 mmol) in THF (4 mL) was added a solution of lithium hydroxide monohydrate (94 mg, 2.24 mmol) in water (6 mL). The mixture was then stirred at room temperature overnight. The mixture was then acidified with 1N HCl and extracted with EtOAc (×3). The extracts were combined, washed with water and brine, dried over sodium sulfate, filtered, and evaporated to pure product, 0.1159 g (93%). MS m/e 565.9 (M+H$^+$).

Example 59

(S)-2-{[5-(3-Hydroxy-benzylcarbamoyl)-3-isopropyl-thiophene-2-carbonyl]-amino}-3-[(thiophene-2-carbonyl)-amino]-propionic acid

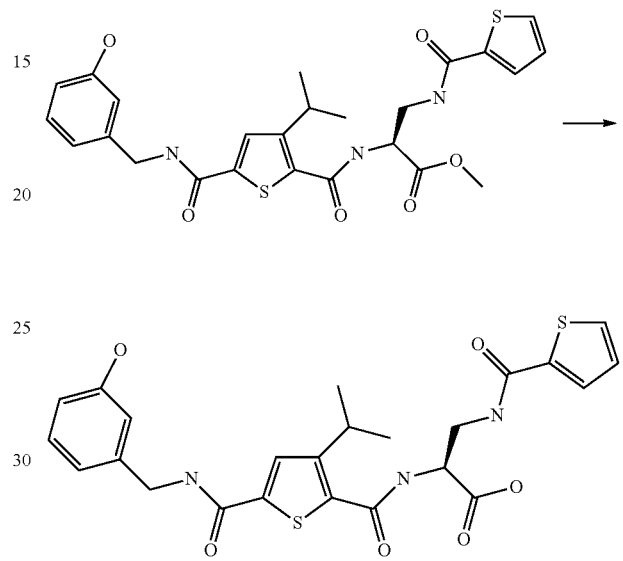

To a solution of (S)-2-{[5-(3-Hydroxy-benzylcarbamoyl)-3-isopropyl-thiophene-2-carbonyl]-amino}-3-[(thiophene-2-carbonyl)-amino]propionic acid methyl ester (40 mg, 0.076 mmol) in THF (2 mL) was added a solution of lithium hydroxide monohydrate (32 mg, 0.76 mmol) in water (3 mL). The mixture was then stirred at room temperature 15 h. The mixture was then acidified with 1N HCl and extracted with EtOAc (×3). The extracts were combined, washed with water and brine, dried over sodium sulfate, filtered, and evaporated to pure product, 29.4 mg (75%). MS m/e 516.0 (M+H$^+$).

Example 60

(S)-2-([5-[(1H-Indazol-4-ylmethyl)-carbamoyl]-3-isopropyl-thiophene-2-carbonyl]-amino)-3-[(thiophene-2-carbonyl)-amino]-propionic acid

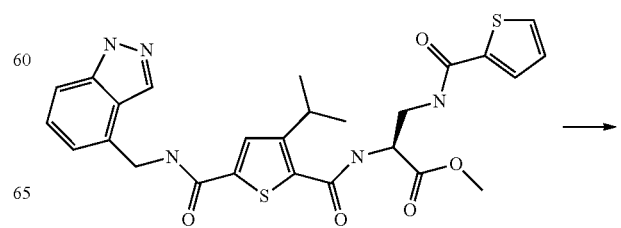

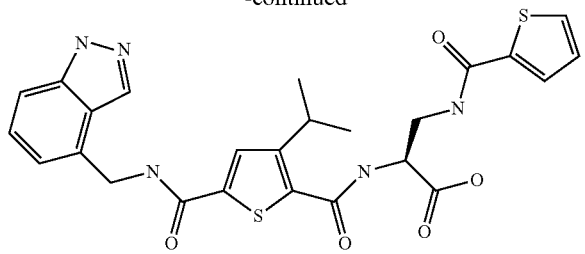

To a solution of (S)-2-({5-[(1H-Indazol-4-ylmethyl)-carbamoyl]-3-isopropyl-thiophene-2-carbonyl}-amino)-3-[(thiophene-2-carbonyl)-amino]-propionic acid methyl ester (109.6 mg, 0.020 mmol) in THF (4 mL) was added a solution of lithium hydroxide monohydrate (84 mg, 2.0 mmol) in water (6 mL). The mixture was then stirred at room temperature 2 d. The mixture was then acidified with 1N HCl and extracted with EtOAc (×3). The extracts were combined, washed with water and brine, dried over sodium sulfate, filtered, and evaporated to pure product, 85.8 mg (79%). MS m/e 540.0 (M+H⁺).

Example 61

(S)-2-{[3-Ethyl-5-(3-hydroxy-benzylcarbamoyl)-thiophene-2-carbonyl]-amino}-3-[(thiophene-2-carbonyl)-amino]-propionic acid

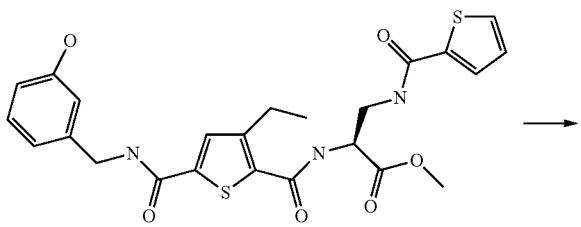

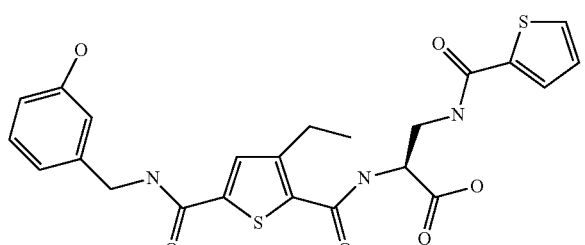

To a solution of (S)-2-{[3-Ethyl-5-(3-hydroxy-benzylcarbamoyl)-thiophene-2-carbonyl]-amino}-3-[(thiophene-2-carbonyl)-amino]-propionic acid methyl ester (74.7 mg, 0.14 mmol) in THF (4 mL) was added a solution of lithium hydroxide monohydrate (61 mg, 1.45 mmol) in water (5 mL). The mixture was then stirred at room temperature 15 h. The mixture was then acidified with 1N HCl and extracted with EtOAc (×3). The extracts were combined, washed with water and brine, dried over sodium sulfate, filtered, and evaporated to pure product, 61.1 mg (87%). MS m/e 501.9 (M+H⁺).

Example 62

(S)-2-({3-Ethyl-5-[(1H-indazol-4-ylmethyl)-carbamoyl]-thiophene-2-carbonyl}-amino)-3-[(thiophene-2-carbonyl)-amino]-propionic acid

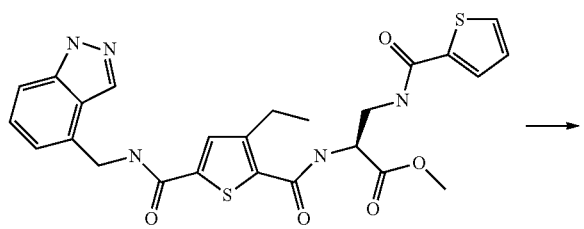

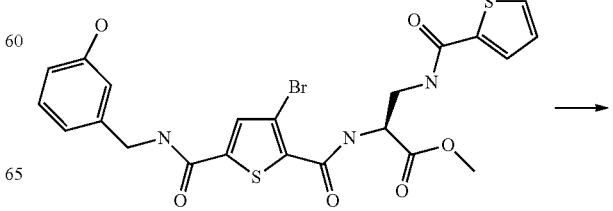

To a solution of (S)-2-({3-Ethyl-5-[(1H-indazol-4-ylmethyl)-carbamoyl]-thiophene-2-carbonyl}-amino)-3-[(thiophene-2-carbonyl)-amino]-propionic acid methyl ester (28.0 mg, 0.052 mmol) in THF (4 mL) was added a solution of lithium hydroxide monohydrate (22 mg, 2.0 mmol) in water (5 mL). The mixture was then stirred at room temperature 2 d. The mixture was then acidified with 1N HCl and extracted with EtOAc (×3). The extracts were combined, washed with water and brine, dried over sodium sulfate, filtered, and evaporated to pure product, 19.2 mg (70%). MS m/e 525.9 (M+H⁺).

Example 63

(S)-2-{[3-Bromo-5-(3-hydroxy-benzylcarbamoyl)-thiophene-2-carbonyl]-amino}-3-[(thiophene-2-carbonyl)-amino]-propionic acid -continued

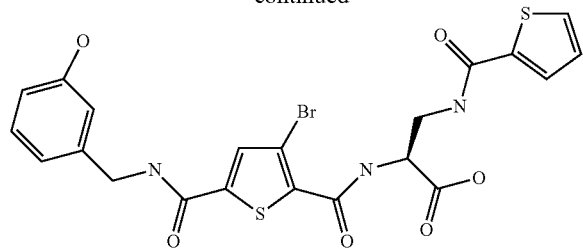

To a solution of (S)-2-{[3-Bromo-5-(3-hydroxy-benzyl-carbamoyl)-thiophene-2-carbonyl]-amino}-3-[(thiophene-2-carbonyl)-amino]-propionic acid methyl ester (24.2 mg, 0.043 mmol) in THF (3 mL) was added a solution of lithium hydroxide monohydrate (120 mg, 2.87 mmol) in water (4 mL). The mixture was then stirred at room temperature 15 h. The mixture was then acidified with 1N HCl and extracted with EtOAc (×3). The extracts were combined, washed with water and brine, dried over sodium sulfate, filtered, and evaporated to pure product, 20.6 mg (87%). MS m/e 553.8 (M+H⁺).

Example 64

(S)-2-{[5-(4-Fluoro-3-hydroxy-benzylcarbamoyl)-3-methyl-thiophene-2-carbonyl]-amino}-3-[(thiophene-2-carbonyl)-amino]-propionic acid

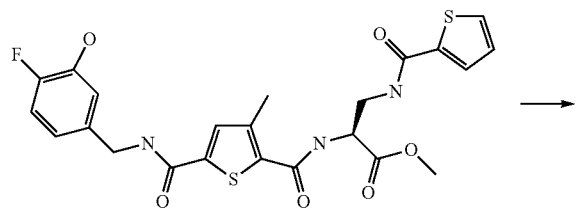

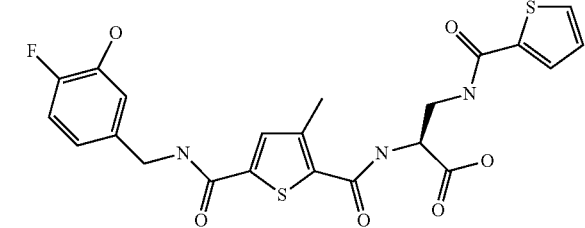

To a solution of (S)-2-{[5-(4-Fluoro-3-hydroxy-benzyl-carbamoyl)-3-methyl-thiophene-2-carbonyl]-amino}-3-[(thiophene-2-carbonyl)-amino]-propionic acidmethyl ester (14 mg, 0.027 mmol) in THF (2 mL) was added a solution of lithium hydroxide monohydrate (11 mg, 0.269 mmol) in water (2.5 mL). The mixture was then stirred at room temperature 15 h. The mixture was then acidified with 1N HCl and extracted with EtOAc (×3). The extracts were combined, washed with water and brine, dried over sodium sulfate, filtered, and evaporated to pure product, 12.3 mg (68%). MS m/e 506.2 (M+H⁺).

Example 65

(S)-2-{[3-Cyano-5-(3-hydroxy-benzylcarbamoyl)-thiophene-2-carbonyl]-amino}-3-[(thiophene-2-carbonyl)-amino]-propionic acid

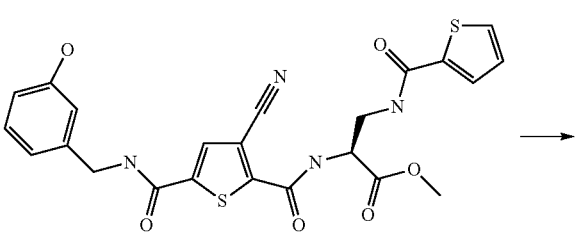

To a solution of (S)-2-{[3-Cyano-5-(3-hydroxy-benzylcarbamoyl)-thiophene-2-carbonyl]-amino}-3-[(thiophene-2-carbonyl)-amino]-propionic acid methyl ester (16.2 mg, 0.032 mmol) in THF (1 mL) was added a solution of lithium hydroxide monohydrate (9 mg, 0.009 mmol) in water (1 mL). The mixture was then stirred at room temperature 15 h. The mixture was then acidified with 1N HCl and extracted with EtOAc (×3). The extracts were combined, washed with water and brine, dried over sodium sulfate, filtered, and evaporated. Material was purified by reverse phase HPLC to afford to pure product, 1.7 mg (11%). MS m/e 498.9 (M+H⁺).

Example 66

(S)-2-({3-Cyano-5-[(1H-indazol-4-ylmethyl)-carbamoyl]-thiophene-2-carbonyl}-amino)-3-(3,5-dihydroxy-benzoylamino)-propionic acid

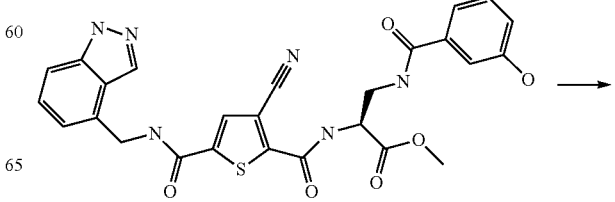

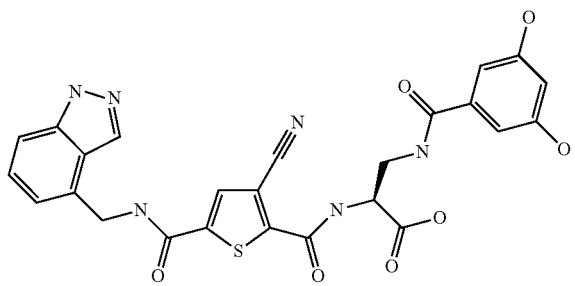

To a solution of (S)-2-({3-Cyano-5-[(1H-indazol-4-ylmethyl)-carbamoyl]-thiophene-2-carbonyl}-amino)-3-(3,5-dihydroxy-benzoylamino)-propionic acid methyl ester (124.1 mg, 0.22 mmol) in THF (10 mL) was added a solution of lithium hydroxide monohydrate (65 mg, 1.54 mmol) in water (12 mL). The mixture was then stirred at room temperature 1.5 h. The mixture was then acidified with 1N HCl and extracted with EtOAc (×3). The extracts were combined, washed with water and brine, dried over sodium sulfate, filtered, and evaporated to afford to pure product, 78.6 mg (65%). MS m/e 549.0 (M+H$^+$).

Example 67

(S)-2-({5-[(1H-Indazol-4-ylmethyl)-carbamoyl}-3-methyl-thiophene-2-carbonyl]-amino)-3-[(thiophene-2-carbonyl)-amino]-propionic acid isobutyl ester

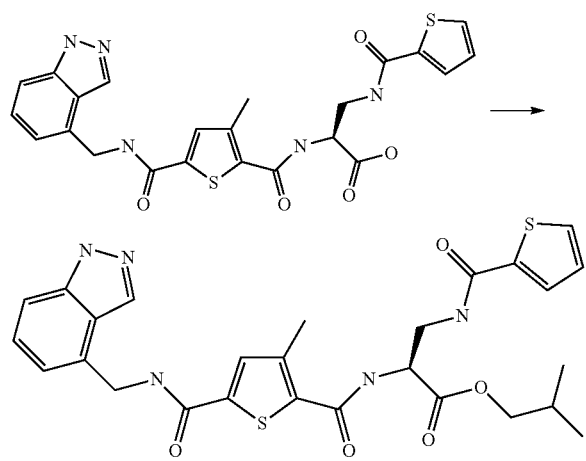

A solution of (S)-2-({5-[(1H-Indazol-4-ylmethyl)-carbamoyl]-3-methyl-thiophene-2-carbonyl}-amino)-3-[(thiophene-2-carbonyl)-amino]-propionic acid (200 mg, 0.39 mmol), 1-Iodo-2-methylpropane (220 mg, 1.17 mmol), and triethylamine (0.16 ml, 1.17 mmol) in DMF (3 mL) was heated in a microwave at 100° C. for 30 min. The mixture was cooled to room temperature, treated with EtOAc (50 mL), washed with brine, dried over sodium sulfate, filtered and evaporated. The residue was purified by column (30-100% EtOAc in hexane) to give 0.1441 g (65%) white solid. MS m/e 567.9 (M+H$^+$).

Example 68

Activity Assays sLFA-1/ICAM-1 ELISA and Mac-1/ICAM-1 ELISA

Plates were coated with either 50 µl/well of 2.0 ug/ml solution of sLFA-1 or Mac-1 receptor in divalent cation buffer (1 mM MnCl$_2$, 0.14M NaCl, 20 mM HEPES pH 7.2) at 4° C. overnight. Two hundred fifty µl of blocking buffer (1% BSA in divalent cation buffer) was added to each well 1 hour at 37° C. Plates were washed 3 times with wash buffer (TBS/0.05% Tween-20/1 mM MnCl$_2$). The compound to be tested was solubilized in DMSO. A series of 1:3 dilutions were performed to achieve a concentration range of 0.45 nM-3 uM. Fifty µl of binding buffer (0.5% BSA in divalent cation buffer)/1% DMSO and 50 µl of the solutions to be tested were added to the appropriate wells and incubated for 1 hour. Fifty µl of 5dICAM-Fc (27 ng/ml) was added to the appropriate wells and 50 µl binding buffer was added to non-specific binding wells and incubated for 2 hours and washed. One hundred µl of 1:4000 HRP-goat anti-huIgG was added to each well and incubated for 1 hour and washed. One hundred µl of 1:1 TMB solution was added to each well and developed for 20 min at room temperature. Color development was stopped by adding 100 µl H$_3$PO$_4$ to each well. Absorbance was measured at 450 nm.

Human Mixed Lymphocyte Reaction (hMLR)

PBMC's were isolated from two healthy donors by Ficoll gradient. Cells were resuspended with 4 mL assay media and counted with a Coulter Counter. Both cell populations were resuspended to 1×107/mL. Stimulator cells were irradiated for 2.5 min (2000 RAD) in cesium irradiator. 5×10$^5$ cells were added to duplicate wells of the plate. Included were quadruplicate wells receiving responder cells alone and stimulator cells alone. The compound to be tested was solubilized in DMSO. A series of 1:3 dilutions were performed to achieve a concentration range of 0.45 nM-3 uM. One hundred µl of the solutions to be tested were added to the cell plate (100 µl of 2% DMSO/media added to control wells). Plates were then incubated for 2.5 days at 37° C. with 5% CO2. Plates were pulsed with 50 µl/well 3H-thymidine at 0.5 uCi/well then incubated for 6 hours at 37° C. with 5% CO2. Cells were harvested using Cell Harvester (TomTec) and counted on TopCount (Perkin Elmer).

Mouse Mixed Lymphocyte Reaction (mMLR)

Spleens were removed from C57Bl/6 and Balb/c mice and placed in Hanks Balanced Salt Solution (HBSS). Red blood cells were removed with ACK lysing buffer and washed two times in assay media. Cells were resuspended with 4 mL assay media and counted with a Coulter Counter. Both cell populations were resuspended to 1×10$^7$/mL. Stimulator cells were irradiated for 2.5 min (2000 RAD) in cesium irradiator. 5×10$^5$ cells were added to duplicate wells of the plate. Included were quadruplicate wells receiving responder cells alone and stimulator cells alone. The compound to be tested was solubilized in DMSO. A series of 1:3 dilutions were performed to achieve a concentration range of 0.45 nM-3 uM. One hundred µl of the solutions to be tested were added to the cell plate (100 µl of 2% DMSO/media added to control wells). Plates were then incubated for 2.5 days at 37° C. with 5% CO$_2$. Plates were pulsed with 50 µl/well $^3$H-thymidine at 0.5 uCi/well then incubated for 6 hours at 37° C. with 5% CO$_2$. Cells were harvested using Cell Harvester (TomTec) and counted on TopCount (Perkin Elmer).

Table 1 provides the in vitro activity for representative LFA-1 antagonists and dual LFA-1/Mac-1 antagonists in the Examples:

TABLE 1

| EXAMPLE | LFA/ICAM (IC50, uM) | MAC-1/ICAM (IC50, uM) |
|---|---|---|
| 1 | 0.017 | |
| 2 | 0.004 | 0.058 |
| 3 | 0.085 | >3 |
| 4 | 0.006 | |
| 5 | 0.002 | 0.3 |
| 6 | 0.003 | |
| 7 | 0.005 | 0.03 |
| 8 | 0.007 | 0.032 |
| 9 | 0.03 | 0.082 |
| 10 | 0.044 | 0.02 |
| 11 | 0.09 | |
| 12 | 0.013 | 0.027 |
| 13 | 0.052 | >3 |
| 14 | 0.008 | 0.089 |
| 15 | 0.003 | 0.012 |
| 16 | 0.017 | |
| 17 | 0.223 | 0.294 |
| 32 | 0.019 | 0.094 |
| 33 | 0.149 | 0.3 |
| 34 | 0.516 | >3 |
| 35 | 0.671 | >3 |
| 36 | 0.024 | 0.048 |
| 37 | 0.027 | |
| 38 | 0.002 | 0.007 |
| 39 | 0.055 | >3 |
| 40 | 0.002 | 0.023 |
| 41 | 0.021 | >3 |
| 42 | 0.035 | >3 |
| 43 | >3 | |
| 44 | 0.017 | |
| 45 | 0.763 | |
| 46 | 0.051 | |
| 47 | 0.289 | |
| 48 | 0.085 | |
| 49 | 0.018 | 0.207 |
| 50 | 0.344 | >3 |
| 51 | 0.164 | >3 |
| 52 | 0.031 | 0.115 |
| 53 | 1.55 | |
| 54 | 0.007 | 0.062 |
| 56 | 0.029 | 0.02 |
| 58 | 0.041 | 0.055 |
| 59 | 0.029 | 0.046 |
| 60 | 0.049 | 0.017 |
| 61 | 0.016 | 0.031 |
| 62 | 0.021 | 0.025 |
| 63 | 0.007 | 0.025 |
| 64 | 0.011 | >3 |
| 65 | 0.003 | |
| 66 | 0.041 | |

It is to be understood that the invention is not limited to the particular embodiments of the invention described above, as variations of the particular embodiments may be made and still fall within the scope of the appended claims.

What is claimed is:

1. A compound of formula (I):

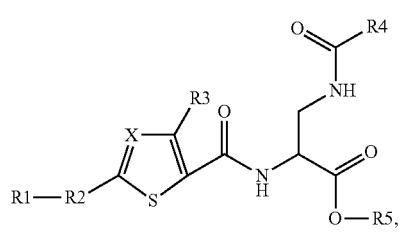

wherein:
X is N or CH;
R1 is indole, oxoindole, indazole or substituted phenyl, said substituted phenyl being mono- or bi-substituted independently with hydroxy, halogen, alkoxy or lower alkyl;
R2 is —(CH$_2$)$_n$C(O)NH—, —(CH$_2$)$_n$NHC(O)—, —(CH$_2$)$_n$NH—, —(CH$_2$)$_n$O— or —CH(CH$_3$)NHC(O)—;
R3 is hydrogen, methyl, trifluoromethyl, halogen or cyano;
R4 is indazole, benzimidazole, unsubstituted heteroaryl, heteroaryl mono- or bi-substituted independently with alkoxy or hydroxy, unsubstituted phenyl or phenyl mono- or bi-substituted independently with hydroxy, methyl, halogen or —COOH;
R5 is hydrogen, lower alkyl, alkoxy, cycloalkyl, heterocycloalkyl, lower alkyl-cycloalkyl, lower alkyl-heterocycloalkyl, —(CH$_2$)$_n$OR6, —CH(CH$_3$)O(O)R6 or —(CH$_2$)—NR7R8;
R6, R7 and R8, independently of each other, are hydrogen, lower alkyl or alkoxy; and
n is 1, 2 or 3,
or a pharmaceutically acceptable salt thereof.

2. The compound according to claim 1, wherein X is N.
3. The compound according to claim 1, wherein X is CH.
4. The compound according to claim 1, wherein R1 is indole, oxoindole or indazole.
5. The compound according to claim 1, wherein R1 is phenyl mono- or bi-substituted independently with hydroxy, halogen, alkoxy or lower alkyl.
6. The compound according to claim 1, wherein R1 is hydroxyphenyl.
7. The compound according to claim 1, wherein R2 is —(CH$_2$)$_n$C(O)NH— or —(CH$_2$)$_n$NHC(O)—.
8. The compound according to claim 1, wherein R2 is —(CH$_2$)$_n$NH—, —(CH$_2$)$_n$O— or —CH(CH$_3$)NHC(O)—.
9. The compound according to claim 1, wherein R3 is methyl.
10. The compound according to claim 1, wherein R4 is indazole or benzimidazole.
11. The compound according to claim 1, wherein R4 is unsubstituted heteroaryl or heteroaryl mono- or bi-substituted independently with alkoxy or hydroxy.
12. The compound according to claim 1, wherein R4 is unsubstituted phenyl or phenyl mono- or bi-substituted independently with hydroxy, methyl, halogen or —COOH.
13. The compound according to claim 1, wherein R4 is thiophene, phenyl, hydroxyphenyl, dihydroxyphenyl or difluorophenyl.
14. The compound according to claim 1, wherein R5 is hydrogen, lower alkyl or alkoxy.
15. The compound according to claim 1, wherein R5 is cycloalkyl, heterocycloalkyl, lower alkyl-cycloalkyl or lower alkyl-heterocycloalkyl.
16. The compound according to claim 1, wherein R5 is —(CH$_2$)$_n$OR6, —CH(CH$_3$)O(O)R6 or —(CH$_2$)$_n$NR7R8.
17. The compound according to claim 1, wherein R5 is hydrogen.
18. The compound according to claim 1, wherein R6 is hydrogen or methyl.
19. The compound according to claim 1, wherein R7 and R8 independently of each other are hydrogen or methyl.
20. The compound according to claim 1, wherein n is 1.
21. The compound according to claim 1, wherein said compound is:
(S)-3-(3,5-Difluoro-benzoylamino)-2-({2-[2-(3-hydroxy-phenyl)-acetylamino]-4-methyl-thiazole-5-carbonyl}-amino)-propionic acid;

(S)-2-({2-[2-(3-Hydroxy-phenyl)-acetylamino]-4-methyl-thiazole-5-carbonyl}-amino)-3-[(thiophene-2-carbonyl)-amino]-propionic acid;
(S)-2-({2-[2-(3-Hydroxy-phenyl)-acetylamino]-thiazole-5-carbonyl}-amino)-3-[(thiophene-2-carbonyl)-amino]-propionic acid;
(S)-3-Benzoylamino-2-({2-[2-(3-hydroxy-phenyl)-acetylamino]-4-methyl-thiazole-5-carbonyl}-amino)-propionic acid;
(S)-3-(3-Hydroxy-benzoylamino)-2-({2-[2-(3-hydroxy-phenyl)-acetylamino]-4-methyl-thiazole-5-carbonyl}-amino)-propionic acid;
(S)-3-(3,5-Dihydroxy-benzoylamino)-2-({2-[2-(3-hydroxy-phenyl)-acetylamino]-4-methyl-thiazole-5-carbonyl}-amino)-propionic acid;
(S)-2-({2-[2-(3-Hydroxy-phenyl)-acetylamino]-4-methyl-thiazole-5-carbonyl}-amino)-3-[(thiophene-3-carbonyl)-amino]-propionic acid;
(S)-2-({4-Chloro-2-[2-(3-hydroxy-phenyl)-acetylamino]-thiazole-5-carbonyl}-amino)-3-[(thiophene-2-carbonyl)-amino]-propionic acid;
(S)-2-({2-[2-(3-Hydroxy-phenyl)-acetylamino]-4-trifluoromethyl-thiazole-5-carbonyl}-amino)-3-[(thiophene-2-carbonyl)-amino]-propionic acid;
(S)-3-(3,5-Dihydroxy-benzoylamino)-2-({2-[3-(3-hydroxy-phenyl)-propionylamino]-4-methyl-thiazole-5-carbonyl}-amino)-propionic acid;
(S)-2-({2-[3-(3-Hydroxy-phenyl)-propionylamino]-4-methyl-thiazole-5-carbonyl}-amino)-3-[(thiophene-2-carbonyl)-amino]-propionic acid;
(S)-3-(3,5-Dihydroxy-benzoylamino)-2-({2-[2-(3-hydroxy-phenyl)-ethylamino]-4-methyl-thiazole-5-carbonyl}-amino)-propionic acid;
(S)-2-({2-[3-(3-Hydroxy-phenyl)-propoxy]-4-methyl-thiazole-5-carbonyl}-amino)-3-[(thiophene-2-carbonyl)-amino]-propionic acid;
(S)-2-{[2-(2-1H-Indazol-4-yl-acetylamino)-4-methyl-thiazole-5-carbonyl]-amino}-3-[(thiophene-2-carbonyl)-amino]-propionic acid;
(S)-3-(3,5-Dihydroxy-benzoylamino)-2-{[2-(2-1H-indazol-4-yl-acetylamino)-4-methyl-thiazole-5-carbonyl]-amino}-propionic acid;
(S)-2-{[2-(2-1H-Indazol-4-yl-acetylamino)-4-trifluoromethyl-thiazole-5-carbonyl]-amino}-3-[(thiophene-2-carbonyl)-amino]-propionic acid;
(S)-2-({2-[3-(1H-Indazol-4-yl)-propylamino]-4-methyl-thiazole-5-carbonyl}-amino)-3-[(thiophene-2-carbonyl)-amino]-propionic acid;
(S)-2-{[2-(2-1H-Indazol-4-yl-acetylamino)-4-methyl-thiazole-5-carbonyl]-amino}-3-[(thiophene-2-carbonyl)-amino]propionic acid 3,3-dimethyl-butyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid ethyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid isobutyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid butyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 1-ethyl-propyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid cyclopentyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 2,2-dimethyl-propyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid cyclopropylmethyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 3-ethoxy-propyl ester;
(S)-2-{[2-(2-1H-Indazol-4-yl-acetylamino)-4-trifluoromethyl-thiazole-5-carbonyl]-amino}-3-[(thiophene-2-carbonyl)-amino]-propionic acid 3-ethoxy-propyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid ethyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 2-morpholin-4-yl-ethyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 1-(2,2-dimethyl-propionyloxy)-ethyl ester;
(S)-2-{[2-(2-1H-Indazol-4-yl-acetylamino)-4-methyl-thiazole-5-carbonyl]-amino}-3-[(thiophene-2-carbonyl)-amino]-propionic acid 2-diethylamino-ethyl ester;
(S)-2-{[5-(3-hydroxy-benzylcarbamoyl)-3-methyl-thiophen-2-carbonyl]-amino}-3-[(thiophene-2-carbonyl)-amino]-propionic acid;
(S)-2-{[2-tert-butyl-5-(3-hydroxy-benzylcarbamoyl)-thiophen-2-carbonyl]-amino}-3-[(thiophene-2-carbonyl)-amino]-propionic acid;
(S)-2-({5-[(1H-indol-4-ylmethyl)carbamoyl]-3-methyl-thiophen-2-carbonyl}-amino)-3-[(thiophene-2-carbonyl)-amino]-propionic acid;
(S)-2-({3-methyl-5-[(2-oxo-2,3-dihydro-1H-indol-4-ylmethyl)carbamoyl]-thiophen-2-carbonyl}-amino)-3-[(thiophene-2-carbonyl)-amino]-propionic acid;
(S)-2-({5-[(1H-indazol-4-ylmethyl)-carbamoyl]-3-methyl-thiophen-2-carbonyl}-amino)-3-[(thiophene-2-carbonyl)-amino]-propionic acid;
(S)-2-({5-[1-(3-hydroxy-phenyl)-ethylcarbamoyl]-3-methyl-thiophen-2-carbonyl}-amino)-3-[(thiophene-2-carbonyl)-amino]-propionic acid;
(S)-3-(3,5-dihydroxy-benzoylamino)-2-{[5-(3-hydroxy-benzylcarbamoyl)-3-methyl-thiophen-2-carbonyl]-amino}-propionic acid;
(S)-3-[(2,6-dioxo-1,2,3,6-tetrahydro-pyrimidine-4-carbonyl)-amino]-2-{[5-(3-hydroxy-benzylcarbamoyl)-3-methyl-thiophene-2-carbonyl-amino]-propionic acid;
(S)-3-(3-hydroxy-benzoylamino)-2-{[5-(3-hydroxy-benzylcarbamoyl)-3-methyl-thiophene-2-carbonyl-amino]-propionic acid;
(S)-3-(3-hydroxy-benzoylamino)-2-{[5-(3-hydroxy-benzylcarbamoyl)-3-methyl-thiophene-2-carbonyl-amino]-propionic acid;
(S)-3-[(1H-benzoimidazole-5-carbonyl)-amino]-2-{[5-(3-hydroxy-benzylcarbamoyl)-3-methyl-thiophene-2-carbonyl-amino]-propionic acid (HCl salt);
(S)-3-[(2,6-dimethoxy-pyrimidine-4-carbonyl)-amino]-2-{[5-(3-hydroxy-benzylcarbamoyl)-3-methyl-thiophene-2-carbonyl]-amino}-propionic acid;
(S)-2-{[5-(3-hydroxy-benzylcarbamoyl)-3-methyl-thiophene-2-carbonyl]-amino}-3-[(1H-indazole-4-carbonyl)-amino]-propionic acid (HCl salt);

(S)-2-{[5-(3-hydroxy-benzylcarbamoyl)-3-methyl-thiophene-2-carbonyl]-amino}-3-[(5-hydroxy-pyrazine-2-carbonyl)-amino]-propionic acid;

(S)-3-[(1H-benzoimidazole-4-carbonyl)-amino]-2-{[5-(3-hydroxy-benzylcarbamoyl)-3-methyl-thiophene-2-carbonyl]-amino}-propionic acid (HCl salt);

(S)-3-[(benzo ic acid-3-carbonyl)-amino]-2-{[5-(3-hydroxy-benzylcarbamoyl)-3-methyl-thiophene-2-carbonyl]-amino}-propionic acid;

(S)-2-({5-[2-(3-hydroxy-phenyl)ethyl-carbamoyl]-3-methyl-thiophen-2-carbonyl}-amino)-3-[(thiophene-2-carbonyl)-amino]-propionic acid;

(S)-3-(3,5-dihydroxy-benzoylamino)-2-({5-[2-(3-hydroxy-phenyl)-ethyl-carbamoyl]-3-methyl-thiophen-2-carbonyl}-amino)-propionic acid;

(S)-2-({5-[(1H-Indol-4-ylmethyl)-carbamoyl]-3-trifluoromethyl-thiophene-2-carbonyl}-amino)-3-[(thiophene-2-carbonyl)-amino]-propionic acid;

(S)-2-({5-[(2-oxo-2,3-dihydro-1H-indol-4-ylmethyl)-carbamoyl]-3-trifluoromethyl-thiophene-2-carbonyl}-amino)-3-[(thiophene-2-carbonyl)-amino]-propionic acid;

(S)-2-{[5-(3-Hydroxy-benzylcarbamoyl)-3-trifluoromethyl-thiophene-2-carbonyl]-amino}-3-[(thiophene-2-carbonyl)-amino]-propionic acid;

(S)-2-{[5-(3-Hydroxy-benzylcarbamoyl)-3-phenyl-thiophene-2-carbonyl]-amino}-3-[(thiophene-2-carbonyl)-amino]-propionic acid;

(S)-2-{[3-Chloro-5-(3-hydroxy-benzylcarbamoyl)-thiophene-2-carbonyl]-amino}-3-[(thiophene-2-carbonyl)-amino]-propionic acid;

(S)-2-{[3-Chloro-5-(3-hydroxy-benzylcarbamoyl)-thiophene-2-carbonyl]-amino}-3-[(thiophene-2-carbonyl)-amino]-propionic acid isobutyl ester;

(S)-2-({3-Chloro-5-[(1H-indazol-4-ylmethyl)-carbamoyl]-thiophene-2-carbonyl}-amino)-3-[(thiophene-2-carbonyl)-amino]-propionic acid;

(S)-2-({3-Chloro-5-[(1H-indazol-4-ylmethyl)-carbamoyl}-thiophene-2-carbonyl]-amino)-3-[(thiophene-2-carbonyl)-amino]-propionic acid isobutyl ester;

(S)-2-({5-[(1H-Indazol-4-ylmethyl)-carbamoyl]-3-trifluoromethyl-thiophene-2-carbonyl}-amino)-3-[(thiophene-2-carbonyl)-amino]-propionic acid;

(S)-2-{[5-(3-Hydroxy-benzylcarbamoyl)-3-isopropyl-thiophene-2-carbonyl]-amino}-3-[(thiophene-2-carbonyl)-amino]-propionic acid;

(S)-2-({5-[(1H-Indazol-4-ylmethyl)-carbamoyl]-3-isopropyl-thiophene-2-carbonyl}-amino)-3-[(thiophene-2-carbonyl)-amino]-propionic acid;

(S)-2-{[3-Ethyl-5-(3-hydroxy-benzylcarbamoyl)-thiophene-2-carbonyl]-amino}-3-[(thiophene-2-carbonyl)-amino]-propionic acid;

(S)-2-({3-Ethyl-5-[(1H-indazol-4-ylmethyl)-carbamoyl]-thiophene-2-carbonyl}-amino)-3-[(thiophene-2-carbonyl)-amino]-propionic acid;

(S)-2-{[3-Bromo-5-(3-hydroxy-benzylcarbamoyl)-thiophene-2-carbonyl]-amino}-3-[(thiophene-2-carbonyl)-amino]-propionic acid;

(S)-2-{[5-(4-Fluoro-3-hydroxy-benzylcarbamoyl)-3-methyl-thiophene-2-carbonyl]-amino}-3-[(thiophene-2-carbonyl)-amino]-propionic acid;

(S)-2-{[3-Cyano-5-(3-hydroxy-benzylcarbamoyl)-thiophene-2-carbonyl]-amino}-3-[(thiophene-2-carbonyl)-amino]-propionic acid;

(S)-2-({3-Cyano-5-[(1H-indazol-4-ylmethyl)-carbamoyl]-thiophene-2-carbonyl}-amino)-3-(3,5-dihydroxy-benzoylamino)-propionic acid; or (S)-2-({5-[(1H-Indazol-4-ylmethyl)-carbamoyl]-3-methyl-thiophene-2-carbonyl}-amino)-3-[(thiophene-2-carbonyl)-amino]-propionic acid isobutyl ester.

22. A process for the preparation of a compound according to claim 1, comprising the steps of:

saponifying a compound of formula (II):

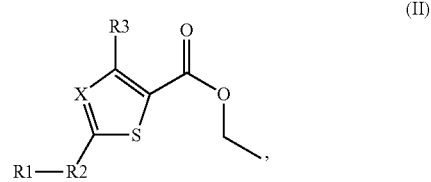

and forming a compound of formula (I):

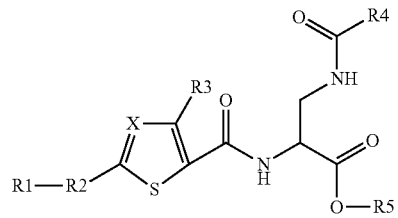

or a pharmaceutically acceptable salt thereof.

23. A pharmaceutical composition, comprising a therapeutically effective amount of a compound in accordance with claim 1 and a therapeutically inert carrier.

24. A method for the treatment of asthma or COPD, which method comprises the step of administering an effective amount of a compound as defined in claim 1 to a patient in need thereof.

* * * * *